(12) United States Patent
Kondou et al.

(10) Patent No.: US 10,619,213 B2
(45) Date of Patent: Apr. 14, 2020

(54) PROSTATE CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Takahiro Ochiya, Tokyo (JP); Nobuyoshi Kosaka, Tokyo (JP)

(73) Assignees: TORAY INDUSTRIES, INC., Tokyo (JP); NATIONAL CANCER CENTER, Tokyo (JP)

(*) Notice: Subject to any disclaimer, the term of this patent is extended or adjusted under 35 U.S.C. 154(b) by 269 days.

(21) Appl. No.: 15/317,882

(22) PCT Filed: Jun. 12, 2015

(86) PCT No.: PCT/JP2015/066964
§ 371 (c)(1),
(2) Date: Dec. 9, 2016

(87) PCT Pub. No.: WO2015/190584
PCT Pub. Date: Dec. 17, 2015

(65) Prior Publication Data
US 2017/0121779 A1    May 4, 2017

(30) Foreign Application Priority Data

Jun. 12, 2014 (JP) .................. 2014-121377
Mar. 31, 2015 (JP) .................. 2015-071756

(51) Int. Cl.
| | | |
|---|---|---|
| C12Q 1/68 | (2018.01) | |
| C12P 19/34 | (2006.01) | |
| C12Q 1/6886 | (2018.01) | |
| G01N 37/00 | (2006.01) | |
| C12N 15/09 | (2006.01) | |
| C12M 1/34 | (2006.01) | |
| G01N 33/574 | (2006.01) | |
| C12M 1/00 | (2006.01) | |
| G01N 33/53 | (2006.01) | |

(52) U.S. Cl.
CPC .......... *C12Q 1/6886* (2013.01); *C12M 1/00* (2013.01); *C12M 1/34* (2013.01); *C12N 15/09* (2013.01); *C12Q 1/68* (2013.01); *G01N 33/53* (2013.01); *G01N 33/574* (2013.01); *G01N 37/00* (2013.01); *C12Q 2600/156* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

FOREIGN PATENT DOCUMENTS

| EP | 2 341 145 A1 | 7/2011 |
|---|---|---|
| JP | 2013-535982 A | 9/2013 |
| WO | WO 2009/108860 A2 | 9/2009 |
| WO | WO 2010/062706 | 6/2010 |
| WO | WO 2011/080315 A1 | 7/2011 |
| WO | WO 2012/027206 A1 | 3/2012 |
| WO | WO 2013/022995 A2 | 2/2013 |
| WO | WO 2014/071205 A1 | 5/2014 |
| WO | WO 2014/071226 A1 | 5/2014 |

OTHER PUBLICATIONS

NCBI GEO Accession Display for Platform GPL7766, public on May 14, 2009. Kyoto Univ. 3D-Gene Human miRNA Oligo chip v11.0. Obtained from https://www.ncbi.nlm.nih.gov/geo/query/acc.cgi?acc=GPL7766 on Aug. 22, 2018. Including full Data Table. 12 pages. (Year: 2009).*
MiScript™ miRNA PCR Array (384-well, 384HC) Human miRBase Profiler HC Plate 4 from Qiagen (2012) (Year: 2012).*
Cheung et al (2003) Nature Genetics, vol. 33, pp. 422-425. (Year: 2003).*
Hoshikawa et al (2003) Phsiol Genomics 12:209-219, 2003 (Year: 2003).*
Cobb et al (2002) Critical Care Medicine. 30(12):2711-2721 (Year: 2002).*
Shen et al. (2013. Cancer Epidemiol Biomarkers Prev; 22(12) Dec. 2013. pp. 2364-2373).*
GenBank Locus NR_039645 (2013).*
American Cancer Society, "Prostate Cancer", 2013, pp. 5, 14-26, 32-54, and 68-70.
Eto et al., "Prospect of microRNA toward laboratory medicine gastrointestinal cancer and microRNA", Clinical Chemistry, vol. 43, 2014, pp. 99-105.
Huang, et al., "Extracellular MicroRNAs in Urologic Malignancies: Chances and Challenges", International Journal of Molecular Sciences, vol. 14, No. 7, 2013, pp. 14785-14799.
International Search Report for PCT/JP2015/066964 (PCT/ISA/210) dated Sep. 1, 2015.
Kozomara et al., "miRBase: annotating high confidence microRNAs using deep sequencing data", Nucleic Acids Research, vol. 42, 2014, Database issue, pp. D68-D73.
Mahn, et al., "Circulating microRNAs (miRNA) in Serum of Patients with Prostate Cancer", Urology, vol. 77, No. 5, 2011, pp. 1265.e9-1265.e16.

(Continued)

*Primary Examiner* — Stephen T Kapushoc
(74) *Attorney, Agent, or Firm* — Birch, Stewart, Kolasch & Birch, LLP

(57) ABSTRACT

An object of the present invention is to provide a kit or a device for the detection of prostate cancer and a method for detecting prostate cancer. The present invention provides a kit or a device for the detection of prostate cancer, comprising a nucleic acid capable of specifically binding to a miRNA in a sample of a subject, and a method for detecting prostate cancer, comprising measuring the miRNA in vitro.

6 Claims, 4 Drawing Sheets
Specification includes a Sequence Listing.

(56) References Cited

OTHER PUBLICATIONS

Mitchell et al., "Circulating microRNAs as stable blood-based markers for cancer detection", Proceedings of the National Academy of Sciences of the United States of America, vol. 105, No. 30, 2008, pp. 10513-10518.
Sobin, et al., "TNM Classification of Malignant Tumours", International Union Against Cancer, 7th edition, 2010, pp. 230 to 234.
Takizawa et al., "miRNA Profiling in Serum Samples Using DNA Chip 3D-Gene", BIO Clinica, vol. 29, No. 6, 2014, pp. 588 to 589.
Wang et al., Tumor-Associated Circulating MicroRNAs as Biomarkers of Cancer, Molecules, vol. 19, No. 2, 2014, pp. 1912-1938.
Wolf et al., "American Cancer Society Guideline for the Early Detection of Prostate Cancer", A Cancer Journal for Clinicians, vol. 60, 2010, pp. 70-98.
Written Opinion of the International Searching Authority for PCT/JP2015/066964 (PCT/ISA/237) dated Sep. 1, 2015.
Berillo et al., "Binding of intronic miRNAs to the mRNAs of host genes encoding intronic miRNAs and proteins that participate in tumourigenesis," Computers in Biology and Medicine, vol. 43, 2013, pp. 1374-1381.
Liu et al., "MicroRNA expression profile of gastric cancer stem cells in the MKN-45 cancer cell line," Acta Biochim. Biophys. Sin., vol. 46, No. 2, 2014 (Advance Access Publication Jan. 2, 2014), pp. 92-99.
Partial Supplementary European Search Report for European Application No. 15806052.5, dated Dec. 15, 2017.
Jima et al., "Deep sequencing of the small RNA transcriptome of normal and malignant human B cells identifies hundreds of novel microRNAs," Blood, vol. 116, No. 23, Dec. 2, 2010 (published online Aug. 23, 2010), pp. 118-127 (11 pages total).

* cited by examiner

SEQUENCE LISTING

```
<160> NUMBER OF SEQ ID NOS: 684

<210> SEQ ID NO 1
<211> LENGTH: 17
<212> TYPE: RNA
<213> ORGANISM: Homo sapiens

<400> SEQUENCE: 1
uuggaggcgu ggguuuu                                              17

<210> SEQ ID NO 2
<211> LENGTH: 21
<212> TYPE: RNA
<213> ORGANISM: Homo sapiens

<400> SEQUENCE: 2
cggcggggac ggcgauuggu c                                         21

<210> SEQ ID NO 3
```

```
<211> LENGTH: 18
<212> TYPE: RNA
<213> ORGANISM: Homo sapiens

<400> SEQUENCE: 3
ccagaggugg ggacugag                                                    18

<210> SEQ ID NO 4
<211> LENGTH: 23
<212> TYPE: RNA
<213> ORGANISM: Homo sapiens

<400> SEQUENCE: 4
ggaggcgcag gcucggaaag gcg                                              23

<210> SEQ ID NO 5
<211> LENGTH: 23
<212> TYPE: RNA
<213> ORGANISM: Homo sapiens

<400> SEQUENCE: 5
agaggcuuug ugcggauacg ggg                                              23

<210> SEQ ID NO 6
<211> LENGTH: 24
<212> TYPE: RNA
<213> ORGANISM: Homo sapiens

<400> SEQUENCE: 6
ugggcgaggg gugggcucuc agag                                             24

<210> SEQ ID NO 7
<211> LENGTH: 22
<212> TYPE: RNA
<213> ORGANISM: Homo sapiens

<400> SEQUENCE: 7
cuccuggggc ccgcacucuc gc                                               22

<210> SEQ ID NO 8
<211> LENGTH: 22
<212> TYPE: RNA
<213> ORGANISM: Homo sapiens

<400> SEQUENCE: 8 acugguagg ugggcucca gg                                                 22

<210> SEQ ID NO 9
<211> LENGTH: 22
<212> TYPE: RNA
<213> ORGANISM: Homo sapiens

<400> SEQUENCE: 9
uggggagcgg cccccgggug gg                                               22

<210> SEQ ID NO 10
<211> LENGTH: 22
<212> TYPE: RNA
<213> ORGANISM: Homo sapiens

<400> SEQUENCE: 10
agacacauuu ggagagggac cc                                               22
```

```
<210> SEQ ID NO 11
<211> LENGTH: 22
<212> TYPE: RNA
<213> ORGANISM: Homo sapiens

<400> SEQUENCE: 11
gugggugcug gugggagccg ug                                              22

<210> SEQ ID NO 12
<211> LENGTH: 23
<212> TYPE: RNA
<213> ORGANISM: Homo sapiens

<400> SEQUENCE: 12 ugagugggc ucccgggacg gcg                                              23

<210> SEQ ID NO 13
<211> LENGTH: 23
<212> TYPE: RNA
<213> ORGANISM: Homo sapiens

<400> SEQUENCE: 13
ucaauaggaa agagguggga ccu                                             23

<210> SEQ ID NO 14
<211> LENGTH: 23
<212> TYPE: RNA
<213> ORGANISM: Homo sapiens

<400> SEQUENCE: 14
ugagcaccac acaggccggg cgc                                             23

<210> SEQ ID NO 15
<211> LENGTH: 23
<212> TYPE: RNA
<213> ORGANISM: Homo sapiens

<400> SEQUENCE: 15
ucgaggacug guggaagggc cuu                                             23

<210> SEQ ID NO 16
<211> LENGTH: 22
<212> TYPE: RNA
<213> ORGANISM: Homo sapiens

<400> SEQUENCE: 16 gggugggau uuguugcauu ac                                               22

<210> SEQ ID NO 17
<211> LENGTH: 17
<212> TYPE: RNA
<213> ORGANISM: Homo sapiens

<400> SEQUENCE: 17
ccccgccacc gccuugg                                                    17

<210> SEQ ID NO 18
<211> LENGTH: 20
<212> TYPE: RNA
<213> ORGANISM: Homo sapiens

<400> SEQUENCE: 18
ggcuccuugg ucuagggua                                                  20
```

```
<210> SEQ ID NO 19
<211> LENGTH: 20
<212> TYPE: RNA
<213> ORGANISM: Homo sapiens

<400> SEQUENCE: 19
gcggaaggcg gagcggcgga                                              20

<210> SEQ ID NO 20
<211> LENGTH: 22
<212> TYPE: RNA
<213> ORGANISM: Homo sapiens

<400> SEQUENCE: 20
ugguggagga agagggcagc uc                                           22

<210> SEQ ID NO 21
<211> LENGTH: 19
<212> TYPE: RNA
<213> ORGANISM: Homo sapiens

<400> SEQUENCE: 21
agcagggcug gggauugca                                               19

<210> SEQ ID NO 22
<211> LENGTH: 22
<212> TYPE: RNA
<213> ORGANISM: Homo sapiens

<400> SEQUENCE: 22
uggcggcggu aguuaugggc uu                                           22

<210> SEQ ID NO 23
<211> LENGTH: 22
<212> TYPE: RNA
<213> ORGANISM: Homo sapiens

<400> SEQUENCE: 23
ucgggccugg gguuggggga gc                                           22

<210> SEQ ID NO 24
<211> LENGTH: 20
<212> TYPE: RNA
<213> ORGANISM: Homo sapiens

<400> SEQUENCE: 24
uaggaugggg gugagaggug                                              20

<210> SEQ ID NO 25
<211> LENGTH: 21
<212> TYPE: RNA
<213> ORGANISM: Homo sapiens

<400> SEQUENCE: 25
accacugcac uccagccuga g                                            21

<210> SEQ ID NO 26
<211> LENGTH: 21
<212> TYPE: RNA
<213> ORGANISM: Homo sapiens

<400> SEQUENCE: 26
agcggugcuc cugcgggccg a                                            21
```

```
<210> SEQ ID NO 27
<211> LENGTH: 22
<212> TYPE: RNA
<213> ORGANISM: Homo sapiens

<400> SEQUENCE: 27 ggagggguc cgcacuggga gg                                              22

<210> SEQ ID NO 28
<211> LENGTH: 21
<212> TYPE: RNA
<213> ORGANISM: Homo sapiens

<400> SEQUENCE: 28
aagggacagg gagggucgug g                                              21

<210> SEQ ID NO 29
<211> LENGTH: 21
<212> TYPE: RNA
<213> ORGANISM: Homo sapiens

<400> SEQUENCE: 29
cgggagcugg ggucugcagg u                                              21

<210> SEQ ID NO 30
<211> LENGTH: 23
<212> TYPE: RNA
<213> ORGANISM: Homo sapiens

<400> SEQUENCE: 30
gggggccgau acacuguacg aga                                            23

<210> SEQ ID NO 31
<211> LENGTH: 20
<212> TYPE: RNA
<213> ORGANISM: Homo sapiens

<400> SEQUENCE: 31
cggggugggu gaggucgggc                                                20

<210> SEQ ID NO 32
<211> LENGTH: 21
<212> TYPE: RNA
<213> ORGANISM: Homo sapiens

<400> SEQUENCE: 32
ucaccuggcu ggcccgccca g                                              21

<210> SEQ ID NO 33
<211> LENGTH: 23
<212> TYPE: RNA
<213> ORGANISM: Homo sapiens

<400> SEQUENCE: 33
agaagaaggc ggucggucug cgg                                            23

<210> SEQ ID NO 34
<211> LENGTH: 18
<212> TYPE: RNA
<213> ORGANISM: Homo sapiens

<400> SEQUENCE: 34
```

```
cggugagcgc ucgcuggc                                                    18

<210> SEQ ID NO 35
<211> LENGTH: 23
<212> TYPE: RNA
<213> ORGANISM: Homo sapiens

<400> SEQUENCE: 35
uggggggaca gauggagagg aca                                              23

<210> SEQ ID NO 36
<211> LENGTH: 21
<212> TYPE: RNA
<213> ORGANISM: Homo sapiens

<400> SEQUENCE: 36 guugggugc agggucugc u                                                  21

<210> SEQ ID NO 37
<211> LENGTH: 22
<212> TYPE: RNA
<213> ORGANISM: Homo sapiens

<400> SEQUENCE: 37
gggaccaucc ugccugcugu gg                                               22

<210> SEQ ID NO 38
<211> LENGTH: 23
<212> TYPE: RNA
<213> ORGANISM: Homo sapiens

<400> SEQUENCE: 38
uggggaaggc uuggcaggga aga                                              23

<210> SEQ ID NO 39
<211> LENGTH: 23
<212> TYPE: RNA
<213> ORGANISM: Homo sapiens

<400> SEQUENCE: 39
gccccggcgc gggcggguuc ugg                                              23

<210> SEQ ID NO 40
<211> LENGTH: 22
<212> TYPE: RNA
<213> ORGANISM: Homo sapiens

<400> SEQUENCE: 40
ucaaaaucag gagucggggc uu                                               22

<210> SEQ ID NO 41
<211> LENGTH: 20
<212> TYPE: RNA
<213> ORGANISM: Homo sapiens

<400> SEQUENCE: 41
ggauccgagu cacggcacca                                                  20

<210> SEQ ID NO 42
<211> LENGTH: 21
<212> TYPE: RNA
<213> ORGANISM: Homo sapiens

<400> SEQUENCE: 42
``` gggggggaugu gcaugcuggu u                                    21

<210> SEQ ID NO 43
<211> LENGTH: 18
<212> TYPE: RNA
<213> ORGANISM: Homo sapiens

<400> SEQUENCE: 43
auccuaguca cggcacca                                         18

<210> SEQ ID NO 44
<211> LENGTH: 22
<212> TYPE: RNA
<213> ORGANISM: Homo sapiens

<400> SEQUENCE: 44
ugcggggcua gggcuaacag ca                                    22

<210> SEQ ID NO 45
<211> LENGTH: 22
<212> TYPE: RNA
<213> ORGANISM: Homo sapiens

<400> SEQUENCE: 45
ggcuggagcg agugcagugg ug                                    22

<210> SEQ ID NO 46
<211> LENGTH: 20
<212> TYPE: RNA
<213> ORGANISM: Homo sapiens

<400> SEQUENCE: 46
ugugggacug caaaugggag                                       20

<210> SEQ ID NO 47
<211> LENGTH: 21
<212> TYPE: RNA
<213> ORGANISM: Homo sapiens

<400> SEQUENCE: 47
uggggcgggg caggucccug c                                     21

<210> SEQ ID NO 48
<211> LENGTH: 23
<212> TYPE: RNA
<213> ORGANISM: Homo sapiens

<400> SEQUENCE: 48
cgggcugucc ggaggggucg gcu                                   23

<210> SEQ ID NO 49
<211> LENGTH: 18
<212> TYPE: RNA
<213> ORGANISM: Homo sapiens

<400> SEQUENCE: 49
cuggcagggg gagaggua                                         18

<210> SEQ ID NO 50
<211> LENGTH: 22
<212> TYPE: RNA
<213> ORGANISM: Homo sapiens -continued

```
<400> SEQUENCE: 50 ccccugggge ugggcaggcg ga                                        22

<210> SEQ ID NO 51
<211> LENGTH: 24
<212> TYPE: RNA
<213> ORGANISM: Homo sapiens

<400> SEQUENCE: 51
ccccgggaac gucgagacug gagc                                      24

<210> SEQ ID NO 52
<211> LENGTH: 18
<212> TYPE: RNA
<213> ORGANISM: Homo sapiens

<400> SEQUENCE: 52
uucccagcca acgcacca                                             18

<210> SEQ ID NO 53
<211> LENGTH: 17
<212> TYPE: RNA
<213> ORGANISM: Homo sapiens

<400> SEQUENCE: 53
cuccgggacg gcuggge                                              17

<210> SEQ ID NO 54
<211> LENGTH: 19
<212> TYPE: RNA
<213> ORGANISM: Homo sapiens

<400> SEQUENCE: 54
ggggagcgag gggcggggc                                            19

<210> SEQ ID NO 55
<211> LENGTH: 21
<212> TYPE: RNA
<213> ORGANISM: Homo sapiens

<400> SEQUENCE: 55
cgggccggag gucaagggcg u                                         21

<210> SEQ ID NO 56
<211> LENGTH: 19
<212> TYPE: RNA
<213> ORGANISM: Homo sapiens

<400> SEQUENCE: 56 uggggggagau gggggguuga                                          19

<210> SEQ ID NO 57
<211> LENGTH: 22
<212> TYPE: RNA
<213> ORGANISM: Homo sapiens

<400> SEQUENCE: 57
ugggcgaggg cggcugagcg gc                                        22

<210> SEQ ID NO 58
<211> LENGTH: 18
<212> TYPE: RNA
<213> ORGANISM: Homo sapiens
```

-continued

```
<400> SEQUENCE: 58
cccagcagga cgggagcg                                                      18

<210> SEQ ID NO 59
<211> LENGTH: 21
<212> TYPE: RNA
<213> ORGANISM: Homo sapiens

<400> SEQUENCE: 59
cguggaggac gaggaggagg c                                                  21

<210> SEQ ID NO 60
<211> LENGTH: 22
<212> TYPE: RNA
<213> ORGANISM: Homo sapiens

<400> SEQUENCE: 60 ugggaggug uggagucagc au                                                  22

<210> SEQ ID NO 61
<211> LENGTH: 21
<212> TYPE: RNA
<213> ORGANISM: Homo sapiens

<400> SEQUENCE: 61
cugggcucgg gacgcgcggc u                                                  21

<210> SEQ ID NO 62
<211> LENGTH: 20
<212> TYPE: RNA
<213> ORGANISM: Homo sapiens

<400> SEQUENCE: 62
gcucggacug agcagguggg                                                    20

<210> SEQ ID NO 63
<211> LENGTH: 22
<212> TYPE: RNA
<213> ORGANISM: Homo sapiens

<400> SEQUENCE: 63
agcccgcccc agccgagguu cu                                                 22

<210> SEQ ID NO 64
<211> LENGTH: 25
<212> TYPE: RNA
<213> ORGANISM: Homo sapiens

<400> SEQUENCE: 64
aggggggcac ugcgcaagca aagcc                                              25

<210> SEQ ID NO 65
<211> LENGTH: 22
<212> TYPE: RNA
<213> ORGANISM: Homo sapiens

<400> SEQUENCE: 65 ugcaggguc ggguggcca gg                                                   22

<210> SEQ ID NO 66
<211> LENGTH: 17
<212> TYPE: RNA
```

```
<213> ORGANISM: Homo sapiens

<400> SEQUENCE: 66
gggagaaggg ucggggc                                                  17

<210> SEQ ID NO 67
<211> LENGTH: 22
<212> TYPE: RNA
<213> ORGANISM: Homo sapiens

<400> SEQUENCE: 67
uagggauggg aggccaggau ga                                            22

<210> SEQ ID NO 68
<211> LENGTH: 22
<212> TYPE: RNA
<213> ORGANISM: Homo sapiens

<400> SEQUENCE: 68
gcccaggacu uugugcgggg ug                                            22

<210> SEQ ID NO 69
<211> LENGTH: 21
<212> TYPE: RNA
<213> ORGANISM: Homo sapiens

<400> SEQUENCE: 69
auccaguucu cugaggggc u                                              21

<210> SEQ ID NO 70
<211> LENGTH: 23
<212> TYPE: RNA
<213> ORGANISM: Homo sapiens

<400> SEQUENCE: 70
aggguggggc uggagguggg gcu                                           23

<210> SEQ ID NO 71
<211> LENGTH: 21
<212> TYPE: RNA
<213> ORGANISM: Homo sapiens

<400> SEQUENCE: 71
guaggugaca gucaggggcg g                                             21

<210> SEQ ID NO 72
<211> LENGTH: 23
<212> TYPE: RNA
<213> ORGANISM: Homo sapiens

<400> SEQUENCE: 72
cucggggcag gcggcuggga gcg                                           23

<210> SEQ ID NO 73
<211> LENGTH: 18
<212> TYPE: RNA
<213> ORGANISM: Homo sapiens

<400> SEQUENCE: 73
gugaaggccc ggcggaga                                                 18

<210> SEQ ID NO 74
<211> LENGTH: 21
```

<212> TYPE: RNA
<213> ORGANISM: Homo sapiens

<400> SEQUENCE: 74
cccaugccuc cugccgcggu c                                              21

<210> SEQ ID NO 75
<211> LENGTH: 22
<212> TYPE: RNA
<213> ORGANISM: Homo sapiens

<400> SEQUENCE: 75
cagggcuggc agugacaugg gu                                             22

<210> SEQ ID NO 76
<211> LENGTH: 18
<212> TYPE: RNA
<213> ORGANISM: Homo sapiens

<400> SEQUENCE: 76
cgggcguggu ggugggg                                                   18

<210> SEQ ID NO 77
<211> LENGTH: 21
<212> TYPE: RNA
<213> ORGANISM: Homo sapiens

<400> SEQUENCE: 77
ccggccgccg gcuccgcccc g                                              21

<210> SEQ ID NO 78
<211> LENGTH: 23
<212> TYPE: RNA
<213> ORGANISM: Homo sapiens

<400> SEQUENCE: 78
ugaggauaug gcagggaagg gga                                            23

<210> SEQ ID NO 79
<211> LENGTH: 17
<212> TYPE: RNA
<213> ORGANISM: Homo sapiens

<400> SEQUENCE: 79
ggauggagga gggucu                                                    17

<210> SEQ ID NO 80
<211> LENGTH: 22
<212> TYPE: RNA
<213> ORGANISM: Homo sapiens

<400> SEQUENCE: 80
ggggcuguga uugaccagca gg                                             22

<210> SEQ ID NO 81
<211> LENGTH: 21
<212> TYPE: RNA
<213> ORGANISM: Homo sapiens

<400> SEQUENCE: 81
guguggccgg caggcgggug g                                              21

<210> SEQ ID NO 82

```
<211> LENGTH: 20
<212> TYPE: RNA
<213> ORGANISM: Homo sapiens

<400> SEQUENCE: 82
ggggaggugu gcagggcugg                                                 20

<210> SEQ ID NO 83
<211> LENGTH: 22
<212> TYPE: RNA
<213> ORGANISM: Homo sapiens

<400> SEQUENCE: 83
caggaggcag ugggcgagca gg                                              22

<210> SEQ ID NO 84
<211> LENGTH: 17
<212> TYPE: RNA
<213> ORGANISM: Homo sapiens

<400> SEQUENCE: 84
ggggcgcggc cggaucg                                                    17

<210> SEQ ID NO 85
<211> LENGTH: 23
<212> TYPE: RNA
<213> ORGANISM: Homo sapiens

<400> SEQUENCE: 85
ccggggcaga uugguguagg gug                                             23

<210> SEQ ID NO 86
<211> LENGTH: 19
<212> TYPE: RNA
<213> ORGANISM: Homo sapiens

<400> SEQUENCE: 86
uggggcggag cuuccggag                                                  19

<210> SEQ ID NO 87
<211> LENGTH: 21
<212> TYPE: RNA
<213> ORGANISM: Homo sapiens

<400> SEQUENCE: 87
cgggggcggg gccgaagcgc g                                               21

<210> SEQ ID NO 88
<211> LENGTH: 23
<212> TYPE: RNA
<213> ORGANISM: Homo sapiens

<400> SEQUENCE: 88
gugaguggga gccggugggg cug                                             23

<210> SEQ ID NO 89
<211> LENGTH: 24
<212> TYPE: RNA
<213> ORGANISM: Homo sapiens

<400> SEQUENCE: 89
ugaggggccu cagaccgagc uuuu                                            24
```

```
<210> SEQ ID NO 90
<211> LENGTH: 17
<212> TYPE: RNA
<213> ORGANISM: Homo sapiens

<400> SEQUENCE: 90
accccacucc ugguacc                                                    17

<210> SEQ ID NO 91
<211> LENGTH: 20
<212> TYPE: RNA
<213> ORGANISM: Homo sapiens

<400> SEQUENCE: 91
gccggggcuu ugggugaggg                                                 20

<210> SEQ ID NO 92
<211> LENGTH: 23
<212> TYPE: RNA
<213> ORGANISM: Homo sapiens

<400> SEQUENCE: 92
cacacaggaa aagcggggcc cug                                             23

<210> SEQ ID NO 93
<211> LENGTH: 22
<212> TYPE: RNA
<213> ORGANISM: Homo sapiens

<400> SEQUENCE: 93
ugggagggcg uggaugaugg ug                                              22

<210> SEQ ID NO 94
<211> LENGTH: 25
<212> TYPE: RNA
<213> ORGANISM: Homo sapiens

<400> SEQUENCE: 94
agcggggagg aagugggcgc ugcuu                                           25

<210> SEQ ID NO 95
<211> LENGTH: 22
<212> TYPE: RNA
<213> ORGANISM: Homo sapiens

<400> SEQUENCE: 95
gggacccagg gagagacgua ag                                              22

<210> SEQ ID NO 96
<211> LENGTH: 18
<212> TYPE: RNA
<213> ORGANISM: Homo sapiens

<400> SEQUENCE: 96
aucccaccuc ugccacca                                                   18

<210> SEQ ID NO 97
<211> LENGTH: 22
<212> TYPE: RNA
<213> ORGANISM: Homo sapiens

<400> SEQUENCE: 97
ccgggagaag gagguggccu gg                                              22
```

```
<210> SEQ ID NO 98
<211> LENGTH: 24
<212> TYPE: RNA
<213> ORGANISM: Homo sapiens

<400> SEQUENCE: 98
ggaggccggg gugggcggg gcgg                                           24

<210> SEQ ID NO 99
<211> LENGTH: 23
<212> TYPE: RNA
<213> ORGANISM: Homo sapiens

<400> SEQUENCE: 99
gugcguggug gcucgaggcg ggg                                           23

<210> SEQ ID NO 100
<211> LENGTH: 22
<212> TYPE: RNA
<213> ORGANISM: Homo sapiens

<400> SEQUENCE: 100 acugggagc agaaggagaa cc                                             22

<210> SEQ ID NO 101
<211> LENGTH: 23
<212> TYPE: RNA
<213> ORGANISM: Homo sapiens

<400> SEQUENCE: 101
ggaugguugg gggcggucgg cgu                                           23

<210> SEQ ID NO 102
<211> LENGTH: 23
<212> TYPE: RNA
<213> ORGANISM: Homo sapiens

<400> SEQUENCE: 102
agggccagag gagccuggag ugg                                           23

<210> SEQ ID NO 103
<211> LENGTH: 20
<212> TYPE: RNA
<213> ORGANISM: Homo sapiens

<400> SEQUENCE: 103
gggaaaagga aggggagga                                                20

<210> SEQ ID NO 104
<211> LENGTH: 17
<212> TYPE: RNA
<213> ORGANISM: Homo sapiens

<400> SEQUENCE: 104
ccccggggag cccggcg                                                  17

<210> SEQ ID NO 105
<211> LENGTH: 17
<212> TYPE: RNA
<213> ORGANISM: Homo sapiens

<400> SEQUENCE: 105
gcugggcgag gcuggca                                                  17
```

```
<210> SEQ ID NO 106
<211> LENGTH: 23
<212> TYPE: RNA
<213> ORGANISM: Homo sapiens

<400> SEQUENCE: 106 ugggaggggga gaggcagcaa gca                                          23

<210> SEQ ID NO 107
<211> LENGTH: 17
<212> TYPE: RNA
<213> ORGANISM: Homo sapiens

<400> SEQUENCE: 107
gcggggcugg gcgcgcg                                                  17

<210> SEQ ID NO 108
<211> LENGTH: 23
<212> TYPE: RNA
<213> ORGANISM: Homo sapiens

<400> SEQUENCE: 108
cggggccgua gcacugucug aga                                           23

<210> SEQ ID NO 109
<211> LENGTH: 22
<212> TYPE: RNA
<213> ORGANISM: Homo sapiens

<400> SEQUENCE: 109
agacugacgg cuggaggccc au                                            22

<210> SEQ ID NO 110
<211> LENGTH: 24
<212> TYPE: RNA
<213> ORGANISM: Homo sapiens

<400> SEQUENCE: 110
uggggggaca ggaugagagg cugu                                          24

<210> SEQ ID NO 111
<211> LENGTH: 22
<212> TYPE: RNA
<213> ORGANISM: Homo sapiens

<400> SEQUENCE: 111
uugaggagac auggugggg cc                                             22

<210> SEQ ID NO 112
<211> LENGTH: 19
<212> TYPE: RNA
<213> ORGANISM: Homo sapiens

<400> SEQUENCE: 112
cuggggagug gcuggggag                                                19

<210> SEQ ID NO 113
<211> LENGTH: 20
<212> TYPE: RNA
<213> ORGANISM: Homo sapiens

<400> SEQUENCE: 113
```

-continued

```
ggcggcgggg agguaggcag                                           20

<210> SEQ ID NO 114
<211> LENGTH: 25
<212> TYPE: RNA
<213> ORGANISM: Homo sapiens

<400> SEQUENCE: 114
gugaggcggg gccaggaggg ugugu                                     25

<210> SEQ ID NO 115
<211> LENGTH: 18
<212> TYPE: RNA
<213> ORGANISM: Homo sapiens

<400> SEQUENCE: 115
gaggcugaag gaagaugg                                             18

<210> SEQ ID NO 116
<211> LENGTH: 19
<212> TYPE: RNA
<213> ORGANISM: Homo sapiens

<400> SEQUENCE: 116
uugaucucgg aagcuaagc                                            19

<210> SEQ ID NO 117
<211> LENGTH: 22
<212> TYPE: RNA
<213> ORGANISM: Homo sapiens

<400> SEQUENCE: 117
ggaggaaccu uggagcuucg gc                                        22

<210> SEQ ID NO 118
<211> LENGTH: 17
<212> TYPE: RNA
<213> ORGANISM: Homo sapiens

<400> SEQUENCE: 118 gugggccag gcggugg                                               17

<210> SEQ ID NO 119
<211> LENGTH: 17
<212> TYPE: RNA
<213> ORGANISM: Homo sapiens

<400> SEQUENCE: 119
ggggcugggc gcgcgcc                                              17

<210> SEQ ID NO 120
<211> LENGTH: 22
<212> TYPE: RNA
<213> ORGANISM: Homo sapiens

<400> SEQUENCE: 120 gagguuggg uggaggcucu cc                                         22

<210> SEQ ID NO 121
<211> LENGTH: 21
<212> TYPE: RNA
<213> ORGANISM: Homo sapiens

<400> SEQUENCE: 121
```

```
agguggguau ggaggagccc u                                              21

<210> SEQ ID NO 122
<211> LENGTH: 23
<212> TYPE: RNA
<213> ORGANISM: Homo sapiens

<400> SEQUENCE: 122
ucggggaguc ugggguccgg aau                                            23

<210> SEQ ID NO 123
<211> LENGTH: 23
<212> TYPE: RNA
<213> ORGANISM: Homo sapiens

<400> SEQUENCE: 123
gagggcagcg ugguguggc gga                                             23

<210> SEQ ID NO 124
<211> LENGTH: 18
<212> TYPE: RNA
<213> ORGANISM: Homo sapiens

<400> SEQUENCE: 124
aggcugggcu gggacgga                                                  18

<210> SEQ ID NO 125
<211> LENGTH: 22
<212> TYPE: RNA
<213> ORGANISM: Homo sapiens

<400> SEQUENCE: 125
cagaagggga guugggagca ga                                             22

<210> SEQ ID NO 126
<211> LENGTH: 21
<212> TYPE: RNA
<213> ORGANISM: Homo sapiens

<400> SEQUENCE: 126
agccgcgggg aucgccgagg g                                              21

<210> SEQ ID NO 127
<211> LENGTH: 17
<212> TYPE: RNA
<213> ORGANISM: Homo sapiens

<400> SEQUENCE: 127
gccggacaag agggagg                                                   17

<210> SEQ ID NO 128
<211> LENGTH: 19
<212> TYPE: RNA
<213> ORGANISM: Homo sapiens

<400> SEQUENCE: 128
gagggcgggu ggaggagga                                                 19

<210> SEQ ID NO 129
<211> LENGTH: 23
<212> TYPE: RNA
<213> ORGANISM: Homo sapiens
```

```
<400> SEQUENCE: 129
ccucccugcc cgccucucug cag                                            23

<210> SEQ ID NO 130
<211> LENGTH: 22
<212> TYPE: RNA
<213> ORGANISM: Homo sapiens

<400> SEQUENCE: 130 uugggugga gggccaagga gc                                              22

<210> SEQ ID NO 131
<211> LENGTH: 17
<212> TYPE: RNA
<213> ORGANISM: Homo sapiens

<400> SEQUENCE: 131
cgcgccgggc ccggguu                                                   17

<210> SEQ ID NO 132
<211> LENGTH: 20
<212> TYPE: RNA
<213> ORGANISM: Homo sapiens

<400> SEQUENCE: 132
ccugagcccg ggccgcgcag                                                20

<210> SEQ ID NO 133
<211> LENGTH: 23
<212> TYPE: RNA
<213> ORGANISM: Homo sapiens

<400> SEQUENCE: 133 cgaggguag aagagcacag ggg                                             23

<210> SEQ ID NO 134
<211> LENGTH: 23
<212> TYPE: RNA
<213> ORGANISM: Homo sapiens

<400> SEQUENCE: 134
ugggcugagg gcaggaggcc ugu                                            23

<210> SEQ ID NO 135
<211> LENGTH: 19
<212> TYPE: RNA
<213> ORGANISM: Homo sapiens

<400> SEQUENCE: 135
ugcggcagag cugggguca                                                 19

<210> SEQ ID NO 136
<211> LENGTH: 22
<212> TYPE: RNA
<213> ORGANISM: Homo sapiens

<400> SEQUENCE: 136
gggggucccc ggugcucgga uc                                             22

<210> SEQ ID NO 137
<211> LENGTH: 21
<212> TYPE: RNA
<213> ORGANISM: Homo sapiens
```

-continued

```
<400> SEQUENCE: 137
cggggcagcu caguacagga u                                      21

<210> SEQ ID NO 138
<211> LENGTH: 22
<212> TYPE: RNA
<213> ORGANISM: Homo sapiens

<400> SEQUENCE: 138
ugagccccug ugccgccccc ag                                     22

<210> SEQ ID NO 139
<211> LENGTH: 20
<212> TYPE: RNA
<213> ORGANISM: Homo sapiens

<400> SEQUENCE: 139
cggcucuggg ucugugggga                                        20

<210> SEQ ID NO 140
<211> LENGTH: 22
<212> TYPE: RNA
<213> ORGANISM: Homo sapiens

<400> SEQUENCE: 140
ggcuacaaca caggacccgg gc                                     22

<210> SEQ ID NO 141
<211> LENGTH: 21
<212> TYPE: RNA
<213> ORGANISM: Homo sapiens

<400> SEQUENCE: 141
cccggagcca ggaugcagcu c                                      21

<210> SEQ ID NO 142
<211> LENGTH: 21
<212> TYPE: RNA
<213> ORGANISM: Homo sapiens

<400> SEQUENCE: 142 uggggugug gggagagaga g                                       21

<210> SEQ ID NO 143
<211> LENGTH: 20
<212> TYPE: RNA
<213> ORGANISM: Homo sapiens

<400> SEQUENCE: 143
acucaaacug uggggcacu                                         20

<210> SEQ ID NO 144
<211> LENGTH: 24
<212> TYPE: RNA
<213> ORGANISM: Homo sapiens

<400> SEQUENCE: 144
uggggagcug aggcucuggg ggug                                   24

<210> SEQ ID NO 145
<211> LENGTH: 19
<212> TYPE: RNA
```

```
<213> ORGANISM: Homo sapiens

<400> SEQUENCE: 145
gagccaguug gacaggagc                                                    19

<210> SEQ ID NO 146
<211> LENGTH: 22
<212> TYPE: RNA
<213> ORGANISM: Homo sapiens

<400> SEQUENCE: 146
agggacggga cgcggugcag ug                                                22

<210> SEQ ID NO 147
<211> LENGTH: 22
<212> TYPE: RNA
<213> ORGANISM: Homo sapiens

<400> SEQUENCE: 147
gugaacgggc gccaucccga gg                                                22

<210> SEQ ID NO 148
<211> LENGTH: 20
<212> TYPE: RNA
<213> ORGANISM: Homo sapiens

<400> SEQUENCE: 148
ggggagcugu ggaagcagua                                                   20

<210> SEQ ID NO 149
<211> LENGTH: 22
<212> TYPE: RNA
<213> ORGANISM: Homo sapiens

<400> SEQUENCE: 149
accuugccuu gcugcccggg cc                                                22

<210> SEQ ID NO 150
<211> LENGTH: 20
<212> TYPE: RNA
<213> ORGANISM: Homo sapiens

<400> SEQUENCE: 150
gugucugggc ggacagcugc                                                   20

<210> SEQ ID NO 151
<211> LENGTH: 22
<212> TYPE: RNA
<213> ORGANISM: Homo sapiens

<400> SEQUENCE: 151
gguggcccgg ccgugccuga gg                                                22

<210> SEQ ID NO 152
<211> LENGTH: 22
<212> TYPE: RNA
<213> ORGANISM: Homo sapiens

<400> SEQUENCE: 152
guggguacgg cccagugggg gg                                                22

<210> SEQ ID NO 153
<211> LENGTH: 24
```

```
<212> TYPE: RNA
<213> ORGANISM: Homo sapiens

<400> SEQUENCE: 153
aggcaggggc uggugcuggg cggg                                          24

<210> SEQ ID NO 154
<211> LENGTH: 17
<212> TYPE: RNA
<213> ORGANISM: Homo sapiens

<400> SEQUENCE: 154
ggcgggugcg ggggugg                                                  17

<210> SEQ ID NO 155
<211> LENGTH: 18
<212> TYPE: RNA
<213> ORGANISM: Homo sapiens

<400> SEQUENCE: 155 aggggcggg cuccggcg                                                  18

<210> SEQ ID NO 156
<211> LENGTH: 22
<212> TYPE: RNA
<213> ORGANISM: Homo sapiens

<400> SEQUENCE: 156
acaggugagg uucuugggag cc                                            22

<210> SEQ ID NO 157
<211> LENGTH: 22
<212> TYPE: RNA
<213> ORGANISM: Homo sapiens

<400> SEQUENCE: 157
cucggcgcgg ggcgcgggcu cc                                            22

<210> SEQ ID NO 158
<211> LENGTH: 21
<212> TYPE: RNA
<213> ORGANISM: Homo sapiens

<400> SEQUENCE: 158
gugggcgggg gcaggugugu g                                             21

<210> SEQ ID NO 159
<211> LENGTH: 23
<212> TYPE: RNA
<213> ORGANISM: Homo sapiens

<400> SEQUENCE: 159 ccaggggau gggcgagcuu ggg                                            23

<210> SEQ ID NO 160
<211> LENGTH: 20
<212> TYPE: RNA
<213> ORGANISM: Homo sapiens

<400> SEQUENCE: 160
cgggcguggu gguggggug                                                20

<210> SEQ ID NO 161
```

<211> LENGTH: 20
<212> TYPE: RNA
<213> ORGANISM: Homo sapiens

<400> SEQUENCE: 161
uagggggugg caggcuggcc                                              20

<210> SEQ ID NO 162
<211> LENGTH: 20
<212> TYPE: RNA
<213> ORGANISM: Homo sapiens

<400> SEQUENCE: 162
ccccagggcg acgcggcggg                                              20

<210> SEQ ID NO 163
<211> LENGTH: 21
<212> TYPE: RNA
<213> ORGANISM: Homo sapiens

<400> SEQUENCE: 163 caggagugggg ggugggacg u                                            21

<210> SEQ ID NO 164
<211> LENGTH: 21
<212> TYPE: RNA
<213> ORGANISM: Homo sapiens

<400> SEQUENCE: 164
uggcagggag gcugggaggg g                                            21

<210> SEQ ID NO 165
<211> LENGTH: 21
<212> TYPE: RNA
<213> ORGANISM: Homo sapiens

<400> SEQUENCE: 165
acaggagugg ggugggaca u                                             21

<210> SEQ ID NO 166
<211> LENGTH: 22
<212> TYPE: RNA
<213> ORGANISM: Homo sapiens

<400> SEQUENCE: 166
cagggcaggg aagguggggag ag                                          22

<210> SEQ ID NO 167
<211> LENGTH: 18
<212> TYPE: RNA
<213> ORGANISM: Homo sapiens

<400> SEQUENCE: 167
ggugggcuuc ccggaggg                                                18

<210> SEQ ID NO 168
<211> LENGTH: 22
<212> TYPE: RNA
<213> ORGANISM: Homo sapiens

<400> SEQUENCE: 168
cugggagagg guuguuuacu cc                                           22

```
<210> SEQ ID NO 169
<211> LENGTH: 21
<212> TYPE: RNA
<213> ORGANISM: Homo sapiens

<400> SEQUENCE: 169
acucggcugc gguggacaag u                                          21

<210> SEQ ID NO 170
<211> LENGTH: 20
<212> TYPE: RNA
<213> ORGANISM: Homo sapiens

<400> SEQUENCE: 170
agagaugaag cggggggggcg                                           20

<210> SEQ ID NO 171
<211> LENGTH: 20
<212> TYPE: RNA
<213> ORGANISM: Homo sapiens

<400> SEQUENCE: 171
ucagggaguc aggggagggc                                            20

<210> SEQ ID NO 172
<211> LENGTH: 25
<212> TYPE: RNA
<213> ORGANISM: Homo sapiens

<400> SEQUENCE: 172
uagggguggg ggaauucagg ggugu                                      25

<210> SEQ ID NO 173
<211> LENGTH: 20
<212> TYPE: RNA
<213> ORGANISM: Homo sapiens

<400> SEQUENCE: 173
accaggaggc ugaggccccu                                            20

<210> SEQ ID NO 174
<211> LENGTH: 22
<212> TYPE: RNA
<213> ORGANISM: Homo sapiens

<400> SEQUENCE: 174
uccuguacug agcugccccg ag                                         22

<210> SEQ ID NO 175
<211> LENGTH: 22
<212> TYPE: RNA
<213> ORGANISM: Homo sapiens

<400> SEQUENCE: 175
caccggggau ggcagagggu cg                                         22

<210> SEQ ID NO 176
<211> LENGTH: 17
<212> TYPE: RNA
<213> ORGANISM: Homo sapiens

<400> SEQUENCE: 176
guggggagaa ggcuguc                                               17
```

```
<210> SEQ ID NO 177
<211> LENGTH: 24
<212> TYPE: RNA
<213> ORGANISM: Homo sapiens

<400> SEQUENCE: 177
uguaggcaug aggcagggcc cagg                                           24

<210> SEQ ID NO 178
<211> LENGTH: 23
<212> TYPE: RNA
<213> ORGANISM: Homo sapiens

<400> SEQUENCE: 178
gaacgccugu ucuugccagg ugg                                            23

<210> SEQ ID NO 179
<211> LENGTH: 23
<212> TYPE: RNA
<213> ORGANISM: Homo sapiens

<400> SEQUENCE: 179
acaggcggcu guagcaaugg ggg                                            23

<210> SEQ ID NO 180
<211> LENGTH: 22
<212> TYPE: RNA
<213> ORGANISM: Homo sapiens

<400> SEQUENCE: 180
ggggggugug gagccagggg gc                                             22

<210> SEQ ID NO 181
<211> LENGTH: 22
<212> TYPE: RNA
<213> ORGANISM: Homo sapiens

<400> SEQUENCE: 181
cucgggaggg caugggccag gc                                             22

<210> SEQ ID NO 182
<211> LENGTH: 22
<212> TYPE: RNA
<213> ORGANISM: Homo sapiens

<400> SEQUENCE: 182 ugggauuug gagaaguggu ga                                              22

<210> SEQ ID NO 183
<211> LENGTH: 21
<212> TYPE: RNA
<213> ORGANISM: Homo sapiens

<400> SEQUENCE: 183
gcagggacag caaagggug c                                               21

<210> SEQ ID NO 184
<211> LENGTH: 22
<212> TYPE: RNA
<213> ORGANISM: Homo sapiens

<400> SEQUENCE: 184
aggcggggcg ccgcgggacc gc                                             22
```

```
<210> SEQ ID NO 185
<211> LENGTH: 22
<212> TYPE: RNA
<213> ORGANISM: Homo sapiens

<400> SEQUENCE: 185
uggggguggu cucuagccaa gg                                              22

<210> SEQ ID NO 186
<211> LENGTH: 21
<212> TYPE: RNA
<213> ORGANISM: Homo sapiens

<400> SEQUENCE: 186
ucuguggagu ggggugccug u                                               21

<210> SEQ ID NO 187
<211> LENGTH: 21
<212> TYPE: RNA
<213> ORGANISM: Homo sapiens

<400> SEQUENCE: 187
cugggagggg cuggguuugg c                                               21

<210> SEQ ID NO 188
<211> LENGTH: 53
<212> TYPE: RNA
<213> ORGANISM: Homo sapiens

<400> SEQUENCE: 188
gguggggguu ggaggcgugg guuuuagaac cuaucccuuu cuagcccuga gca            53

<210> SEQ ID NO 189
<211> LENGTH: 80
<212> TYPE: RNA
<213> ORGANISM: Homo sapiens

<400> SEQUENCE: 189
cgggaaugcc gcggcgggga cggcgauugg uccguaugug uggugccacc ggccgccggc     60
uccgccccgg ccccgcccc                                                  80

<210> SEQ ID NO 190
<211> LENGTH: 86
<212> TYPE: RNA
<213> ORGANISM: Homo sapiens

<400> SEQUENCE: 190
ggcuuagaaa caguccuag guaggauuug gggaggagcu aagaagcccc uacagggccc      60
agaggugggg acugagccuu aguugg                                          86

<210> SEQ ID NO 191
<211> LENGTH: 73
<212> TYPE: RNA
<213> ORGANISM: Homo sapiens

<400> SEQUENCE: 191
ggcgagggga ggcgcaggcu cggaaaggcg cgcgaggcuc caggcuccuu cccgauccac     60
cgcucuccuc gcu                                                        73

<210> SEQ ID NO 192
```

```
<211> LENGTH: 85
<212> TYPE: RNA
<213> ORGANISM: Homo sapiens

<400> SEQUENCE: 192
ggcgccuccu gcucugcugu gccgccaggg ccuccccuag cgcgccuucu ggagaggcuu    60
ugugcggaua cggggcugga ggccu                                         85

<210> SEQ ID NO 193
<211> LENGTH: 64
<212> TYPE: RNA
<213> ORGANISM: Homo sapiens

<400> SEQUENCE: 193
ucugggcgag ggugggcuc ucagaggggc uggcaguacu gcucugaggc cugccucucc    60
ccag                                                                64

<210> SEQ ID NO 194
<211> LENGTH: 84
<212> TYPE: RNA
<213> ORGANISM: Homo sapiens

<400> SEQUENCE: 194
gcuggcgucg gugcugggga gcggcccccg gguggaccuc ugcucuggcc ccuccugggg    60
cccgcacucu cgcucugggc ccgc                                          84

<210> SEQ ID NO 195
<211> LENGTH: 64
<212> TYPE: RNA
<213> ORGANISM: Homo sapiens

<400> SEQUENCE: 195
gaggcacugg guaggugggg cuccagggcu ccugacaccu ggaccucucc ucccaggcc    60 caca                                                                64

<210> SEQ ID NO 196
<211> LENGTH: 77
<212> TYPE: RNA
<213> ORGANISM: Homo sapiens

<400> SEQUENCE: 196
gaguugggag guucccucuc caaauguguc uugauccccc accccaagac acauuggag    60 agggacccuc ccaacuc                                                  77

<210> SEQ ID NO 197
<211> LENGTH: 63
<212> TYPE: RNA
<213> ORGANISM: Homo sapiens

<400> SEQUENCE: 197 aaugggugggg ugcugguggg agccgugccc uggccacuca uucggcucuc ucccucaccc    60
uag                                                                 63

<210> SEQ ID NO 198
<211> LENGTH: 62
<212> TYPE: RNA
<213> ORGANISM: Homo sapiens

<400> SEQUENCE: 198
gugagugggg cucccgggac ggcgcccgcc cuggcccugg cccggcgacg ucucacgguc    60
``` cc 62

<210> SEQ ID NO 199
<211> LENGTH: 98
<212> TYPE: RNA
<213> ORGANISM: Homo sapiens

<400> SEQUENCE: 199
cuuggucaau aggaaagagg ugggaccucc uggcuuuucc ucugcagcau ggcucggacc    60
uagugcaaug uuuaagcucc ccucucuuuc cuguucag    98

<210> SEQ ID NO 200
<211> LENGTH: 97
<212> TYPE: RNA
<213> ORGANISM: Homo sapiens

<400> SEQUENCE: 200
cccgggaccu ugguccaggc gcuggucugc guggugcucg gguggauaag ucugaucuga    60
gcaccacaca ggccgggcgc cgggaccaag ggggcuc    97

<210> SEQ ID NO 201
<211> LENGTH: 63
<212> TYPE: RNA
<213> ORGANISM: Homo sapiens

<400> SEQUENCE: 201
gagucgagga cugguggaag ggccuuuccc cucagaccaa ggcccuggcc ccagcuucuu    60
cuc    63

<210> SEQ ID NO 202
<211> LENGTH: 75
<212> TYPE: RNA
<213> ORGANISM: Homo sapiens

<400> SEQUENCE: 202
ucaucccugg gugggauuu guugcauuac uuguguucua auaaaguau ugcacuuguc    60 ccggccugug gaaga    75

<210> SEQ ID NO 203
<211> LENGTH: 91
<212> TYPE: RNA
<213> ORGANISM: Homo sapiens

<400> SEQUENCE: 203
acgccccccg ccccgccacc gccuuggagg cugaccucuu acuuucgguc ggucuucuuc    60
ccugggcuug guuuggggc gggggagugu c    91

<210> SEQ ID NO 204
<211> LENGTH: 86
<212> TYPE: RNA
<213> ORGANISM: Homo sapiens

<400> SEQUENCE: 204
aggagugacc aaaagacaag agugcgagcc uucuauuaug cccagacagg gccaccagag    60
ggcuccuugg ucuaggggua augcca    86

<210> SEQ ID NO 205
<211> LENGTH: 96
<212> TYPE: RNA

<213> ORGANISM: Homo sapiens

<400> SEQUENCE: 205
gcucuggggc gugccgccgc cgucgcugcc accuccccua ccgcuagugg aagaagaugg     60
cggaaggcgg agcggcggau cuggacaccc agcggu                               96

<210> SEQ ID NO 206
<211> LENGTH: 62
<212> TYPE: RNA
<213> ORGANISM: Homo sapiens

<400> SEQUENCE: 206 gagguggug gaggaagagg gcagcuccca ugacugccug accgccuucu cuccucccc       60 ag                                                                    62

<210> SEQ ID NO 207
<211> LENGTH: 109
<212> TYPE: RNA
<213> ORGANISM: Homo sapiens

<400> SEQUENCE: 207
ugcuauuguc uuacugcuac agcagggcug gggauugcag uauccgcugu ugcugcugcu     60
cccagaccug ccccugcugc uaccuagucc agccucaccg caucccaga                109

<210> SEQ ID NO 208
<211> LENGTH: 63
<212> TYPE: RNA
<213> ORGANISM: Homo sapiens

<400> SEQUENCE: 208
ugguggcggc gguaguuaug ggcuucucuu ucucaccagc agccccuggg ccgccgccuc     60
ccu                                                                   63

<210> SEQ ID NO 209
<211> LENGTH: 69
<212> TYPE: RNA
<213> ORGANISM: Homo sapiens

<400> SEQUENCE: 209
ggcccucggg ccugggguug ggggagcucu guccugucuc acucauugcu ccuccccugc     60
cuggcccag                                                             69

<210> SEQ ID NO 210
<211> LENGTH: 84
<212> TYPE: RNA
<213> ORGANISM: Homo sapiens

<400> SEQUENCE: 210
auggucccuc ccaauccagc cauuccucag accaggugc ucccgagcca ccccaggcug      60
uaggaugggg gugagaggug cuag                                            84

<210> SEQ ID NO 211
<211> LENGTH: 100
<212> TYPE: RNA
<213> ORGANISM: Homo sapiens

<400> SEQUENCE: 211
gaggugggag gauugcuuga gucagggugg uugaggcugc aguaaguugu gaucauacca     60
cugcacucca gccugaguga cagagcaaga ccuugucuca                          100

<210> SEQ ID NO 212
<211> LENGTH: 71
<212> TYPE: RNA
<213> ORGANISM: Homo sapiens

<400> SEQUENCE: 212
gugucugugc cggucccagg agaaccugca gaggcaucgg gucagcggug cuccugcggg     60
ccgacacuca c                                                         71

<210> SEQ ID NO 213
<211> LENGTH: 80
<212> TYPE: RNA
<213> ORGANISM: Homo sapiens

<400> SEQUENCE: 213
cgugugagcc cgcccugugc ccggcccacu ucugcuuccu cuuagcgcag gagggguccc     60
gcacugggag gggcccucac                                                80

<210> SEQ ID NO 214
<211> LENGTH: 99
<212> TYPE: RNA
<213> ORGANISM: Homo sapiens

<400> SEQUENCE: 214
gcaagggaca gggagggucg uggcgacacu cgcgccagcu cccgggacgg cugggcucgg     60
gcuggucgcc gaccuccgac ccuccacuag augccuggc                           99

<210> SEQ ID NO 215
<211> LENGTH: 61
<212> TYPE: RNA
<213> ORGANISM: Homo sapiens

<400> SEQUENCE: 215
gggggcggga gcuggggucu gcagguucgc acugaugccu gcucgcccug ucccgcua      60 g                                                                    61

<210> SEQ ID NO 216
<211> LENGTH: 84
<212> TYPE: RNA
<213> ORGANISM: Homo sapiens

<400> SEQUENCE: 216
ugugcagugg gaaggggggc cgauacacug uacgagagug aguagcaggu cucacaguga     60
accggucucu uucccuacug uguc                                           84

<210> SEQ ID NO 217
<211> LENGTH: 73
<212> TYPE: RNA
<213> ORGANISM: Homo sapiens

<400> SEQUENCE: 217
cggcgacggc ggggugggug aggucgggcc ccaagacucg ggguuugccg ggcgccucag     60
uucaccgcgg ccg                                                       73

<210> SEQ ID NO 218
<211> LENGTH: 87
<212> TYPE: RNA
<213> ORGANISM: Homo sapiens

```
<400> SEQUENCE: 218
gugaggcggg gccaggaggg uguguggcgu gggugcugcg gggccgucag ggugccugcg    60
ggacgcucac cuggcuggcc cgcccag                                        87

<210> SEQ ID NO 219
<211> LENGTH: 68
<212> TYPE: RNA
<213> ORGANISM: Homo sapiens

<400> SEQUENCE: 219
gaauggaaga agaaggcggu cggucugcgg gagccaggcc gcagagccau ccgccuucug    60
uccauguc                                                             68

<210> SEQ ID NO 220
<211> LENGTH: 74
<212> TYPE: RNA
<213> ORGANISM: Homo sapiens

<400> SEQUENCE: 220
gcagcccggu gagcgcucgc uggccuggca gugcgucgga agaacagggc ggguggggcc    60
gcgcacaucu cugc                                                      74

<210> SEQ ID NO 221
<211> LENGTH: 65
<212> TYPE: RNA
<213> ORGANISM: Homo sapiens

<400> SEQUENCE: 221
gagaaugggg ggacagaugg agaggacaca ggcuggcacu gagguccccu ccacuuuccu    60
ccuag                                                                65

<210> SEQ ID NO 222
<211> LENGTH: 137
<212> TYPE: RNA
<213> ORGANISM: Homo sapiens

<400> SEQUENCE: 222
agccagacaa gagggucaug gggagucacu gucaacccag agcaggcacu gccccugcga    60
ccagccuggg gcaucgguug gggugcaggg gucugcuggu gaugcuuucc aucucuuugc   120
uuuguccuga uuguagc                                                  137

<210> SEQ ID NO 223
<211> LENGTH: 83
<212> TYPE: RNA
<213> ORGANISM: Homo sapiens

<400> SEQUENCE: 223
acggcaucuu ugcacucagc aggcaggcug gugcagcccg ugguggggga ccauccugcc    60
ugcugugggg uaaggacggc ugu                                            83

<210> SEQ ID NO 224
<211> LENGTH: 79
<212> TYPE: RNA
<213> ORGANISM: Homo sapiens

<400> SEQUENCE: 224
cagccugggg aaggcuuggc agggaagaca caugagcagu gccuccacuu cacgccucuc    60
ccuugucucc uuucccuag                                                 79
```

<210> SEQ ID NO 225
<211> LENGTH: 80
<212> TYPE: RNA
<213> ORGANISM: Homo sapiens

<400> SEQUENCE: 225
gguuccggag ccccggcgcg ggcgggguucu gggguguaga cgcugcuggc cagcccgccc    60
cagccgaggu ucucggcacc                                                80

<210> SEQ ID NO 226
<211> LENGTH: 81
<212> TYPE: RNA
<213> ORGANISM: Homo sapiens

<400> SEQUENCE: 226
uagaggcagu uucaacagau guguagacuu uugauaugag aaauugguuu caaaaucagg    60
agucggggcu uuacugcuuu u                                              81

<210> SEQ ID NO 227
<211> LENGTH: 55
<212> TYPE: RNA
<213> ORGANISM: Homo sapiens

<400> SEQUENCE: 227
ccggauccga gucacggcac caaauuucau gcguguccgu gugaagagac cacca         55

<210> SEQ ID NO 228
<211> LENGTH: 75
<212> TYPE: RNA
<213> ORGANISM: Homo sapiens

<400> SEQUENCE: 228
gucagagggg ggaugugcau gcugguuggg gugggcugcc ugggaccaa ucagcgugca     60 cuuccccacc cugaa                                                     75

<210> SEQ ID NO 229
<211> LENGTH: 68
<212> TYPE: RNA
<213> ORGANISM: Homo sapiens

<400> SEQUENCE: 229
gugcaaagag caggaggaca ggggauuuau cucccaaggg agguccccug auccaguca     60 cggcacca                                                             68

<210> SEQ ID NO 230
<211> LENGTH: 98
<212> TYPE: RNA
<213> ORGANISM: Homo sapiens

<400> SEQUENCE: 230
uugggcaagg ugcggggcua gggcuaacag cagucuuacu gaagguuucc uggaaaccac    60
gcacaugcug uugccacuaa ccucaaccuu acucgguc                            98

<210> SEQ ID NO 231
<211> LENGTH: 68
<212> TYPE: RNA
<213> ORGANISM: Homo sapiens

<400> SEQUENCE: 231

```
ugcccaggcu ggagcgagug caguggugca gucagcccua gcucacugca gccucgaacu      60
ccugggcu                                                              68

<210> SEQ ID NO 232
<211> LENGTH: 72
<212> TYPE: RNA
<213> ORGANISM: Homo sapiens

<400> SEQUENCE: 232
ugugggacug caaaugggag cucagcaccu gccugccacc cacgcagacc agccccugcu      60 cguucccac ag                                                          72

<210> SEQ ID NO 233
<211> LENGTH: 66
<212> TYPE: RNA
<213> ORGANISM: Homo sapiens

<400> SEQUENCE: 233 ccgaguggg cggggcaggu cccugcaggg acugugacac ugaaggaccu gcaccuucgc       60
ccacag                                                                66

<210> SEQ ID NO 234
<211> LENGTH: 90
<212> TYPE: RNA
<213> ORGANISM: Homo sapiens

<400> SEQUENCE: 234 cgggcgggc ggguccggcc gccuccgagc ccggccggca gccccggcc uuaaagcgcg        60 ggcuguccgg aggggucggc uuucccaccg                                      90

<210> SEQ ID NO 235
<211> LENGTH: 94
<212> TYPE: RNA
<213> ORGANISM: Homo sapiens

<400> SEQUENCE: 235
cacggugucc ccuggguggaa ccuggcaggg ggagagguaa ggucuuucag ccucuccaaa    60
gcccaugguc agguacucag gugggggagc ccug                                 94

<210> SEQ ID NO 236
<211> LENGTH: 67
<212> TYPE: RNA
<213> ORGANISM: Homo sapiens

<400> SEQUENCE: 236
ccagaccccu ggggcugggc aggcggaaag aggucugaac ugccucugcc uccuuggucu     60
ccggcag                                                               67

<210> SEQ ID NO 237
<211> LENGTH: 136
<212> TYPE: RNA
<213> ORGANISM: Homo sapiens

<400> SEQUENCE: 237
ccgcuugccu cgcccagcgc agccccggcc gcugggcgca ccgucccgu ucgucccgg       60 acguugcucu cuaccccggg aacgucgaga cuggagcgcc cgaacugagc caccuucgcg    120
gaccccgaga gcggcg                                                    136
```

```
<210> SEQ ID NO 238
<211> LENGTH: 49
<212> TYPE: RNA
<213> ORGANISM: Homo sapiens

<400> SEQUENCE: 238 ucccagcca acgcaccaaa aaugauaugg gucuguuguc uggagaaac        49

<210> SEQ ID NO 239
<211> LENGTH: 89
<212> TYPE: RNA
<213> ORGANISM: Homo sapiens

<400> SEQUENCE: 239
accuccggga cggcugggcg ccggcggccg ggagauccgc gcuuccugaa ucccggccgg    60 cccgccggc gcccguccgc ccgcggguc                                       89

<210> SEQ ID NO 240
<211> LENGTH: 60
<212> TYPE: RNA
<213> ORGANISM: Homo sapiens

<400> SEQUENCE: 240
cgcugggucc gcgcgcccug ggccgggcga uguccgcuug ggggagcgag gggcggggcg    60

<210> SEQ ID NO 241
<211> LENGTH: 64
<212> TYPE: RNA
<213> ORGANISM: Homo sapiens

<400> SEQUENCE: 241
aaccccgggc cggaggucaa gggcgucgcu ucccccuaau guugccucuu uuccacggcc    60
ucag                                                                 64

<210> SEQ ID NO 242
<211> LENGTH: 60
<212> TYPE: RNA
<213> ORGANISM: Homo sapiens

<400> SEQUENCE: 242
caaggugggg gagauggggg uugaacuuca uuucucaugc ucauccccau cuccuuucag    60

<210> SEQ ID NO 243
<211> LENGTH: 65
<212> TYPE: RNA
<213> ORGANISM: Homo sapiens

<400> SEQUENCE: 243
gagggugggc gagggcggcu gagcggcucc auccccggc cugcucaucc cccucgcccu     60
cucag                                                                65

<210> SEQ ID NO 244
<211> LENGTH: 56
<212> TYPE: RNA
<213> ORGANISM: Homo sapiens

<400> SEQUENCE: 244
cgaccgcacc cgcccgaagc ugggucaagg agcccagcag gacgggagcg cggcgc        56

<210> SEQ ID NO 245
<211> LENGTH: 103
<212> TYPE: RNA
```

<213> ORGANISM: Homo sapiens

<400> SEQUENCE: 245
gugucggcug uggcgugacu gucccucugu gucccccacu aggcccacug cucaguggag    60
cguggaggac gaggaggagg ccguccacga gcaaugccag cau                    103

<210> SEQ ID NO 246
<211> LENGTH: 66
<212> TYPE: RNA
<213> ORGANISM: Homo sapiens

<400> SEQUENCE: 246
gggcaugggg aggguggag ucagcauggg gcuaggaggc cccgcgcuga cccgccuucu    60
ccgcag                                                              66

<210> SEQ ID NO 247
<211> LENGTH: 87
<212> TYPE: RNA
<213> ORGANISM: Homo sapiens

<400> SEQUENCE: 247
cccaggcgcc cgcucccgac ccacgccgcg ccgccggguc ccuccucccc ggagaggcug    60
ggcucgggac gcgcggcuca gcucggg                                       87

<210> SEQ ID NO 248
<211> LENGTH: 93
<212> TYPE: RNA
<213> ORGANISM: Homo sapiens

<400> SEQUENCE: 248
ggcgcuuuug ugcgcgcccg ggucuguugg ugcucagagu guggucaggc ggcucggacu    60
gagcaggugg gugcggggcu cggaggaggc ggc                                93

<210> SEQ ID NO 249
<211> LENGTH: 66
<212> TYPE: RNA
<213> ORGANISM: Homo sapiens

<400> SEQUENCE: 249
ccuggagggg ggcacugcgc aagcaaagcc agggacccug agaggcuuug cuuccugcuc    60
cccuag                                                              66

<210> SEQ ID NO 250
<211> LENGTH: 78
<212> TYPE: RNA
<213> ORGANISM: Homo sapiens

<400> SEQUENCE: 250
ggccucaggc aggcgcaccc gaccacaugc auggcuggug gcggcgugca ggggucgggu    60
gggccaggcu gugggcg                                                  78

<210> SEQ ID NO 251
<211> LENGTH: 86
<212> TYPE: RNA
<213> ORGANISM: Homo sapiens

<400> SEQUENCE: 251
agggagaagg gucggggcag ggagggcagg gcaggcucug ggguggggg ucugugaguc    60 agccacggcu cugcccacgu cucccc                                        86

<210> SEQ ID NO 252
<211> LENGTH: 69
<212> TYPE: RNA
<213> ORGANISM: Homo sapiens

<400> SEQUENCE: 252
gggcuuaggg augggaggcc aggaugaaga uuaaucccua auccccaaca cuggccuugc    60
uaucccag                                                            69

<210> SEQ ID NO 253
<211> LENGTH: 71
<212> TYPE: RNA
<213> ORGANISM: Homo sapiens

<400> SEQUENCE: 253
ugaccacccc cgggcaaaga ccugcagauc cccuguuaga gacgggccca ggacuuugug    60
cggggugccc a                                                        71

<210> SEQ ID NO 254
<211> LENGTH: 115
<212> TYPE: RNA
<213> ORGANISM: Homo sapiens

<400> SEQUENCE: 254
gagcaaaaac cagagaacaa caugggagcg uuccuaaccc cuaaggcaac uggaugggag    60
accugaccca uccaguucuc ugaggggcu cuugugugu cuacaagguu guuca         115

<210> SEQ ID NO 255
<211> LENGTH: 63
<212> TYPE: RNA
<213> ORGANISM: Homo sapiens

<400> SEQUENCE: 255
acccuagggu ggggcuggag gugggcuga ggcugagucu uccucccuu ccucccugcc     60 cag                                                                 63

<210> SEQ ID NO 256
<211> LENGTH: 82
<212> TYPE: RNA
<213> ORGANISM: Homo sapiens

<400> SEQUENCE: 256
accuguaggu gacagucagg ggcggggugu gguggggcug ggcuggcccc ccuccucaca    60
ccucuccugg caucgccccc ag                                            82

<210> SEQ ID NO 257
<211> LENGTH: 65
<212> TYPE: RNA
<213> ORGANISM: Homo sapiens

<400> SEQUENCE: 257
gggugcucgg ggcaggcggc ugggagcggc ccucacauug auggcuccug ccaccuccuc    60
cgcag                                                               65

<210> SEQ ID NO 258
<211> LENGTH: 89
<212> TYPE: RNA
<213> ORGANISM: Homo sapiens

```
<400> SEQUENCE: 258 agccugugggaaagagaagagcagggcagggugaaggcccggcggagacacucugcccac    60 cccacacccugccauggggccacacagcu                                 89

<210> SEQ ID NO 259
<211> LENGTH: 62
<212> TYPE: RNA
<213> ORGANISM: Homo sapiens

<400> SEQUENCE: 259 gugggucucgcaucaggaggcaaggccaggacccgcugaccaugccuccugccgcgguc    60 ag                                                            62

<210> SEQ ID NO 260
<211> LENGTH: 67
<212> TYPE: RNA
<213> ORGANISM: Homo sapiens

<400> SEQUENCE: 260 cugguccauucccugccauucccuuggcucaauuuacucccagggcugcagugacau    60 gggucaa                                                       67

<210> SEQ ID NO 261
<211> LENGTH: 52
<212> TYPE: RNA
<213> ORGANISM: Homo sapiens

<400> SEQUENCE: 261 uagccgggcguggugguggggccuguggucccagcuacuuuggaggcugag           52

<210> SEQ ID NO 262
<211> LENGTH: 68
<212> TYPE: RNA
<213> ORGANISM: Homo sapiens

<400> SEQUENCE: 262 cguggugaggauauggcagggaaggggaguuucccucuauucccuuccccccaguaaucu    60 ucaucaug                                                      68

<210> SEQ ID NO 263
<211> LENGTH: 60
<212> TYPE: RNA
<213> ORGANISM: Homo sapiens

<400> SEQUENCE: 263 ugugaaugaccccuuccagagccaaaauccagggaugggaggagggucuuggguacu    60

<210> SEQ ID NO 264
<211> LENGTH: 77
<212> TYPE: RNA
<213> ORGANISM: Homo sapiens

<400> SEQUENCE: 264 caugagaaauccugcuggucaaccauagcccuggucagacucuccggggcugugauugac    60 cagcaggacuucucaug                                             77

<210> SEQ ID NO 265
<211> LENGTH: 87
<212> TYPE: RNA
<213> ORGANISM: Homo sapiens
```

<400> SEQUENCE: 265
guguggccgg caggcgggug ggcggggggcg gccggvggga acccccgcccc gccccgcgcc    60 cgcacucacc cgcccgucuc cccacag                                          87

<210> SEQ ID NO 266
<211> LENGTH: 69
<212> TYPE: RNA
<213> ORGANISM: Homo sapiens

<400> SEQUENCE: 266
gaggagggga ggugugcagg gcuggggucu cugacucugc uuccccugcc cugcauggug      60
uccccacag                                                              69

<210> SEQ ID NO 267
<211> LENGTH: 74
<212> TYPE: RNA
<213> ORGANISM: Homo sapiens

<400> SEQUENCE: 267
ccugcaggag gcagugggcg agcaggcggg gcagcccaau gccaugggcc ugaucucacc      60
gcugccuccu uccc                                                        74

<210> SEQ ID NO 268
<211> LENGTH: 84
<212> TYPE: RNA
<213> ORGANISM: Homo sapiens

<400> SEQUENCE: 268
gaggcugggc ggggcgcggc cggaucgguc gagagcgucc uggcugauga cggucucccg      60
ugcccacgcc ccaaacgcag ucuc                                             84

<210> SEQ ID NO 269
<211> LENGTH: 85
<212> TYPE: RNA
<213> ORGANISM: Homo sapiens

<400> SEQUENCE: 269
ucugagguac ccggggcaga uugguguagg gugcaaagcc ugcccgcccc cuaagccuuc      60
ugcccccaac uccagccugu cagga                                            85

<210> SEQ ID NO 270
<211> LENGTH: 153
<212> TYPE: RNA
<213> ORGANISM: Homo sapiens

<400> SEQUENCE: 270
gcuccgcccc acgucgcaug cgccccggga acgcgugggg cggagcuucc ggaggccccg      60
cucugcugcc gacccugugg agcggagggu gaagccuccg gaugccaguc ccucaucgcu     120
ggccuggucg cgcuguggcg aaggggggcgg agc                                 153

<210> SEQ ID NO 271
<211> LENGTH: 153
<212> TYPE: RNA
<213> ORGANISM: Homo sapiens

<400> SEQUENCE: 271
gcuccgcccc acgucgcaug cgccccggga acgcgugggg cggagcuucc ggaggccccg      60

```
cccugcugcc gacccugugg agcggagggu gaagccuccg gaugccaguc ccucaucgcu    120
ggcccggucg cgcuguggcg aaggggggcgg agc                                153
```

<210> SEQ ID NO 272
<211> LENGTH: 102
<212> TYPE: RNA
<213> ORGANISM: Homo sapiens

<400> SEQUENCE: 272

```
gugggagggc ccaggcgcgg gcaggggugg ggguggcaga gcgcuguccc ggggggcgggg   60 ccgaagcgcg gcgaccguaa cuccuucugc uccguccccc ag                      102
```

<210> SEQ ID NO 273
<211> LENGTH: 71
<212> TYPE: RNA
<213> ORGANISM: Homo sapiens

<400> SEQUENCE: 273

```
ggugaguggg agccgguggg gcuggaguaa gggcacgccc ggggcugccc caccugcuga    60
ccacccuccc c                                                        71
```

<210> SEQ ID NO 274
<211> LENGTH: 75
<212> TYPE: RNA
<213> ORGANISM: Homo sapiens

<400> SEQUENCE: 274

```
aagcaagacu gaggggccuc agaccgagcu uuuggaaaau agaaaagucu cgcucucugc    60
cccucagccu aacuu                                                    75
```

<210> SEQ ID NO 275
<211> LENGTH: 93
<212> TYPE: RNA
<213> ORGANISM: Homo sapiens

<400> SEQUENCE: 275

```
uacuuauggc accccacucc ugguaccaua gucauaaguu aggagauguu agagcuguga    60
guaccaugac uuaagugugg uggcuuaaac aug                                 93
```

<210> SEQ ID NO 276
<211> LENGTH: 67
<212> TYPE: RNA
<213> ORGANISM: Homo sapiens

<400> SEQUENCE: 276

```
uacaggccgg ggcuuugggu gagggacccc cggagucugu cacggcucca ccccaacucu    60
gccccag                                                             67
```

<210> SEQ ID NO 277
<211> LENGTH: 72
<212> TYPE: RNA
<213> ORGANISM: Homo sapiens

<400> SEQUENCE: 277

```
ccaggcacac aggaaaagcg gggcccuggg uucggcugcu accccaaagg ccacauucuc    60
cugugcacac ag                                                       72
```

<210> SEQ ID NO 278
<211> LENGTH: 81

```
<212> TYPE: RNA
<213> ORGANISM: Homo sapiens

<400> SEQUENCE: 278
cucccuggga gggcguggau gaugguggga gaggagcccc acuguggaag ucgaccccc      60 acaucgcccc accuuccca g                                                81

<210> SEQ ID NO 279
<211> LENGTH: 82
<212> TYPE: RNA
<213> ORGANISM: Homo sapiens

<400> SEQUENCE: 279
gcuacgggga gcggggagga agugggcgcu gcuucugcgu uaucuggaag gagcagccca      60
cuccuguccu gggcucugug gu                                              82

<210> SEQ ID NO 280
<211> LENGTH: 76
<212> TYPE: RNA
<213> ORGANISM: Homo sapiens

<400> SEQUENCE: 280
acugacuuug agucucuccu cagggugcug caggcaaagc uggggaccca gggagagacg      60
uaagugaggg gagaug                                                     76

<210> SEQ ID NO 281
<211> LENGTH: 73
<212> TYPE: RNA
<213> ORGANISM: Homo sapiens

<400> SEQUENCE: 281
accuuuccag cucaucccac cucugccacc aaaacacuca ucgcggguc agagggagug       60 ccaaaaaagg uaa                                                        73

<210> SEQ ID NO 282
<211> LENGTH: 63
<212> TYPE: RNA
<213> ORGANISM: Homo sapiens

<400> SEQUENCE: 282
cuugcccggg agaaggaggu ggccuggaga gcugcugucu ccagccgccg ccugucucca      60
cag                                                                   63

<210> SEQ ID NO 283
<211> LENGTH: 64
<212> TYPE: RNA
<213> ORGANISM: Homo sapiens

<400> SEQUENCE: 283
ccccgggccc ggcguucccu ccccuuccgu gcgccagugg aggccggggu ggggcgggc       60 gggg                                                                  64

<210> SEQ ID NO 284
<211> LENGTH: 64
<212> TYPE: RNA
<213> ORGANISM: Homo sapiens

<400> SEQUENCE: 284
ccccgggccc ggcguucccu ccccuuccgu gcgccagugg aggccggggu ggggcgggc       60
```

```
gggg                                                                       64

<210> SEQ ID NO 285
<211> LENGTH: 74
<212> TYPE: RNA
<213> ORGANISM: Homo sapiens

<400> SEQUENCE: 285
gugcguggug gcucgaggcg ggguggggg ccucgcccug cuugggcccu cccugaccuc          60
uccgcuccgc acag                                                            74

<210> SEQ ID NO 286
<211> LENGTH: 66
<212> TYPE: RNA
<213> ORGANISM: Homo sapiens

<400> SEQUENCE: 286
ugacugggga gcagaaggag aacccaagaa aagcugacuu ggaggucccu ccuucugucc          60
ccacag                                                                     66

<210> SEQ ID NO 287
<211> LENGTH: 86
<212> TYPE: RNA
<213> ORGANISM: Homo sapiens

<400> SEQUENCE: 287
cgccugagcg ugcagcagga caucuuccug accugguaau aauuagguga gaaggauggu          60 uggggcggu cggcguaacu caggga                                                86

<210> SEQ ID NO 288
<211> LENGTH: 58
<212> TYPE: RNA
<213> ORGANISM: Homo sapiens

<400> SEQUENCE: 288
agggccagag gagccuggag uggucggguc gacugaaccc agguucccuc uggccgca            58

<210> SEQ ID NO 289
<211> LENGTH: 85
<212> TYPE: RNA
<213> ORGANISM: Homo sapiens

<400> SEQUENCE: 289 gggagguag ggaaaaggaa gggggaggag aaggugagac caauguccug ggugccacuc           60
cugcccagug ccucccuucc ucguu                                                85

<210> SEQ ID NO 290
<211> LENGTH: 51
<212> TYPE: RNA
<213> ORGANISM: Homo sapiens

<400> SEQUENCE: 290
acagaccccg gggagcccgg cggugaagcu ccugguaucc uggguguug a                   51

<210> SEQ ID NO 291
<211> LENGTH: 63
<212> TYPE: RNA
<213> ORGANISM: Homo sapiens

<400> SEQUENCE: 291
gcaugcuggg cgaggcuggc aucuagcaca ggcgguagau gcuugcucuu gccauugcaa         60
```

```
uga                                                                63

<210> SEQ ID NO 292
<211> LENGTH: 67
<212> TYPE: RNA
<213> ORGANISM: Homo sapiens

<400> SEQUENCE: 292
gugggagggg agaggcagca agcacacagg gccugggacu agcaugcuga ccuccccuccu   60 gccccag                                                            67

<210> SEQ ID NO 293
<211> LENGTH: 70
<212> TYPE: RNA
<213> ORGANISM: Homo sapiens

<400> SEQUENCE: 293
aggacccagc ggggcugggc gcgcggagca gcgcugggug cagcgccugc gccggcagcu   60
gcaagggccg                                                         70

<210> SEQ ID NO 294
<211> LENGTH: 82
<212> TYPE: RNA
<213> ORGANISM: Homo sapiens

<400> SEQUENCE: 294
ugagcuguug gauucggggc cguagcacug ucugagaggu uuacauuucu cacagugaac   60
cggucucuuu uucagcugcu uc                                           82

<210> SEQ ID NO 295
<211> LENGTH: 86
<212> TYPE: RNA
<213> ORGANISM: Homo sapiens

<400> SEQUENCE: 295
auucuaggug gggagacuga cggcuggagg cccauaagcu gucuaaaacu ucggccccca   60
gauuucuggu cucccacuu cagaac                                        86

<210> SEQ ID NO 296
<211> LENGTH: 68
<212> TYPE: RNA
<213> ORGANISM: Homo sapiens

<400> SEQUENCE: 296
aggguugggg ggacaggaug agaggcuguc uucauucccu cuugaccacc ccucguuucu   60
uccccag                                                            68

<210> SEQ ID NO 297
<211> LENGTH: 70
<212> TYPE: RNA
<213> ORGANISM: Homo sapiens

<400> SEQUENCE: 297
gguuucuccu ugaggagaca uggugggggc cggucaggca gcccaugcca uguguccuca   60
uggagaggcc                                                         70

<210> SEQ ID NO 298
<211> LENGTH: 65
<212> TYPE: RNA
```

<213> ORGANISM: Homo sapiens

<400> SEQUENCE: 298
uucuccuggg gaguggcugg ggagcagaca gacccaaccu caugcuccccc ggccucugcc    60 cccag    65

<210> SEQ ID NO 299
<211> LENGTH: 80
<212> TYPE: RNA
<213> ORGANISM: Homo sapiens

<400> SEQUENCE: 299
gcgucaagau ggcggcgggg agguaggcag agcaggacgc cgcugcugcc gccgccaccg    60
ccgccuccgc uccagucgcc    80

<210> SEQ ID NO 300
<211> LENGTH: 68
<212> TYPE: RNA
<213> ORGANISM: Homo sapiens

<400> SEQUENCE: 300
cucaggcuca guggugcaug cuuauagucc cagccacucu ggaggcugaa ggaagauggc    60
uugagccu    68

<210> SEQ ID NO 301
<211> LENGTH: 61
<212> TYPE: RNA
<213> ORGANISM: Homo sapiens

<400> SEQUENCE: 301
ucucguuuga ucucggaagc uaagcagggu ugggccuggu aguacuugg augggaaacu    60 u    61

<210> SEQ ID NO 302
<211> LENGTH: 53
<212> TYPE: RNA
<213> ORGANISM: Homo sapiens

<400> SEQUENCE: 302
guuugaucuc ggaagcuaag cagggucggg ccugguuagu acuggaugg gag    53

<210> SEQ ID NO 303
<211> LENGTH: 58
<212> TYPE: RNA
<213> ORGANISM: Homo sapiens

<400> SEQUENCE: 303
gcugaagcuc uaagguuccg ccugcgggca ggaagcggag gaaccuugga gcuucggc    58

<210> SEQ ID NO 304
<211> LENGTH: 88
<212> TYPE: RNA
<213> ORGANISM: Homo sapiens

<400> SEQUENCE: 304 gugggggccag gcgguggugg gcacugcugg gguggggcaca gcagccaugc agagcgggca    60
uuugaccccg ugccacccuu uucccccag    88

<210> SEQ ID NO 305
<211> LENGTH: 80

```
<212> TYPE: RNA
<213> ORGANISM: Homo sapiens

<400> SEQUENCE: 305
cugcagcgug cuucuccagg ccccgcgcgc ggacagacac acggacaagu cccgccaggg    60
gcugggcgcg cgccagccgg                                                80

<210> SEQ ID NO 306
<211> LENGTH: 80
<212> TYPE: RNA
<213> ORGANISM: Homo sapiens

<400> SEQUENCE: 306
aggacccuuc cagagggccc ccccucaauc cuguugugcc uaauucagag gguugggugg    60
aggcucuccu gaagggcucu                                                80

<210> SEQ ID NO 307
<211> LENGTH: 73
<212> TYPE: RNA
<213> ORGANISM: Homo sapiens

<400> SEQUENCE: 307
aggccaggug gguauggagg agcccucaua uggcaguugg cgagggccca gugagccccu    60
cucugcucuc cag                                                       73

<210> SEQ ID NO 308
<211> LENGTH: 59
<212> TYPE: RNA
<213> ORGANISM: Homo sapiens

<400> SEQUENCE: 308
cugugucggg gagucugggg uccggaauuc uccagagccu cugugccccu acuucccag     59

<210> SEQ ID NO 309
<211> LENGTH: 61
<212> TYPE: RNA
<213> ORGANISM: Homo sapiens

<400> SEQUENCE: 309
gagggcagcg uggguguggc ggaggcaggc gugaccguuu gccgcccucu cgcugcucua    60
g                                                                    61

<210> SEQ ID NO 310
<211> LENGTH: 73
<212> TYPE: RNA
<213> ORGANISM: Homo sapiens

<400> SEQUENCE: 310
ggaggcuggg cugggacgga cacccggccu ccacuuucug uggcagguac cuccuccaug    60
ucggcccgcc uug                                                       73

<210> SEQ ID NO 311
<211> LENGTH: 84
<212> TYPE: RNA
<213> ORGANISM: Homo sapiens

<400> SEQUENCE: 311
ggccccuccu ucucagcccc agcucccgcu caccccugcc acgucaaagg aggcagaagg    60
ggaguuggga gcagagaggg gacc                                           84
```

```
<210> SEQ ID NO 312
<211> LENGTH: 180
<212> TYPE: RNA
<213> ORGANISM: Homo sapiens

<400> SEQUENCE: 312
cgcgacugcg gcggcggugg uggggggagc cgcggggauc gccgagggcc ggucggccgc      60
cccgggugcc gcgcggugcc gccggcggcg gugaggcccc gcgcgugugu cccggcugcg     120
gucggccgcg cucgagggu ccccguggcg uccccuuccc cgccggccgc cuuucucgcg     180

<210> SEQ ID NO 313
<211> LENGTH: 67
<212> TYPE: RNA
<213> ORGANISM: Homo sapiens

<400> SEQUENCE: 313
gcgcccuccc ucucccccg gugugcaaau gugugugugc ggugunaugc cggacaagag      60
ggaggug                                                                67

<210> SEQ ID NO 314
<211> LENGTH: 61
<212> TYPE: RNA
<213> ORGANISM: Homo sapiens

<400> SEQUENCE: 314
ucacccggug agggcgggug gaggaggagg gucccccacca ucagccuuca cugggacggg      60
a                                                                      61

<210> SEQ ID NO 315
<211> LENGTH: 59
<212> TYPE: RNA
<213> ORGANISM: Homo sapiens

<400> SEQUENCE: 315
cuccagggag acagugugug aggccucuug ccauggccuc ccugcccgcc ucucugcag       59

<210> SEQ ID NO 316
<211> LENGTH: 61
<212> TYPE: RNA
<213> ORGANISM: Homo sapiens

<400> SEQUENCE: 316
gaggguuggg guggagggcc aaggagcugg guggggugcc aagccucugu ccccaccca       60 g                                                                      61

<210> SEQ ID NO 317
<211> LENGTH: 84
<212> TYPE: RNA
<213> ORGANISM: Homo sapiens

<400> SEQUENCE: 317
ccgcagccgc cgcgccgggc ccggguuggc cgcugacccc cgcggggccc ccggcggccg      60 gggcggggc gggggcugcc ccgg                                              84

<210> SEQ ID NO 318
<211> LENGTH: 119
<212> TYPE: RNA
<213> ORGANISM: Homo sapiens

<400> SEQUENCE: 318
```
agccugcgcc ggagccgggg ccugagcccg ggccgcgcag gccgugaacu cgucgagcug        60
cgcgugcggc cggugcucaa ccugccgggu ccuggccccg cgcucccgcg cgcccugga        119

<210> SEQ ID NO 319
<211> LENGTH: 64
<212> TYPE: RNA
<213> ORGANISM: Homo sapiens

<400> SEQUENCE: 319
gaaggcgagg gguagaagag cacaggggnu cugauaaacc cuucugccug cauucuacuc        60
ccag        64

<210> SEQ ID NO 320
<211> LENGTH: 75
<212> TYPE: RNA
<213> ORGANISM: Homo sapiens

<400> SEQUENCE: 320
aggcuggcgu gggcugaggg caggaggccu guggccgguc ccaggccucc ugcuuccugg        60
gcucaggcuc gguuu        75

<210> SEQ ID NO 321
<211> LENGTH: 62
<212> TYPE: RNA
<213> ORGANISM: Homo sapiens

<400> SEQUENCE: 321
ccuucugcgg cagagcuggg gucaccagcc cucauguacu ugugacuucu ccccugccac        60
ag        62

<210> SEQ ID NO 322
<211> LENGTH: 96
<212> TYPE: RNA
<213> ORGANISM: Homo sapiens

<400> SEQUENCE: 322
cucgggaggg gcgggagggg ggucccccggu gcucggaucu cgagggugcu uauuguucgg        60
uccgagccug ggucucccuc uucccccccaa cccccc        96

<210> SEQ ID NO 323
<211> LENGTH: 68
<212> TYPE: RNA
<213> ORGANISM: Homo sapiens

<400> SEQUENCE: 323
gcauccugua cugagcugcc ccgaggcccu ucaugcugcc cagcucgggg cagcucagua        60
caggauac        68

<210> SEQ ID NO 324
<211> LENGTH: 64
<212> TYPE: RNA
<213> ORGANISM: Homo sapiens

<400> SEQUENCE: 324
uccuguacug agcugccccg agcugggcag caugaagggc cucggggcag cucaguacag        60
gaug        64

<210> SEQ ID NO 325

```
<211> LENGTH: 90
<212> TYPE: RNA
<213> ORGANISM: Homo sapiens

<400> SEQUENCE: 325
gugggurcgg cccagugggg gggagaggga cacgcccugg gcucugccca gggugcagcc    60
ggacugacug agccccugug ccgccccag                                     90

<210> SEQ ID NO 326
<211> LENGTH: 80
<212> TYPE: RNA
<213> ORGANISM: Homo sapiens

<400> SEQUENCE: 326
ggcgcgucgc cccccucagu ccaccagagc ccggauaccu cagaaauucg gcucggguc    60 uguggggagc gaaaugcaac                                               80

<210> SEQ ID NO 327
<211> LENGTH: 109
<212> TYPE: RNA
<213> ORGANISM: Homo sapiens

<400> SEQUENCE: 327
ggucgggcuc accaugacac agugugagac cucgggcuac aacacaggac ccgggcgcug    60
cucugacccc ucgugucuug guugcagcc ggagggacg agguccgca                109

<210> SEQ ID NO 328
<211> LENGTH: 85
<212> TYPE: RNA
<213> ORGANISM: Homo sapiens

<400> SEQUENCE: 328 uccucccgg agccaggaug cagcucaagc cacagcaggg uguuuagcgc ucuucagugg     60
cuccagauug uggcgcuggu gcagg                                         85

<210> SEQ ID NO 329
<211> LENGTH: 86
<212> TYPE: RNA
<213> ORGANISM: Homo sapiens

<400> SEQUENCE: 329
ggggcugggg guguggggag agagagugca cagccagcuc agggauuaaa gcucuuucuc    60
ucucucucuc ucccacuucc cugcag                                        86

<210> SEQ ID NO 330
<211> LENGTH: 67
<212> TYPE: RNA
<213> ORGANISM: Homo sapiens

<400> SEQUENCE: 330
guggcacuca aacugugggg gcacuuucug cucucuggug aaagugccgc caucuuuuga    60
guguuac                                                             67

<210> SEQ ID NO 331
<211> LENGTH: 82
<212> TYPE: RNA
<213> ORGANISM: Homo sapiens

<400> SEQUENCE: 331
ugugggcagg gcccuggggga gcugaggcuc ugggggguggc cggggcugac ccugggccuc    60
``` ugcucccag ugucugaccg cg                                          82

<210> SEQ ID NO 332
<211> LENGTH: 94
<212> TYPE: RNA
<213> ORGANISM: Homo sapiens

<400> SEQUENCE: 332
aauucagccc ugccacuggc uuaugucaug accuugggcu acucaggcug ucugcacaau    60
gagccaguug gacaggagca gugccacuca acuc                                94

<210> SEQ ID NO 333
<211> LENGTH: 96
<212> TYPE: RNA
<213> ORGANISM: Homo sapiens

<400> SEQUENCE: 333
cgggccccgg gcgggcggga gggacgggac gcggugcagu guuguuuuuu ccccgccaa    60 uauugcacuc gucccggccu ccggcccccc cggccc                              96

<210> SEQ ID NO 334
<211> LENGTH: 79
<212> TYPE: RNA
<213> ORGANISM: Homo sapiens

<400> SEQUENCE: 334
gugcagaucc uugggagccc uguuagacuc uggauuuuac acuggagug aacgggcgcc    60 aucccgaggc uuugcacag                                                 79

<210> SEQ ID NO 335
<211> LENGTH: 75
<212> TYPE: RNA
<213> ORGANISM: Homo sapiens

<400> SEQUENCE: 335
guaguuguuc uacagaagac cuggaugugu aggagcuaag acacaccca ggggagcugu    60 ggaagcagua acacg                                                     75

<210> SEQ ID NO 336
<211> LENGTH: 80
<212> TYPE: RNA
<213> ORGANISM: Homo sapiens

<400> SEQUENCE: 336
ugagaggccg caccuugccu ugcugcccgg gccgugcacc cgugggcccc agggcgacgc    60
ggcgggggcg gcccuagcga                                                80

<210> SEQ ID NO 337
<211> LENGTH: 92
<212> TYPE: RNA
<213> ORGANISM: Homo sapiens

<400> SEQUENCE: 337
gucagugucu gggcggacag cugcaggaaa gggaagacca aggcuugcug ucuguccagu    60
cugccacccu acccugucug uucuugccac ag                                  92

<210> SEQ ID NO 338
<211> LENGTH: 115
<212> TYPE: RNA

-continued

<213> ORGANISM: Homo sapiens

<400> SEQUENCE: 338
ggugccgagg gccguccggc auccuaggcg ggucgcugcg guaccucccu ccugucugug    60 gcgguggau cccguggccg uguuuuccug guggcccggc cgugccugag guuuc         115

<210> SEQ ID NO 339
<211> LENGTH: 92
<212> TYPE: RNA
<213> ORGANISM: Homo sapiens

<400> SEQUENCE: 339
ccugucccuc cugcccugcg ccugcccagc ccuccugcuc uggugacuga ggaccgccag    60 gcagggcug gugcugggcg gggggcggcg gg                                  92

<210> SEQ ID NO 340
<211> LENGTH: 69
<212> TYPE: RNA
<213> ORGANISM: Homo sapiens

<400> SEQUENCE: 340 cuucggcca gcgggacggc auccgaggug ggcuaggcuc gggcccgugg cgggugcggg    60
ggugggagg                                                           69

<210> SEQ ID NO 341
<211> LENGTH: 62
<212> TYPE: RNA
<213> ORGANISM: Homo sapiens

<400> SEQUENCE: 341 gguaggggc gggcuccggc gcugggaccc cacuagggug gcgccuuggc cccgccccgc    60
cc                                                                  62

<210> SEQ ID NO 342
<211> LENGTH: 86
<212> TYPE: RNA
<213> ORGANISM: Homo sapiens

<400> SEQUENCE: 342
ugccagucuc uaggucccug agacccuuua accgugagg acauccaggg ucacagguga    60
gguucuuggg agccuggcgu cuggcc                                        86

<210> SEQ ID NO 343
<211> LENGTH: 47
<212> TYPE: RNA
<213> ORGANISM: Homo sapiens

<400> SEQUENCE: 343
cucggcgcgg ggcgcgggcu ccggguuggg gcgagccaac gccgggg                 47

<210> SEQ ID NO 344
<211> LENGTH: 73
<212> TYPE: RNA
<213> ORGANISM: Homo sapiens

<400> SEQUENCE: 344
gugggcgggg gcaggugugu ggugggguggu ggccugcggu gagcagggcc cucacaccug   60
ccucgccccc cag                                                      73

```
<210> SEQ ID NO 345
<211> LENGTH: 67
<212> TYPE: RNA
<213> ORGANISM: Homo sapiens

<400> SEQUENCE: 345
ggcagccagg gggaugggcg agcuugggcc cauuccuuuc cuuacccuac ccccaucccc    60
ccuguag                                                              67

<210> SEQ ID NO 346
<211> LENGTH: 50
<212> TYPE: RNA
<213> ORGANISM: Homo sapiens

<400> SEQUENCE: 346
acccgggcgu ggugguggggg gugggugccu guaauuccag cuaguuggga              50

<210> SEQ ID NO 347
<211> LENGTH: 60
<212> TYPE: RNA
<213> ORGANISM: Homo sapiens

<400> SEQUENCE: 347
aggccuaggg gguggcaggc uggccaucag uguggcuaa cccuguccuc ucccucccag      60

<210> SEQ ID NO 348
<211> LENGTH: 102
<212> TYPE: RNA
<213> ORGANISM: Homo sapiens

<400> SEQUENCE: 348
uguguucccu auccuccuua ugucccaccc ccacuccugu uugaauauuu caccagaaac    60 aggaguggg gguggacgu aaggaggaug ggggaaagaa ca                        102

<210> SEQ ID NO 349
<211> LENGTH: 87
<212> TYPE: RNA
<213> ORGANISM: Homo sapiens

<400> SEQUENCE: 349
gcagggcugg cagggaggcu gggaggggcu ggcugggucu gguaguggc aucagcuggc     60 ccucauuucu uaagacagca cuucugu                                        87

<210> SEQ ID NO 350
<211> LENGTH: 81
<212> TYPE: RNA
<213> ORGANISM: Homo sapiens

<400> SEQUENCE: 350
cauccuccuu acgucccacc cccacuccu guuucggug aaauauucaa acaggagugg      60 ggguggaca uaaggaggau a                                               81

<210> SEQ ID NO 351
<211> LENGTH: 66
<212> TYPE: RNA
<213> ORGANISM: Homo sapiens

<400> SEQUENCE: 351
cagagcaggg cagggaaggu gggagagggg cccagcugac ccuccuguca cccgcuccuu    60
gcccag                                                               66
```

```
<210> SEQ ID NO 352
<211> LENGTH: 73
<212> TYPE: RNA
<213> ORGANISM: Homo sapiens

<400> SEQUENCE: 352
gaaaacaacc aggugggcuu cccggagggc ggaacaccca gccccagcau ccagggcuca      60
ccuaccacgu uug                                                        73

<210> SEQ ID NO 353
<211> LENGTH: 89
<212> TYPE: RNA
<213> ORGANISM: Homo sapiens

<400> SEQUENCE: 353
accaugcugu agugugugua aacauccuac acucucagcu gugagcucaa gguggcuggg      60
agaggguugu uuacuccuuc ugccaugga                                       89

<210> SEQ ID NO 354
<211> LENGTH: 68
<212> TYPE: RNA
<213> ORGANISM: Homo sapiens

<400> SEQUENCE: 354
gacucggcug cgguggacaa guccggcucc agaaccugga caccgcucag ccggccgcgg      60
cagggguc                                                              68

<210> SEQ ID NO 355
<211> LENGTH: 51
<212> TYPE: RNA
<213> ORGANISM: Homo sapiens

<400> SEQUENCE: 355
agagaugaag cgggggggcg gggucuugcu cuauugccua cgcugaucuc a               51

<210> SEQ ID NO 356
<211> LENGTH: 70
<212> TYPE: RNA
<213> ORGANISM: Homo sapiens

<400> SEQUENCE: 356
acaaauagcu ucagggaguc aggggagggc agaaauagau ggccuucccc ugcugggaag      60
aaaguggguc                                                            70

<210> SEQ ID NO 357
<211> LENGTH: 69
<212> TYPE: RNA
<213> ORGANISM: Homo sapiens

<400> SEQUENCE: 357 uggguaggg gugggggaau caggggugu cgaacucaug gcugccaccu uugucccc          60 auccugcag                                                             69

<210> SEQ ID NO 358
<211> LENGTH: 72
<212> TYPE: RNA
<213> ORGANISM: Homo sapiens

<400> SEQUENCE: 358
ucuccucgag gggucucugc cucuacccag gacucuuuca ugaccaggag gcugaggccc      60
```

```
cucacaggcg gc                                                              72

<210> SEQ ID NO 359
<211> LENGTH: 74
<212> TYPE: RNA
<213> ORGANISM: Homo sapiens

<400> SEQUENCE: 359
ccaagggcac accggggaug gcagaggguc gugggaaagu guugacccuc gucaggcccc          60
cggggagccc cugg                                                            74

<210> SEQ ID NO 360
<211> LENGTH: 80
<212> TYPE: RNA
<213> ORGANISM: Homo sapiens

<400> SEQUENCE: 360
ccucugugag aaagggugug ggggagaggc ugucuugugu cuguaaguau gccaaacuua          60
uuuuccccaa ggcagaggga                                                      80

<210> SEQ ID NO 361
<211> LENGTH: 64
<212> TYPE: RNA
<213> ORGANISM: Homo sapiens

<400> SEQUENCE: 361
ugcucuguag gcaugaggca gggcccaggu uccaugugau gcugaagcuc ugacauuccu          60
gcag                                                                       64

<210> SEQ ID NO 362
<211> LENGTH: 90
<212> TYPE: RNA
<213> ORGANISM: Homo sapiens

<400> SEQUENCE: 362
ucuaagaaac gcagguggucu cugaagccug caggggcagg ccagcccugc acugaacgcc         60
uguucuugcc agguggcaga agguugcugc                                           90

<210> SEQ ID NO 363
<211> LENGTH: 106
<212> TYPE: RNA
<213> ORGANISM: Homo sapiens

<400> SEQUENCE: 363
agaagaaugc ccaaccagcc cucaguugcu acaguucccu guuguuucag cucgacaaca          60
acaggcggcu guagcaaugg ggggcuggau gggcaucuca augugc                         106

<210> SEQ ID NO 364
<211> LENGTH: 71
<212> TYPE: RNA
<213> ORGANISM: Homo sapiens

<400> SEQUENCE: 364 auggagggg guguggagcc aggggccca ggucuacagc uucuccccgc uccugcccc             60 cauacuccca g                                                               71

<210> SEQ ID NO 365
<211> LENGTH: 60
<212> TYPE: RNA
```

```
<213> ORGANISM: Homo sapiens

<400> SEQUENCE: 365
ggugccucgg gagggcaugg gccaggccac auaaugagcc aaacccugu cuacccgcag      60

<210> SEQ ID NO 366
<211> LENGTH: 65
<212> TYPE: RNA
<213> ORGANISM: Homo sapiens

<400> SEQUENCE: 366
ugucugggga uuuggagaag uggugagcgc aggucuuugg caccaucucc ccuggucccu      60
uggcu                                                                 65

<210> SEQ ID NO 367
<211> LENGTH: 110
<212> TYPE: RNA
<213> ORGANISM: Homo sapiens

<400> SEQUENCE: 367
ucaccuggcc augugacuug ugggcuuccc uuugucaucc uucgccuagg gcucugagca      60
gggcagggac agcaaagggg ugcucaguug ucacuuccca cagcacggag                110

<210> SEQ ID NO 368
<211> LENGTH: 93
<212> TYPE: RNA
<213> ORGANISM: Homo sapiens

<400> SEQUENCE: 368
ccuuccggcg ucccaggcgg ggcgccgcgg gaccgcccuc gugucugugg cgguggggauc     60 ccgcggccgu guuuccugg uggcccggcc aug                                   93

<210> SEQ ID NO 369
<211> LENGTH: 65
<212> TYPE: RNA
<213> ORGANISM: Homo sapiens

<400> SEQUENCE: 369
agcccugggg guggucucua gccaaggcuc uggggucuca cccuuggcug gucucugcuc     60
cgcag                                                                 65

<210> SEQ ID NO 370
<211> LENGTH: 61
<212> TYPE: RNA
<213> ORGANISM: Homo sapiens

<400> SEQUENCE: 370
uccgcucugu ggagugggu gccuguccccc ugccacuggg ugacccaccc cucuccacca     60
g                                                                     61

<210> SEQ ID NO 371
<211> LENGTH: 64
<212> TYPE: RNA
<213> ORGANISM: Homo sapiens

<400> SEQUENCE: 371
gagcucuggg aggggcuggg uuuggcagga caguuccaa gcccugcuc cucccaucuu      60 ccag                                                                  64
```

-continued

```
<210> SEQ ID NO 372
<211> LENGTH: 21
<212> TYPE: RNA
<213> ORGANISM: Homo sapiens

<400> SEQUENCE: 372
guuggaggcg uggguuuuag a                                              21

<210> SEQ ID NO 373
<211> LENGTH: 15
<212> TYPE: RNA
<213> ORGANISM: Homo sapiens

<400> SEQUENCE: 373
guuggaggcg ugggu                                                     15

<210> SEQ ID NO 374
<211> LENGTH: 22
<212> TYPE: RNA
<213> ORGANISM: Homo sapiens

<400> SEQUENCE: 374
cgcggcgggg acggcgauug gu                                             22

<210> SEQ ID NO 375
<211> LENGTH: 17
<212> TYPE: RNA
<213> ORGANISM: Homo sapiens

<400> SEQUENCE: 375
cggcggggac ggcgauu                                                   17

<210> SEQ ID NO 376
<211> LENGTH: 23
<212> TYPE: RNA
<213> ORGANISM: Homo sapiens

<400> SEQUENCE: 376
ggaggcgcag gcucggaaag gcg                                            23

<210> SEQ ID NO 377
<211> LENGTH: 15
<212> TYPE: RNA
<213> ORGANISM: Homo sapiens

<400> SEQUENCE: 377
gcaggcucgg aaagg                                                     15

<210> SEQ ID NO 378
<211> LENGTH: 26
<212> TYPE: RNA
<213> ORGANISM: Homo sapiens

<400> SEQUENCE: 378
ccuucuggag aggcuuugug cggaua                                         26

<210> SEQ ID NO 379
<211> LENGTH: 15
<212> TYPE: RNA
<213> ORGANISM: Homo sapiens

<400> SEQUENCE: 379
ccuucuggag aggcu                                                     15
```

```
<210> SEQ ID NO 380
<211> LENGTH: 15
<212> TYPE: RNA
<213> ORGANISM: Homo sapiens

<400> SEQUENCE: 380
ucugggcgag gggug                                                    15

<210> SEQ ID NO 381
<211> LENGTH: 15
<212> TYPE: RNA
<213> ORGANISM: Homo sapiens

<400> SEQUENCE: 381
ucugggcgag gggug                                                    15

<210> SEQ ID NO 382
<211> LENGTH: 23
<212> TYPE: RNA
<213> ORGANISM: Homo sapiens

<400> SEQUENCE: 382
cuccuggggc ccgcacucuc gcu                                           23

<210> SEQ ID NO 383
<211> LENGTH: 18
<212> TYPE: RNA
<213> ORGANISM: Homo sapiens

<400> SEQUENCE: 383
cuccuggggc ccgcacuc                                                 18

<210> SEQ ID NO 384
<211> LENGTH: 20
<212> TYPE: RNA
<213> ORGANISM: Homo sapiens

<400> SEQUENCE: 384
aagacacauu uggagaggga                                               20

<210> SEQ ID NO 385
<211> LENGTH: 16
<212> TYPE: RNA
<213> ORGANISM: Homo sapiens

<400> SEQUENCE: 385
agacacauuu ggagag                                                   16

<210> SEQ ID NO 386
<211> LENGTH: 20
<212> TYPE: RNA
<213> ORGANISM: Homo sapiens

<400> SEQUENCE: 386
ugaguggggc ucccgggacg                                               20

<210> SEQ ID NO 387
<211> LENGTH: 20
<212> TYPE: RNA
<213> ORGANISM: Homo sapiens

<400> SEQUENCE: 387
ugaguggggc ucccgggacg                                               20
```

```
<210> SEQ ID NO 388
<211> LENGTH: 24
<212> TYPE: RNA
<213> ORGANISM: Homo sapiens

<400> SEQUENCE: 388
ucgaggacug guggaagggc cuuu                                          24

<210> SEQ ID NO 389
<211> LENGTH: 16
<212> TYPE: RNA
<213> ORGANISM: Homo sapiens

<400> SEQUENCE: 389
ucgaggacug guggaa                                                   16

<210> SEQ ID NO 390
<211> LENGTH: 25
<212> TYPE: RNA
<213> ORGANISM: Homo sapiens

<400> SEQUENCE: 390
ggguggggau uuguugcauu acuug                                         25

<210> SEQ ID NO 391
<211> LENGTH: 20
<212> TYPE: RNA
<213> ORGANISM: Homo sapiens

<400> SEQUENCE: 391
ggguggggau uuguugcauu                                               20

<210> SEQ ID NO 392
<211> LENGTH: 20
<212> TYPE: RNA
<213> ORGANISM: Homo sapiens

<400> SEQUENCE: 392
ggcuccuugg ucuagggua                                                20

<210> SEQ ID NO 393
<211> LENGTH: 15
<212> TYPE: RNA
<213> ORGANISM: Homo sapiens

<400> SEQUENCE: 393
cuuggucuag gggua                                                    15

<210> SEQ ID NO 394
<211> LENGTH: 23
<212> TYPE: RNA
<213> ORGANISM: Homo sapiens

<400> SEQUENCE: 394 cuagguggaag aagauggcgg aag                                          23

<210> SEQ ID NO 395
<211> LENGTH: 15
<212> TYPE: RNA
<213> ORGANISM: Homo sapiens

<400> SEQUENCE: 395
```

-continued uaguggaaga agaug                                                    15

<210> SEQ ID NO 396
<211> LENGTH: 23
<212> TYPE: RNA
<213> ORGANISM: Homo sapiens

<400> SEQUENCE: 396
acagcagggc uggggauugc agu                                           23

<210> SEQ ID NO 397
<211> LENGTH: 19
<212> TYPE: RNA
<213> ORGANISM: Homo sapiens

<400> SEQUENCE: 397
ugcugcuccc aguccugcc                                                19

<210> SEQ ID NO 398
<211> LENGTH: 25
<212> TYPE: RNA
<213> ORGANISM: Homo sapiens

<400> SEQUENCE: 398
uggcggcggu aguaugggc uucuc                                          25

<210> SEQ ID NO 399
<211> LENGTH: 25
<212> TYPE: RNA
<213> ORGANISM: Homo sapiens

<400> SEQUENCE: 399
uggcggcggu aguaugggc uucuc                                          25

<210> SEQ ID NO 400
<211> LENGTH: 20
<212> TYPE: RNA
<213> ORGANISM: Homo sapiens

<400> SEQUENCE: 400
uaggaugggg gugagaggug                                               20

<210> SEQ ID NO 401
<211> LENGTH: 18
<212> TYPE: RNA
<213> ORGANISM: Homo sapiens

<400> SEQUENCE: 401
uaggaugggg gugagagg                                                 18

<210> SEQ ID NO 402
<211> LENGTH: 21
<212> TYPE: RNA
<213> ORGANISM: Homo sapiens

<400> SEQUENCE: 402
cagccugagu gacagagcaa g                                             21

<210> SEQ ID NO 403
<211> LENGTH: 15
<212> TYPE: RNA
<213> ORGANISM: Homo sapiens

<400> SEQUENCE: 403

```
acugcacucc agccu                                                    15

<210> SEQ ID NO 404
<211> LENGTH: 23
<212> TYPE: RNA
<213> ORGANISM: Homo sapiens

<400> SEQUENCE: 404
aggagggguc ccgcacuggg agg                                           23

<210> SEQ ID NO 405
<211> LENGTH: 15
<212> TYPE: RNA
<213> ORGANISM: Homo sapiens

<400> SEQUENCE: 405
ugggaggggc ccuca                                                    15

<210> SEQ ID NO 406
<211> LENGTH: 23
<212> TYPE: RNA
<213> ORGANISM: Homo sapiens

<400> SEQUENCE: 406
gggggccgau acacuguacg aga                                           23

<210> SEQ ID NO 407
<211> LENGTH: 20
<212> TYPE: RNA
<213> ORGANISM: Homo sapiens

<400> SEQUENCE: 407
gggggccgau acacuguacg                                               20

<210> SEQ ID NO 408
<211> LENGTH: 23
<212> TYPE: RNA
<213> ORGANISM: Homo sapiens

<400> SEQUENCE: 408
ggugggugag gucgggcccc aag                                           23

<210> SEQ ID NO 409
<211> LENGTH: 20
<212> TYPE: RNA
<213> ORGANISM: Homo sapiens

<400> SEQUENCE: 409
cggggugggu gaggucgggc                                               20

<210> SEQ ID NO 410
<211> LENGTH: 23
<212> TYPE: RNA
<213> ORGANISM: Homo sapiens

<400> SEQUENCE: 410
agaagaaggc ggucggucug cgg                                           23

<210> SEQ ID NO 411
<211> LENGTH: 21
<212> TYPE: RNA
<213> ORGANISM: Homo sapiens
```

```
<400> SEQUENCE: 411
aagaaggcgg ucggucugcg g                                              21

<210> SEQ ID NO 412
<211> LENGTH: 17
<212> TYPE: RNA
<213> ORGANISM: Homo sapiens

<400> SEQUENCE: 412
ggugagcgcu cgcuggc                                                   17

<210> SEQ ID NO 413
<211> LENGTH: 15
<212> TYPE: RNA
<213> ORGANISM: Homo sapiens

<400> SEQUENCE: 413
cggugagcgc ucgcu                                                     15

<210> SEQ ID NO 414
<211> LENGTH: 16
<212> TYPE: RNA
<213> ORGANISM: Homo sapiens

<400> SEQUENCE: 414
ugcuggugau gcuuuc                                                    16

<210> SEQ ID NO 415
<211> LENGTH: 16
<212> TYPE: RNA
<213> ORGANISM: Homo sapiens

<400> SEQUENCE: 415
ugcuggugau gcuuuc                                                    16

<210> SEQ ID NO 416
<211> LENGTH: 23
<212> TYPE: RNA
<213> ORGANISM: Homo sapiens

<400> SEQUENCE: 416
gccccggcgc gggcggguuc ugg                                            23

<210> SEQ ID NO 417
<211> LENGTH: 16
<212> TYPE: RNA
<213> ORGANISM: Homo sapiens

<400> SEQUENCE: 417
ggagccccgg cgcggg                                                    16

<210> SEQ ID NO 418
<211> LENGTH: 21
<212> TYPE: RNA
<213> ORGANISM: Homo sapiens

<400> SEQUENCE: 418
cggauccgag ucacggcacc a                                              21

<210> SEQ ID NO 419
<211> LENGTH: 15
<212> TYPE: RNA
<213> ORGANISM: Homo sapiens
```

```
<400> SEQUENCE: 419
ggauccgagu cacgg                                                    15

<210> SEQ ID NO 420
<211> LENGTH: 23
<212> TYPE: RNA
<213> ORGANISM: Homo sapiens

<400> SEQUENCE: 420 gggggggaugu gcaugcuggu ugg                                          23

<210> SEQ ID NO 421
<211> LENGTH: 15
<212> TYPE: RNA
<213> ORGANISM: Homo sapiens

<400> SEQUENCE: 421
aucagcgugc acuuc                                                    15

<210> SEQ ID NO 422
<211> LENGTH: 17
<212> TYPE: RNA
<213> ORGANISM: Homo sapiens

<400> SEQUENCE: 422
uccuagucac ggcacca                                                  17

<210> SEQ ID NO 423
<211> LENGTH: 17
<212> TYPE: RNA
<213> ORGANISM: Homo sapiens

<400> SEQUENCE: 423
uccuagucac ggcacca                                                  17

<210> SEQ ID NO 424
<211> LENGTH: 25
<212> TYPE: RNA
<213> ORGANISM: Homo sapiens

<400> SEQUENCE: 424
ugcggggcua gggcuaacag caguc                                         25

<210> SEQ ID NO 425
<211> LENGTH: 15
<212> TYPE: RNA
<213> ORGANISM: Homo sapiens

<400> SEQUENCE: 425
ugcggggcua gggcu                                                    15

<210> SEQ ID NO 426
<211> LENGTH: 21
<212> TYPE: RNA
<213> ORGANISM: Homo sapiens

<400> SEQUENCE: 426
cccaggcugg agcgagugca g                                             21

<210> SEQ ID NO 427
<211> LENGTH: 15
<212> TYPE: RNA
```

```
<213> ORGANISM: Homo sapiens

<400> SEQUENCE: 427
agcucacugc agccu                                                    15

<210> SEQ ID NO 428
<211> LENGTH: 22
<212> TYPE: RNA
<213> ORGANISM: Homo sapiens

<400> SEQUENCE: 428
ugugggacug caaaugggag cu                                            22

<210> SEQ ID NO 429
<211> LENGTH: 22
<212> TYPE: RNA
<213> ORGANISM: Homo sapiens

<400> SEQUENCE: 429
ugugggacug caaaugggag cu                                            22

<210> SEQ ID NO 430
<211> LENGTH: 26
<212> TYPE: RNA
<213> ORGANISM: Homo sapiens

<400> SEQUENCE: 430
gcgggcuguc cggaggdgguc ggcuuu                                       26

<210> SEQ ID NO 431
<211> LENGTH: 16
<212> TYPE: RNA
<213> ORGANISM: Homo sapiens

<400> SEQUENCE: 431
gcuguccgga gggguc                                                   16

<210> SEQ ID NO 432
<211> LENGTH: 22
<212> TYPE: RNA
<213> ORGANISM: Homo sapiens

<400> SEQUENCE: 432
ccgggaacgu cgagacugga gc                                            22

<210> SEQ ID NO 433
<211> LENGTH: 15
<212> TYPE: RNA
<213> ORGANISM: Homo sapiens

<400> SEQUENCE: 433
cgggaacguc gagac                                                    15

<210> SEQ ID NO 434
<211> LENGTH: 17
<212> TYPE: RNA
<213> ORGANISM: Homo sapiens

<400> SEQUENCE: 434
ccuccgggac ggcuggg                                                  17

<210> SEQ ID NO 435
<211> LENGTH: 15
```

<212> TYPE: RNA
<213> ORGANISM: Homo sapiens

<400> SEQUENCE: 435
cuccgggacg gcugg                                             15

<210> SEQ ID NO 436
<211> LENGTH: 21
<212> TYPE: RNA
<213> ORGANISM: Homo sapiens

<400> SEQUENCE: 436
cccagcagga cgggagcgcg g                                      21

<210> SEQ ID NO 437
<211> LENGTH: 16
<212> TYPE: RNA
<213> ORGANISM: Homo sapiens

<400> SEQUENCE: 437
aagcuggguc aaggag                                            16

<210> SEQ ID NO 438
<211> LENGTH: 22
<212> TYPE: RNA
<213> ORGANISM: Homo sapiens

<400> SEQUENCE: 438
cugggcucgg gacgcgcggc uc                                     22

<210> SEQ ID NO 439
<211> LENGTH: 19
<212> TYPE: RNA
<213> ORGANISM: Homo sapiens

<400> SEQUENCE: 439
cugggcucgg gacgcgcgg                                         19

<210> SEQ ID NO 440
<211> LENGTH: 29
<212> TYPE: RNA
<213> ORGANISM: Homo sapiens

<400> SEQUENCE: 440
ggucaggcgg cucggacuga gcagguggg                              29

<210> SEQ ID NO 441
<211> LENGTH: 15
<212> TYPE: RNA
<213> ORGANISM: Homo sapiens

<400> SEQUENCE: 441
agaguguggu caggc                                             15

<210> SEQ ID NO 442
<211> LENGTH: 23
<212> TYPE: RNA
<213> ORGANISM: Homo sapiens

<400> SEQUENCE: 442
cagcccgccc cagccgaggu ucu                                    23

<210> SEQ ID NO 443

```
<211> LENGTH: 17
<212> TYPE: RNA
<213> ORGANISM: Homo sapiens

<400> SEQUENCE: 443
agcccgcccc agccgag                                                    17

<210> SEQ ID NO 444
<211> LENGTH: 23
<212> TYPE: RNA
<213> ORGANISM: Homo sapiens

<400> SEQUENCE: 444
agggucgggg cagggagggc agg                                             23

<210> SEQ ID NO 445
<211> LENGTH: 15
<212> TYPE: RNA
<213> ORGANISM: Homo sapiens

<400> SEQUENCE: 445
gggagaaggg ucggg                                                      15

<210> SEQ ID NO 446
<211> LENGTH: 21
<212> TYPE: RNA
<213> ORGANISM: Homo sapiens

<400> SEQUENCE: 446
auccaguucu cugagggggc u                                               21

<210> SEQ ID NO 447
<211> LENGTH: 21
<212> TYPE: RNA
<213> ORGANISM: Homo sapiens

<400> SEQUENCE: 447
auccaguucu cugagggggc u                                               21

<210> SEQ ID NO 448
<211> LENGTH: 16
<212> TYPE: RNA
<213> ORGANISM: Homo sapiens

<400> SEQUENCE: 448
gugaaggccc ggcgga                                                     16

<210> SEQ ID NO 449
<211> LENGTH: 15
<212> TYPE: RNA
<213> ORGANISM: Homo sapiens

<400> SEQUENCE: 449
gugaaggccc ggcgg                                                      15

<210> SEQ ID NO 450
<211> LENGTH: 23
<212> TYPE: RNA
<213> ORGANISM: Homo sapiens

<400> SEQUENCE: 450
ccagggcugg cagugacaug ggu                                             23
```

```
<210> SEQ ID NO 451
<211> LENGTH: 19
<212> TYPE: RNA
<213> ORGANISM: Homo sapiens

<400> SEQUENCE: 451
cagggcuggc agugacaug                                              19

<210> SEQ ID NO 452
<211> LENGTH: 21
<212> TYPE: RNA
<213> ORGANISM: Homo sapiens

<400> SEQUENCE: 452
gccgggcgug guguggggg c                                            21

<210> SEQ ID NO 453
<211> LENGTH: 15
<212> TYPE: RNA
<213> ORGANISM: Homo sapiens

<400> SEQUENCE: 453
uagccgggcg uggug                                                  15

<210> SEQ ID NO 454
<211> LENGTH: 21
<212> TYPE: RNA
<213> ORGANISM: Homo sapiens

<400> SEQUENCE: 454
ccggccgccg gcuccgcccc g                                           21

<210> SEQ ID NO 455
<211> LENGTH: 17
<212> TYPE: RNA
<213> ORGANISM: Homo sapiens

<400> SEQUENCE: 455
ccggccgccg gcuccgc                                                17

<210> SEQ ID NO 456
<211> LENGTH: 23
<212> TYPE: RNA
<213> ORGANISM: Homo sapiens

<400> SEQUENCE: 456
ugaggauaug gcagggaagg gga                                         23

<210> SEQ ID NO 457
<211> LENGTH: 19
<212> TYPE: RNA
<213> ORGANISM: Homo sapiens

<400> SEQUENCE: 457
ugaggauaug gcagggaag                                              19

<210> SEQ ID NO 458
<211> LENGTH: 21
<212> TYPE: RNA
<213> ORGANISM: Homo sapiens

<400> SEQUENCE: 458
aggaggcagu gggcgagcag g                                           21
```

```
<210> SEQ ID NO 459
<211> LENGTH: 21
<212> TYPE: RNA
<213> ORGANISM: Homo sapiens

<400> SEQUENCE: 459
aggaggcagu gggcgagcag g                                              21

<210> SEQ ID NO 460
<211> LENGTH: 24
<212> TYPE: RNA
<213> ORGANISM: Homo sapiens

<400> SEQUENCE: 460
gaucggucga gagcguccug gcug                                           24

<210> SEQ ID NO 461
<211> LENGTH: 15
<212> TYPE: RNA
<213> ORGANISM: Homo sapiens

<400> SEQUENCE: 461
gcugggcggg gcgcg                                                     15

<210> SEQ ID NO 462
<211> LENGTH: 24
<212> TYPE: RNA
<213> ORGANISM: Homo sapiens

<400> SEQUENCE: 462
cccggggcag auugguguag ggug                                           24

<210> SEQ ID NO 463
<211> LENGTH: 17
<212> TYPE: RNA
<213> ORGANISM: Homo sapiens

<400> SEQUENCE: 463
cggggcagau uggugua                                                   17

<210> SEQ ID NO 464
<211> LENGTH: 23
<212> TYPE: RNA
<213> ORGANISM: Homo sapiens

<400> SEQUENCE: 464
uggggcggag cuuccggagg ccc                                            23

<210> SEQ ID NO 465
<211> LENGTH: 16
<212> TYPE: RNA
<213> ORGANISM: Homo sapiens

<400> SEQUENCE: 465
aucgcuggcc uggucg                                                    16

<210> SEQ ID NO 466
<211> LENGTH: 15
<212> TYPE: RNA
<213> ORGANISM: Homo sapiens

<400> SEQUENCE: 466
uggcagagcg cuguc                                                     15
```

```
<210> SEQ ID NO 467
<211> LENGTH: 15
<212> TYPE: RNA
<213> ORGANISM: Homo sapiens

<400> SEQUENCE: 467
uggcagagcg cuguc                                                    15

<210> SEQ ID NO 468
<211> LENGTH: 24
<212> TYPE: RNA
<213> ORGANISM: Homo sapiens

<400> SEQUENCE: 468
gugaguggga gccggugggg cugg                                          24

<210> SEQ ID NO 469
<211> LENGTH: 15
<212> TYPE: RNA
<213> ORGANISM: Homo sapiens

<400> SEQUENCE: 469
ggggcuggag uaagg                                                    15

<210> SEQ ID NO 470
<211> LENGTH: 22
<212> TYPE: RNA
<213> ORGANISM: Homo sapiens

<400> SEQUENCE: 470
accccacucc ugguaccaua gu                                            22

<210> SEQ ID NO 471
<211> LENGTH: 15
<212> TYPE: RNA
<213> ORGANISM: Homo sapiens

<400> SEQUENCE: 471
accccacucc uggua                                                    15

<210> SEQ ID NO 472
<211> LENGTH: 25
<212> TYPE: RNA
<213> ORGANISM: Homo sapiens

<400> SEQUENCE: 472
agcggggagg aagugggcgc ugcuu                                         25

<210> SEQ ID NO 473
<211> LENGTH: 21
<212> TYPE: RNA
<213> ORGANISM: Homo sapiens

<400> SEQUENCE: 473
agcggggagg aagugggcgc u                                             21

<210> SEQ ID NO 474
<211> LENGTH: 16
<212> TYPE: RNA
<213> ORGANISM: Homo sapiens

<400> SEQUENCE: 474
```

```
ggacccaggg agagac                                                    16

<210> SEQ ID NO 475
<211> LENGTH: 16
<212> TYPE: RNA
<213> ORGANISM: Homo sapiens

<400> SEQUENCE: 475
ggacccaggg agagac                                                    16

<210> SEQ ID NO 476
<211> LENGTH: 20
<212> TYPE: RNA
<213> ORGANISM: Homo sapiens

<400> SEQUENCE: 476
aucccaccuc ugccaccaaa                                                20

<210> SEQ ID NO 477
<211> LENGTH: 15
<212> TYPE: RNA
<213> ORGANISM: Homo sapiens

<400> SEQUENCE: 477
aucccaccuc ugcca                                                     15

<210> SEQ ID NO 478
<211> LENGTH: 16
<212> TYPE: RNA
<213> ORGANISM: Homo sapiens

<400> SEQUENCE: 478
cgggcccggc guuccc                                                    16

<210> SEQ ID NO 479
<211> LENGTH: 15
<212> TYPE: RNA
<213> ORGANISM: Homo sapiens

<400> SEQUENCE: 479
ccgggcccgg cguuc                                                     15

<210> SEQ ID NO 480
<211> LENGTH: 24
<212> TYPE: RNA
<213> ORGANISM: Homo sapiens

<400> SEQUENCE: 480
ugacugggga gcagaaggag aacc                                           24

<210> SEQ ID NO 481
<211> LENGTH: 15
<212> TYPE: RNA
<213> ORGANISM: Homo sapiens

<400> SEQUENCE: 481
gacuggggag cagaa                                                     15

<210> SEQ ID NO 482
<211> LENGTH: 27
<212> TYPE: RNA
<213> ORGANISM: Homo sapiens

<400> SEQUENCE: 482
```
agggccagag gagccuggag uggucgg                                    27

<210> SEQ ID NO 483
<211> LENGTH: 23
<212> TYPE: RNA
<213> ORGANISM: Homo sapiens

<400> SEQUENCE: 483
agggccagag gagccuggag ugg                                        23

<210> SEQ ID NO 484
<211> LENGTH: 18
<212> TYPE: RNA
<213> ORGANISM: Homo sapiens

<400> SEQUENCE: 484
aaaaggaagg gggaggag                                              18

<210> SEQ ID NO 485
<211> LENGTH: 16
<212> TYPE: RNA
<213> ORGANISM: Homo sapiens

<400> SEQUENCE: 485
aaggaagggg gaggag                                                16

<210> SEQ ID NO 486
<211> LENGTH: 20
<212> TYPE: RNA
<213> ORGANISM: Homo sapiens

<400> SEQUENCE: 486
ccccggggag cccggcggug                                            20

<210> SEQ ID NO 487
<211> LENGTH: 15
<212> TYPE: RNA
<213> ORGANISM: Homo sapiens

<400> SEQUENCE: 487
accccgggga gcccg                                                 15

<210> SEQ ID NO 488
<211> LENGTH: 19
<212> TYPE: RNA
<213> ORGANISM: Homo sapiens

<400> SEQUENCE: 488
gcugggcgag gcuggcauc                                             19

<210> SEQ ID NO 489
<211> LENGTH: 17
<212> TYPE: RNA
<213> ORGANISM: Homo sapiens

<400> SEQUENCE: 489
gcugggcgag gcuggca                                               17

<210> SEQ ID NO 490
<211> LENGTH: 22
<212> TYPE: RNA
<213> ORGANISM: Homo sapiens -continued

```
<400> SEQUENCE: 490
ugggagggga gaggcagcaa gc                                              22

<210> SEQ ID NO 491
<211> LENGTH: 22
<212> TYPE: RNA
<213> ORGANISM: Homo sapiens

<400> SEQUENCE: 491
ugggagggga gaggcagcaa gc                                              22

<210> SEQ ID NO 492
<211> LENGTH: 18
<212> TYPE: RNA
<213> ORGANISM: Homo sapiens

<400> SEQUENCE: 492
cagcggggcu gggcgcgc                                                   18

<210> SEQ ID NO 493
<211> LENGTH: 15
<212> TYPE: RNA
<213> ORGANISM: Homo sapiens

<400> SEQUENCE: 493
cagcggggcu gggcg                                                      15

<210> SEQ ID NO 494
<211> LENGTH: 23
<212> TYPE: RNA
<213> ORGANISM: Homo sapiens

<400> SEQUENCE: 494
cggggccgua gcacugucug aga                                             23

<210> SEQ ID NO 495
<211> LENGTH: 20
<212> TYPE: RNA
<213> ORGANISM: Homo sapiens

<400> SEQUENCE: 495
cggggccgua gcacugucug                                                 20

<210> SEQ ID NO 496
<211> LENGTH: 18
<212> TYPE: RNA
<213> ORGANISM: Homo sapiens

<400> SEQUENCE: 496
ucuagguggg gagacuga                                                   18

<210> SEQ ID NO 497
<211> LENGTH: 16
<212> TYPE: RNA
<213> ORGANISM: Homo sapiens

<400> SEQUENCE: 497
guggggagac ugacgg                                                     16

<210> SEQ ID NO 498
<211> LENGTH: 21
<212> TYPE: RNA
<213> ORGANISM: Homo sapiens
```

-continued

<400> SEQUENCE: 498
uugaggagac auggugggggg c                                              21

<210> SEQ ID NO 499
<211> LENGTH: 15
<212> TYPE: RNA
<213> ORGANISM: Homo sapiens

<400> SEQUENCE: 499
uugaggagac auggu                                                      15

<210> SEQ ID NO 500
<211> LENGTH: 18
<212> TYPE: RNA
<213> ORGANISM: Homo sapiens

<400> SEQUENCE: 500
gaggcugaag gaagaugg                                                   18

<210> SEQ ID NO 501
<211> LENGTH: 15
<212> TYPE: RNA
<213> ORGANISM: Homo sapiens

<400> SEQUENCE: 501
gaggcugaag gaaga                                                      15

<210> SEQ ID NO 502
<211> LENGTH: 22
<212> TYPE: RNA
<213> ORGANISM: Homo sapiens

<400> SEQUENCE: 502
ggcaggaagc ggaggaaccu ug                                              22

<210> SEQ ID NO 503
<211> LENGTH: 17
<212> TYPE: RNA
<213> ORGANISM: Homo sapiens

<400> SEQUENCE: 503
ggaggaaccu uggagcu                                                    17

<210> SEQ ID NO 504
<211> LENGTH: 17
<212> TYPE: RNA
<213> ORGANISM: Homo sapiens

<400> SEQUENCE: 504
aggggcuggg cgcgcgc                                                    17

<210> SEQ ID NO 505
<211> LENGTH: 15
<212> TYPE: RNA
<213> ORGANISM: Homo sapiens

<400> SEQUENCE: 505
caggggcugg gcgcg                                                      15

<210> SEQ ID NO 506
<211> LENGTH: 22
<212> TYPE: RNA

```
<213> ORGANISM: Homo sapiens

<400> SEQUENCE: 506
gaggguuggg uggaggcucu cc                                    22

<210> SEQ ID NO 507
<211> LENGTH: 15
<212> TYPE: RNA
<213> ORGANISM: Homo sapiens

<400> SEQUENCE: 507
gaggguuggg uggag                                            15

<210> SEQ ID NO 508
<211> LENGTH: 21
<212> TYPE: RNA
<213> ORGANISM: Homo sapiens

<400> SEQUENCE: 508
gagggcagcg uggguguggc g                                     21

<210> SEQ ID NO 509
<211> LENGTH: 21
<212> TYPE: RNA
<213> ORGANISM: Homo sapiens

<400> SEQUENCE: 509
gagggcagcg uggguguggc g                                     21

<210> SEQ ID NO 510
<211> LENGTH: 30
<212> TYPE: RNA
<213> ORGANISM: Homo sapiens

<400> SEQUENCE: 510
gcugggcugg gacggacacc cggccuccac                            30

<210> SEQ ID NO 511
<211> LENGTH: 19
<212> TYPE: RNA
<213> ORGANISM: Homo sapiens

<400> SEQUENCE: 511
gaggcugggc ugggacgga                                        19

<210> SEQ ID NO 512
<211> LENGTH: 22
<212> TYPE: RNA
<213> ORGANISM: Homo sapiens

<400> SEQUENCE: 512
cagaagggga guugggagca ga                                    22

<210> SEQ ID NO 513
<211> LENGTH: 16
<212> TYPE: RNA
<213> ORGANISM: Homo sapiens

<400> SEQUENCE: 513 gaagggagu ugggag                                            16

<210> SEQ ID NO 514
<211> LENGTH: 29
```

<212> TYPE: RNA
<213> ORGANISM: Homo sapiens

<400> SEQUENCE: 514
gggagccgcg gggaucgccg agggccggu                29

<210> SEQ ID NO 515
<211> LENGTH: 15
<212> TYPE: RNA
<213> ORGANISM: Homo sapiens

<400> SEQUENCE: 515
ggcggcggug guggg                15

<210> SEQ ID NO 516
<211> LENGTH: 20
<212> TYPE: RNA
<213> ORGANISM: Homo sapiens

<400> SEQUENCE: 516
cuccccggug ugcaaaugug                20

<210> SEQ ID NO 517
<211> LENGTH: 15
<212> TYPE: RNA
<213> ORGANISM: Homo sapiens

<400> SEQUENCE: 517
gugugcggug uuaug                15

<210> SEQ ID NO 518
<211> LENGTH: 19
<212> TYPE: RNA
<213> ORGANISM: Homo sapiens

<400> SEQUENCE: 518
gagggcgggu ggaggagga                19

<210> SEQ ID NO 519
<211> LENGTH: 15
<212> TYPE: RNA
<213> ORGANISM: Homo sapiens

<400> SEQUENCE: 519
gcggguggag gagga                15

<210> SEQ ID NO 520
<211> LENGTH: 17
<212> TYPE: RNA
<213> ORGANISM: Homo sapiens

<400> SEQUENCE: 520
ggggcggggg cggggc                17

<210> SEQ ID NO 521
<211> LENGTH: 15
<212> TYPE: RNA
<213> ORGANISM: Homo sapiens

<400> SEQUENCE: 521
cgcgccgggc ccggg                15

<210> SEQ ID NO 522

```
<211> LENGTH: 23
<212> TYPE: RNA
<213> ORGANISM: Homo sapiens

<400> SEQUENCE: 522
gggggucccc ggugcucgga ucu                                              23

<210> SEQ ID NO 523
<211> LENGTH: 16
<212> TYPE: RNA
<213> ORGANISM: Homo sapiens

<400> SEQUENCE: 523
ucgggagggg cgggag                                                      16

<210> SEQ ID NO 524
<211> LENGTH: 23
<212> TYPE: RNA
<213> ORGANISM: Homo sapiens

<400> SEQUENCE: 524
cggggcagcu caguacagga uac                                              23

<210> SEQ ID NO 525
<211> LENGTH: 15
<212> TYPE: RNA
<213> ORGANISM: Homo sapiens

<400> SEQUENCE: 525
agcucaguac aggau                                                       15

<210> SEQ ID NO 526
<211> LENGTH: 23
<212> TYPE: RNA
<213> ORGANISM: Homo sapiens

<400> SEQUENCE: 526
ucggcucugg gucugugggg agc                                              23

<210> SEQ ID NO 527
<211> LENGTH: 15
<212> TYPE: RNA
<213> ORGANISM: Homo sapiens

<400> SEQUENCE: 527
gcccggauac cucag                                                       15

<210> SEQ ID NO 528
<211> LENGTH: 23
<212> TYPE: RNA
<213> ORGANISM: Homo sapiens

<400> SEQUENCE: 528
ggcuacaaca caggacccgg gcg                                              23

<210> SEQ ID NO 529
<211> LENGTH: 21
<212> TYPE: RNA
<213> ORGANISM: Homo sapiens

<400> SEQUENCE: 529
ggcuacaaca caggacccgg g                                                21
```

```
<210> SEQ ID NO 530
<211> LENGTH: 22
<212> TYPE: RNA
<213> ORGANISM: Homo sapiens

<400> SEQUENCE: 530
acucaaacug uggggcacu uu                                            22

<210> SEQ ID NO 531
<211> LENGTH: 19
<212> TYPE: RNA
<213> ORGANISM: Homo sapiens

<400> SEQUENCE: 531
acucaaacug uggggcac                                                19

<210> SEQ ID NO 532
<211> LENGTH: 24
<212> TYPE: RNA
<213> ORGANISM: Homo sapiens

<400> SEQUENCE: 532
uggggagcug aggcucuggg ggug                                         24

<210> SEQ ID NO 533
<211> LENGTH: 15
<212> TYPE: RNA
<213> ORGANISM: Homo sapiens

<400> SEQUENCE: 533
ggcccugggg agcug                                                   15

<210> SEQ ID NO 534
<211> LENGTH: 27
<212> TYPE: RNA
<213> ORGANISM: Homo sapiens

<400> SEQUENCE: 534
gugaacgggc gccaucccga ggcuuug                                      27

<210> SEQ ID NO 535
<211> LENGTH: 16
<212> TYPE: RNA
<213> ORGANISM: Homo sapiens

<400> SEQUENCE: 535
gugaacgggc gccauc                                                  16

<210> SEQ ID NO 536
<211> LENGTH: 23
<212> TYPE: RNA
<213> ORGANISM: Homo sapiens

<400> SEQUENCE: 536
caccuugccu ugcugcccgg gcc                                          23

<210> SEQ ID NO 537
<211> LENGTH: 22
<212> TYPE: RNA
<213> ORGANISM: Homo sapiens

<400> SEQUENCE: 537
caccuugccu ugcugcccgg gc                                           22
```

```
<210> SEQ ID NO 538
<211> LENGTH: 23
<212> TYPE: RNA
<213> ORGANISM: Homo sapiens

<400> SEQUENCE: 538
ggcccggccg ugccugaggu uuc                                           23

<210> SEQ ID NO 539
<211> LENGTH: 15
<212> TYPE: RNA
<213> ORGANISM: Homo sapiens

<400> SEQUENCE: 539
ggcgguggga ucccg                                                    15

<210> SEQ ID NO 540
<211> LENGTH: 24
<212> TYPE: RNA
<213> ORGANISM: Homo sapiens

<400> SEQUENCE: 540
aggcaggggc uggugcuggg cggg                                          24

<210> SEQ ID NO 541
<211> LENGTH: 15
<212> TYPE: RNA
<213> ORGANISM: Homo sapiens

<400> SEQUENCE: 541 gggcggggggg cggcg                                                   15

<210> SEQ ID NO 542
<211> LENGTH: 19
<212> TYPE: RNA
<213> ORGANISM: Homo sapiens

<400> SEQUENCE: 542
uggcgggugc gggggguggg                                               19

<210> SEQ ID NO 543
<211> LENGTH: 15
<212> TYPE: RNA
<213> ORGANISM: Homo sapiens

<400> SEQUENCE: 543
uggcgggugc ggggg                                                    15

<210> SEQ ID NO 544
<211> LENGTH: 19
<212> TYPE: RNA
<213> ORGANISM: Homo sapiens

<400> SEQUENCE: 544 aggggggcggg cuccggcgc                                               19

<210> SEQ ID NO 545
<211> LENGTH: 15
<212> TYPE: RNA
<213> ORGANISM: Homo sapiens

<400> SEQUENCE: 545
guagggggcg ggcuc                                                    15
```

```
<210> SEQ ID NO 546
<211> LENGTH: 23
<212> TYPE: RNA
<213> ORGANISM: Homo sapiens

<400> SEQUENCE: 546
cacaggugag guucuuggga gcc                                          23

<210> SEQ ID NO 547
<211> LENGTH: 15
<212> TYPE: RNA
<213> ORGANISM: Homo sapiens

<400> SEQUENCE: 547
acaggugagg uucuu                                                   15

<210> SEQ ID NO 548
<211> LENGTH: 22
<212> TYPE: RNA
<213> ORGANISM: Homo sapiens

<400> SEQUENCE: 548
gugggcgggg gcaggugugu gg                                           22

<210> SEQ ID NO 549
<211> LENGTH: 15
<212> TYPE: RNA
<213> ORGANISM: Homo sapiens

<400> SEQUENCE: 549
cgggggcagg ugugu                                                   15

<210> SEQ ID NO 550
<211> LENGTH: 24
<212> TYPE: RNA
<213> ORGANISM: Homo sapiens

<400> SEQUENCE: 550
cgggcguggu gguggggug ggug                                          24

<210> SEQ ID NO 551
<211> LENGTH: 15
<212> TYPE: RNA
<213> ORGANISM: Homo sapiens

<400> SEQUENCE: 551
cgggcguggu ggugg                                                   15

<210> SEQ ID NO 552
<211> LENGTH: 20
<212> TYPE: RNA
<213> ORGANISM: Homo sapiens

<400> SEQUENCE: 552
ccccagggcg acgcggcggg                                              20

<210> SEQ ID NO 553
<211> LENGTH: 15
<212> TYPE: RNA
<213> ORGANISM: Homo sapiens

<400> SEQUENCE: 553
```
cgcggcgggg gcggc 15

<210> SEQ ID NO 554
<211> LENGTH: 23
<212> TYPE: RNA
<213> ORGANISM: Homo sapiens

<400> SEQUENCE: 554
acaggagugg ggugggaca uaa 23

<210> SEQ ID NO 555
<211> LENGTH: 20
<212> TYPE: RNA
<213> ORGANISM: Homo sapiens

<400> SEQUENCE: 555
acaggagugg ggugggaca 20

<210> SEQ ID NO 556
<211> LENGTH: 18
<212> TYPE: RNA
<213> ORGANISM: Homo sapiens

<400> SEQUENCE: 556
ggugggcuuc ccgagggg 18

<210> SEQ ID NO 557
<211> LENGTH: 15
<212> TYPE: RNA
<213> ORGANISM: Homo sapiens

<400> SEQUENCE: 557
ggugggcuuc ccgga 15

<210> SEQ ID NO 558
<211> LENGTH: 27
<212> TYPE: RNA
<213> ORGANISM: Homo sapiens

<400> SEQUENCE: 558
caagguggcu gggagagggu uguuuac 27

<210> SEQ ID NO 559
<211> LENGTH: 15
<212> TYPE: RNA
<213> ORGANISM: Homo sapiens

<400> SEQUENCE: 559
gugagcucaa ggugg 15

<210> SEQ ID NO 560
<211> LENGTH: 22
<212> TYPE: RNA
<213> ORGANISM: Homo sapiens

<400> SEQUENCE: 560
acucggcugc gguggacaag uc 22

<210> SEQ ID NO 561
<211> LENGTH: 20
<212> TYPE: RNA
<213> ORGANISM: Homo sapiens

<400> SEQUENCE: 561

```
acucggcugc gguggacaag                                               20

<210> SEQ ID NO 562
<211> LENGTH: 15
<212> TYPE: RNA
<213> ORGANISM: Homo sapiens

<400> SEQUENCE: 562
ugaagcgggg gggcg                                                    15

<210> SEQ ID NO 563
<211> LENGTH: 15
<212> TYPE: RNA
<213> ORGANISM: Homo sapiens

<400> SEQUENCE: 563
ugaagcgggg gggcg                                                    15

<210> SEQ ID NO 564
<211> LENGTH: 22
<212> TYPE: RNA
<213> ORGANISM: Homo sapiens

<400> SEQUENCE: 564
accaggaggc ugaggcsccu ca                                            22

<210> SEQ ID NO 565
<211> LENGTH: 15
<212> TYPE: RNA
<213> ORGANISM: Homo sapiens

<400> SEQUENCE: 565
accaggaggc ugagg                                                    15

<210> SEQ ID NO 566
<211> LENGTH: 25
<212> TYPE: RNA
<213> ORGANISM: Homo sapiens

<400> SEQUENCE: 566
uccuguacug agcugccccg aggcc                                         25

<210> SEQ ID NO 567
<211> LENGTH: 15
<212> TYPE: RNA
<213> ORGANISM: Homo sapiens

<400> SEQUENCE: 567
uccuguacug agcug                                                    15

<210> SEQ ID NO 568
<211> LENGTH: 22
<212> TYPE: RNA
<213> ORGANISM: Homo sapiens

<400> SEQUENCE: 568
acaccgggga uggcagaggg uc                                            22

<210> SEQ ID NO 569
<211> LENGTH: 20
<212> TYPE: RNA
<213> ORGANISM: Homo sapiens
```

```
<400> SEQUENCE: 569
caccggggau ggcagagggu                                              20

<210> SEQ ID NO 570
<211> LENGTH: 23
<212> TYPE: RNA
<213> ORGANISM: Homo sapiens

<400> SEQUENCE: 570 guggggaga ggcugucuug ugu                                           23

<210> SEQ ID NO 571
<211> LENGTH: 15
<212> TYPE: RNA
<213> ORGANISM: Homo sapiens

<400> SEQUENCE: 571
guguggggga gaggc                                                   15

<210> SEQ ID NO 572
<211> LENGTH: 17
<212> TYPE: RNA
<213> ORGANISM: Homo sapiens

<400> SEQUENCE: 572
ugcaggggca ggccagc                                                 17

<210> SEQ ID NO 573
<211> LENGTH: 17
<212> TYPE: RNA
<213> ORGANISM: Homo sapiens

<400> SEQUENCE: 573
ugcaggggca ggccagc                                                 17

<210> SEQ ID NO 574
<211> LENGTH: 22
<212> TYPE: RNA
<213> ORGANISM: Homo sapiens

<400> SEQUENCE: 574 ugggauuug gagaaguggu ga                                            22

<210> SEQ ID NO 575
<211> LENGTH: 22
<212> TYPE: RNA
<213> ORGANISM: Homo sapiens

<400> SEQUENCE: 575 ugggauuug gagaaguggu ga                                            22

<210> SEQ ID NO 576
<211> LENGTH: 22
<212> TYPE: RNA
<213> ORGANISM: Homo sapiens

<400> SEQUENCE: 576
ggcagggaca gcaaaggggu gc                                           22

<210> SEQ ID NO 577
<211> LENGTH: 18
<212> TYPE: RNA
<213> ORGANISM: Homo sapiens
```

-continued

```
<400> SEQUENCE: 577
gcagggacag caaagggg                                              18

<210> SEQ ID NO 578
<211> LENGTH: 26
<212> TYPE: RNA
<213> ORGANISM: Homo sapiens

<400> SEQUENCE: 578 cgugggauc ccgcggccgu guuuuc                                      26

<210> SEQ ID NO 579
<211> LENGTH: 15
<212> TYPE: RNA
<213> ORGANISM: Homo sapiens

<400> SEQUENCE: 579
ggggcgccgc gggac                                                 15

<210> SEQ ID NO 580
<211> LENGTH: 21
<212> TYPE: RNA
<213> ORGANISM: Homo sapiens

<400> SEQUENCE: 580
gcugggaagg caaagggacg u                                          21

<210> SEQ ID NO 581
<211> LENGTH: 22
<212> TYPE: RNA
<213> ORGANISM: Homo sapiens

<400> SEQUENCE: 581
agacacauuu ggagagggaa cc                                         22

<210> SEQ ID NO 582
<211> LENGTH: 22
<212> TYPE: RNA
<213> ORGANISM: Homo sapiens

<400> SEQUENCE: 582
ggggcugggg ccggggccga gc                                         22

<210> SEQ ID NO 583
<211> LENGTH: 21
<212> TYPE: RNA
<213> ORGANISM: Homo sapiens

<400> SEQUENCE: 583
gugccagcug cagugggga g                                           21

<210> SEQ ID NO 584
<211> LENGTH: 23
<212> TYPE: RNA
<213> ORGANISM: Homo sapiens

<400> SEQUENCE: 584
uuagggagua gaagguggg gag                                         23

<210> SEQ ID NO 585
<211> LENGTH: 18
<212> TYPE: RNA
```

```
<213> ORGANISM: Homo sapiens

<400> SEQUENCE: 585
cggggcggca ggggccuc                                              18

<210> SEQ ID NO 586
<211> LENGTH: 22
<212> TYPE: RNA
<213> ORGANISM: Homo sapiens

<400> SEQUENCE: 586
caggcacggg agcucaggug ag                                         22

<210> SEQ ID NO 587
<211> LENGTH: 18
<212> TYPE: RNA
<213> ORGANISM: Homo sapiens

<400> SEQUENCE: 587
agcaggugcg gggcggcg                                              18

<210> SEQ ID NO 588
<211> LENGTH: 20
<212> TYPE: RNA
<213> ORGANISM: Homo sapiens

<400> SEQUENCE: 588
guggguuggg gcgggcucug                                            20

<210> SEQ ID NO 589
<211> LENGTH: 17
<212> TYPE: RNA
<213> ORGANISM: Homo sapiens

<400> SEQUENCE: 589
gggagucuac agcaggg                                               17

<210> SEQ ID NO 590
<211> LENGTH: 18
<212> TYPE: RNA
<213> ORGANISM: Homo sapiens

<400> SEQUENCE: 590
gggugcgggc cggcgggg                                              18

<210> SEQ ID NO 591
<211> LENGTH: 22
<212> TYPE: RNA
<213> ORGANISM: Homo sapiens

<400> SEQUENCE: 591
caggaaggau uuagggacag gc                                         22

<210> SEQ ID NO 592
<211> LENGTH: 24
<212> TYPE: RNA
<213> ORGANISM: Homo sapiens

<400> SEQUENCE: 592 uggggggagcc augagauaag agca                                      24

<210> SEQ ID NO 593
<211> LENGTH: 22
```

```
<212> TYPE: RNA
<213> ORGANISM: Homo sapiens

<400> SEQUENCE: 593 ugggaaggc gucagugucg gg                                              22

<210> SEQ ID NO 594
<211> LENGTH: 23
<212> TYPE: RNA
<213> ORGANISM: Homo sapiens

<400> SEQUENCE: 594
cuggcggagc ccauuccaug cca                                            23

<210> SEQ ID NO 595
<211> LENGTH: 25
<212> TYPE: RNA
<213> ORGANISM: Homo sapiens

<400> SEQUENCE: 595
aagggaggag gagcggaggg gcccu                                          25

<210> SEQ ID NO 596
<211> LENGTH: 22
<212> TYPE: RNA
<213> ORGANISM: Homo sapiens

<400> SEQUENCE: 596 gcggggugg cggcggcauc cc                                              22

<210> SEQ ID NO 597
<211> LENGTH: 20
<212> TYPE: RNA
<213> ORGANISM: Homo sapiens

<400> SEQUENCE: 597
gggcuggggc gcggggaggu                                                20

<210> SEQ ID NO 598
<211> LENGTH: 19
<212> TYPE: RNA
<213> ORGANISM: Homo sapiens

<400> SEQUENCE: 598
aaggggcugg gggagcaca                                                 19

<210> SEQ ID NO 599
<211> LENGTH: 22
<212> TYPE: RNA
<213> ORGANISM: Homo sapiens

<400> SEQUENCE: 599
aggcgaugug gggauguaga ga                                             22

<210> SEQ ID NO 600
<211> LENGTH: 23
<212> TYPE: RNA
<213> ORGANISM: Homo sapiens

<400> SEQUENCE: 600
cugggcccgc ggcgggcgug ggg                                            23

<210> SEQ ID NO 601
```

<211> LENGTH: 23
<212> TYPE: RNA
<213> ORGANISM: Homo sapiens

<400> SEQUENCE: 601
acggggaguc aggcaguggu gga                                              23

<210> SEQ ID NO 602
<211> LENGTH: 22
<212> TYPE: RNA
<213> ORGANISM: Homo sapiens

<400> SEQUENCE: 602
agugggagga caggaggcag gu                                               22

<210> SEQ ID NO 603
<211> LENGTH: 22
<212> TYPE: RNA
<213> ORGANISM: Homo sapiens

<400> SEQUENCE: 603
uggcgggggu agagcuggcu gc                                               22

<210> SEQ ID NO 604
<211> LENGTH: 24
<212> TYPE: RNA
<213> ORGANISM: Homo sapiens

<400> SEQUENCE: 604
guaggggcgu cccgggcgcg cggg                                             24

<210> SEQ ID NO 605
<211> LENGTH: 19
<212> TYPE: RNA
<213> ORGANISM: Homo sapiens

<400> SEQUENCE: 605
cggggccaga gcagagagc                                                   19

<210> SEQ ID NO 606
<211> LENGTH: 21
<212> TYPE: RNA
<213> ORGANISM: Homo sapiens

<400> SEQUENCE: 606
caggcaggug uaggguggag c                                                21

<210> SEQ ID NO 607
<211> LENGTH: 22
<212> TYPE: RNA
<213> ORGANISM: Homo sapiens

<400> SEQUENCE: 607
uagcagcacg uaaauauugg cg                                               22

<210> SEQ ID NO 608
<211> LENGTH: 23
<212> TYPE: RNA
<213> ORGANISM: Homo sapiens

<400> SEQUENCE: 608
ugaggggcag agagcgagac uuu                                              23

```
<210> SEQ ID NO 609
<211> LENGTH: 22
<212> TYPE: RNA
<213> ORGANISM: Homo sapiens

<400> SEQUENCE: 609
aaaccguuac cauuacugag uu                                              22

<210> SEQ ID NO 610
<211> LENGTH: 19
<212> TYPE: RNA
<213> ORGANISM: Homo sapiens

<400> SEQUENCE: 610
aggcacggug ucagcaggc                                                  19

<210> SEQ ID NO 611
<211> LENGTH: 23
<212> TYPE: RNA
<213> ORGANISM: Homo sapiens

<400> SEQUENCE: 611
aggaagcccu ggaggggcug gag                                             23

<210> SEQ ID NO 612
<211> LENGTH: 110
<212> TYPE: RNA
<213> ORGANISM: Homo sapiens

<400> SEQUENCE: 612
ggcuacaguc uuucuucaug ugacucgugg acuucccuuu gucauccuau gccugagaau     60
auaugaagga ggcugggaag gcaaagggac guucaauugu caucacuggc                110

<210> SEQ ID NO 613
<211> LENGTH: 97
<212> TYPE: RNA
<213> ORGANISM: Homo sapiens

<400> SEQUENCE: 613
aucugaguug ggagggucccc ucuccaaaug ugucuugggg uggggaauca agacacauuu    60
ggagagggaa ccucccaacu cggccucugc caucauu                              97

<210> SEQ ID NO 614
<211> LENGTH: 83
<212> TYPE: RNA
<213> ORGANISM: Homo sapiens

<400> SEQUENCE: 614
ggcccggcuc cgggucucgg cccguacagu ccggccggcc augcuggcgg ggcuggggcc     60
ggggccgagc ccgcggcggg gcc                                             83

<210> SEQ ID NO 615
<211> LENGTH: 83
<212> TYPE: RNA
<213> ORGANISM: Homo sapiens

<400> SEQUENCE: 615
ccugcugcag aggugccagc ugcaguggg gaggcacugc cagggcugcc cacucugcuu      60
agccagcagg ugccaagaac agg                                             83

<210> SEQ ID NO 616
```

```
<211> LENGTH: 82
<212> TYPE: RNA
<213> ORGANISM: Homo sapiens

<400> SEQUENCE: 616
cugacuuuuu uagggaguag aaggguggg agcaugaaca auguuucuca cucccuaccc      60
cuccacuccc caaaaaaguc ag                                              82

<210> SEQ ID NO 617
<211> LENGTH: 64
<212> TYPE: RNA
<213> ORGANISM: Homo sapiens

<400> SEQUENCE: 617 ggguggggc gggcggcag gggccucccc cagugccagg ccccauucug cuucucuccc       60
agcu                                                                  64

<210> SEQ ID NO 618
<211> LENGTH: 83
<212> TYPE: RNA
<213> ORGANISM: Homo sapiens

<400> SEQUENCE: 618
aauagagggu gcacaggcac gggagcucag gugaggcagg gagcugagcu caccugaccu     60
cccaugccug ugcacccucu auu                                             83

<210> SEQ ID NO 619
<211> LENGTH: 105
<212> TYPE: RNA
<213> ORGANISM: Homo sapiens

<400> SEQUENCE: 619
gcgggcggcg gcggcggcag cagcagcagg ugcggggcgg cggccgcgcu ggccgcucga     60
cuccgcagcu gcucguucug cuucuccagc uugcgcacca gcucc                     105

<210> SEQ ID NO 620
<211> LENGTH: 102
<212> TYPE: RNA
<213> ORGANISM: Homo sapiens

<400> SEQUENCE: 620
gcuuaucgag gaaaagaucg aggugggung gggcgggcuc uggggauuug gucucacagc     60
ccggauccca gcccacuuac cuugguuacu cuccuuccuu cu                        102

<210> SEQ ID NO 621
<211> LENGTH: 76
<212> TYPE: RNA
<213> ORGANISM: Homo sapiens

<400> SEQUENCE: 621
ccgaugccuc gggagucuac agcagggcca ugucugugag ggcccaaggg ugcaugnguc     60
ucccagguuu cggugc                                                     76

<210> SEQ ID NO 622
<211> LENGTH: 54
<212> TYPE: RNA
<213> ORGANISM: Homo sapiens

<400> SEQUENCE: 622 acgcggguge gggccggcgg gguagaagcc acccggcccg gcccggcccg gcga           54
```

<210> SEQ ID NO 623
<211> LENGTH: 70
<212> TYPE: RNA
<213> ORGANISM: Homo sapiens

<400> SEQUENCE: 623
aaaagccugu cccuaagucc cucccagccu uccagaguug gugccaggaa ggauuuaggg      60
acaggcuuug      70

<210> SEQ ID NO 624
<211> LENGTH: 81
<212> TYPE: RNA
<213> ORGANISM: Homo sapiens

<400> SEQUENCE: 624
aguuggvggg ggagccauga gauaagagca ccuccuagag aauguugaac uaaaggugcc      60
cucucuggcu ccuccccaaa g      81

<210> SEQ ID NO 625
<211> LENGTH: 90
<212> TYPE: RNA
<213> ORGANISM: Homo sapiens

<400> SEQUENCE: 625
gugucucucu ggagacccug cagccuuccc acccaccagg gagcuuucca ugggcugugg      60
ggaaggcguc agucggggu gagggaacac      90

<210> SEQ ID NO 626
<211> LENGTH: 76
<212> TYPE: RNA
<213> ORGANISM: Homo sapiens

<400> SEQUENCE: 626
cgcaggccuc uggcggagcc cauuccaugc cagaugcuga gcgauggcug gugugugcug      60
cuccacaggc cuggug      76

<210> SEQ ID NO 627
<211> LENGTH: 74
<212> TYPE: RNA
<213> ORGANISM: Homo sapiens

<400> SEQUENCE: 627
gggaggaaga agggaggagg agcggagggg cccuugucuu cccagagccu cucccuuccu      60
cccucccccc uccc      74

<210> SEQ ID NO 628
<211> LENGTH: 84
<212> TYPE: RNA
<213> ORGANISM: Homo sapiens

<400> SEQUENCE: 628
cgguccagac guggcggggg uggcggcggc aucccggacg gccugugagg gaugcgccgc      60
ccacugcccc gcgccgccug accg      84

<210> SEQ ID NO 629
<211> LENGTH: 55
<212> TYPE: RNA
<213> ORGANISM: Homo sapiens

```
<400> SEQUENCE: 629
gggggcuggg gcgcggggag gugcuagguc ggccucggcu cccgcgccgc acccc        55

<210> SEQ ID NO 630
<211> LENGTH: 110
<212> TYPE: RNA
<213> ORGANISM: Homo sapiens

<400> SEQUENCE: 630
gucuaccagg uguggcccca gcuuuacaua guucaugcug aggccgggau uucaugcaga    60
aaacugguug caaaaggugc ugaaggggcu gggggagcac aagggagaag             110

<210> SEQ ID NO 631
<211> LENGTH: 73
<212> TYPE: RNA
<213> ORGANISM: Homo sapiens

<400> SEQUENCE: 631
cugguguuug aggcgaugug gggauguaga gacaacuucc cagucucauu uccucauccu    60
gccaggccac cau                                                     73

<210> SEQ ID NO 632
<211> LENGTH: 92
<212> TYPE: RNA
<213> ORGANISM: Homo sapiens

<400> SEQUENCE: 632
cgcugcgcuu cugggcccgc ggcggcgcug gggcugcccg ggccggucga ccagcgcgcc    60
guagcucccg aggcccgagc cgcgacccgc gg                                92

<210> SEQ ID NO 633
<211> LENGTH: 66
<212> TYPE: RNA
<213> ORGANISM: Homo sapiens

<400> SEQUENCE: 633
ucaagacggg gagucaggca gugguggaga uggagagccc ugagccucca cucuccuggc    60
ccccag                                                             66

<210> SEQ ID NO 634
<211> LENGTH: 73
<212> TYPE: RNA
<213> ORGANISM: Homo sapiens

<400> SEQUENCE: 634
guucaagugg gaggacagga ggcaggugug guuggaggaa gcagccugaa ccugccuccc    60
ugacauucca cag                                                     73

<210> SEQ ID NO 635
<211> LENGTH: 61
<212> TYPE: RNA
<213> ORGANISM: Homo sapiens

<400> SEQUENCE: 635
ucggcuggcg ggguagagc uggcugcagg cccggcccu cucagcugcu gcccucucca     60
g                                                                  61

<210> SEQ ID NO 636
<211> LENGTH: 98
```

```
<212> TYPE: RNA
<213> ORGANISM: Homo sapiens

<400> SEQUENCE: 636
cgagguaggg gcgucccggg cgcgcgggcg gguccaggc ugggcccuc ggaggccggg     60 ugcucacugc cccguccgg cgccguguc uccuccag                            98

<210> SEQ ID NO 637
<211> LENGTH: 61
<212> TYPE: RNA
<213> ORGANISM: Homo sapiens

<400> SEQUENCE: 637
aacugcgggg ccagagcaga gagcccuugc acaccaccag ccucuccucc cugugcccca   60
g                                                                   61

<210> SEQ ID NO 638
<211> LENGTH: 69
<212> TYPE: RNA
<213> ORGANISM: Homo sapiens

<400> SEQUENCE: 638
ccgggcaggc agguguaggg uggagcccac uguggcuccu gacucagccc ugcugccuuc   60
accugccag                                                           69

<210> SEQ ID NO 639
<211> LENGTH: 89
<212> TYPE: RNA
<213> ORGANISM: Homo sapiens

<400> SEQUENCE: 639
gucagcagug ccuuagcagc acguaaauau uggcguuaag auucuaaaau uaucuccagu   60
auuaacugug cugcugaagu aagguugac                                     89

<210> SEQ ID NO 640
<211> LENGTH: 81
<212> TYPE: RNA
<213> ORGANISM: Homo sapiens

<400> SEQUENCE: 640
guuccacucu agcagcacgu aaauauuggc guagugaaau auauuaaaa caccauauu     60 acugugcugc uuuaguguga c                                             81

<210> SEQ ID NO 641
<211> LENGTH: 94
<212> TYPE: RNA
<213> ORGANISM: Homo sapiens

<400> SEQUENCE: 641
auaaaggaag uuaggcugag ggcagagag cgagacuuuu cuauuuccca aaagcucggu    60
cugaggcccc ucagucuugc uuccuaaccc gcgc                               94

<210> SEQ ID NO 642
<211> LENGTH: 72
<212> TYPE: RNA
<213> ORGANISM: Homo sapiens

<400> SEQUENCE: 642
cuugggaaug gcaaggaaac cguuaccauu acugaguuua guaaugguaa ugguucucuu   60
```

```
gcuauaccca ga                                                   72

<210> SEQ ID NO 643
<211> LENGTH: 94
<212> TYPE: RNA
<213> ORGANISM: Homo sapiens

<400> SEQUENCE: 643
cgggcagcgg gugccaggca cggugucagc aggcaacaug gccgagaggc cggggccucc  60
gggcggcgcc guguccgcga ccgcguaccc ugac                             94

<210> SEQ ID NO 644
<211> LENGTH: 118
<212> TYPE: RNA
<213> ORGANISM: Homo sapiens

<400> SEQUENCE: 644
gcaggugaac uggcaggcca ggaagaggag gaagcccugg aggggcugga ggugauggau  60
guuuuccucc gguucucagg gcuccaccuc uuucgggccg uagagccagg gcuggugc   118

<210> SEQ ID NO 645
<211> LENGTH: 24
<212> TYPE: RNA
<213> ORGANISM: Homo sapiens

<400> SEQUENCE: 645
gaggcuggga aggcaaaggg acgu                                       24

<210> SEQ ID NO 646
<211> LENGTH: 15
<212> TYPE: RNA
<213> ORGANISM: Homo sapiens

<400> SEQUENCE: 646
cugggaaggc aaagg                                                 15

<210> SEQ ID NO 647
<211> LENGTH: 24
<212> TYPE: RNA
<213> ORGANISM: Homo sapiens

<400> SEQUENCE: 647
agacacauuu ggagagggaa ccuc                                       24

<210> SEQ ID NO 648
<211> LENGTH: 16
<212> TYPE: RNA
<213> ORGANISM: Homo sapiens

<400> SEQUENCE: 648
agacacauuu ggagag                                                16

<210> SEQ ID NO 649
<211> LENGTH: 15
<212> TYPE: RNA
<213> ORGANISM: Homo sapiens

<400> SEQUENCE: 649
gcugcagugg gggag                                                 15

<210> SEQ ID NO 650
<211> LENGTH: 23
```

<212> TYPE: RNA
<213> ORGANISM: Homo sapiens

<400> SEQUENCE: 650
agggaguaga agguugggga gca                                    23

<210> SEQ ID NO 651
<211> LENGTH: 16
<212> TYPE: RNA
<213> ORGANISM: Homo sapiens

<400> SEQUENCE: 651
uagggaguag aagggu                                            16

<210> SEQ ID NO 652
<211> LENGTH: 17
<212> TYPE: RNA
<213> ORGANISM: Homo sapiens

<400> SEQUENCE: 652
gcggggcggc aggggcc                                           17

<210> SEQ ID NO 653
<211> LENGTH: 15
<212> TYPE: RNA
<213> ORGANISM: Homo sapiens

<400> SEQUENCE: 653
gggggcgggg cggca                                             15

<210> SEQ ID NO 654
<211> LENGTH: 18
<212> TYPE: RNA
<213> ORGANISM: Homo sapiens

<400> SEQUENCE: 654
gcacgggagc ucagguga                                          18

<210> SEQ ID NO 655
<211> LENGTH: 18
<212> TYPE: RNA
<213> ORGANISM: Homo sapiens

<400> SEQUENCE: 655
gcggcggcgg cggcagca                                          18

<210> SEQ ID NO 656
<211> LENGTH: 15
<212> TYPE: RNA
<213> ORGANISM: Homo sapiens

<400> SEQUENCE: 656
gcgggcggcg gcggc                                             15

<210> SEQ ID NO 657
<211> LENGTH: 19
<212> TYPE: RNA
<213> ORGANISM: Homo sapiens

<400> SEQUENCE: 657
guggguuggg gcgggcucu                                         19

<210> SEQ ID NO 658

```
<211> LENGTH: 19
<212> TYPE: RNA
<213> ORGANISM: Homo sapiens

<400> SEQUENCE: 658
guggguuggg gcgggcucu                                                   19

<210> SEQ ID NO 659
<211> LENGTH: 19
<212> TYPE: RNA
<213> ORGANISM: Homo sapiens

<400> SEQUENCE: 659
gggugcgggc cggcggggu                                                   19

<210> SEQ ID NO 660
<211> LENGTH: 15
<212> TYPE: RNA
<213> ORGANISM: Homo sapiens

<400> SEQUENCE: 660
ugcgggccgg cgggg                                                       15

<210> SEQ ID NO 661
<211> LENGTH: 22
<212> TYPE: RNA
<213> ORGANISM: Homo sapiens

<400> SEQUENCE: 661
aaggauuuag ggacaggcuu ug                                               22

<210> SEQ ID NO 662
<211> LENGTH: 19
<212> TYPE: RNA
<213> ORGANISM: Homo sapiens

<400> SEQUENCE: 662
caggaaggau uuagggaca                                                   19

<210> SEQ ID NO 663
<211> LENGTH: 22
<212> TYPE: RNA
<213> ORGANISM: Homo sapiens

<400> SEQUENCE: 663
guuggugggg gagccaugag au                                               22

<210> SEQ ID NO 664
<211> LENGTH: 22
<212> TYPE: RNA
<213> ORGANISM: Homo sapiens

<400> SEQUENCE: 664
ggggagccau gagauaagag ca                                               22

<210> SEQ ID NO 665
<211> LENGTH: 23
<212> TYPE: RNA
<213> ORGANISM: Homo sapiens

<400> SEQUENCE: 665
uggggaaggc gucagugucg ggu                                              23
```

```
<210> SEQ ID NO 666
<211> LENGTH: 16
<212> TYPE: RNA
<213> ORGANISM: Homo sapiens

<400> SEQUENCE: 666 ugggaaggc gucagu                                                    16

<210> SEQ ID NO 667
<211> LENGTH: 22
<212> TYPE: RNA
<213> ORGANISM: Homo sapiens

<400> SEQUENCE: 667
uggcggagcc cauuccaugc ca                                            22

<210> SEQ ID NO 668
<211> LENGTH: 21
<212> TYPE: RNA
<213> ORGANISM: Homo sapiens

<400> SEQUENCE: 668
cuggcggagc ccauuccaug c                                             21

<210> SEQ ID NO 669
<211> LENGTH: 23
<212> TYPE: RNA
<213> ORGANISM: Homo sapiens

<400> SEQUENCE: 669
aagggaggag gagcggaggg gcc                                           23

<210> SEQ ID NO 670
<211> LENGTH: 15
<212> TYPE: RNA
<213> ORGANISM: Homo sapiens

<400> SEQUENCE: 670
gggaggagga gcgga                                                    15

<210> SEQ ID NO 671
<211> LENGTH: 15
<212> TYPE: RNA
<213> ORGANISM: Homo sapiens

<400> SEQUENCE: 671
ggcgcgggga ggugc                                                    15

<210> SEQ ID NO 672
<211> LENGTH: 15
<212> TYPE: RNA
<213> ORGANISM: Homo sapiens

<400> SEQUENCE: 672
ggcgcgggga ggugc                                                    15

<210> SEQ ID NO 673
<211> LENGTH: 21
<212> TYPE: RNA
<213> ORGANISM: Homo sapiens

<400> SEQUENCE: 673
gaggcgaugu ggggauguag a                                             21
```

```
<210> SEQ ID NO 674
<211> LENGTH: 20
<212> TYPE: RNA
<213> ORGANISM: Homo sapiens

<400> SEQUENCE: 674
cccagucuca uuuccucauc                                              20

<210> SEQ ID NO 675
<211> LENGTH: 25
<212> TYPE: RNA
<213> ORGANISM: Homo sapiens

<400> SEQUENCE: 675
uucugggccc gcggcgggcg ugggg                                        25

<210> SEQ ID NO 676
<211> LENGTH: 15
<212> TYPE: RNA
<213> ORGANISM: Homo sapiens

<400> SEQUENCE: 676
cgcggcgggc guggg                                                   15

<210> SEQ ID NO 677
<211> LENGTH: 27
<212> TYPE: RNA
<213> ORGANISM: Homo sapiens

<400> SEQUENCE: 677
uagcagcacg uaaauauugg cguuaag                                      27

<210> SEQ ID NO 678
<211> LENGTH: 15
<212> TYPE: RNA
<213> ORGANISM: Homo sapiens

<400> SEQUENCE: 678
cacguaaaua uuggc                                                   15

<210> SEQ ID NO 679
<211> LENGTH: 30
<212> TYPE: RNA
<213> ORGANISM: Homo sapiens

<400> SEQUENCE: 679
ugaggggcag agagcgagac uuuucuauuu                                   30

<210> SEQ ID NO 680
<211> LENGTH: 15
<212> TYPE: RNA
<213> ORGANISM: Homo sapiens

<400> SEQUENCE: 680
cagagagcga gacuu                                                   15

<210> SEQ ID NO 681
<211> LENGTH: 27
<212> TYPE: RNA
<213> ORGANISM: Homo sapiens

<400> SEQUENCE: 681
aaaccguuac cauuacugag uuuagua                                      27
```

```
<210> SEQ ID NO 682
<211> LENGTH: 15
<212> TYPE: RNA
<213> ORGANISM: Homo sapiens

<400> SEQUENCE: 682
uaccauuacu gaguu                                                    15

<210> SEQ ID NO 683
<211> LENGTH: 25
<212> TYPE: RNA
<213> ORGANISM: Homo sapiens

<400> SEQUENCE: 683
aggaagcccu ggaggggcug gaggu                                         25

<210> SEQ ID NO 684
<211> LENGTH: 15
<212> TYPE: RNA
<213> ORGANISM: Homo sapiens

<400> SEQUENCE: 684
aggaagagga ggaag                                                    15
```

PROSTATE CANCER DETECTION KIT OR DEVICE, AND DETECTION METHOD

TECHNICAL FIELD

The present invention relates to a kit or a device for the detection of prostate cancer, comprising a nucleic acid capable of specifically binding to a particular miRNA, which is used for examining the presence or absence of prostate cancer in a subject, and a method for detecting prostate cancer, comprising measuring an expression level of the miRNA using the nucleic acid.

BACKGROUND ART

The prostate is an organ that produces a component of the semen in males, and is positioned underneath the urinary bladder and in front of the rectum. Prostate cancer is a disease caused by the disorganized and repeated proliferation of cells of this prostate. According to the 2011 statistics of cancer type specific mortality in Japan disclosed by the Center for Cancer Control and Information Services, National Cancer Center, the number of individuals affected by prostate cancer was 51,534 people. Namely, it is estimated that one out of 14 Japanese males will experience prostate cancer. The number of incidences of this cancer in males takes the 4th place by cancer type. Also, the number of prostate cancer deaths climbed to 10,823 people and takes the 6th place by cancer type in males. It is estimated that one out of 7 American males will experience prostate cancer. Prostate cancer is particularly common in elderly people, and 6 out of 10 men aged 65 or older are diagnosed with prostate cancer (Non-Patent Literature 1). The estimated number of American individuals affected by prostate cancer climbed to 233,000 people in 2014, among which approximately 29,480 people reportedly died (Non-Patent Literature 1).

The progression stages of prostate cancer are specified in Non-Patent Literature 2 and classified into stage I (T1 to T2a/N0/M0), stage II (T2b to T2c/N0/M0), stage III (T3/N0/M0), and stage IV (T4/N0/M0 and N1 and cM1) according to tumor spread (T1a to T1c, T2a to T2c, T3a to T3b, and T4), lymph node metastasis (N0 and N1), distant metastasis (M0 and M1a to M1c), etc.

Since prostate cancer progresses relatively slowly in most cases, its 5-year relative survival rate is almost 100%, indicating one of cancers having the best prognosis (Non-Patent Literature 1). Some of prostate cancer cases, however, progress relatively fast and cause various disorders or symptoms. Prostate cancer found to have distant metastasis at stage 4 exhibits a 5-year relative survival rate as significantly low as 28% (Non-Patent Literature 1).

The treatment of prostate cancer in regular protocols includes surgical treatment, radiotherapy, endocrine therapy (hormone therapy), and palliative treatment which continues follow-up while monitoring a tumor marker PSA without special treatment. Particularly, the treatment of early prostate cancer has some options such as external beam radiotherapy, internal radiotherapy (brachytherapy), radical prostatectomy, and cryosurgery, in addition to palliative treatment (Non-Patent Literature 1).

As described in Non-Patent Literature 1, a test of PSA, a tumor marker in blood, is widely used as a primary test for prostate cancer. Rectal examination or transrectal ultrasonography of the prostate is carried out when the PSA measurement value is high. Biopsy is further carried out as definite diagnosis when a subject is suspected of having prostate cancer. An imaging test such as CT scan, MRI scan, or bone scintigraphy is also conducted when a subject is suspected of having distant metastasis.

The prostate-specific antigen (PSA) is produced by the prostate and contained in the semen, but is also present in blood, albeit slightly. The PSA concentration in blood of ordinary males is usually 4 ng/mL or lower, and a subject is suspected of having prostate cancer when the measurement value exceeds this reference value (Non-Patent Literature 1). The PSA concentration in blood is reportedly useful and widely implemented, for example, because this concentration elevates even in asymptomatic early prostate cancer and correlates with the stages of cancer progression. The American Cancer Society promotes the early detection of prostate cancer and recommends that subjects who desire screening of prostate cancer should undergo the PSA test (Non-Patent Literature 1).

As shown in Patent Literatures 1 to 3, there are reports, albeit at a research stage, on the detection of prostate cancer using the expression levels of microRNAs (miRNAs) or combinations of the expression levels of miRNAs and the expression levels of additional markers in biological samples including blood.

Patent Literature 1 discloses a method for detecting prostate cancer as well as Wilms tumor and COPD using hsa-miR-760, hsa-miR-920, hsa-miR-887-3p, hsa-miR-486-3p, hsa-miR-663b, hsa-miR-187-5p, hsa-miR-1231, hsa-miR-371a-5p, hsa-miR-575, hsa-miR-615-5p, hsa-miR-711, hsa-miR-939-5p, hsa-miR-1203, hsa-miR-1225-3p, hsa-miR-1225-5p, hsa-miR-1915-5p and the like in blood.

Patent Literature 2 discloses a method for detecting prostate cancer, etc., comprising isolating a vesicle from blood using EpCam and using a miRNA such as hsa-miR-92b-5p contained in the vesicle, for the detection.

Patent Literature 3 has reported that prostate cancer is determined by combining the expression level of PCA3 gene with the expression level of miR-141.

CITATION LIST

Patent Literature

Patent Literature 1: European Patent Application Publication No. 2341145
Patent Literature 2: International Publication No. WO 2013/022995
Patent Literature 3: International Publication No. WO 2010/062706

Non-Patent Literature

Non-Patent Literature 1: American Cancer Society "Prostate Cancer", 2013, p. 5, 14 to 26, 32 to 54, and 68 to 70
Non-Patent Literature 2: Sobin, L. et al., "TNM Classification of Malignant Tumours, the 7th edition", 2010, p. 230 to 234
Non-Patent Literature 3: Wolf, A M. et al., 2010, A Cancer Journal for Clinicians, Vol. 60 (2), p. 70-98
Non-Patent Literature 4: Mitchell P S. et al., 2008, Proceedings of the National Academy of Sciences of the United States of America, Vol. 105 (30), p. 10513-10518

SUMMARY OF INVENTION

Technical Problem

An object of the present invention is to find a novel tumor marker for prostate cancer and to provide a method that can effectively detect prostate cancer using a nucleic acid capable of specifically binding to the marker. The PSA test is widely used as a tumor marker test for prostate cancer. The PSA test is, however, known that 15% of males having a PSA concentration in blood corresponding to the reference value 4 ng/mL or lower are confirmed to be prostate cancer-positive as a result of biopsy. On the other hand, it is also known that the PSA concentration in blood elevates in males having benign prostatic hyperplasia or prostatitis and in ordinary elderly men, leading to a high probability of false positives even in the absence of cancer (Non-Patent Literature 1). Furthermore, the false detection of a cancer other than prostate cancer also leads to false positives. Such a high probability of false positives in the PSA test leads to overdiagnosis and overtreatment, and various aftereffects ascribable to the unnecessary treatment of prostate cancer has been viewed as problems in recent years (Non-Patent Literature 3). According to the large-scale research using 5000 or more recruited subjects (Non-Patent Literature 3), the specific performance of the PSA test showed the sensitivity as low as 20.5% for the overall prostate cancer cases and the sensitivity of merely 51% even limited for highly malignant prostate cancer cases, suggesting that the tumor marker measurement is less significant as a preoperative test.

As described below, there are reports, albeit at a research stage, on the determination of prostate cancer using the expression levels of microRNAs (miRNAs) in biological samples including blood, none of which, however, have yet been brought into practical use.

Patent Literature 1 discloses a method for detecting prostate cancer as well as Wilms tumor and COPD using hsa-miR-760, hsa-miR-920, hsa-miR-887-3p, hsa-miR-486-3p, hsa-miR-663b, hsa-miR-187-5p, hsa-miR-1231, hsa-miR-371a-5p, hsa-miR-575, hsa-miR-615-5p, hsa-miR-711, hsa-miR-939-5p, hsa-miR-1203, hsa-miR-1225-3p, hsa-miR-1225-5p, hsa-miR-1915-5p and the like in blood. Patent Literature 1 describes many miRNAs, whereas this literature lacks a direct statement showing that these miRNA markers are markers for prostate cancer, and includes insufficient evidence for the usefulness of the miRNA markers as prostate cancer markers.

Patent Literature 2 discloses a method for detecting prostate cancer, etc., comprising isolating a vesicle from blood using EpCam and using a miRNA such as hsa-miR-92b-5p contained in the vesicle, for the detection. This literature, however, is less reliable because the miRNA marker was not reproducibly validated in an independent sample group and the literature has no mention about a threshold for detecting prostate cancer.

Patent Literature 3 specifically states that prostate cancer can be determined with 100% sensitivity and specificity by combining the expression levels of miR-141 and PCA3. This literature, however, does not state that prostate cancer can be determined conveniently and highly accurately using a single marker. In fact, Non-Patent Literature 4 is cited in Patent Literature 3. Non-Patent Literature 4 has reported the determination of prostate cancer using miR-141 in serum and states that the accuracy of the determination is 60% sensitivity when the specificity is 100%. In addition, a sample that is subjected to the PCA3 test currently used generally is urine, particularly urine after digital rectal examination. On the other hand, the sample that is subjected to the determination of prostate cancer using miR-141 is blood (serum) as mentioned above. Thus, for obtaining highly sensitive and specific results by combining them, it is necessary to collect two samples.

Solution to Problem

The present inventors have conducted diligent studies to attain the object and consequently completed the present invention by finding several genes usable as markers for the detection of prostate cancer from blood, which can be collected with limited invasiveness, and finding that prostate cancer can be significantly detected by using nucleic acids capable of specifically binding to any of these markers.

SUMMARY OF INVENTION

Specifically, the present invention has the following features:

(1) A kit for the detection of prostate cancer, comprising a nucleic acid capable of specifically binding to at least one or more polynucleotide(s) selected from the group consisting of prostate cancer markers miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

(2) The kit according to (1), wherein miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other prostate cancer markers miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

(5) The kit according to (4), wherein miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, any variant thereof, any derivative thereof, or any fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other prostate cancer markers miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

(8) The kit according to (7), wherein miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c-1-3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR-486-5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two or more nucleic acids capable of specifically binding to at least two or more polynucleotides, respectively, selected from all of the prostate cancer markers according to (1) or (2).

(11) A device for the detection of prostate cancer, comprising a nucleic acid capable of specifically binding to at least one or more polynucleotide(s) selected from the group consisting of prostate cancer markers miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-5p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

(12) The device according to (11), wherein miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

(13) The device according to (11) or (12), wherein the nucleic acid is a polynucleotide selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s) selected from the group consisting of other prostate cancer markers miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564, and miR-671-5p.

(15) The device according to (14), wherein miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other prostate cancer markers miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

(18) The device according to (17), wherein miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c-1-3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR-486-5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the prostate cancer markers according to (11) or (12).

(23) A method for detecting prostate cancer, comprising measuring an expression level of a target nucleic acid in a sample from a subject using a kit according to any one of (1) to (10) or a device according to any one of (11) to (22), and evaluating in vitro whether or not the subject has prostate cancer using the measured expression level and a control expression level in a sample from a healthy subject measured in the same way as above.

(24) The method according to (23), wherein the subject is a human.

(25) The method according to (23) or (24), wherein the sample is blood, serum, or plasma.

Definition of Term

The terms used in the present specification are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

In the present specification, the term "polynucleotide" is used for a nucleic acid including all of RNA, DNA, and RNA/DNA (chimera). The DNA includes all of cDNA, genomic DNA, and synthetic DNA. The RNA includes all of total RNA, mRNA, rRNA, miRNA, siRNA, snoRNA, snRNA, non-coding RNA and synthetic RNA. In the present specification, the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). In the present specification, the "non-natural sequence" is intended to be used in a broad sense and includes, for example, a sequence containing substitution, deletion, insertion, and/or addition of one or more nucleotide(s) (i.e., a variant sequence) and a sequence containing one or more modified nucleotide(s) (i.e., a modified sequence), which are different from the natural sequence. In the present specification, the polynucleotide is used interchangeably with a nucleic acid.

In the present specification, the term "fragment" is a polynucleotide having a nucleotide sequence having a consecutive portion of a polynucleotide and desirably has a length of 15 or more nucleotides, preferably 17 or more nucleotides, more preferably 19 or more nucleotides.

In the present specification, the term "gene" is intended to include not only RNA and double-stranded DNA but also each single-stranded DNA such as a plus strand (or a sense strand) or a complementary strand (or an antisense strand) constituting the duplex. The gene is not particularly limited by its length.

Thus, in the present specification, the "gene" includes all of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 684 or a nucleotide sequence derived from the nucleotide sequence by the replacement of u with t. The "gene" is not particularly limited by its functional region and can contain, for example, an expression control region, a coding region, an exon, or an intron. The "gene" may be contained in a cell or may exist alone after being released into the outside of a cell. Alternatively, the "gene" may be in a state enclosed in a vesicle called exosome.

In the present specification, the term "exosome" is a vesicle that is capsulated with a lipid bilayer and secreted from a cell. The exosome is derived from a multivesicular endosome and may incorporate a biomaterial such as a "gene" (e.g., RNA or DNA) or a protein when released into an extracellular environment. The exosome is known to be contained in a body fluid such as blood, serum, plasma, or lymph.

In the present specification, the term "transcript" refers to an RNA synthesized with the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a poly A sequence, including an expression regulatory region, a coding region, an exon, or an intron.

In the present specification, the term "microRNA (miRNA)" is intended to mean a 15- to 25-nucleotide non-coding RNA that is transcribed as an RNA precursor having a hairpin-like structure, cleaved by a dsRNA-cleaving enzyme which has RNase III cleavage activity, integrated into a protein complex called RISC, and involved in the suppression of translation of mRNA, unless otherwise specified. The term "miRNA" used in the present specification includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 684. The term "miRNA" used in the present specification may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

In the present specification, the term "probe" includes a polynucleotide that is used for specifically detecting an RNA resulting from the expression of a gene or a polynucleotide derived from the RNA, and/or a polynucleotide complementary thereto.

In the present specification, the term "primer" includes a polynucleotide that specifically recognizes and amplifies an RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship based on A:T (U) and G:C base pairs with the full-length sequence of a polynucleotide consisting of a nucleotide sequence defined by any of SEQ ID NOs: 1 to 684 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

In the present specification, the term "stringent conditions" refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

In the present specification, the term "Tm value" means a temperature at which the double-stranded moiety of a polynucleotide is denatured into single strands so that the double strands and the single strands exist at a ratio of 1:1.

In the present specification, the term "variant" means, in the case of a nucleic acid, a natural variant attributed to polymorphism, mutation, or the like; a variant containing the deletion, substitution, addition, or insertion of 1, 2, or 3 or more nucleotides in a nucleotide sequence represented by any of SEQ ID NOs: 1 to 684 or a nucleotide sequence derived from the nucleotide sequence by the replacement of u with t, or a partial sequence thereof; a variant containing the deletion, substitution, addition, or insertion of 1 or 2 or more nucleotides in a nucleotide sequence of a premature miRNA of a sequence represented by any of SEQ ID NOs: 1 to 684 or a nucleotide sequence derived from the nucleotide sequence by the replacement of u with t, or a partial sequence thereof; a variant that exhibits % identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

In the present specification, the term "several" means an integer of approximately 10, 9, 8, 7, 6, 5, 4, 3, or 2.

In the present specification, the variant can be prepared by use of a well-known technique such as site-directed mutagenesis or PCR-based mutagenesis.

In the present specification, the term "percent (%) identity" can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

In the present specification, the term "derivative" is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

In the present specification, the "nucleic acid" capable of specifically binding to a polynucleotide selected from the prostate cancer marker miRNAs described above is a synthesized or prepared nucleic acid and specifically includes a "nucleic acid probe" or a "primer". The "nucleic acid" is utilized directly or indirectly for detecting the presence or absence of prostate cancer in a subject, for diagnosing the severity, the degree of amelioration, or the therapeutic sensitivity of prostate cancer, or for screening for a candidate substance useful in the prevention, amelioration, or treatment of prostate cancer. The "nucleic acid" includes a nucleotide, an oligonucleotide, and a polynucleotide capable of specifically recognizing and binding to a transcript represented by any of SEQ ID NOs: 1 to 684, or a synthetic cDNA nucleic acid thereof in vivo, particularly, in a sample such as a body fluid (e.g., blood or urine), in relation to the development of prostate cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used in the present specification is interchangeable with the term "examination", "measurement", or "detection or decision support". In the present specification, the term "evaluation" is meant to include diagnosis or evaluation support on the basis of examination results or measurement results.

The term "subject" used in the present specification means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used in the present specification refers to a probability at which a more extreme statistic than that actually calculated from data under a null hypothesis is observed in a statistical test. Thus, smaller "P" or "P value" means more significant difference between subjects to be compared.

In the present specification, the term "sensitivity" means a value of (the number of true positives)/(the number of true positives+the number of false negatives). High sensitivity allows prostate cancer to be detected early, leading to the complete resection of cancer sites and reduction in the rate of recurrence.

In the present specification, the term "specificity" means a value of (the number of true negatives)/(the number of true negatives+the number of false positives). High specificity prevents needless extra examination for healthy subjects misjudged as being prostate cancer patients, leading to reduction in burden on patients and reduction in medical expense.

In the present specification, the term "accuracy" means a value of (the number of true positives+the number of true negatives)/(the total number of cases). The accuracy indicates the ratio of samples that were correctly identified to all samples and serves as a primary index to evaluate detection performance.

In the present specification, the "sample" that is subjected to determination, detection, or diagnosis refers to a tissue and a biological material in which the expression of the gene of the present invention varies as prostate cancer develops, prostate cancer progresses, and therapeutic effects on prostate cancer are exerted. Specifically, the "sample" refers to a prostatic tissue, a periprostatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4443 gene" or "hsa-miR-4443" used in the present specification includes the hsa-miR-4443 gene (miRBase Accession No. MIMAT0018961) described in SEQ ID NO: 1, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 188) having a hairpin-like structure is known as a precursor of "hsa-miR-4443".

The term "hsa-miR-1908-5p gene" or "hsa-miR-1908-5p" used in the present specification includes the hsa-miR-1908-5p gene (miRBase Accession No. MIMAT0007881) described in SEQ ID NO: 2, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 189) having a hairpin-like structure is known as a precursor of "hsa-miR-1908-5p".

The term "hsa-miR-4257 gene" or "hsa-miR-4257" used in the present specification includes the hsa-miR-4257 gene (miRBase Accession No. MIMAT0016878) described in SEQ ID NO: 3, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 190) having a hairpin-like structure is known as a precursor of "hsa-miR-4257".

The term "hsa-miR-3197 gene" or "hsa-miR-3197" used in the present specification includes the hsa-miR-3197 gene (miRBase Accession No. MIMAT0015082) described in SEQ ID NO: 4, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 191) having a hairpin-like structure is known as a precursor of "hsa-miR-3197".

The term "hsa-miR-3188 gene" or "hsa-miR-3188" used in the present specification includes the hsa-miR-3188 gene (miRBase Accession No. MIMAT0015070) described in SEQ ID NO: 5, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 192) having a hairpin-like structure is known as a precursor of "hsa-miR-3188".

The term "hsa-miR-4649-5p gene" or "hsa-miR-4649-5p" used in the present specification includes the hsa-miR-4649-5p gene (miRBase Accession No. MIMAT0019711) described in SEQ ID NO: 6, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 193) having a hairpin-like structure is known as a precursor of "hsa-miR-4649-5p".

The term "hsa-miR-1343-3p gene" or "hsa-miR-1343-3p" used in the present specification includes the hsa-miR-1343-3p gene (miRBase Accession No. MIMAT0019776) described in SEQ ID NO: 7, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 194) having a hairpin-like structure is known as a precursor of "hsa-miR-1343-3p".

The term "hsa-miR-6861-5p gene" or "hsa-miR-6861-5p" used in the present specification includes the hsa-miR-6861-5p gene (miRBase Accession No. MIMAT0027623) described in SEQ ID NO: 8, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 195) having a hairpin-like structure is known as a precursor of "hsa-miR-6861-5p".

The term "hsa-miR-1343-5p gene" or "hsa-miR-1343-5p" used in the present specification includes the hsa-miR-1343-5p gene (miRBase Accession No. MIMAT0027038) described in SEQ ID NO: 9, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 194) having a hairpin-like structure is known as a precursor of "hsa-miR-1343-5p".

The term "hsa-miR-642b-3p gene" or "hsa-miR-642b-3p" used in the present specification includes the hsa-miR-642b-3p gene (miRBase Accession No. MIMAT0018444) described in SEQ ID NO: 10, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 196) having a hairpin-like structure is known as a precursor of "hsa-miR-642b-3p".

The term "hsa-miR-6741-5p gene" or "hsa-miR-6741-5p" used in the present specification includes the hsa-miR-6741-5p gene (miRBase Accession No. MIMAT0027383) described in SEQ ID NO: 11, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 197) having a hairpin-like structure is known as a precursor of "hsa-miR-6741-5p".

The term "hsa-miR-4745-5p gene" or "hsa-miR-4745-5p" used in the present specification includes the hsa-miR-4745-5p gene (miRBase Accession No. MIMAT0019878) described in SEQ ID NO: 12, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 198) having a hairpin-like structure is known as a precursor of "hsa-miR-4745-5p".

The term "hsa-miR-6826-5p gene" or "hsa-miR-6826-5p" used in the present specification includes the hsa-miR-6826-5p gene (miRBase Accession No. MIMAT0027552) described in SEQ ID NO: 13, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 199) having a hairpin-like structure is known as a precursor of "hsa-miR-6826-5p".

The term "hsa-miR-3663-3p gene" or "hsa-miR-3663-3p" used in the present specification includes the hsa-miR-3663-3p gene (miRBase Accession No. MIMAT0018085) described in SEQ ID NO: 14, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 200) having a hairpin-like structure is known as a precursor of "hsa-miR-3663-3p".

The term "hsa-miR-3131 gene" or "hsa-miR-3131" used in the present specification includes the hsa-miR-3131 gene (miRBase Accession No. MIMAT0014996) described in SEQ ID NO: 15, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 201) having a hairpin-like structure is known as a precursor of "hsa-miR-3131".

The term "hsa-miR-92a-2-5p gene" or "hsa-miR-92a-2-5p" used in the present specification includes the hsa-miR-92a-2-5p gene (miRBase Accession No. MIMAT0004508) described in SEQ ID NO: 16, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 202) having a hairpin-like structure is known as a precursor of "hsa-miR-92a-2-5p".

The term "hsa-miR-4258 gene" or "hsa-miR-4258" used in the present specification includes the hsa-miR-4258 gene (miRBase Accession No. MIMAT0016879) described in SEQ ID NO: 17, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 203) having a hairpin-like structure is known as a precursor of "hsa-miR-4258".

The term "hsa-miR-4448 gene" or "hsa-miR-4448" used in the present specification includes the hsa-miR-4448 gene (miRBase Accession No. MIMAT0018967) described in SEQ ID NO: 18, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 204) having a hairpin-like structure is known as a precursor of "hsa-miR-4448".

The term "hsa-miR-6125 gene" or "hsa-miR-6125" used in the present specification includes the hsa-miR-6125 gene (miRBase Accession No. MIMAT0024598) described in SEQ ID NO: 19, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 205) having a hairpin-like structure is known as a precursor of "hsa-miR-6125".

The term "hsa-miR-6880-5p gene" or "hsa-miR-6880-5p" used in the present specification includes the hsa-miR-6880-5p gene (miRBase Accession No. MIMAT0027660) described in SEQ ID NO: 20, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 206) having a hairpin-like structure is known as a precursor of "hsa-miR-6880-5p".

The term "hsa-miR-6132 gene" or "hsa-miR-6132" used in the present specification includes the hsa-miR-6132 gene (miRBase Accession No. MIMAT0024616) described in SEQ ID NO: 21, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 207) having a hairpin-like structure is known as a precursor of "hsa-miR-6132".

The term "hsa-miR-4467 gene" or "hsa-miR-4467" used in the present specification includes the hsa-miR-4467 gene (miRBase Accession No. MIMAT0018994) described in SEQ ID NO: 22, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 208) having a hairpin-like structure is known as a precursor of "hsa-miR-4467".

The term "hsa-miR-6749-5p gene" or "hsa-miR-6749-5p" used in the present specification includes the hsa-miR-6749-5p gene (miRBase Accession No. MIMAT0027398) described in SEQ ID NO: 23, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 209) having a hairpin-like structure is known as a precursor of "hsa-miR-6749-5p".

The term "hsa-miR-2392 gene" or "hsa-miR-2392" used in the present specification includes the hsa-miR-2392 gene (miRBase Accession No. MIMAT0019043) described in SEQ ID NO: 24, a homolog or an ortholog of a different organism species, and the like. The hsa-miR-2392 gene can be obtained by a method described in Jima D D et al., 2010, Blood, Vol. 116, e118-e127. Also, "hsa-mir-2392" (miRBase Accession No. MI0016870, SEQ ID NO: 210) having a hairpin-like structure is known as a precursor of "hsa-miR-2392".

The term "hsa-miR-1273g-3p gene" or "hsa-miR-1273g-3p" used in the present specification includes the hsa-miR-1273g-3p gene (miRBase Accession No. MIMAT0022742) described in SEQ ID NO: 25, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 211) having a hairpin-like structure is known as a precursor of "hsa-miR-1273g-3p".

The term "hsa-miR-4746-3p gene" or "hsa-miR-4746-3p" used in the present specification includes the hsa-miR-4746-3p gene (miRBase Accession No. MIMAT0019881) described in SEQ ID NO: 26, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 212) having a hairpin-like structure is known as a precursor of "hsa-miR-4746-3p".

The term "hsa-miR-1914-3p gene" or "hsa-miR-1914-3p" used in the present specification includes the hsa-miR-1914-3p gene (miRBase Accession No. MIMAT0007890) described in SEQ ID NO: 27, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 213) having a hairpin-like structure is known as a precursor of "hsa-miR-1914-3p".

The term "hsa-miR-7845-5p gene" or "hsa-miR-7845-5p" used in the present specification includes the hsa-miR-7845-5p gene (miRBase Accession No. MIMAT0030420) described in SEQ ID NO: 28, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 214) having a hairpin-like structure is known as a precursor of "hsa-miR-7845-5p".

The term "hsa-miR-6726-5p gene" or "hsa-miR-6726-5p" used in the present specification includes the hsa-miR-6726-5p gene (miRBase Accession No. MIMAT0027353) described in SEQ ID NO: 29, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 215) having a hairpin-like structure is known as a precursor of "hsa-miR-6726-5p".

The term "hsa-miR-128-2-5p gene" or "hsa-miR-128-2-5p" used in the present specification includes the hsa-miR-128-2-5p gene (miRBase Accession No. MIMAT0031095) described in SEQ ID NO: 30, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No.

MI0000727, SEQ ID NO: 216) having a hairpin-like structure is known as a precursor of "hsa-miR-128-2-5p".

The term "hsa-miR-4651 gene" or "hsa-miR-4651" used in the present specification includes the hsa-miR-4651 gene (miRBase Accession No. MIMAT0019715) described in SEQ ID NO: 31, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 217) having a hairpin-like structure is known as a precursor of "hsa-miR-4651".

The term "hsa-miR-6765-3p gene" or "hsa-miR-6765-3p" used in the present specification includes the hsa-miR-6765-3p gene (miRBase Accession No. MIMAT0027431) described in SEQ ID NO: 32, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 218) having a hairpin-like structure is known as a precursor of "hsa-miR-6765-3p".

The term "hsa-miR-3185 gene" or "hsa-miR-3185" used in the present specification includes the hsa-miR-3185 gene (miRBase Accession No. MIMAT0015065) described in SEQ ID NO: 33, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 219) having a hairpin-like structure is known as a precursor of "hsa-miR-3185".

The term "hsa-miR-4792 gene" or "hsa-miR-4792" used in the present specification includes the hsa-miR-4792 gene (miRBase Accession No. MIMAT0019964) described in SEQ ID NO: 34, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 220) having a hairpin-like structure is known as a precursor of "hsa-miR-4792".

The term "hsa-miR-6887-5p gene" or "hsa-miR-6887-5p" used in the present specification includes the hsa-miR-6887-5p gene (miRBase Accession No. MIMAT0027674) described in SEQ ID NO: 35, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 221) having a hairpin-like structure is known as a precursor of "hsa-miR-6887-5p".

The term "hsa-miR-5572 gene" or "hsa-miR-5572" used in the present specification includes the hsa-miR-5572 gene (miRBase Accession No. MIMAT0022260) described in SEQ ID NO: 36, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 222) having a hairpin-like structure is known as a precursor of "hsa-miR-5572".

The term "hsa-miR-3619-3p gene" or "hsa-miR-3619-3p" used in the present specification includes the hsa-miR-3619-3p gene (miRBase Accession No. MIMAT0019219) described in SEQ ID NO: 37, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 223) having a hairpin-like structure is known as a precursor of "hsa-miR-3619-3p".

The term "hsa-miR-6780b-5p gene" or "hsa-miR-6780b-5p" used in the present specification includes the hsa-miR-6780b-5p gene (miRBase Accession No. MIMAT0027572) described in SEQ ID NO: 38, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 224) having a hairpin-like structure is known as a precursor of "hsa-miR-6780b-5p".

The term "hsa-miR-4707-5p gene" or "hsa-miR-4707-5p" used in the present specification includes the hsa-miR-4707-5p gene (miRBase Accession No. MIMAT0019807) described in SEQ ID NO: 39, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 225) having a hairpin-like structure is known as a precursor of "hsa-miR-4707-5p".

The term "hsa-miR-8063 gene" or "hsa-miR-8063" used in the present specification includes the hsa-miR-8063 gene (miRBase Accession No. MIMAT0030990) described in SEQ ID NO: 40, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 226) having a hairpin-like structure is known as a precursor of "hsa-miR-8063".

The term "hsa-miR-4454 gene" or "hsa-miR-4454" used in the present specification includes the hsa-miR-4454 gene (miRBase Accession No. MIMAT0018976) described in SEQ ID NO: 41, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 227) having a hairpin-like structure is known as a precursor of "hsa-miR-4454".

The term "hsa-miR-4525 gene" or "hsa-miR-4525" used in the present specification includes the hsa-miR-4525 gene (miRBase Accession No. MIMAT0019064) described in SEQ ID NO: 42, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 228) having a hairpin-like structure is known as a precursor of "hsa-miR-4525".

The term "hsa-miR-7975 gene" or "hsa-miR-7975" used in the present specification includes the hsa-miR-7975 gene (miRBase Accession No. MIMAT0031178) described in SEQ ID NO: 43, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 229) having a hairpin-like structure is known as a precursor of "hsa-miR-7975".

The term "hsa-miR-744-5p gene" or "hsa-miR-744-5p" used in the present specification includes the hsa-miR-744-

5p gene (miRBase Accession No. MIMAT0004945) described in SEQ ID NO: 44, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 230) having a hairpin-like structure is known as a precursor of "hsa-miR-744-5p".

The term "hsa-miR-3135b gene" or "hsa-miR-3135b" used in the present specification includes the hsa-miR-3135b gene (miRBase Accession No. MIMAT0018985) described in SEQ ID NO: 45, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 231) having a hairpin-like structure is known as a precursor of "hsa-miR-3135b".

The term "hsa-miR-4648 gene" or "hsa-miR-4648" used in the present specification includes the hsa-miR-4648 gene (miRBase Accession No. MIMAT0019710) described in SEQ ID NO: 46, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 232) having a hairpin-like structure is known as a precursor of "hsa-miR-4648".

The term "hsa-miR-6816-5p gene" or "hsa-miR-6816-5p" used in the present specification includes the hsa-miR-6816-5p gene (miRBase Accession No. MIMAT0027532) described in SEQ ID NO: 47, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 233) having a hairpin-like structure is known as a precursor of "hsa-miR-6816-5p".

The term "hsa-miR-4741 gene" or "hsa-miR-4741" used in the present specification includes the hsa-miR-4741 gene (miRBase Accession No. MIMAT0019871) described in SEQ ID NO: 48, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 234) having a hairpin-like structure is known as a precursor of "hsa-miR-4741".

The term "hsa-miR-7150 gene" or "hsa-miR-7150" used in the present specification includes the hsa-miR-7150 gene (miRBase Accession No. MIMAT0028211) described in SEQ ID NO: 49, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 235) having a hairpin-like structure is known as a precursor of "hsa-miR-7150".

The term "hsa-miR-6791-5p gene" or "hsa-miR-6791-5p" used in the present specification includes the hsa-miR-6791-5p gene (miRBase Accession No. MIMAT0027482) described in SEQ ID NO: 50, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 236) having a hairpin-like structure is known as a precursor of "hsa-miR-6791-5p".

The term "hsa-miR-1247-3p gene" or "hsa-miR-1247-3p" used in the present specification includes the hsa-miR-1247-3p gene (miRBase Accession No. MIMAT0022721) described in SEQ ID NO: 51, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 237) having a hairpin-like structure is known as a precursor of "hsa-miR-1247-3p".

The term "hsa-miR-7977 gene" or "hsa-miR-7977" used in the present specification includes the hsa-miR-7977 gene (miRBase Accession No. MIMAT0031180) described in SEQ ID NO: 52, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 238) having a hairpin-like structure is known as a precursor of "hsa-miR-7977".

The term "hsa-miR-4497 gene" or "hsa-miR-4497" used in the present specification includes the hsa-miR-4497 gene (miRBase Accession No. MIMAT0019032) described in SEQ ID NO: 53, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 239) having a hairpin-like structure is known as a precursor of "hsa-miR-4497".

The term "hsa-miR-6090 gene" or "hsa-miR-6090" used in the present specification includes the hsa-miR-6090 gene (miRBase Accession No. MIMAT0023715) described in SEQ ID NO: 54, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 240) having a hairpin-like structure is known as a precursor of "hsa-miR-6090".

The term "hsa-miR-6781-5p gene" or "hsa-miR-6781-5p" used in the present specification includes the hsa-miR-6781-5p gene (miRBase Accession No. MIMAT0027462) described in SEQ ID NO: 55, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 241) having a hairpin-like structure is known as a precursor of "hsa-miR-6781-5p".

The term "hsa-miR-6870-5p gene" or "hsa-miR-6870-5p" used in the present specification includes the hsa-miR-6870-5p gene (miRBase Accession No. MIMAT0027640) described in SEQ ID NO: 56, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 242) having a hairpin-like structure is known as a precursor of "hsa-miR-6870-5p".

The term "hsa-miR-6729-5p gene" or "hsa-miR-6729-5p" used in the present specification includes the hsa-miR-6729-5p gene (miRBase Accession No. MIMAT0027359) described in SEQ ID NO: 57, a homolog or an ortholog of a different organism species, and the like. The hsa-miR- 6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 243) having a hairpin-like structure is known as a precursor of "hsa-miR-6729-5p".

The term "hsa-miR-4530 gene" or "hsa-miR-4530" used in the present specification includes the hsa-miR-4530 gene (miRBase Accession No. MIMAT0019069) described in SEQ ID NO: 58, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 244) having a hairpin-like structure is known as a precursor of "hsa-miR-4530".

The term "hsa-miR-7847-3p gene" or "hsa-miR-7847-3p" used in the present specification includes the hsa-miR-7847-3p gene (miRBase Accession No. MIMAT0030422) described in SEQ ID NO: 59, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 245) having a hairpin-like structure is known as a precursor of "hsa-miR-7847-3p".

The term "hsa-miR-6825-5p gene" or "hsa-miR-6825-5p" used in the present specification includes the hsa-miR-6825-5p gene (miRBase Accession No. MIMAT0027550) described in SEQ ID NO: 60, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 246) having a hairpin-like structure is known as a precursor of "hsa-miR-6825-5p".

The term "hsa-miR-4674 gene" or "hsa-miR-4674" used in the present specification includes the hsa-miR-4674 gene (miRBase Accession No. MIMAT0019756) described in SEQ ID NO: 61, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 247) having a hairpin-like structure is known as a precursor of "hsa-miR-4674".

The term "hsa-miR-3917 gene" or "hsa-miR-3917" used in the present specification includes the hsa-miR-3917 gene (miRBase Accession No. MIMAT0018191) described in SEQ ID NO: 62, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 248) having a hairpin-like structure is known as a precursor of "hsa-miR-3917".

The term "hsa-miR-4707-3p gene" or "hsa-miR-4707-3p" used in the present specification includes the hsa-miR-4707-3p gene (miRBase Accession No. MIMAT0019808) described in SEQ ID NO: 63, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 225) having a hairpin-like structure is known as a precursor of "hsa-miR-4707-3p".

The term "hsa-miR-6885-5p gene" or "hsa-miR-6885-5p" used in the present specification includes the hsa-miR-6885-5p gene (miRBase Accession No. MIMAT0027670) described in SEQ ID NO: 64, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 249) having a hairpin-like structure is known as a precursor of "hsa-miR-6885-5p".

The term "hsa-miR-6722-3p gene" or "hsa-miR-6722-3p" used in the present specification includes the hsa-miR-6722-3p gene (miRBase Accession No. MIMAT0025854) described in SEQ ID NO: 65, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 250) having a hairpin-like structure is known as a precursor of "hsa-miR-6722-3p".

The term "hsa-miR-4516 gene" or "hsa-miR-4516" used in the present specification includes the hsa-miR-4516 gene (miRBase Accession No. MIMAT0019053) described in SEQ ID NO: 66, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 251) having a hairpin-like structure is known as a precursor of "hsa-miR-4516".

The term "hsa-miR-6757-5p gene" or "hsa-miR-6757-5p" used in the present specification includes the hsa-miR-6757-5p gene (miRBase Accession No. MIMAT0027414) described in SEQ ID NO: 67, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 252) having a hairpin-like structure is known as a precursor of "hsa-miR-6757-5p".

The term "hsa-miR-6840-3p gene" or "hsa-miR-6840-3p" used in the present specification includes the hsa-miR-6840-3p gene (miRBase Accession No. MIMAT0027583) described in SEQ ID NO: 68, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 253) having a hairpin-like structure is known as a precursor of "hsa-miR-6840-3p".

The term "hsa-miR-5195-3p gene" or "hsa-miR-5195-3p" used in the present specification includes the hsa-miR-5195-3p gene (miRBase Accession No. MIMAT0021127) described in SEQ ID NO: 69, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 254) having a hairpin-like structure is known as a precursor of "hsa-miR-5195-3p".

The term "hsa-miR-6756-5p gene" or "hsa-miR-6756-5p" used in the present specification includes the hsa-miR-6756-5p gene (miRBase Accession No. MIMAT0027412) described in SEQ ID NO: 70, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 255) having a hairpin-like structure is known as a precursor of "hsa-miR-6756-5p".

The term "hsa-miR-6800-5p gene" or "hsa-miR-6800-5p" used in the present specification includes the hsa-miR-6800-5p gene (miRBase Accession No. MIMAT0027500) described in SEQ ID NO: 71, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 256) having a hairpin-like structure is known as a precursor of "hsa-miR-6800-5p".

The term "hsa-miR-6727-5p gene" or "hsa-miR-6727-5p" used in the present specification includes the hsa-miR-6727-5p gene (miRBase Accession No. MIMAT0027355) described in SEQ ID NO: 72, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 257) having a hairpin-like structure is known as a precursor of "hsa-miR-6727-5p".

The term "hsa-miR-6126 gene" or "hsa-miR-6126" used in the present specification includes the hsa-miR-6126 gene (miRBase Accession No. MIMAT0024599) described in SEQ ID NO: 73, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 258) having a hairpin-like structure is known as a precursor of "hsa-miR-6126".

The term "hsa-miR-6872-3p gene" or "hsa-miR-6872-3p" used in the present specification includes the hsa-miR-6872-3p gene (miRBase Accession No. MIMAT0027645) described in SEQ ID NO: 74, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 259) having a hairpin-like structure is known as a precursor of "hsa-miR-6872-3p".

The term "hsa-miR-4446-3p gene" or "hsa-miR-4446-3p" used in the present specification includes the hsa-miR-4446-3p gene (miRBase Accession No. MIMAT0018965) described in SEQ ID NO: 75, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 260) having a hairpin-like structure is known as a precursor of "hsa-miR-4446-3p".

The term "hsa-miR-1268a gene" or "hsa-miR-1268a" used in the present specification includes the hsa-miR-1268a gene (miRBase Accession No. MIMAT0005922) described in SEQ ID NO: 76, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 261) having a hairpin-like structure is known as a precursor of "hsa-miR-1268a".

The term "hsa-miR-1908-3p gene" or "hsa-miR-1908-3p" used in the present specification includes the hsa-miR-1908-3p gene (miRBase Accession No. MIMAT0026916) described in SEQ ID NO: 77, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 189) having a hairpin-like structure is known as a precursor of "hsa-miR-1908-3p".

The term "hsa-miR-3679-5p gene" or "hsa-miR-3679-5p" used in the present specification includes the hsa-miR-3679-5p gene (miRBase Accession No. MIMAT0018104) described in SEQ ID NO: 78, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 262) having a hairpin-like structure is known as a precursor of "hsa-miR-3679-5p".

The term "hsa-miR-4534 gene" or "hsa-miR-4534" used in the present specification includes the hsa-miR-4534 gene (miRBase Accession No. MIMAT0019073) described in SEQ ID NO: 79, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 263) having a hairpin-like structure is known as a precursor of "hsa-miR-4534".

The term "hsa-miR-4675 gene" or "hsa-miR-4675" used in the present specification includes the hsa-miR-4675 gene (miRBase Accession No. MIMAT0019757) described in SEQ ID NO: 80, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 264) having a hairpin-like structure is known as a precursor of "hsa-miR-4675".

The term "hsa-miR-7108-5p gene" or "hsa-miR-7108-5p" used in the present specification includes the hsa-miR-7108-5p gene (miRBase Accession No. MIMAT0028113) described in SEQ ID NO: 81, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 265) having a hairpin-like structure is known as a precursor of "hsa-miR-7108-5p".

The term "hsa-miR-6799-5p gene" or "hsa-miR-6799-5p" used in the present specification includes the hsa-miR-6799-5p gene (miRBase Accession No. MIMAT0027498) described in SEQ ID NO: 82, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 266) having a hairpin-like structure is known as a precursor of "hsa-miR-6799-5p".

The term "hsa-miR-4695-5p gene" or "hsa-miR-4695-5p" used in the present specification includes the hsa-miR-4695-5p gene (miRBase Accession No. MIMAT0019788) described in SEQ ID NO: 83, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 267) having a hairpin-like structure is known as a precursor of "hsa-miR-4695-5p".

The term "hsa-miR-3178 gene" or "hsa-miR-3178" used in the present specification includes the hsa-miR-3178 gene (miRBase Accession No. MIMAT0015055) described in SEQ ID NO: 84, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 268) having a hairpin-like structure is known as a precursor of "hsa-miR-3178".

The term "hsa-miR-5090 gene" or "hsa-miR-5090" used in the present specification includes the hsa-miR-5090 gene (miRBase Accession No. MIMAT0021082) described in SEQ ID NO: 85, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 269) having a hairpin-like structure is known as a precursor of "hsa-miR-5090".

The term "hsa-miR-3180 gene" or "hsa-miR-3180" used in the present specification includes the hsa-miR-3180 gene (miRBase Accession No. MIMAT0018178) described in SEQ ID NO: 86, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 270 and 271) having a hairpin-like structure is known as precursors of "hsa-miR-3180".

The term "hsa-miR-1237-5p gene" or "hsa-miR-1237-5p" used in the present specification includes the hsa-miR-1237-5p gene (miRBase Accession No. MIMAT0022946) described in SEQ ID NO: 87, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 272) having a hairpin-like structure is known as a precursor of "hsa-miR-1237-5p".

The term "hsa-miR-4758-5p gene" or "hsa-miR-4758-5p" used in the present specification includes the hsa-miR-4758-5p gene (miRBase Accession No. MIMAT0019903) described in SEQ ID NO: 88, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 273) having a hairpin-like structure is known as a precursor of "hsa-miR-4758-5p".

The term "hsa-miR-3184-5p gene" or "hsa-miR-3184-5p" used in the present specification includes the hsa-miR-3184-5p gene (miRBase Accession No. MIMAT0015064) described in SEQ ID NO: 89, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 274) having a hairpin-like structure is known as a precursor of "hsa-miR-3184-5p".

The term "hsa-miR-4286 gene" or "hsa-miR-4286" used in the present specification includes the hsa-miR-4286 gene (miRBase Accession No. MIMAT0016916) described in SEQ ID NO: 90, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 275) having a hairpin-like structure is known as a precursor of "hsa-miR-4286".

The term "hsa-miR-6784-5p gene" or "hsa-miR-6784-5p" used in the present specification includes the hsa-miR-6784-5p gene (miRBase Accession No. MIMAT0027468) described in SEQ ID NO: 91, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 276) having a hairpin-like structure is known as a precursor of "hsa-miR-6784-5p".

The term "hsa-miR-6768-5p gene" or "hsa-miR-6768-5p" used in the present specification includes the hsa-miR-6768-5p gene (miRBase Accession No. MIMAT0027436) described in SEQ ID NO: 92, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. MI0022613, SEQ ID NO: 277) having a hairpin-like structure is known as a precursor of "hsa-miR-6768-5p".

The term "hsa-miR-6785-5p gene" or "hsa-miR-6785-5p" used in the present specification includes the hsa-miR-6785-5p gene (miRBase Accession No. MIMAT0027470) described in SEQ ID NO: 93, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 278) having a hairpin-like structure is known as a precursor of "hsa-miR-6785-5p".

The term "hsa-miR-4706 gene" or "hsa-miR-4706" used in the present specification includes the hsa-miR-4706 gene (miRBase Accession No. MIMAT0019806) described in SEQ ID NO: 94, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 279) having a hairpin-like structure is known as a precursor of "hsa-miR-4706".

The term "hsa-miR-711 gene" or "hsa-miR-711" used in the present specification includes the hsa-miR-711 gene (miRBase Accession No. MIMAT0012734) described in SEQ ID NO: 95, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 280) having a hairpin-like structure is known as a precursor of "hsa-miR-711".

The term "hsa-miR-1260a gene" or "hsa-miR-1260a" used in the present specification includes the hsa-miR-1260a gene (miRBase Accession No. MIMAT0005911) described in SEQ ID NO: 96, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 281) having a hairpin-like structure is known as a precursor of "hsa-miR-1260a".

The term "hsa-miR-6746-5p gene" or "hsa-miR-6746-5p" used in the present specification includes the hsa-miR-6746-5p gene (miRBase Accession No. MIMAT0027392) described in SEQ ID NO: 97, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 282) having a hairpin-like structure is known as a precursor of "hsa-miR-6746-5p".

The term "hsa-miR-6089 gene" or "hsa-miR-6089" used in the present specification includes the hsa-miR-6089 gene (miRBase Accession No. MIMAT0023714) described in SEQ ID NO: 98, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 283 and 284) having a hairpin-like structure are known as precursors of "hsa-miR-6089".

The term "hsa-miR-6821-5p gene" or "hsa-miR-6821-5p" used in the present specification includes the hsa-miR-6821-5p gene (miRBase Accession No. MIMAT0027542) described in SEQ ID NO: 99, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 285) having a hairpin-like structure is known as a precursor of "hsa-miR-6821-5p".

The term "hsa-miR-4667-5p gene" or "hsa-miR-4667-5p" used in the present specification includes the hsa-miR-4667-5p gene (miRBase Accession No. MIMAT0019743) described in SEQ ID NO: 100, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 286) having a hairpin-like structure is known as a precursor of "hsa-miR-4667-5p".

The term "hsa-miR-8069 gene" or "hsa-miR-8069" used in the present specification includes the hsa-miR-8069 gene (miRBase Accession No. MIMAT0030996) described in SEQ ID NO: 101, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 287) having a hairpin-like structure is known as a precursor of "hsa-miR-8069".

The term "hsa-miR-4726-5p gene" or "hsa-miR-4726-5p" used in the present specification includes the hsa-miR-4726-5p gene (miRBase Accession No. MIMAT0019845) described in SEQ ID NO: 102, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 288) having a hairpin-like structure is known as a precursor of "hsa-miR-4726-5p".

The term "hsa-miR-6124 gene" or "hsa-miR-6124" used in the present specification includes the hsa-miR-6124 gene (miRBase Accession No. MIMAT0024597) described in SEQ ID NO: 103, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 289) having a hairpin-like structure is known as a precursor of "hsa-miR-6124".

The term "hsa-miR-4532 gene" or "hsa-miR-4532" used in the present specification includes the hsa-miR-4532 gene (miRBase Accession No. MIMAT0019071) described in SEQ ID NO: 104, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 290) having a hairpin-like structure is known as a precursor of "hsa-miR-4532".

The term "hsa-miR-4486 gene" or "hsa-miR-4486" used in the present specification includes the hsa-miR-4486 gene (miRBase Accession No. MIMAT0019020) described in SEQ ID NO: 105, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 291) having a hairpin-like structure is known as a precursor of "hsa-miR-4486".

The term "hsa-miR-4728-5p gene" or "hsa-miR-4728-5p" used in the present specification includes the hsa-miR-4728-5p gene (miRBase Accession No. MIMAT0019849) described in SEQ ID NO: 106, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 292) having a hairpin-like structure is known as a precursor of "hsa-miR-4728-5p".

The term "hsa-miR-4508 gene" or "hsa-miR-4508" used in the present specification includes the hsa-miR-4508 gene (miRBase Accession No. MIMAT0019045) described in SEQ ID NO: 107, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 293) having a hairpin-like structure is known as a precursor of "hsa-miR-4508".

The term "hsa-miR-128-1-5p gene" or "hsa-miR-128-1-5p" used in the present specification includes the hsa-miR-128-1-5p gene (miRBase Accession No. MIMAT0026477) described in SEQ ID NO: 108, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 294) having a hairpin-like structure is known as a precursor of "hsa-miR-128-1-5p".

The term "hsa-miR-4513 gene" or "hsa-miR-4513" used in the present specification includes the hsa-miR-4513 gene (miRBase Accession No. MIMAT0019050) described in SEQ ID NO: 109, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 295) having a hairpin-like structure is known as a precursor of "hsa-miR-4513".

The term "hsa-miR-6795-5p gene" or "hsa-miR-6795-5p" used in the present specification includes the hsa-miR-6795-5p gene (miRBase Accession No. MIMAT0027490) described in SEQ ID NO: 110, a homolog or an ortholog of a different organism species, and the like. The hsa-miR-6795-5p gene can be obtained by a method described in Ladewig E et al., 2012, Genome Res, Vol. 22, p. 1634-1645.

Also, "hsa-mir-6795" (miRBase Accession No. MI0022640, SEQ ID NO: 296) having a hairpin-like structure is known as a precursor of "hsa-miR-6795-5p".

The term "hsa-miR-4689 gene" or "hsa-miR-4689" used in the present specification includes the hsa-miR-4689 gene (miRBase Accession No. MIMAT0019778) described in SEQ ID NO: 111, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 297) having a hairpin-like structure is known as a precursor of "hsa-miR-4689".

The term "hsa-miR-6763-5p gene" or "hsa-miR-6763-5p" used in the present specification includes the hsa-miR-6763-5p gene (miRBase Accession No. MIMAT0027426) described in SEQ ID NO: 112, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 298) having a hairpin-like structure is known as a precursor of "hsa-miR-6763-5p".

The term "hsa-miR-8072 gene" or "hsa-miR-8072" used in the present specification includes the hsa-miR-8072 gene (miRBase Accession No. MIMAT0030999) described in SEQ ID NO: 113, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 299) having a hairpin-like structure is known as a precursor of "hsa-miR-8072".

The term "hsa-miR-6765-5p gene" or "hsa-miR-6765-5p" used in the present specification includes the hsa-miR-6765-5p gene (miRBase Accession No. MIMAT0027430) described in SEQ ID NO: 114, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 218) having a hairpin-like structure is known as a precursor of "hsa-miR-6765-5p".

The term "hsa-miR-4419b gene" or "hsa-miR-4419b" used in the present specification includes the hsa-miR-4419b gene (miRBase Accession No. MIMAT0019034) described in SEQ ID NO: 115, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 300) having a hairpin-like structure is known as a precursor of "hsa-miR-4419b".

The term "hsa-miR-7641 gene" or "hsa-miR-7641" used in the present specification includes the hsa-miR-7641 gene (miRBase Accession No. MIMAT0029782) described in SEQ ID NO: 116, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 301 and 302) having a hairpin-like structure are known as precursors of "hsa-miR-7641".

The term "hsa-miR-3928-3p gene" or "hsa-miR-3928-3p" used in the present specification includes the hsa-miR-3928-3p gene (miRBase Accession No. MIMAT0018205) described in SEQ ID NO: 117, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438, SEQ ID NO: 303) having a hairpin-like structure is known as a precursor of "hsa-miR-3928-3p".

The term "hsa-miR-1227-5p gene" or "hsa-miR-1227-5p" used in the present specification includes the hsa-miR-1227-5p gene (miRBase Accession No. MIMAT0022941) described in SEQ ID NO: 118, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 304) having a hairpin-like structure is known as a precursor of "hsa-miR-1227-5p"

The term "hsa-miR-4492 gene" or "hsa-miR-4492" used in the present specification includes the hsa-miR-4492 gene (miRBase Accession No. MIMAT0019027) described in SEQ ID NO: 119, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 305) having a hairpin-like structure is known as a precursor of "hsa-miR-4492".

The term "hsa-miR-296-3p gene" or "hsa-miR-296-3p" used in the present specification includes the hsa-miR-296-3p gene (miRBase Accession No. MIMAT0004679) described in SEQ ID NO: 120, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 306) having a hairpin-like structure is known as a precursor of "hsa-miR-296-3p".

The term "hsa-miR-6769a-5p gene" or "hsa-miR-6769a-5p" used in the present specification includes the hsa-miR-6769a-5p gene (miRBase Accession No. MIMAT0027438) described in SEQ ID NO: 121, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 307) having a hairpin-like structure is known as a precursor of "hsa-miR-6769a-5p".

The term "hsa-miR-6889-5p gene" or "hsa-miR-6889-5p" used in the present specification includes the hsa-miR-6889-5p gene (miRBase Accession No. MIMAT0027678) described in SEQ ID NO: 122, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 308) having a hairpin-like structure is known as a precursor of "hsa-miR-6889-5p".

The term "hsa-miR-4632-5p gene" or "hsa-miR-4632-5p" used in the present specification includes the hsa-miR-4632-5p gene (miRBase Accession No. MIMAT0022977) described in SEQ ID NO: 123, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 309) having a hairpin-like structure is known as a precursor of "hsa-miR-4632-5p".

The term "hsa-miR-4505 gene" or "hsa-miR-4505" used in the present specification includes the hsa-miR-4505 gene (miRBase Accession No. MIMAT0019041) described in SEQ ID NO: 124, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 310) having a hairpin-like structure is known as a precursor of "hsa-miR-4505".

The term "hsa-miR-3154 gene" or "hsa-miR-3154" used in the present specification includes the hsa-miR-3154 gene (miRBase Accession No. MIMAT0015028) described in SEQ ID NO: 125, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 311) having a hairpin-like structure is known as a precursor of "hsa-miR-3154".

The term "hsa-miR-3648 gene" or "hsa-miR-3648" used in the present specification includes the hsa-miR-3648 gene (miRBase Accession No. MIMAT0018068) described in SEQ ID NO: 126, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 312) having a hairpin-like structure is known as a precursor of "hsa-miR-3648".

The term "hsa-miR-4442 gene" or "hsa-miR-4442" used in the present specification includes the hsa-miR-4442 gene (miRBase Accession No. MIMAT0018960) described in SEQ ID NO: 127, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 313) having a hairpin-like structure is known as a precursor of "hsa-miR-4442".

The term "hsa-miR-3141 gene" or "hsa-miR-3141" used in the present specification includes the hsa-miR-3141 gene (miRBase Accession No. MIMAT0015010) described in SEQ ID NO: 128, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 314) having a hairpin-like structure is known as a precursor of "hsa-miR-3141".

The term "hsa-miR-7113-3p gene" or "hsa-miR-7113-3p" used in the present specification includes the hsa-miR-7113-3p gene (miRBase Accession No. MIMAT0028124) described in SEQ ID NO: 129, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 315) having a hairpin-like structure is known as a precursor of "hsa-miR-7113-3p".

The term "hsa-miR-6819-5p gene" or "hsa-miR-6819-5p" used in the present specification includes the hsa-miR-6819-5p gene (miRBase Accession No. MIMAT0027538) described in SEQ ID NO: 130, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 316) having a hairpin-like structure is known as a precursor of "hsa-miR-6819-5p".

The term "hsa-miR-3195 gene" or "hsa-miR-3195" used in the present specification includes the hsa-miR-3195 gene (miRBase Accession No. MIMAT0015079) described in SEQ ID NO: 131, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 317) having a hairpin-like structure is known as a precursor of "hsa-miR-3195".

The term "hsa-miR-1199-5p gene" or "hsa-miR-1199-5p" used in the present specification includes the hsa-miR-1199-5p gene (miRBase Accession No. MIMAT0031119) described in SEQ ID NO: 132, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 318) having a hairpin-like structure is known as a precursor of "hsa-miR-1199-5p".

The term "hsa-miR-6738-5p gene" or "hsa-miR-6738-5p" used in the present specification includes the hsa-miR-6738-5p gene (miRBase Accession No. MIMAT0027377) described in SEQ ID NO: 133, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 319) having a hairpin-like structure is known as a precursor of "hsa-miR-6738-5p".

The term "hsa-miR-4656 gene" or "hsa-miR-4656" used in the present specification includes the hsa-miR-4656 gene (miRBase Accession No. MIMAT0019723) described in SEQ ID NO: 134, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 320) having a hairpin-like structure is known as a precursor of "hsa-miR-4656".

The term "hsa-miR-6820-5p gene" or "hsa-miR-6820-5p" used in the present specification includes the hsa-miR-6820-5p gene (miRBase Accession No. MIMAT0027540) described in SEQ ID NO: 135, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 321) having a hairpin-like structure is known as a precursor of "hsa-miR-6820-5p".

The term "hsa-miR-615-5p gene" or "hsa-miR-615-5p" used in the present specification includes the hsa-miR-615-5p gene (miRBase Accession No. MIMAT0004804) described in SEQ ID NO: 136, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 322) having a hairpin-like structure is known as a precursor of "hsa-miR-615-5p".

The term "hsa-miR-486-3p gene" or "hsa-miR-486-3p" used in the present specification includes the hsa-miR-486-3p gene (miRBase Accession No. MIMAT0004762) described in SEQ ID NO: 137, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NO: 323 and 324) having a hairpin-like structure are known as precursors of "hsa-miR-486-3p".

The term "hsa-miR-1225-3p gene" or "hsa-miR-1225-3p" used in the present specification includes the hsa-miR-1225-3p gene (miRBase Accession No. MIMAT0005573) described in SEQ ID NO: 138, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 325) having a hairpin-like structure is known as a precursor of "hsa-miR-1225-3p".

The term "hsa-miR-760 gene" or "hsa-miR-760" used in the present specification includes the hsa-miR-760 gene (miRBase Accession No. MIMAT0004957) described in SEQ ID NO: 139, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 326) having a hairpin-like structure is known as a precursor of "hsa-miR-760".

The term "hsa-miR-187-5p gene" or "hsa-miR-187-5p" used in the present specification includes the hsa-miR-187-5p gene (miRBase Accession No. MIMAT0004561) described in SEQ ID NO: 140, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 327) having a hairpin-like structure is known as a precursor of "hsa-miR-187-5p".

The term "hsa-miR-1203 gene" or "hsa-miR-1203" used in the present specification includes the hsa-miR-1203 gene (miRBase Accession No. MIMAT0005866) described in SEQ ID NO: 141, a homolog or an ortholog of a different organism species, and the like. The hsa-miR-1203 gene can be obtained by a method described in Marton S et al., 2008, Leukemia, Vol. 22, p. 330-338. Also, "hsa-mir-1203" (miRBase Accession No. MI0006335, SEQ ID NO: 328) having a hairpin-like structure is known as a precursor of "hsa-miR-1203".

The term "hsa-miR-7110-5p gene" or "hsa-miR-7110-5p" used in the present specification includes the hsa-miR-7110-5p gene (miRBase Accession No. MIMAT0028117) described in SEQ ID NO: 142, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 329) having a hairpin-like structure is known as a precursor of "hsa-miR-7110-5p".

The term "hsa-miR-371a-5p gene" or "hsa-miR-371a-5p" used in the present specification includes the hsa-miR-371a-5p gene (miRBase Accession No. MIMAT0004687) described in SEQ ID NO: 143, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 330) having a hairpin-like structure is known as a precursor of "hsa-miR-371a-5p".

The term "hsa-miR-939-5p gene" or "hsa-miR-939-5p" used in the present specification includes the hsa-miR-939-5p gene (miRBase Accession No. MIMAT0004982) described in SEQ ID NO: 144, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 331) having a hairpin-like structure is known as a precursor of "hsa-miR-939-5p".

The term "hsa-miR-575 gene" or "hsa-miR-575" used in the present specification includes the hsa-miR-575 gene (miRBase Accession No. MIMAT0003240) described in SEQ ID NO: 145, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 332) having a hairpin-like structure is known as a precursor of "hsa-miR-575".

The term "hsa-miR-92b-5p gene" or "hsa-miR-92b-5p" used in the present specification includes the hsa-miR-92b-5p gene (miRBase Accession No. MIMAT0004792) described in SEQ ID NO: 146, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 333) having a hairpin-like structure is known as a precursor of "hsa-miR-92b-5p".

The term "hsa-miR-887-3p gene" or "hsa-miR-887-3p" used in the present specification includes the hsa-miR-887-3p gene (miRBase Accession No. MIMAT0004951) described in SEQ ID NO: 147, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 334) having a hairpin-like structure is known as a precursor of "hsa-miR-887-3p".

The term "hsa-miR-920 gene" or "hsa-miR-920" used in the present specification includes the hsa-miR-920 gene (miRBase Accession No. MIMAT0004970) described in SEQ ID NO: 148, a homolog or an ortholog of a different organism species, and the like. The hsa-miR-920 gene can be obtained by a method described in Novotny G W et al., 2007, Int J Androl, Vol. 30, p. 316-326. Also, "hsa-miR-920" (miRBase Accession No. MI0005712, SEQ ID NO: 335) having a hairpin-like structure is known as a precursor of "hsa-miR-920".

The term "hsa-miR-1915-5p gene" or "hsa-miR-1915-5p" used in the present specification includes the hsa-miR-1915-5p gene (miRBase Accession No. MIMAT0007891) described in SEQ ID NO: 149, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 336) having a hairpin-like structure is known as a precursor of "hsa-miR-1915-5p".

The term "hsa-miR-1231 gene" or "hsa-miR-1231" used in the present specification includes the hsa-miR-1231 gene (miRBase Accession No. MIMAT0005586) described in SEQ ID NO: 150, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231"

(miRBase Accession No. MI0006321, SEQ ID NO: 337) having a hairpin-like structure is known as a precursor of "hsa-miR-1231".

The term "hsa-miR-663b gene" or "hsa-miR-663b" used in the present specification includes the hsa-miR-663b gene (miRBase Accession No. MIMAT0005867) described in SEQ ID NO: 151, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 338) having a hairpin-like structure is known as a precursor of "hsa-miR-663b".

The term "hsa-miR-1225-5p gene" or "hsa-miR-1225-5p" used in the present specification includes the hsa-miR-1225-5p gene (miRBase Accession No. MIMAT0005572) described in SEQ ID NO: 152, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 325) having a hairpin-like structure is known as a precursor of "hsa-miR-1225-5p".

The term "hsa-miR-4763-3p gene" or "hsa-miR-4763-3p" used in the present specification includes the hsa-miR-4763-3p gene (miRBase Accession No. MIMAT0019913) described in SEQ ID NO: 153, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 339) having a hairpin-like structure is known as a precursor of "hsa-miR-4763-3p".

The term "hsa-miR-3656 gene" or "hsa-miR-3656" used in the present specification includes the hsa-miR-3656 gene (miRBase Accession No. MIMAT0018076) described in SEQ ID NO: 154, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 340) having a hairpin-like structure is known as a precursor of "hsa-miR-3656".

The term "hsa-miR-4488 gene" or "hsa-miR-4488" used in the present specification includes the hsa-miR-4488 gene (miRBase Accession No. MIMAT0019022) described in SEQ ID NO: 155, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 341) having a hairpin-like structure is known as a precursor of "hsa-miR-4488".

The term "hsa-miR-125a-3p gene" or "hsa-miR-125a-3p" used in the present specification includes the hsa-miR-125a-3p gene (miRBase Accession No. MIMAT0004602) described in SEQ ID NO: 156, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 342) having a hairpin-like structure is known as a precursor of "hsa-miR-125a-3p".

The term "hsa-miR-1469 gene" or "hsa-miR-1469" used in the present specification includes the hsa-miR-1469 gene (miRBase Accession No. MIMAT0007347) described in SEQ ID NO: 157, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 343) having a hairpin-like structure is known as a precursor of "hsa-miR-1469".

The term "hsa-miR-1228-5p gene" or "hsa-miR-1228-5p" used in the present specification includes the hsa-miR-1228-5p gene (miRBase Accession No. MIMAT0005582) described in SEQ ID NO: 158, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 344) having a hairpin-like structure is known as a precursor of "hsa-miR-1228-5p".

The term "hsa-miR-6798-5p gene" or "hsa-miR-6798-5p" used in the present specification includes the hsa-miR-6798-5p gene (miRBase Accession No. MIMAT0027496) described in SEQ ID NO: 159, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 345) having a hairpin-like structure is known as a precursor of "hsa-miR-6798-5p".

The term "hsa-miR-1268b gene" or "hsa-miR-1268b" used in the present specification includes the hsa-miR-1268b gene (miRBase Accession No. MIMAT0018925) described in SEQ ID NO: 160, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 346) having a hairpin-like structure is known as a precursor of "hsa-miR-1268b".

The term "hsa-miR-6732-5p gene" or "hsa-miR-6732-5p" used in the present specification includes the hsa-miR-6732-5p gene (miRBase Accession No. MIMAT0027365) described in SEQ ID NO: 161, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 347) having a hairpin-like structure is known as a precursor of "hsa-miR-6732-5p".

The term "hsa-miR-1915-3p gene" or "hsa-miR-1915-3p" used in the present specification includes the hsa-miR-1915-3p gene (miRBase Accession No. MIMAT0007892) described in SEQ ID NO: 162, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 336) having a hairpin-like structure is known as a precursor of "hsa-miR-1915-3p".

The term "hsa-miR-4433b-3p gene" or "hsa-miR-4433b-3p" used in the present specification includes the hsa-miR-4433b-3p gene (miRBase Accession No. MIMAT0030414) described in SEQ ID NO: 163, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 348) having a hairpin-like structure is known as a precursor of "hsa-miR-4433b-3p".

The term "hsa-miR-1207-5p gene" or "hsa-miR-1207-5p" used in the present specification includes the hsa-miR-1207-5p gene (miRBase Accession No. MIMAT0005871) described in SEQ ID NO: 164, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. MI0006340, SEQ ID NO: 349) having a hairpin-like structure is known as a precursor of "hsa-miR-1207-5p".

The term "hsa-miR-4433-3p gene" or "hsa-miR-4433-3p" used in the present specification includes the hsa-miR-4433-3p gene (miRBase Accession No. MIMAT0018949) described in SEQ ID NO: 165, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 350) having a hairpin-like structure is known as a precursor of "hsa-miR-4433-3p".

The term "hsa-miR-6879-5p gene" or "hsa-miR-6879-5p" used in the present specification includes the hsa-miR-6879-5p gene (miRBase Accession No. MIMAT0027658) described in SEQ ID NO: 166, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 351) having a hairpin-like structure is known as a precursor of "hsa-miR-6879-5p".

The term "hsa-miR-4417 gene" or "hsa-miR-4417" used in the present specification includes the hsa-miR-4417 gene (miRBase Accession No. MIMAT0018929) described in SEQ ID NO: 167, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 352) having a hairpin-like structure is known as a precursor of "hsa-miR-4417".

The term "hsa-miR-30c-1-3p gene" or "hsa-miR-30c-1-3p" used in the present specification includes the hsa-miR-30c-1-3p gene (miRBase Accession No. MIMAT0004674) described in SEQ ID NO: 168, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 353) having a hairpin-like structure is known as a precursor of "hsa-miR-30c-1-3p".

The term "hsa-miR-4638-5p gene" or "hsa-miR-4638-5p" used in the present specification includes the hsa-miR-4638-5p gene (miRBase Accession No. MIMAT0019695) described in SEQ ID NO: 169, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 354) having a hairpin-like structure is known as a precursor of "hsa-miR-4638-5p".

The term "hsa-miR-6088 gene" or "hsa-miR-6088" used in the present specification includes the hsa-miR-6088 gene (miRBase Accession No. MIMAT0023713) described in SEQ ID NO: 170, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 355) having a hairpin-like structure is known as a precursor of "hsa-miR-6088".

The term "hsa-miR-4270 gene" or "hsa-miR-4270" used in the present specification includes the hsa-miR-4270 gene (miRBase Accession No. MIMAT0016900) described in SEQ ID NO: 171, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 356) having a hairpin-like structure is known as a precursor of "hsa-miR-4270".

The term "hsa-miR-6782-5p gene" or "hsa-miR-6782-5p" used in the present specification includes the hsa-miR-6782-5p gene (miRBase Accession No. MIMAT0027464) described in SEQ ID NO: 172, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 357) having a hairpin-like structure is known as a precursor of "hsa-miR-6782-5p".

The term "hsa-miR-665 gene" or "hsa-miR-665" used in the present specification includes the hsa-miR-665 gene (miRBase Accession No. MIMAT0004952) described in SEQ ID NO: 173, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 358) having a hairpin-like structure is known as a precursor of "hsa-miR-665".

The term "hsa-miR-486-5p gene" or "hsa-miR-486-5p" used in the present specification includes the hsa-miR-486-5p gene (miRBase Accession No. MIMAT0002177) described in SEQ ID NO: 174, a homolog or an ortholog of a different organism species, and the like. The hsa-miR-486-5p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 323 and 324) having a hairpin-like structure are known as precursors of "hsa-miR-486-5p".

The term "hsa-miR-4655-5p gene" or "hsa-miR-4655-5p" used in the present specification includes the hsa-miR-4655-5p gene (miRBase Accession No. MIMAT0019721) described in SEQ ID NO: 175, a homolog or an ortholog of a different organism species, and the like. The hsa-miR-4655-5p gene can be obtained by a method described in Persson H et al., 2011, Cancer Res, Vol. 71, p. 78-86. Also, "hsa-mir-4655" (miRBase Accession No. MI0017283, SEQ ID NO: 359) having a hairpin-like structure is known as a precursor of "hsa-miR-4655-5p".

The term "hsa-miR-1275 gene" or "hsa-miR-1275" used in the present specification includes the hsa-miR-1275 gene (miRBase Accession No. MIMAT0005929) described in SEQ ID NO: 176, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 360) having a hairpin-like structure is known as a precursor of "hsa-miR-1275".

The term "hsa-miR-6806-5p gene" or "hsa-miR-6806-5p" used in the present specification includes the hsa-miR-6806-5p gene (miRBase Accession No. MIMAT0027512)

described in SEQ ID NO: 177, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 361) having a hairpin-like structure is known as a precursor of "hsa-miR-6806-5p".

The term "hsa-miR-614 gene" or "hsa-miR-614" used in the present specification includes the hsa-miR-614 gene (miRBase Accession No. MIMAT0003282) described in SEQ ID NO: 178, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 362) having a hairpin-like structure is known as a precursor of "hsa-miR-614".

The term "hsa-miR-3937 gene" or "hsa-miR-3937" used in the present specification includes the hsa-miR-3937 gene (miRBase Accession No. MIMAT0018352) described in SEQ ID NO: 179, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 363) having a hairpin-like structure is known as a precursor of "hsa-miR-3937".

The term "hsa-miR-6752-5p gene" or "hsa-miR-6752-5p" used in the present specification includes the hsa-miR-6752-5p gene (miRBase Accession No. MIMAT0027404) described in SEQ ID NO: 180, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 364) having a hairpin-like structure is known as a precursor of "hsa-miR-6752-5p".

The term "hsa-miR-6771-5p gene" or "hsa-miR-6771-5p" used in the present specification includes the hsa-miR-6771-5p gene (miRBase Accession No. MIMAT0027442) described in SEQ ID NO: 181, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771" (miRBase Accession No. MI0022616, SEQ ID NO: 365) having a hairpin-like structure is known as a precursor of "hsa-miR-6771-5p".

The term "hsa-miR-4450 gene" or "hsa-miR-4450" used in the present specification includes the hsa-miR-4450 gene (miRBase Accession No. MIMAT0018971) described in SEQ ID NO: 182, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795, SEQ ID NO: 366) having a hairpin-like structure is known as a precursor of "hsa-miR-4450".

The term "hsa-miR-211-3p gene" or "hsa-miR-211-3p" used in the present specification includes the hsa-miR-211-3p gene (miRBase Accession No. MIMAT0022694) described in SEQ ID NO: 183, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 367) having a hairpin-like structure is known as a precursor of "hsa-miR-211-3p".

The term "hsa-miR-663a gene" or "hsa-miR-663a" used in the present specification includes the hsa-miR-663a gene (miRBase Accession No. MIMAT0003326) described in SEQ ID NO: 184, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 368) having a hairpin-like structure is known as a precursor of "hsa-miR-663a".

The term "hsa-miR-6842-5p gene" or "hsa-miR-6842-5p" used in the present specification includes the hsa-miR-6842-5p gene (miRBase Accession No. MIMAT0027586) described in SEQ ID NO: 185, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 369) having a hairpin-like structure is known as a precursor of "hsa-miR-6842-5p".

The term "hsa-miR-7114-5p gene" or "hsa-miR-7114-5p" used in the present specification includes the hsa-miR-7114-5p gene (miRBase Accession No. MIMAT0028125) described in SEQ ID NO: 186, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 370) having a hairpin-like structure is known as a precursor of "hsa-miR-7114-5p".

The term "hsa-miR-6779-5p gene" or "hsa-miR-6779-5p" used in the present specification includes the hsa-miR-6779-5p gene (miRBase Accession No. MIMAT0027458) described in SEQ ID NO: 187, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 371) having a hairpin-like structure is known as a precursor of "hsa-miR-6779-5p".

The term "hsa-miR-204-3p gene" or "hsa-miR-204-3p" used in the present specification includes the hsa-miR-204-3p gene (miRBase Accession No. MIMAT0022693) described in SEQ ID NO: 580, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 612) having a hairpin-like structure is known as a precursor of "hsa-miR-204-3p".

The term "hsa-miR-642a-3p gene" or "hsa-miR-642a-3p" used in the present specification includes the hsa-miR-642a-3p gene (miRBase Accession No. MIMAT0020924) described in SEQ ID NO: 581, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 613) having a hairpin-like structure is known as a precursor of "hsa-miR-642a-3p".

The term "hsa-miR-762 gene" or "hsa-miR-762" used in the present specification includes the hsa-miR-762 gene (miRBase Accession No. MIMAT0010313) described in SEQ ID NO: 582, a homolog or an ortholog of a different organism species, and the like. The hsa-miR-762 gene can be obtained by a method described in Berezikov E et al., 2006, Genome Res, Vol. 16, p. 1289-1298. Also, "hsa-mir- 762" (miRBase Accession No. MI0003892, SEQ ID NO: 614) having a hairpin-like structure is known as a precursor of "hsa-miR-762".

The term "hsa-miR-1202 gene" or "hsa-miR-1202" used in the present specification includes the hsa-miR-1202 gene (miRBase Accession No. MIMAT0005865) described in SEQ ID NO: 583, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 615) having a hairpin-like structure is known as a precursor of "hsa-miR-1202".

The term "hsa-miR-3162-5p gene" or "hsa-miR-3162-5p" used in the present specification includes the hsa-miR-3162-5p gene (miRBase Accession No. MIMAT0015036) described in SEQ ID NO: 584, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 616) having a hairpin-like structure is known as a precursor of "hsa-miR-3162-5p".

The term "hsa-miR-3196 gene" or "hsa-miR-3196" used in the present specification includes the hsa-miR-3196 gene (miRBase Accession No. MIMAT0015080) described in SEQ ID NO: 585, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 617) having a hairpin-like structure is known as a precursor of "hsa-miR-3196".

The term "hsa-miR-3622a-5p gene" or "hsa-miR-3622a-5p" used in the present specification includes the hsa-miR-3622a-5p gene (miRBase Accession No. MIMAT0018003) described in SEQ ID NO: 586, a homolog or an ortholog of a different organism species, and the like. The hsa-miR-3622a-5p gene can be obtained by a method described in Witten D et al., 2010, BMC Biol., Vol. 8, p. 58. Also, "hsa-mir-3622a" (miRBase Accession No. MI0016013, SEQ ID NO: 618) having a hairpin-like structure is known as a precursor of "hsa-miR-3622a-5p".

The term "hsa-miR-3665 gene" or "hsa-miR-3665" used in the present specification includes the hsa-miR-3665 gene (miRBase Accession No. MIMAT0018087) described in SEQ ID NO: 587, a homolog or an ortholog of a different organism species, and the like. The hsa-miR-3665 gene can be obtained by a method described in Xie X et al., 2005, Nature, Vol. 434, p. 338-345. Also, "hsa-mir-3665" (miRBase Accession No. MI0016066, SEQ ID NO: 619) having a hairpin-like structure is known as a precursor of "hsa-miR-3665".

The term "hsa-miR-3940-5p gene" or "hsa-miR-3940-5p" used in the present specification includes the hsa-miR-3940-5p gene (miRBase Accession No. MIMAT0019229) described in SEQ ID NO: 588, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 620) having a hairpin-like structure is known as a precursor of "hsa-miR-3940-5p".

The term "hsa-miR-4294 gene" or "hsa-miR-4294" used in the present specification includes the hsa-miR-4294 gene (miRBase Accession No. MIMAT0016849) described in SEQ ID NO: 589, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827, SEQ ID NO: 621) having a hairpin-like structure is known as a precursor of "hsa-miR-4294".

The term "hsa-miR-4466 gene" or "hsa-miR-4466" used in the present specification includes the hsa-miR-4466 gene (miRBase Accession No. MIMAT0018993) described in SEQ ID NO: 590, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 622) having a hairpin-like structure is known as a precursor of "hsa-miR-4466".

The term "hsa-miR-4476 gene" or "hsa-miR-4476" used in the present specification includes the hsa-miR-4476 gene (miRBase Accession No. MIMAT0019003) described in SEQ ID NO: 591, a homolog or an ortholog of a different organism species, and the like. The hsa-miR-4476 gene can be obtained by a method described in Jima D D et al., 2010, Blood, Vol. 116, e118-e127. Also, "hsa-miR-4476" (miRBase Accession No. MI0016828, SEQ ID NO: 623) having a hairpin-like structure is known as a precursor of "hsa-miR-4476".

The term "hsa-miR-4723-5p gene" or "hsa-miR-4723-5p" used in the present specification includes the hsa-miR-4723-5p gene (miRBase Accession No. MIMAT0019838) described in SEQ ID NO: 592, a homolog or an ortholog of a different organism species, and the like. The hsa-miR-4723-5p gene can be obtained by a method described in Persson H et al., 2011, Cancer Res., Vol. 71, p. 78-86. Also, "hsa-mir-4723" (miRBase Accession No. MI0017359, SEQ ID NO: 624) having a hairpin-like structure is known as a precursor of "hsa-miR-4723-5p".

The term "hsa-miR-4725-3p gene" or "hsa-miR-4725-3p" used in the present specification includes the hsa-miR-4725-3p gene (miRBase Accession No. MIMAT0019844) described in SEQ ID NO: 593, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 625) having a hairpin-like structure is known as a precursor of "hsa-miR-4725-3p".

The term "hsa-miR-4730 gene" or "hsa-miR-4730" used in the present specification includes the hsa-miR-4730 gene (miRBase Accession No. MIMAT0019852) described in SEQ ID NO: 594, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 626) having a hairpin-like structure is known as a precursor of "hsa-miR-4730".

The term "hsa-miR-4739 gene" or "hsa-miR-4739" used in the present specification includes the hsa-miR-4739 gene (miRBase Accession No. MIMAT0019868) described in SEQ ID NO: 595, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 627) having a hairpin-like structure is known as a precursor of "hsa-miR-4739".

The term "hsa-miR-4787-5p gene" or "hsa-miR-4787-5p" used in the present specification includes the hsa-miR-4787-5p gene (miRBase Accession No. MIMAT0019956) described in SEQ ID NO: 596, a homolog or an ortholog of a different organism species, and the like. The hsa-miR-4787-5p gene can be obtained by a method described in Persson H et al., 2011, Cancer Res, Vol. 71, p. 78-86. Also, "hsa-mir-4787" (miRBase Accession No. MI0017434, SEQ ID NO: 628) having a hairpin-like structure is known as a precursor of "hsa-miR-4787-5p".

The term "hsa-miR-5787 gene" or "hsa-miR-5787" used in the present specification includes the hsa-miR-5787 gene (miRBase Accession No. MIMAT0023252) described in SEQ ID NO: 597, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 629) having a hairpin-like structure is known as a precursor of "hsa-miR-5787".

The term "hsa-miR-6085 gene" or "hsa-miR-6085" used in the present specification includes the hsa-miR-6085 gene (miRBase Accession No. MIMAT0023710) described in SEQ ID NO: 598, a homolog or an ortholog of a different organism species, and the like. The hsa-miR-6085 gene can be obtained by a method described in Voellenkle C et al., 2012, RNA., Vol. 18, p. 472-484. Also, "hsa-mir-6085" (miRBase Accession No. MI0020362, SEQ ID NO: 630) having a hairpin-like structure is known as a precursor of "hsa-miR-6085".

The term "hsa-miR-6717-5p gene" or "hsa-miR-6717-5p" used in the present specification includes the hsa-miR-6717-5p gene (miRBase Accession No. MIMAT0025846) described in SEQ ID NO: 599, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 631) having a hairpin-like structure is known as a precursor of "hsa-miR-6717-5p".

The term "hsa-miR-6724-5p gene" or "hsa-miR-6724-5p" used in the present specification includes the hsa-miR-6724-5p gene (miRBase Accession No. MIMAT0025856) described in SEQ ID NO: 600, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 632) having a hairpin-like structure is known as a precursor of "hsa-miR-6724-5p".

The term "hsa-miR-6777-5p gene" or "hsa-miR-6777-5p" used in the present specification includes the hsa-miR-6777-5p gene (miRBase Accession No. MIMAT0027454) described in SEQ ID NO: 601, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 633) having a hairpin-like structure is known as a precursor of "hsa-miR-6777-5p".

The term "hsa-miR-6778-5p gene" or "hsa-miR-6778-5p" used in the present specification includes the hsa-miR-6778-5p gene (miRBase Accession No. MIMAT0027456) described in SEQ ID NO: 602, a homolog or an ortholog of a different organism species, and the like. The hsa-miR-6778-5p gene can be obtained by a method described in Ladewig E et al., 2012, Genome Res., Vol. 22, p. 1634-1645. Also, "hsa-mir-6778" (miRBase Accession No. MI0022623, SEQ ID NO: 634) having a hairpin-like structure is known as a precursor of "hsa-miR-6778-5p".

The term "hsa-miR-6787-5p gene" or "hsa-miR-6787-5p" used in the present specification includes the hsa-miR-6787-5p gene (miRBase Accession No. MIMAT0027474) described in SEQ ID NO: 603, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 635) having a hairpin-like structure is known as a precursor of "hsa-miR-6787-5p".

The term "hsa-miR-6789-5p gene" or "hsa-miR-6789-5p" used in the present specification includes the hsa-miR-6789-5p gene (miRBase Accession No. MIMAT0027478) described in SEQ ID NO: 604, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 636) having a hairpin-like structure is known as a precursor of "hsa-miR-6789-5p".

The term "hsa-miR-6845-5p gene" or "hsa-miR-6845-5p" used in the present specification includes the hsa-miR-6845-5p gene (miRBase Accession No. MIMAT0027590) described in SEQ ID NO: 605, a homolog or an ortholog of a different organism species, and the like. The hsa-miR-6845-5p gene can be obtained by a method described in Ladewig E et al., 2012, Genome Res., Vol. 22, p. 1634-1645. Also, "hsa-mir-6845" (miRBase Accession No. MI0022691, SEQ ID NO: 637) having a hairpin-like structure is known as a precursor of "hsa-miR-6845-5p".

The term "hsa-miR-6893-5p gene" or "hsa-miR-6893-5p" used in the present specification includes the hsa-miR-6893-5p gene (miRBase Accession No. MIMAT0027686) described in SEQ ID NO: 606, a homolog or an ortholog of a different organism species, and the like. The hsa-miR-6893-5p gene can be obtained by a method described in Ladewig E et al., 2012, Genome Res., Vol. 22, p. 1634-1645. Also, "hsa-mir-6893" (miRBase Accession No. MI0022740, SEQ ID NO: 638) having a hairpin-like structure is known as a precursor of "hsa-miR-6893-5p".

The term "hsa-miR-16-5p gene" or "hsa-miR-16-5p" used in the present specification includes the hsa-miR-16-5p gene (miRBase Accession No. MIMAT0000069) described in SEQ ID NO: 607, a homolog or an ortholog of a different organism species, and the like. The hsa-miR-16-5p gene can be obtained by a method described in Lagos-Quintana M et al., 2002, Curr Biol., Vol. 12, p. 735-739. Also, "hsa-mir-16-1 and hsa-mir-16-2" (miRBase Accession Nos. MI0000070 and MI0000115, SEQ ID NOs: 639 and 640) having a hairpin-like structure are known as precursors of "hsa-miR-16-5p".

The term "hsa-miR-423-5p gene" or "hsa-miR-423-5p" used in the present specification includes the hsa-miR-423-5p gene (miRBase Accession No. MIMAT0004748) described in SEQ ID NO: 608, a homolog or an ortholog of a different organism species, and the like. The hsa-miR-423-5p gene can be obtained by a method described in Kasashima K et al., 2004, Biochem Biophys Res Commun., Vol. 322, p. 403-410. Also, "hsa-mir-423" (miRBase Accession No. MI0001445, SEQ ID NO: 641) having a hairpin-like structure is known as a precursor of "hsa-miR-423-5p".

The term "hsa-miR-451a gene" or "hsa-miR-451a" used in the present specification includes the hsa-miR-451a gene (miRBase Accession No. MIMAT0001631) described in SEQ ID NO: 609, a homolog or an ortholog of a different organism species, and the like. The hsa-miR-451a gene can be obtained by a method described in Altuvia Y et al., 2005, Nucleic Acids Res., Vol. 33, p. 2697-2706. Also, "hsa-mir-451a" (miRBase Accession No. MI0001729, SEQ ID NO: 642) having a hairpin-like structure is known as a precursor of "hsa-miR-451a".

The term "hsa-miR-564 gene" or "hsa-miR-564" used in the present specification includes the hsa-miR-564 gene (miRBase Accession No. MIMAT0003228) described in SEQ ID NO: 610, a homolog or an ortholog of a different organism species, and the like. The hsa-miR-564 gene can be obtained by a method described in Cummins J M, 2006, Proc Natl Acad Sci, Vol. 103, p. 3687-3692. Also, "hsa-mir-564" (miRBase Accession No. MI0003570, SEQ ID NO: 643) having a hairpin-like structure is known as a precursor of "hsa-miR-564".

The term "hsa-miR-671-5p gene" or "hsa-miR-671-5p" used in the present specification includes the hsa-miR-671-5p gene (miRBase Accession No. MIMAT0003880) described in SEQ ID NO: 611, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 644) having a hairpin-like structure is known as a precursor of "hsa-miR-671-5p".

A mature miRNA may become a variant due to the sequence cleaved shorter or longer by one to several upstream or downstream bases or base substitution when cleaved as the mature miRNA from its RNA precursor that has a hairpin-like structure. This variant is called isomiR (Morin R D. et al., 2008, Genome Res., Vol. 18, p. 610-621). miRBase Release 20 shows the nucleotide sequences represented by SEQ ID NOs: 1 to 187 and 580 to 611 as well as a large number of the nucleotide sequence variants and fragments represented by SEQ ID NOs: 137 to 579 and 645 to 684, called isomiRs. These variants can also be obtained as miRNAs having a nucleotide sequence represented by any of SEQ ID NOs: 1 to 187 and 580 to 611. Specifically, among the variants of polynucleotides consisting of a nucleotide sequence represented by any of SEQ ID NOs: 1, 2, 4, 5, 6, 7, 10, 12, 15, 16, 18, 19, 21, 22, 24, 25, 27, 30, 31, 33, 34, 36, 39, 41, 42, 43, 44, 45, 46, 48, 51, 53, 58, 61, 62, 63, 66, 69, 73, 75, 76, 77, 78, 83, 84, 85, 86, 87, 88, 90, 94, 95, 96, 98, 100, 102, 103, 104, 105, 106, 107, 108, 109, 111, 115, 117, 119, 120, 123, 124, 125, 126, 127, 128, 131, 136, 137, 139, 140, 143, 144, 147, 149, 151, 153, 154, 155, 156, 158, 160, 162, 165, 167, 168, 169, 170, 173, 174, 175, 176, 178, 182, 183, 184, 580, 581, 584, 585, 587, 588, 590, 591, 592, 593, 594, 595, 597, 599, 600, 607, 608, 609 and 611 or a nucleotide sequence derived from the nucleotide sequence by the replacement of u with t according to the present invention, examples of the longest variants registered in miRBase Release 20 include polynucleotides represented by SEQ ID NOs: 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 645, 647, 650, 652, 655, 657, 659, 661, 663, 665, 667, 669, 671, 673, 675, 677, 679, 681 and 683, respectively. Also, among the variants of polynucleotides consisting of a nucleotide sequence represented by any of SEQ ID NOs: 1, 2, 4, 5, 6, 7, 10, 12, 15, 16, 18, 19, 21, 22, 24, 25, 27, 30, 31, 33, 34, 36, 39, 41, 42, 43, 44, 45, 46, 48, 51, 53, 58, 61, 62, 63, 66, 69, 73, 75, 76, 77, 78, 83, 84, 85, 86, 87, 88, 90, 94, 95, 96, 98, 100, 102, 103, 104, 105, 106, 107, 108, 109, 111, 115, 117, 119, 120, 123, 124, 125, 126, 127, 128, 131, 136, 137, 139, 140, 143, 144, 147, 149, 151, 153, 154, 155, 156, 158, 160, 162, 165, 167, 168, 169, 170, 173, 174, 175, 176, 178, 182, 183, 184, 580, 581, 583, 584, 585, 586, 587, 588, 590, 591, 592, 593, 594, 595, 597, 599, 600, 607, 608, 609 and 611 or a nucleotide sequence derived from the nucleotide sequence by the replacement of u with t according to the present invention, examples of the shortest variants registered in miRBase Release 20 include polynucleotides having sequences represented by SEQ ID NOs: 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 646, 648, 649, 651, 653, 654, 656, 658, 660, 662, 664, 666, 668, 670, 672, 674, 676, 678, 680, 682 and 684, respectively. In addition to these variants and fragments, examples thereof include a large number of isomiR polynucleotides of SEQ ID NOs: 1 to 187 and 580 to 611 registered in miRBase. Examples of the polynucleotide comprising a nucleotide sequence represented by any of SEQ ID NOs: 1 to 187 and 580 to 611 include a polynucleotide represented by any of SEQ ID NOs: 188 to 371, and 612 to 644, which are their respective precursors.

The names and miRBase Accession Nos. (registration numbers) of the genes represented by SEQ ID NOs: 1 to 684 are shown in Table 1.

In the present specification, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-4443 | MIMAT0018961 |
| 2 | hsa-miR-1908-5p | MIMAT0007881 |
| 3 | hsa-miR-4257 | MIMAT0016878 |
| 4 | hsa-miR-3197 | MIMAT0015082 |
| 5 | hsa-miR-3188 | MIMAT0015070 |
| 6 | hsa-miR-4649-5p | MIMAT0019711 |
| 7 | hsa-miR-1343-3p | MIMAT0019776 |
| 8 | hsa-miR-6861-5p | MIMAT0027623 |
| 9 | hsa-miR-1343-5p | MIMAT0027038 |
| 10 | hsa-miR-642b-3p | MIMAT0018444 |
| 11 | hsa-miR-6741-5p | MIMAT0027383 |
| 12 | hsa-miR-4745-5p | MIMAT0019878 |
| 13 | hsa-miR-6826-5p | MIMAT0027552 |
| 14 | hsa-miR-3663-3p | MIMAT0018085 |
| 15 | hsa-miR-3131 | MIMAT0014996 |
| 16 | hsa-miR-92a-2-5p | MIMAT0004508 |
| 17 | hsa-miR-4258 | MIMAT0016879 |
| 18 | hsa-miR-4448 | MIMAT0018967 |
| 19 | hsa-miR-6125 | MIMAT0024598 |
| 20 | hsa-miR-6880-5p | MIMAT0027660 |
| 21 | hsa-miR-6132 | MIMAT0024616 |
| 22 | hsa-miR-4467 | MIMAT0018994 |
| 23 | hsa-miR-6749-5p | MIMAT0027398 |

TABLE 1-continued

| SEQ ID NO: | Gene name | miRBase registration No. |
|---|---|---|
| 24 | hsa-miR-2392 | MIMAT0019043 |
| 25 | hsa-miR-1273g-3p | MIMAT0022742 |
| 26 | hsa-miR-4746-3p | MIMAT0019881 |
| 27 | hsa-miR-1914-3p | MIMAT0007890 |
| 28 | hsa-miR-7845-5p | MIMAT0030420 |
| 29 | hsa-miR-6726-5p | MIMAT0027353 |
| 30 | hsa-miR-128-2-5p | MIMAT0031095 |
| 31 | hsa-miR-4651 | MIMAT0019715 |
| 32 | hsa-miR-6765-3p | MIMAT0027431 |
| 33 | hsa-miR-3185 | MIMAT0015065 |
| 34 | hsa-miR-4792 | MIMAT0019964 |
| 35 | hsa-miR-6887-5p | MIMAT0027674 |
| 36 | hsa-miR-5572 | MIMAT0022260 |
| 37 | hsa-miR-3619-3p | MIMAT0019219 |
| 38 | hsa-miR-6780b-5p | MIMAT0027572 |
| 39 | hsa-miR-4707-5p | MIMAT0019807 |
| 40 | hsa-miR-8063 | MIMAT0030990 |
| 41 | hsa-miR-4454 | MIMAT0018976 |
| 42 | hsa-miR-4525 | MIMAT0019064 |
| 43 | hsa-miR-7975 | MIMAT0031178 |
| 44 | hsa-miR-744-5p | MIMAT0004945 |
| 45 | hsa-miR-3135b | MIMAT0018985 |
| 46 | hsa-miR-4648 | MIMAT0019710 |
| 47 | hsa-miR-6816-5p | MIMAT0027532 |
| 48 | hsa-miR-4741 | MIMAT0019871 |
| 49 | hsa-miR-7150 | MIMAT0028211 |
| 50 | hsa-miR-6791-5p | MIMAT0027482 |
| 51 | hsa-miR-1247-3p | MIMAT0022721 |
| 52 | hsa-miR-7977 | MIMAT0031180 |
| 53 | hsa-miR-4497 | MIMAT0019032 |
| 54 | hsa-miR-6090 | MIMAT0023715 |
| 55 | hsa-miR-6781-5p | MIMAT0027462 |
| 56 | hsa-miR-6870-5p | MIMAT0027640 |
| 57 | hsa-miR-6729-5p | MIMAT0027359 |
| 58 | hsa-miR-4530 | MIMAT0019069 |
| 59 | hsa-miR-7847-3p | MIMAT0030422 |
| 60 | hsa-miR-6825-5p | MIMAT0027550 |
| 61 | hsa-miR-4674 | MIMAT0019756 |
| 62 | hsa-miR-3917 | MIMAT0018191 |
| 63 | hsa-miR-4707-3p | MIMAT0019808 |
| 64 | hsa-miR-6885-5p | MIMAT0027670 |
| 65 | hsa-miR-6722-3p | MIMAT0025854 |
| 66 | hsa-miR-4516 | MIMAT0019053 |
| 67 | hsa-miR-6757-5p | MIMAT0027414 |
| 68 | hsa-miR-6840-3p | MIMAT0027583 |
| 69 | hsa-miR-5195-3p | MIMAT0021127 |
| 70 | hsa-miR-6756-5p | MIMAT0027412 |
| 71 | hsa-miR-6800-5p | MIMAT0027500 |
| 72 | hsa-miR-6727-5p | MIMAT0027355 |
| 73 | hsa-miR-6126 | MIMAT0024599 |
| 74 | hsa-miR-6872-3p | MIMAT0027645 |
| 75 | hsa-miR-4446-3p | MIMAT0018965 |
| 76 | hsa-miR-1268a | MIMAT0005922 |
| 77 | hsa-miR-1908-3p | MIMAT0026916 |
| 78 | hsa-miR-3679-5p | MIMAT0018104 |
| 79 | hsa-miR-4534 | MIMAT0019073 |
| 80 | hsa-miR-4675 | MIMAT0019757 |
| 81 | hsa-miR-7108-5p | MIMAT0028113 |
| 82 | hsa-miR-6799-5p | MIMAT0027498 |
| 83 | hsa-miR-4695-5p | MIMAT0019788 |
| 84 | hsa-miR-3178 | MIMAT0015055 |
| 85 | hsa-miR-5090 | MIMAT0021082 |
| 86 | hsa-miR-3180 | MIMAT0018178 |
| 87 | hsa-miR-1237-3p | MIMAT0022946 |
| 88 | hsa-miR-4758-5p | MIMAT0019903 |
| 89 | hsa-miR-3184-5p | MIMAT0015064 |
| 90 | hsa-miR-4286 | MIMAT0016916 |
| 91 | hsa-miR-6784-5p | MIMAT0027468 |
| 92 | hsa-miR-6768-5p | MIMAT0027436 |
| 93 | hsa-miR-6785-5p | MIMAT0027470 |
| 94 | hsa-miR-4706 | MIMAT0019806 |
| 95 | hsa-miR-711 | MIMAT0012734 |
| 96 | hsa-miR-1260a | MIMAT0005911 |
| 97 | hsa-miR-6746-5p | MIMAT0027392 |
| 98 | hsa-miR-6089 | MIMAT0023714 |
| 99 | hsa-miR-6821-5p | MIMAT0027542 |
| 100 | hsa-miR-4667-5p | MIMAT0019743 |
| 101 | hsa-miR-8069 | MIMAT0030996 |
| 102 | hsa-miR-4726-5p | MIMAT0019845 |
| 103 | hsa-miR-6124 | MIMAT0024597 |
| 104 | hsa-miR-4532 | MIMAT0019071 |
| 105 | hsa-miR-4486 | MIMAT0019020 |
| 106 | hsa-miR-4728-5p | MIMAT0019849 |
| 107 | hsa-miR-4508 | MIMAT0019045 |
| 108 | hsa-miR-128-1-5p | MIMAT0026477 |
| 109 | hsa-miR-4513 | MIMAT0019050 |
| 110 | hsa-miR-6795-5p | MIMAT0027490 |
| 111 | hsa-miR-4689 | MIMAT0019778 |
| 112 | hsa-miR-6763-5p | MIMAT0027426 |
| 113 | hsa-miR-8072 | MIMAT0030999 |
| 114 | hsa-miR-6765-5p | MIMAT0027430 |
| 115 | hsa-miR-4419b | MIMAT0019034 |
| 116 | hsa-miR-7641 | MIMAT0029782 |
| 117 | hsa-miR-3928-3p | MIMAT0018205 |
| 118 | hsa-miR-1227-5p | MIMAT0022941 |
| 119 | hsa-miR-4492 | MIMAT0019027 |
| 120 | hsa-miR-296-3p | MIMAT0004679 |
| 121 | hsa-miR-6769a-5p | MIMAT0027438 |
| 122 | hsa-miR-6889-5p | MIMAT0027678 |
| 123 | hsa-miR-4632-5p | MIMAT0022977 |
| 124 | hsa-miR-4505 | MIMAT0019041 |
| 125 | hsa-miR-3154 | MIMAT0015028 |
| 126 | hsa-miR-3648 | MIMAT0018068 |
| 127 | hsa-miR-4442 | MIMAT0018960 |
| 128 | hsa-miR-3141 | MIMAT0015010 |
| 129 | hsa-miR-7113-3p | MIMAT0028124 |
| 130 | hsa-miR-6819-5p | MIMAT0027538 |
| 131 | hsa-miR-3195 | MIMAT0015079 |
| 132 | hsa-miR-1199-5p | MIMAT0031119 |
| 133 | hsa-miR-6738-5p | MIMAT0027377 |
| 134 | hsa-miR-4656 | MIMAT0019723 |
| 135 | hsa-miR-6820-5p | MIMAT0027540 |
| 136 | hsa-miR-615-5p | MIMAT0004804 |
| 137 | hsa-miR-486-3p | MIMAT0004762 |
| 138 | hsa-miR-1225-3p | MIMAT0005573 |
| 139 | hsa-miR-760 | MIMAT0004957 |
| 140 | hsa-miR-187-5p | MIMAT0004561 |
| 141 | hsa-miR-1203 | MIMAT0005866 |
| 142 | hsa-miR-7110-5p | MIMAT0028117 |
| 143 | hsa-miR-371a-5p | MIMAT0004687 |
| 144 | hsa-miR-939-5p | MIMAT0004982 |
| 145 | hsa-miR-575 | MIMAT0003240 |
| 146 | hsa-miR-92b-5p | MIMAT0004792 |
| 147 | hsa-miR-887-3p | MIMAT0004951 |
| 148 | hsa-miR-920 | MIMAT0004970 |
| 149 | hsa-miR-1915-5p | MIMAT0007891 |
| 150 | hsa-miR-1231 | MIMAT0005586 |
| 151 | hsa-miR-663b | MIMAT0005867 |
| 152 | hsa-miR-1225-5p | MIMAT0005572 |
| 153 | hsa-miR-4763-3p | MIMAT0019913 |
| 154 | hsa-miR-3656 | MIMAT0018076 |
| 155 | hsa-miR-4488 | MIMAT0019022 |
| 156 | hsa-miR-125a-3p | MIMAT0004602 |
| 157 | hsa-miR-1469 | MIMAT0007347 |
| 158 | hsa-miR-1228-5p | MIMAT0005582 |
| 159 | hsa-miR-6798-5p | MIMAT0027496 |
| 160 | hsa-miR-1268b | MIMAT0018925 |
| 161 | hsa-miR-6732-5p | MIMAT0027365 |
| 162 | hsa-miR-1915-3p | MIMAT0007892 |
| 163 | hsa-miR-4433b-3p | MIMAT0030414 |
| 164 | hsa-miR-1207-5p | MIMAT0005871 |
| 165 | hsa-miR-4433-3p | MIMAT0018949 |
| 166 | hsa-miR-6879-5p | MIMAT0027658 |
| 167 | hsa-miR-4417 | MIMAT0018929 |
| 168 | hsa-miR-30c-1-3p | MIMAT0004674 |
| 169 | hsa-miR-4638-5p | MIMAT0019695 |
| 170 | hsa-miR-6088 | MIMAT0023713 |
| 171 | hsa-miR-4270 | MIMAT0016900 |
| 172 | hsa-miR-6782-5p | MIMAT0027464 |
| 173 | hsa-miR-665 | MIMAT0004952 |
| 174 | hsa-miR-486-5p | MIMAT0002177 |
| 175 | hsa-miR-4655-5p | MIMAT0019721 |
| 176 | hsa-miR-1275 | MIMAT0005929 |
| 177 | hsa-miR-6806-5p | MIMAT0027512 |

TABLE 1-continued

| SEQ ID NO: | Gene name | miRBase registration No. |
|---|---|---|
| 178 | hsa-miR-614 | MIMAT0003282 |
| 179 | hsa-miR-3937 | MIMAT0018352 |
| 180 | hsa-miR-6752-5p | MIMAT0027404 |
| 181 | hsa-miR-6771-5p | MIMAT0027442 |
| 182 | hsa-miR-4450 | MIMAT0018971 |
| 183 | hsa-miR-211-3p | MIMAT0022694 |
| 184 | hsa-miR-663a | MIMAT0003326 |
| 185 | hsa-miR-6842-5p | MIMAT0027586 |
| 186 | hsa-miR-7114-5p | MIMAT0028125 |
| 187 | hsa-miR-6779-5p | MIMAT0027458 |
| 188 | hsa-mir-4443 | MI0016786 |
| 189 | hsa-mir-1908 | MI0008329 |
| 190 | hsa-mir-4257 | MI0015856 |
| 191 | hsa-mir-3197 | MI0014245 |
| 192 | hsa-mir-3188 | MI0014232 |
| 193 | hsa-mir-4649 | MI0017276 |
| 194 | hsa-mir-1343 | MI0017320 |
| 195 | hsa-mir-6861 | MI0022708 |
| 196 | hsa-mir-642b | MI0016685 |
| 197 | hsa-mir-6741 | MI0022586 |
| 198 | hsa-mir-4745 | MI0017384 |
| 199 | hsa-mir-6826 | MI0022671 |
| 200 | hsa-mir-3663 | MI0016064 |
| 201 | hsa-mir-3131 | MI0014151 |
| 202 | hsa-mir-92a-2 | MI0000094 |
| 203 | hsa-mir-4258 | MI0015857 |
| 204 | hsa-mir-4448 | MI0016791 |
| 205 | hsa-mir-6125 | MI0021259 |
| 206 | hsa-mir-6880 | MI0022727 |
| 207 | hsa-mir-6132 | MI0021277 |
| 208 | hsa-mir-4467 | MI0016818 |
| 209 | hsa-mir-6749 | MI0022594 |
| 210 | hsa-mir-2392 | MI0016870 |
| 211 | hsa-mir-1273g | MI0018003 |
| 212 | hsa-mir-4746 | MI0017385 |
| 213 | hsa-mir-1914 | MI0008335 |
| 214 | hsa-mir-7845 | MI0025515 |
| 215 | hsa-mir-6726 | MI0022571 |
| 216 | hsa-mir-128-2 | MI0000727 |
| 217 | hsa-mir-4651 | MI0017279 |
| 218 | hsa-mir-6765 | MI0022610 |
| 219 | hsa-mir-3185 | MI0014227 |
| 220 | hsa-mir-4792 | MI0017439 |
| 221 | hsa-mir-6887 | MI0022734 |
| 222 | hsa-mir-5572 | MI0019117 |
| 223 | hsa-mir-3619 | MI0016009 |
| 224 | hsa-mir-6780b | MI0022681 |
| 225 | hsa-mir-4707 | MI0017340 |
| 226 | hsa-mir-8063 | MI0025899 |
| 227 | hsa-mir-4454 | MI0016800 |
| 228 | hsa-mir-4525 | MI0016892 |
| 229 | hsa-mir-7975 | MI0025751 |
| 230 | hsa-mir-744 | MI0005559 |
| 231 | hsa-mir-3135b | MI0016809 |
| 232 | hsa-mir-4648 | MI0017275 |
| 233 | hsa-mir-6816 | MI0022661 |
| 234 | hsa-mir-4741 | MI0017379 |
| 235 | hsa-mir-7150 | MI0023610 |
| 236 | hsa-mir-6791 | MI0022636 |
| 237 | hsa-mir-1247 | MI0006382 |
| 238 | hsa-mir-7977 | MI0025753 |
| 239 | hsa-mir-4497 | MI0016859 |
| 240 | hsa-mir-6090 | MI0020367 |
| 241 | hsa-mir-6781 | MI0022626 |
| 242 | hsa-mir-6870 | MI0022717 |
| 243 | hsa-mir-6729 | MI0022574 |
| 244 | hsa-mir-4530 | MI0016897 |
| 245 | hsa-mir-7847 | MI0025517 |
| 246 | hsa-mir-6825 | MI0022670 |
| 247 | hsa-mir-4674 | MI0017305 |
| 248 | hsa-mir-3917 | MI0016423 |
| 249 | hsa-mir-6885 | MI0022732 |
| 250 | hsa-mir-6722 | MI0022557 |
| 251 | hsa-mir-4516 | MI0016882 |
| 252 | hsa-mir-6757 | MI0022602 |
| 253 | hsa-mir-6840 | MI0022686 |
| 254 | hsa-mir-5195 | MI0018174 |
| 255 | hsa-mir-6756 | MI0022601 |
| 256 | hsa-mir-6800 | MI0022645 |
| 257 | hsa-mir-6727 | MI0022572 |
| 258 | hsa-mir-6126 | MI0021260 |
| 259 | hsa-mir-6872 | MI0022719 |
| 260 | hsa-mir-4446 | MI0016789 |
| 261 | hsa-mir-1268a | MI0006405 |
| 262 | hsa-mir-3679 | MI0016080 |
| 263 | hsa-mir-4534 | MI0016901 |
| 264 | hsa-mir-4675 | MI0017306 |
| 265 | hsa-mir-7108 | MI0022959 |
| 266 | hsa-mir-6799 | MI0022644 |
| 267 | hsa-mir-4695 | MI0017328 |
| 268 | hsa-mir-3178 | MI0014212 |
| 269 | hsa-mir-5090 | MI0017979 |
| 270 | hsa-mir-3180-4 | MI0016408 |
| 271 | hsa-mir-3180-5 | MI0016409 |
| 272 | hsa-mir-1237 | MI0006327 |
| 273 | hsa-mir-4758 | MI0017399 |
| 274 | hsa-mir-3184 | MI0014226 |
| 275 | hsa-mir-4286 | MI0015894 |
| 276 | hsa-mir-6784 | MI0022629 |
| 277 | hsa-mir-6768 | MI0022613 |
| 278 | hsa-mir-6785 | MI0022630 |
| 279 | hsa-mir-4706 | MI0017339 |
| 280 | hsa-mir-711 | MI0012488 |
| 281 | hsa-mir-1260a | MI0006394 |
| 282 | hsa-mir-6746 | MI0022591 |
| 283 | hsa-mir-6089-1 | MI0020366 |
| 284 | hsa-mir-6089-2 | MI0023563 |
| 285 | hsa-mir-6821 | MI0022666 |
| 286 | hsa-mir-4667 | MI0017297 |
| 287 | hsa-mir-8069 | MI0025905 |
| 288 | hsa-mir-4726 | MI0017363 |
| 289 | hsa-mir-6124 | MI0021258 |
| 290 | hsa-mir-4532 | MI0016899 |
| 291 | hsa-mir-4486 | MI0016847 |
| 292 | hsa-mir-4728 | MI0017365 |
| 293 | hsa-mir-4508 | MI0016872 |
| 294 | hsa-mir-128-1 | MI0000447 |
| 295 | hsa-mir-4513 | MI0016879 |
| 296 | hsa-mir-6795 | MI0022640 |
| 297 | hsa-mir-4689 | MI0017322 |
| 298 | hsa-mir-6763 | MI0022608 |
| 299 | hsa-mir-8072 | MI0025908 |
| 300 | hsa-mir-4419b | MI0016861 |
| 301 | hsa-mir-7641-1 | MI0024975 |
| 302 | hsa-mir-7641-2 | MI0024976 |
| 303 | hsa-mir-3928 | MI0016438 |
| 304 | hsa-mir-1227 | MI0006316 |
| 305 | hsa-mir-4492 | MI0016854 |
| 306 | hsa-mir-296 | MI0000747 |
| 307 | hsa-mir-6769a | MI0022614 |
| 308 | hsa-mir-6889 | MI0022736 |
| 309 | hsa-mir-4632 | MI0017259 |
| 310 | hsa-mir-4505 | MI0016868 |
| 311 | hsa-mir-3154 | MI0014182 |
| 312 | hsa-mir-3648 | MI0016048 |
| 313 | hsa-mir-4442 | MI0016785 |
| 314 | hsa-mir-3141 | MI0014165 |
| 315 | hsa-mir-7113 | MI0022964 |
| 316 | hsa-mir-6819 | MI0022664 |
| 317 | hsa-mir-3195 | MI0014240 |
| 318 | hsa-mir-1199 | MI0020340 |
| 319 | hsa-mir-6738 | MI0022583 |
| 320 | hsa-mir-4656 | MI0017284 |
| 321 | hsa-mir-6820 | MI0022665 |
| 322 | hsa-mir-615 | MI0003628 |
| 323 | hsa-mir-486 | MI0002470 |
| 324 | hsa-mir-486-2 | MI0023622 |
| 325 | hsa-mir-1225 | MI0006311 |
| 326 | hsa-mir-760 | MI0005567 |
| 327 | hsa-mir-187 | MI0000274 |
| 328 | hsa-mir-1203 | MI0006335 |
| 329 | hsa-mir-7110 | MI0022961 |
| 330 | hsa-mir-371a | MI0000779 |
| 331 | hsa-mir-939 | MI0005761 |

TABLE 1-continued

| SEQ ID NO: | Gene name | miRBase registration No. |
|---|---|---|
| 332 | hsa-mir-575 | MI0003582 |
| 333 | hsa-mir-92b | MI0003560 |
| 334 | hsa-mir-887 | MI0005562 |
| 335 | hsa-mir-920 | MI0005712 |
| 336 | hsa-mir-1915 | MI0008336 |
| 337 | hsa-mir-1231 | MI0006321 |
| 338 | hsa-mir-663b | MI0006336 |
| 339 | hsa-mir-4763 | MI0017404 |
| 340 | hsa-mir-3656 | MI0016056 |
| 341 | hsa-mir-4488 | MI0016849 |
| 342 | hsa-mir-125a | MI0000469 |
| 343 | hsa-mir-1469 | MI0007074 |
| 344 | hsa-mir-1228 | MI0006318 |
| 345 | hsa-mir-6798 | MI0022643 |
| 346 | hsa-mir-1268b | MI0016748 |
| 347 | hsa-mir-6732 | MI0022577 |
| 348 | hsa-mir-4433b | MI0025511 |
| 349 | hsa-mir-1207 | MI0006340 |
| 350 | hsa-mir-4433 | MI0016773 |
| 351 | hsa-mir-6879 | MI0022726 |
| 352 | hsa-mir-4417 | MI0016753 |
| 353 | hsa-mir-30c-1 | MI0000736 |
| 354 | hsa-mir-4638 | MI0017265 |
| 355 | hsa-mir-6088 | MI0020365 |
| 356 | hsa-mir-4270 | MI0015878 |
| 357 | hsa-mir-6782 | MI0022627 |
| 358 | hsa-mir-665 | MI0005563 |
| 359 | hsa-mir-4655 | MI0017283 |
| 360 | hsa-mir-1275 | MI0006415 |
| 361 | hsa-mir-6806 | MI0022651 |
| 362 | hsa-mir-614 | MI0003627 |
| 363 | hsa-mir-3937 | MI0016593 |
| 364 | hsa-mir-6752 | MI0022597 |
| 365 | hsa-mir-6771 | MI0022616 |
| 366 | hsa-mir-4450 | MI0016795 |
| 367 | hsa-mir-211 | MI0000287 |
| 368 | hsa-mir-663a | MI0003672 |
| 369 | hsa-mir-6842 | MI0022688 |
| 370 | hsa-mir-7114 | MI0022965 |
| 371 | hsa-mir-6779 | MI0022624 |
| 372 | isomiR example 1 of SEQ ID NO: 1 | — |
| 373 | isomiR example 2 of SEQ ID NO: 1 | — |
| 374 | isomiR example 1 of SEQ ID NO: 2 | — |
| 375 | isomiR example 2 of SEQ ID NO: 2 | — |
| 376 | isomiR example 1 of SEQ ID NO: 4 | — |
| 377 | isomiR example 2 of SEQ ID NO: 4 | — |
| 378 | isomiR example 1 of SEQ ID NO: 5 | — |
| 379 | isomiR example 2 of SEQ ID NO: 5 | — |
| 380 | isomiR example 1 of SEQ ID NO: 6 | — |
| 381 | isomiR example 2 of SEQ ID NO: 6 | — |
| 382 | isomiR example 1 of SEQ ID NO: 7 | — |
| 383 | isomiR example 2 of SEQ ID NO: 7 | — |
| 384 | isomiR example 1 of SEQ ID NO: 10 | — |
| 385 | isomiR example 2 of SEQ ID NO: 10 | — |
| 386 | isomiR example 1 of SEQ ID NO: 12 | — |
| 387 | isomiR example 2 of SEQ ID NO: 12 | — |
| 388 | isomiR example 1 of SEQ ID NO: 15 | — |
| 389 | isomiR example 2 of SEQ ID NO: 15 | — |
| 390 | isomiR example 1 of SEQ ID NO: 16 | — |
| 391 | isomiR example 2 of SEQ ID NO: 16 | — |
| 392 | isomiR example 1 of SEQ ID NO: 18 | — |
| 393 | isomiR example 2 of SEQ ID NO: 18 | — |
| 394 | isomiR example 1 of SEQ ID NO: 19 | — |
| 395 | isomiR example 2 of SEQ ID NO: 19 | — |
| 396 | isomiR example 1 of SEQ ID NO: 21 | — |
| 397 | isomiR example 2 of SEQ ID NO: 21 | — |
| 398 | isomiR example 1 of SEQ ID NO: 22 | — |
| 399 | isomiR example 2 of SEQ ID NO: 22 | — |
| 400 | isomiR example 1 of SEQ ID NO: 24 | — |
| 401 | isomiR example 2 of SEQ ID NO: 24 | — |
| 402 | isomiR example 1 of SEQ ID NO: 25 | — |
| 403 | isomiR example 2 of SEQ ID NO: 25 | — |
| 404 | isomiR example 1 of SEQ ID NO: 27 | — |
| 405 | isomiR example 2 of SEQ ID NO: 27 | — |
| 406 | isomiR example 1 of SEQ ID NO: 30 | — |
| 407 | isomiR example 2 of SEQ ID NO: 30 | — |
| 408 | isomiR example 1 of SEQ ID NO: 31 | — |
| 409 | isomiR example 2 of SEQ ID NO: 31 | — |
| 410 | isomiR example 1 of SEQ ID NO: 33 | — |
| 411 | isomiR example 2 of SEQ ID NO: 33 | — |
| 412 | isomiR example 1 of SEQ ID NO: 34 | — |
| 413 | isomiR example 2 of SEQ ID NO: 34 | — |
| 414 | isomiR example 1 of SEQ ID NO: 36 | — |
| 415 | isomiR example 2 of SEQ ID NO: 36 | — |
| 416 | isomiR example 1 of SEQ ID NO: 39 | — |
| 417 | isomiR example 2 of SEQ ID NO: 39 | — |
| 418 | isomiR example 1 of SEQ ID NO: 41 | — |
| 419 | isomiR example 2 of SEQ ID NO: 41 | — |
| 420 | isomiR example 1 of SEQ ID NO: 42 | — |
| 421 | isomiR example 2 of SEQ ID NO: 42 | — |
| 422 | isomiR example 1 of SEQ ID NO: 43 | — |
| 423 | isomiR example 2 of SEQ ID NO: 43 | — |
| 424 | isomiR example 1 of SEQ ID NO: 44 | — |
| 425 | isomiR example 2 of SEQ ID NO: 44 | — |
| 426 | isomiR example 1 of SEQ ID NO: 45 | — |
| 427 | isomiR example 2 of SEQ ID NO: 45 | — |
| 428 | isomiR example 1 of SEQ ID NO: 46 | — |
| 429 | isomiR example 2 of SEQ ID NO: 46 | — |
| 430 | isomiR example 1 of SEQ ID NO: 48 | — |
| 431 | isomiR example 2 of SEQ ID NO: 48 | — |
| 432 | isomiR example 1 of SEQ ID NO: 51 | — |
| 433 | isomiR example 2 of SEQ ID NO: 51 | — |
| 434 | isomiR example 1 of SEQ ID NO: 53 | — |
| 435 | isomiR example 2 of SEQ ID NO: 53 | — |
| 436 | isomiR example 1 of SEQ ID NO: 58 | — |
| 437 | isomiR example 2 of SEQ ID NO: 58 | — |
| 438 | isomiR example 1 of SEQ ID NO: 61 | — |
| 439 | isomiR example 2 of SEQ ID NO: 61 | — |
| 440 | isomiR example 1 of SEQ ID NO: 62 | — |
| 441 | isomiR example 2 of SEQ ID NO: 62 | — |
| 442 | isomiR example 1 of SEQ ID NO: 63 | — |
| 443 | isomiR example 2 of SEQ ID NO: 63 | — |
| 444 | isomiR example 1 of SEQ ID NO: 66 | — |
| 445 | isomiR example 2 of SEQ ID NO: 66 | — |
| 446 | isomiR example 1 of SEQ ID NO: 69 | — |
| 447 | isomiR example 2 of SEQ ID NO: 69 | — |
| 448 | isomiR example 1 of SEQ ID NO: 73 | — |
| 449 | isomiR example 2 of SEQ ID NO: 73 | — |
| 450 | isomiR example 1 of SEQ ID NO: 75 | — |
| 451 | isomiR example 2 of SEQ ID NO: 75 | — |
| 452 | isomiR example 1 of SEQ ID NO: 76 | — |
| 453 | isomiR example 2 of SEQ ID NO: 76 | — |
| 454 | isomiR example 1 of SEQ ID NO: 77 | — |
| 455 | isomiR example 2 of SEQ ID NO: 77 | — |
| 456 | isomiR example 1 of SEQ ID NO: 78 | — |
| 457 | isomiR example 2 of SEQ ID NO: 78 | — |
| 458 | isomiR example 1 of SEQ ID NO: 83 | — |
| 459 | isomiR example 2 of SEQ ID NO: 83 | — |
| 460 | isomiR example 1 of SEQ ID NO: 84 | — |
| 461 | isomiR example 2 of SEQ ID NO: 84 | — |
| 462 | isomiR example 1 of SEQ ID NO: 85 | — |
| 463 | isomiR example 2 of SEQ ID NO: 85 | — |
| 464 | isomiR example 1 of SEQ ID NO: 86 | — |
| 465 | isomiR example 2 of SEQ ID NO: 86 | — |
| 466 | isomiR example 1 of SEQ ID NO: 87 | — |
| 467 | isomiR example 2 of SEQ ID NO: 87 | — |
| 468 | isomiR example 1 of SEQ ID NO: 88 | — |
| 469 | isomiR example 2 of SEQ ID NO: 88 | — |
| 470 | isomiR example 1 of SEQ ID NO: 90 | — |
| 471 | isomiR example 2 of SEQ ID NO: 90 | — |
| 472 | isomiR example 1 of SEQ ID NO: 94 | — |
| 473 | isomiR example 2 of SEQ ID NO: 94 | — |
| 474 | isomiR example 1 of SEQ ID NO: 95 | — |
| 475 | isomiR example 2 of SEQ ID NO: 95 | — |
| 476 | isomiR example 1 of SEQ ID NO: 96 | — |
| 477 | isomiR example 2 of SEQ ID NO: 96 | — |
| 478 | isomiR example 1 of SEQ ID NO: 98 | — |
| 479 | isomiR example 2 of SEQ ID NO: 98 | — |
| 480 | isomiR example 1 of SEQ ID NO: 100 | — |
| 481 | isomiR example 2 of SEQ ID NO: 100 | — |
| 482 | isomiR example 1 of SEQ ID NO: 102 | — |
| 483 | isomiR example 2 of SEQ ID NO: 102 | — |
| 484 | isomiR example 1 of SEQ ID NO: 103 | — |
| 485 | isomiR example 2 of SEQ ID NO: 103 | — |

TABLE 1-continued

| SEQ ID NO: | Gene name | miRBase registration No. |
|---|---|---|
| 486 | isomiR example 1 of SEQ ID NO: 104 | — |
| 487 | isomiR example 2 of SEQ ID NO: 104 | — |
| 488 | isomiR example 1 of SEQ ID NO: 105 | — |
| 489 | isomiR example 2 of SEQ ID NO: 105 | — |
| 490 | isomiR example 1 of SEQ ID NO: 106 | — |
| 491 | isomiR example 2 of SEQ ID NO: 106 | — |
| 492 | isomiR example 1 of SEQ ID NO: 107 | — |
| 493 | isomiR example 2 of SEQ ID NO: 107 | — |
| 494 | isomiR example 1 of SEQ ID NO: 108 | — |
| 495 | isomiR example 2 of SEQ ID NO: 108 | — |
| 496 | isomiR example 1 of SEQ ID NO: 109 | — |
| 497 | isomiR example 2 of SEQ ID NO: 109 | — |
| 498 | isomiR example 1 of SEQ ID NO: 111 | — |
| 499 | isomiR example 2 of SEQ ID NO: 111 | — |
| 500 | isomiR example 1 of SEQ ID NO: 115 | — |
| 501 | isomiR example 2 of SEQ ID NO: 115 | — |
| 502 | isomiR example 1 of SEQ ID NO: 117 | — |
| 503 | isomiR example 2 of SEQ ID NO: 117 | — |
| 504 | isomiR example 1 of SEQ ID NO: 119 | — |
| 505 | isomiR example 2 of SEQ ID NO: 119 | — |
| 506 | isomiR example 1 of SEQ ID NO: 120 | — |
| 507 | isomiR example 2 of SEQ ID NO: 120 | — |
| 508 | isomiR example 1 of SEQ ID NO: 123 | — |
| 509 | isomiR example 2 of SEQ ID NO: 123 | — |
| 510 | isomiR example 1 of SEQ ID NO: 124 | — |
| 511 | isomiR example 2 of SEQ ID NO: 124 | — |
| 512 | isomiR example 1 of SEQ ID NO: 125 | — |
| 513 | isomiR example 2 of SEQ ID NO: 125 | — |
| 514 | isomiR example 1 of SEQ ID NO: 126 | — |
| 515 | isomiR example 2 of SEQ ID NO: 126 | — |
| 516 | isomiR example 1 of SEQ ID NO: 127 | — |
| 517 | isomiR example 2 of SEQ ID NO: 127 | — |
| 518 | isomiR example 1 of SEQ ID NO: 128 | — |
| 519 | isomiR example 2 of SEQ ID NO: 128 | — |
| 520 | isomiR example 1 of SEQ ID NO: 131 | — |
| 521 | isomiR example 2 of SEQ ID NO: 131 | — |
| 522 | isomiR example 1 of SEQ ID NO: 136 | — |
| 523 | isomiR example 2 of SEQ ID NO: 136 | — |
| 524 | isomiR example 1 of SEQ ID NO: 137 | — |
| 525 | isomiR example 2 of SEQ ID NO: 137 | — |
| 526 | isomiR example 1 of SEQ ID NO: 139 | — |
| 527 | isomiR example 2 of SEQ ID NO: 139 | — |
| 528 | isomiR example 1 of SEQ ID NO: 140 | — |
| 529 | isomiR example 2 of SEQ ID NO: 140 | — |
| 530 | isomiR example 1 of SEQ ID NO: 143 | — |
| 531 | isomiR example 2 of SEQ ID NO: 143 | — |
| 532 | isomiR example 1 of SEQ ID NO: 144 | — |
| 533 | isomiR example 2 of SEQ ID NO: 144 | — |
| 534 | isomiR example 1 of SEQ ID NO: 147 | — |
| 535 | isomiR example 2 of SEQ ID NO: 147 | — |
| 536 | isomiR example 1 of SEQ ID NO: 149 | — |
| 537 | isomiR example 2 of SEQ ID NO: 149 | — |
| 538 | isomiR example 1 of SEQ ID NO: 151 | — |
| 539 | isomiR example 2 of SEQ ID NO: 151 | — |
| 540 | isomiR example 1 of SEQ ID NO: 153 | — |
| 541 | isomiR example 2 of SEQ ID NO: 153 | — |
| 542 | isomiR example 1 of SEQ ID NO: 154 | — |
| 543 | isomiR example 2 of SEQ ID NO: 154 | — |
| 544 | isomiR example 1 of SEQ ID NO: 155 | — |
| 545 | isomiR example 2 of SEQ ID NO: 155 | — |
| 546 | isomiR example 1 of SEQ ID NO: 156 | — |
| 547 | isomiR example 2 of SEQ ID NO: 156 | — |
| 548 | isomiR example 1 of SEQ ID NO: 158 | — |
| 549 | isomiR example 2 of SEQ ID NO: 158 | — |
| 550 | isomiR example 1 of SEQ ID NO: 160 | — |
| 551 | isomiR example 2 of SEQ ID NO: 160 | — |
| 552 | isomiR example 1 of SEQ ID NO: 162 | — |
| 553 | isomiR example 2 of SEQ ID NO: 162 | — |
| 554 | isomiR example 1 of SEQ ID NO: 165 | — |
| 555 | isomiR example 2 of SEQ ID NO: 165 | — |
| 556 | isomiR example 1 of SEQ ID NO: 167 | — |
| 557 | isomiR example 2 of SEQ ID NO: 167 | — |
| 558 | isomiR example 1 of SEQ ID NO: 168 | — |
| 559 | isomiR example 2 of SEQ ID NO: 168 | — |
| 560 | isomiR example 1 of SEQ ID NO: 169 | — |
| 561 | isomiR example 2 of SEQ ID NO: 169 | — |
| 562 | isomiR example 1 of SEQ ID NO: 170 | — |
| 563 | isomiR example 2 of SEQ ID NO: 170 | — |
| 564 | isomiR example 1 of SEQ ID NO: 173 | — |
| 565 | isomiR example 2 of SEQ ID NO: 173 | — |
| 566 | isomiR example 1 of SEQ ID NO: 174 | — |
| 567 | isomiR example 2 of SEQ ID NO: 174 | — |
| 568 | isomiR example 1 of SEQ ID NO: 175 | — |
| 569 | isomiR example 2 of SEQ ID NO: 175 | — |
| 570 | isomiR example 1 of SEQ ID NO: 176 | — |
| 571 | isomiR example 2 of SEQ ID NO: 176 | — |
| 572 | isomiR example 1 of SEQ ID NO: 178 | — |
| 573 | isomiR example 2 of SEQ ID NO: 178 | — |
| 574 | isomiR example 1 of SEQ ID NO: 182 | — |
| 575 | isomiR example 2 of SEQ ID NO: 182 | — |
| 576 | isomiR example 1 of SEQ ID NO: 183 | — |
| 577 | isomiR example 2 of SEQ ID NO: 183 | — |
| 578 | isomiR example 1 of SEQ ID NO: 184 | — |
| 579 | isomiR example 1 of SEQ ID NO: 184 | — |
| 580 | hsa-miR-204-3p | MIMAT0022693 |
| 581 | hsa-miR-642a-3p | MIMAT0020924 |
| 582 | hsa-miR-762 | MIMAT0010313 |
| 583 | hsa-miR-1202 | MIMAT0005865 |
| 584 | hsa-miR-3162-5p | MIMAT0015036 |
| 585 | hsa-miR-3196 | MIMAT0015080 |
| 586 | hsa-miR-3622a-5p | MIMAT0018003 |
| 587 | hsa-miR-3665 | MIMAT0018087 |
| 588 | hsa-miR-3940-5p | MIMAT0019229 |
| 589 | hsa-miR-4294 | MIMAT0016849 |
| 590 | hsa-miR-4466 | MIMAT0018993 |
| 591 | hsa-miR-4476 | MIMAT0019003 |
| 592 | hsa-miR-4723-5p | MIMAT0019838 |
| 593 | hsa-miR-4725-3p | MIMAT0019844 |
| 594 | hsa-miR-4730 | MIMAT0019852 |
| 595 | hsa-miR-4739 | MIMAT0019868 |
| 596 | hsa-miR-4787-5p | MIMAT0019956 |
| 597 | hsa-miR-5787 | MIMAT0023252 |
| 598 | hsa-miR-6085 | MIMAT0023710 |
| 599 | hsa-miR-6717-5p | MIMAT0025846 |
| 600 | hsa-miR-6724-5p | MIMAT0025856 |
| 601 | hsa-miR-6777-5p | MIMAT0027454 |
| 602 | hsa-miR-6778-5p | MIMAT0027456 |
| 603 | hsa-miR-6787-5p | MIMAT0027474 |
| 604 | hsa-miR-6789-5p | MIMAT0027478 |
| 605 | hsa-miR-6845-5p | MIMAT0027590 |
| 606 | hsa-miR-6893-5p | MIMAT0027686 |
| 607 | hsa-miR-16-5p | MIMAT0000069 |
| 608 | hsa-miR-423-5p | MIMAT0004748 |
| 609 | hsa-miR-451a | MIMAT0001631 |
| 610 | hsa-miR-564 | MIMAT0003228 |
| 611 | hsa-miR-671-5p | MIMAT0003880 |
| 612 | hsa-mir-204 | MI0000284 |
| 613 | hsa-mir-642a | MI0003657 |
| 614 | hsa-mir-762 | MI0003892 |
| 615 | hsa-mir-1202 | MI0006334 |
| 616 | hsa-mir-3162 | MI0014192 |
| 617 | hsa-mir-3196 | MI0014241 |
| 618 | hsa-mir-3622a | MI0016013 |
| 619 | hsa-mir-3665 | MI0016066 |
| 620 | hsa-mir-3940 | MI0016597 |
| 621 | hsa-mir-4294 | MI0015827 |
| 622 | hsa-mir-4466 | MI0016817 |
| 623 | hsa-mir-4476 | MI0016828 |
| 624 | hsa-mir-4723 | MI0017359 |
| 625 | hsa-mir-4725 | MI0017362 |
| 626 | hsa-mir-4730 | MI0017367 |
| 627 | hsa-mir-4739 | MI0017377 |
| 628 | hsa-mir-4787 | MI0017434 |
| 629 | hsa-mir-5787 | MI0019797 |
| 630 | hsa-mir-6085 | MI0020362 |
| 631 | hsa-mir-6717 | MI0022551 |
| 632 | hsa-mir-6724 | MI0022559 |
| 633 | hsa-mir-6777 | MI0022622 |
| 634 | hsa-mir-6778 | MI0022623 |
| 635 | hsa-mir-6787 | MI0022632 |
| 636 | hsa-mir-6789 | MI0022634 |
| 637 | hsa-mir-6845 | MI0022691 |
| 638 | hsa-mir-6893 | MI0022740 |
| 639 | hsa-mir-16-1 | MI0000070 |

TABLE 1-continued

| SEQ ID NO: | Gene name | miRBase registration No. |
|---|---|---|
| 640 | hsa-mir-16-2 | MI0000115 |
| 641 | hsa-mir-423 | MI0001445 |
| 642 | hsa-mir-451a | MI0001729 |
| 643 | hsa-mir-564 | MI0003570 |
| 644 | hsa-mir-671 | MI0003760 |
| 645 | isomiR example 1 of SEQ ID NO: 580 | — |
| 646 | isomiR example 2 of SEQ ID NO: 580 | — |
| 647 | isomiR example 1 of SEQ ID NO: 581 | — |
| 648 | isomiR example 2 of SEQ ID NO: 581 | — |
| 649 | isomiR example 1 of SEQ ID NO: 583 | — |
| 650 | isomiR example 1 of SEQ ID NO: 584 | — |
| 651 | isomiR example 2 of SEQ ID NO: 584 | — |
| 652 | isomiR example 1 of SEQ ID NO: 585 | — |
| 653 | isomiR example 2 of SEQ ID NO: 585 | — |
| 654 | isomiR example 1 of SEQ ID NO: 586 | — |
| 655 | isomiR example 1 of SEQ ID NO: 587 | — |
| 656 | isomiR example 2 of SEQ ID NO: 587 | — |
| 657 | isomiR example 1 of SEQ ID NO: 588 | — |
| 658 | isomiR example 2 of SEQ ID NO: 588 | — |
| 659 | isomiR example 1 of SEQ ID NO: 590 | — |
| 660 | isomiR example 2 of SEQ ID NO: 590 | — |
| 661 | isomiR example 1 of SEQ ID NO: 591 | — |
| 662 | isomiR example 2 of SEQ ID NO: 591 | — |
| 663 | isomiR example 1 of SEQ ID NO: 592 | — |
| 664 | isomiR example 2 of SEQ ID NO: 592 | — |
| 665 | isomiR example 1 of SEQ ID NO: 593 | — |
| 666 | isomiR example 2 of SEQ ID NO: 593 | — |
| 667 | isomiR example 1 of SEQ ID NO: 594 | — |
| 668 | isomiR example 2 of SEQ ID NO: 594 | — |
| 669 | isomiR example 1 of SEQ ID NO: 595 | — |
| 670 | isomiR example 2 of SEQ ID NO: 595 | — |
| 671 | isomiR example 1 of SEQ ID NO: 597 | — |
| 672 | isomiR example 2 of SEQ ID NO: 597 | — |
| 673 | isomiR example 1 of SEQ ID NO: 599 | — |
| 674 | isomiR example 2 of SEQ ID NO: 599 | — |
| 675 | isomiR example 1 of SEQ ID NO: 600 | — |
| 676 | isomiR example 2 of SEQ ID NO: 600 | — |
| 677 | isomiR example 1 of SEQ ID NO: 607 | — |
| 678 | isomiR example 2 of SEQ ID NO: 607 | — |
| 679 | isomiR example 1 of SEQ ID NO: 608 | — |
| 680 | isomiR example 2 of SEQ ID NO: 608 | — |
| 681 | isomiR example 1 of SEQ ID NO: 609 | — |
| 682 | isomiR example 2 of SEQ ID NO: 609 | — |
| 683 | isomiR example 1 of SEQ ID NO: 611 | — |
| 684 | isomiR example 2 of SEQ ID NO: 611 | — |

The present application claims the priority of Japanese Patent Application No. 2014-121377 filed on Jun. 12, 2014 and Japanese Patent Application No. 2015-71756 filed on Mar. 31, 2015, and encompasses the contents described in the specifications of these patent applications.

Advantageous Effects of Invention

According to the present invention, prostate cancer can be detected easily and highly accurately. For example, the presence or absence of prostate cancer in a patient can be easily detected by using, as an index, the measurement values of several miRNAs in blood, serum, and/or plasma of the patient, which can be collected with limited invasiveness.

DESCRIPTION OF EMBODIMENTS

Figure 1:
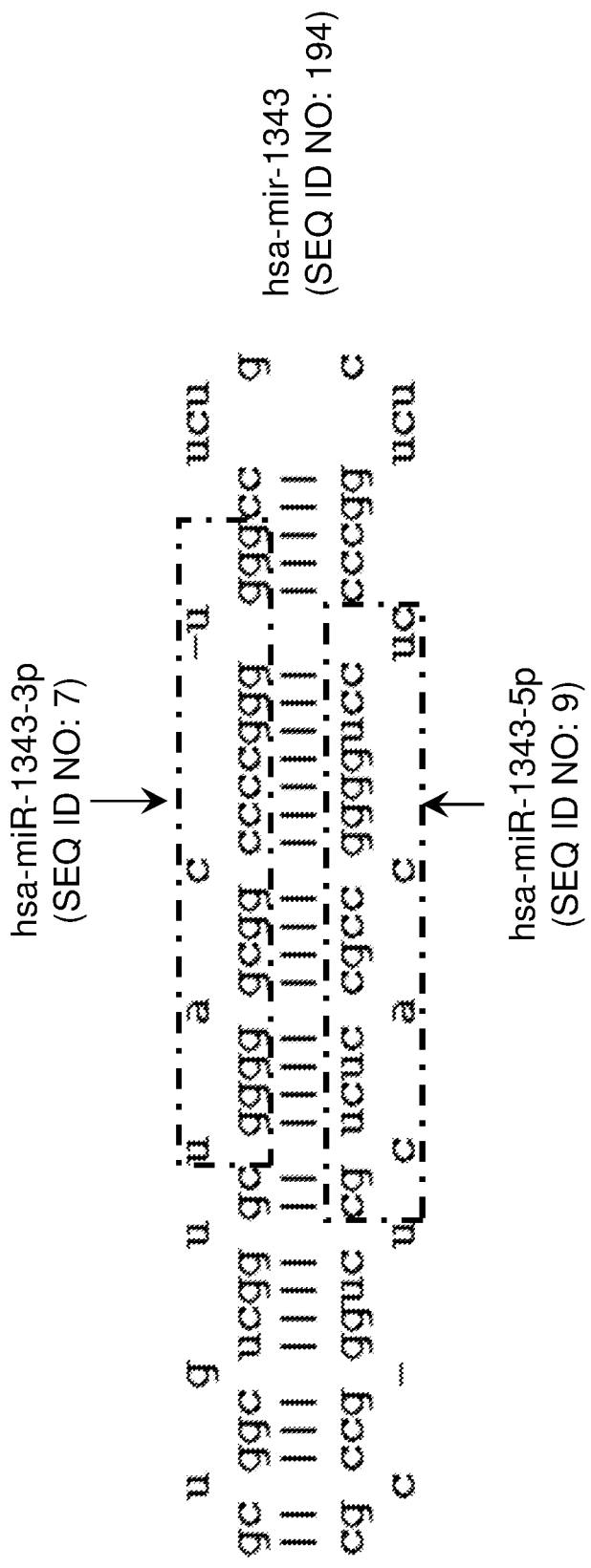
FIG. 1 This figure shows the relationship between the nucleotide sequences of hsa-miR-1343-3p represented by SEQ ID NO: 7 and hsa-miR-1343-5p represented by SEQ ID NO: 9, which are formed from a precursor hsa-mir-1343 represented by SEQ ID NO: 194.

Hereinafter, the present invention will be described further specifically.

1. Target Nucleic Acid for Prostate Cancer

A primary target nucleic acid as a prostate cancer marker for detecting the presence and/or absence of prostate cancer or prostate cancer cells using the nucleic acid probe or the primer for the detection of prostate cancer defined above according to the present invention comprises at least one or more miRNA(s) selected from the group consisting of hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p and hsa-miR-6893-5p. Furthermore, at least one or more miRNA(s) selected from the group consisting of other prostate cancer markers that can be combined with these miRNAs, i.e., hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564 and hsa-miR-671-5p can also be preferably used as a target nucleic acid(s). Moreover, at least one or more miRNA(s) selected from the group consisting of other prostate cancer markers that can be combined with these miRNAs, i.e., hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p can also be preferably used as a target nucleic acid(s).

These miRNAs include, for example, a human gene comprising a nucleotide sequence represented by any of SEQ ID NOs: 1 to 187 and 580 to 611 (i.e., hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p and hsa-miR-6893-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564 and hsa-miR-671-5p, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p, respectively), any congener thereof, any transcript thereof, and any variant or any derivative thereof. In this context, the gene, the congener, the transcript, the variant, and the derivative are as defined above.

The target nucleic acid is preferably a human gene comprising a nucleotide sequence represented by any of SEQ ID NOs: 1 to 684 or a transcript thereof, more preferably the transcript, i.e., a miRNA or its precursor RNA (pri-miRNA or pre-miRNA).

The first target gene is the hsa-miR-4443 gene, a congener thereof, a transcript thereof, or a variant or a derivative thereof. None of the previously known reports show that change in the expression of the gene or the transcript thereof can serve as a marker for prostate cancer.

The second target gene is the hsa-miR-1908-5p gene, a congener thereof, a transcript thereof, or a variant or a derivative thereof. None of the previously known reports show that change in the expression of the gene or the transcript thereof can serve as a marker for prostate cancer.

The third target gene is the hsa-miR-4257 gene, a congener thereof, a transcript thereof, or a variant or a derivative thereof. None of the previously known reports show that change in the expression of the gene or the transcript thereof can serve as a marker for prostate cancer.

The fourth target gene is the hsa-miR-3197 gene, a congener thereof, a transcript thereof, or a variant or a derivative thereof. None of the previously known reports show that change in the expression of the gene or the transcript thereof can serve as a marker for prostate cancer.

The fifth target gene is the hsa-miR-3188 gene, a congener thereof, a transcript thereof, or a variant or a derivative thereof. None of the previously known reports show that change in the expression of the gene or the transcript thereof can serve as a marker for prostate cancer.

The sixth target gene is the hsa-miR-4649-5p gene, a congener thereof, a transcript thereof, or a variant or a derivative thereof. None of the previously known reports show that change in the expression of the gene or the transcript thereof can serve as a marker for prostate cancer.

The seventh target gene is the hsa-miR-1343-3p gene, a congener thereof, a transcript thereof, or a variant or a derivative thereof. None of the previously known reports show that change in the expression of the gene or the transcript thereof can serve as a marker for prostate cancer.

The eighth target gene is the hsa-miR-6861-5p gene, a congener thereof, a transcript thereof, or a variant or a derivative thereof. None of the previously known reports show that change in the expression of the gene or the transcript thereof can serve as a marker for prostate cancer.

The ninth target gene is the hsa-miR-1343-5p gene, a congener thereof, a transcript thereof, or a variant or a derivative thereof. None of the previously known reports show that change in the expression of the gene or the transcript thereof can serve as a marker for prostate cancer.

The 10th target gene is the hsa-miR-642b-3p gene, a congener thereof, a transcript thereof, or a variant or a derivative thereof. None of the previously known reports show that change in the expression of the gene or the transcript thereof can serve as a marker for prostate cancer.

The 11th target gene is the hsa-miR-6741-5p gene, a congener thereof, a transcript thereof, or a variant or a derivative thereof. None of the previously known reports show that change in the expression of the gene or the transcript thereof can serve as a marker for prostate cancer.

The 12th target gene is the hsa-miR-4745-5p gene, a congener thereof, a transcript thereof, or a variant or a derivative thereof. None of the previously known reports show that change in the expression of the gene or the transcript thereof can serve as a marker for prostate cancer.

The 13th target gene is the hsa-miR-6826-5p gene, a congener thereof, a transcript thereof, or a variant or a derivative thereof. None of the previously known reports show that change in the expression of the gene or the transcript thereof can serve as a marker for prostate cancer.

The 14th target gene is the hsa-miR-3663-3p gene, a congener thereof, a transcript thereof, or a variant or a derivative thereof. None of the previously known reports show that change in the expression of the gene or the transcript thereof can serve as a marker for prostate cancer.

The 15th target gene is the hsa-miR-3131 gene, a congener thereof, a transcript thereof, or a variant or a derivative thereof. None of the previously known reports show that change in the expression of the gene or the transcript thereof can serve as a marker for prostate cancer.

The 16th target gene is the hsa-miR-92a-2-5p gene, a congener thereof, a transcript thereof, or a variant or a derivative thereof. None of the previously known reports show that change in the expression of the gene or the transcript thereof can serve as a marker for prostate cancer.

The 17th target gene is the hsa-miR-4258 gene, a congener thereof, a transcript thereof, or a variant or a derivative thereof. None of the previously known reports show that change in the expression of the gene or the transcript thereof can serve as a marker for prostate cancer.

The 18th target gene is the hsa-miR-4448 gene, a congener thereof, a transcript thereof, or a variant or a derivative thereof. None of the previously known reports show that change in the expression of the gene or the transcript thereof can serve as a marker for prostate cancer.

The 19th target gene is the hsa-miR-6125 gene, a congener thereof, a transcript thereof, or a variant or a derivative thereof. None of the previously known reports show that change in the expression of the gene or the transcript thereof can serve as a marker for prostate cancer.

The 20th target gene is the hsa-miR-6880-5p gene, a congener thereof, a transcript thereof, or a variant or a derivative thereof. None of the previously known reports show that change in the expression of the gene or the transcript thereof can serve as a marker for prostate cancer.

The 21st target gene is the hsa-miR-6132 gene, a congener thereof, a transcript thereof, or a variant or a derivative thereof. None of the previously known reports show that change in the expression of the gene or the transcript thereof can serve as a marker for prostate cancer.

The 22nd target gene is the hsa-miR-4467 gene, a congener thereof, a transcript thereof, or a variant or a derivative thereof. None of the previously known reports show that change in the expression of the gene or the transcript thereof can serve as a marker for prostate cancer.

The 23rd target gene is the hsa-miR-6749-5p gene, a congener thereof, a transcript thereof, or a variant or a derivative thereof. None of the previously known reports show that change in the expression of the gene or the transcript thereof can serve as a marker for prostate cancer.

The 24th target gene is the hsa-miR-2392 gene, a congener thereof, a transcript thereof, or a variant or a derivative thereof. None of the previously known reports show that change in the expression of the gene or the transcript thereof can serve as a marker for prostate cancer.

The 25th target gene is the hsa-miR-1273g-3p gene, a congener thereof, a transcript thereof, or a variant or a derivative thereof. None of the previously known reports show that change in the expression of the gene or the transcript thereof can serve as a marker for prostate cancer.

The 26th target gene is the hsa-miR-4746-3p gene, a congener thereof, a transcript thereof, or a variant or a derivative thereof. None of the previously known reports show that change in the expression of the gene or the transcript thereof can serve as a marker for prostate cancer.

The 27th target gene is the hsa-miR-1914-3p gene, a congener thereof, a transcript thereof, or a variant or a derivative thereof. None of the previously known reports show that change in the expression of the gene or the transcript thereof can serve as a marker for prostate cancer.

The 28th target gene is the hsa-miR-7845-5p gene, a congener thereof, a transcript thereof, or a variant or a derivative thereof. None of the previously known reports show that change in the expression of the gene or the transcript thereof can serve as a marker for prostate cancer.

The 29th target gene is the hsa-miR-6726-5p gene, a congener thereof, a transcript thereof, or a variant or a derivative thereof. None of the previously known reports show that change in the expression of the gene or the transcript thereof can serve as a marker for prostate cancer.

The 30th target gene is the hsa-miR-128-2-5p gene, a congener thereof, a transcript thereof, or a variant or a derivative thereof. None of the previously known reports show that change in the expression of the gene or the transcript thereof can serve as a marker for prostate cancer.

The 31st target gene is the hsa-miR-4651 gene, a congener thereof, a transcript thereof, or a variant or a derivative thereof. None of the previously known reports show that change in the expression of the gene or the transcript thereof can serve as a marker for prostate cancer.

The 32nd target gene is the hsa-miR-6765-3p gene, a congener thereof, a transcript thereof, or a variant or a derivative thereof. None of the previously known reports show that change in the expression of the gene or the transcript thereof can serve as a marker for prostate cancer.

The 33rd target gene is the hsa-miR-3185 gene, a congener thereof, a transcript thereof, or a variant or a derivative thereof. None of the previously known reports show that change in the expression of the gene or the transcript thereof can serve as a marker for prostate cancer.

The 34th target gene is the hsa-miR-4792 gene, a congener thereof, a transcript thereof, or a variant or a derivative thereof. None of the previously known reports show that change in the expression of the gene or the transcript thereof can serve as a marker for prostate cancer.

The 35th target gene is the hsa-miR-6887-5p gene, a congener thereof, a transcript thereof, or a variant or a derivative thereof. None of the previously known reports show that change in the expression of the gene or the transcript thereof can serve as a marker for prostate cancer.

The 36th target gene is the hsa-miR-5572 gene, a congener thereof, a transcript thereof, or a variant or a derivative thereof. None of the previously known reports show that change in the expression of the gene or the transcript thereof can serve as a marker for prostate cancer.

The 37th target gene is the hsa-miR-3619-3p gene, a congener thereof, a transcript thereof, or a variant or a derivative thereof. None of the previously known reports show that change in the expression of the gene or the transcript thereof can serve as a marker for prostate cancer.

The 38th target gene is the hsa-miR-6780b-5p gene, a congener thereof, a transcript thereof, or a variant or a derivative thereof. None of the previously known reports show that change in the expression of the gene or the transcript thereof can serve as a marker for prostate cancer.

The 39th target gene is the hsa-miR-4707-5p gene, a congener thereof, a transcript thereof, or a variant or a derivative thereof. None of the previously known reports show that change in the expression of the gene or the transcript thereof can serve as a marker for prostate cancer.

The 40th target gene is the hsa-miR-8063 gene, a congener thereof, a transcript thereof, or a variant or a derivative thereof. None of the previously known reports show that change in the expression of the gene or the transcript thereof can serve as a marker for prostate cancer.

The 41st target gene is the hsa-miR-4454 gene, a congener thereof, a transcript thereof, or a variant or a derivative thereof. None of the previously known reports show that change in the expression of the gene or the transcript thereof can serve as a marker for prostate cancer.

The 42nd target gene is the hsa-miR-4525 gene, a congener thereof, a transcript thereof, or a variant or a derivative thereof. None of the previously known reports show that change in the expression of the gene or the transcript thereof can serve as a marker for prostate cancer.

The 43rd target gene is the hsa-miR-7975 gene, a congener thereof, a transcript thereof, or a variant or a derivative thereof. None of the previously known reports show that change in the expression of the gene or the transcript thereof can serve as a marker for prostate cancer.

The 44th target gene is the hsa-miR-744-5p gene, a congener thereof, a transcript thereof, or a variant or a derivative thereof. None of the previously known reports show that change in the expression of the gene or the transcript thereof can serve as a marker for prostate cancer.

The 45th target gene is the hsa-miR-3135b gene, a congener thereof, a transcript thereof, or a variant or a derivative thereof. None of the previously known reports show that change in the expression of the gene or the transcript thereof can serve as a marker for prostate cancer.

The 46th target gene is the hsa-miR-4648 gene, a congener thereof, a transcript thereof, or a variant or a derivative thereof. None of the previously known reports show that change in the expression of the gene or the transcript thereof can serve as a marker for prostate cancer.

The 47th target gene is the hsa-miR-6816-5p gene, a congener thereof, a transcript thereof, or a variant or a derivative thereof. None of the previously known reports show that change in the expression of the gene or the transcript thereof can serve as a marker for prostate cancer.

The 48th target gene is the hsa-miR-4741 gene, a congener thereof, a transcript thereof, or a variant or a derivative thereof. None of the previously known reports show that change in the expression of the gene or the transcript thereof can serve as a marker for prostate cancer.

The 49th target gene is the hsa-miR-7150 gene, a congener thereof, a transcript thereof, or a variant or a derivative thereof. None of the previously known reports show that change in the expression of the gene or the transcript thereof can serve as a marker for prostate cancer.

The 50th target gene is the hsa-miR-6791-5p gene, a congener thereof, a transcript thereof, or a variant or a derivative thereof. None of the previously known reports show that change in the expression of the gene or the transcript thereof can serve as a marker for prostate cancer.

The 51st target gene is the hsa-miR-1247-3p gene, a congener thereof, a transcript thereof, or a variant or a derivative thereof. None of the previously known reports show that change in the expression of the gene or the transcript thereof can serve as a marker for prostate cancer.

The 52nd target gene is the hsa-miR-7977 gene, a congener thereof, a transcript thereof, or a variant or a derivative thereof. None of the previously known reports show that change in the expression of the gene or the transcript thereof can serve as a marker for prostate cancer.

The 53rd target gene is the hsa-miR-4497 gene, a congener thereof, a transcript thereof, or a variant or a derivative thereof. None of the previously known reports show that change in the expression of the gene or the transcript thereof can serve as a marker for prostate cancer.

The 54th target gene is the hsa-miR-6090 gene, a congener thereof, a transcript thereof, or a variant or a derivative thereof. None of the previously known reports show that change in the expression of the gene or the transcript thereof can serve as a marker for prostate cancer.

The 55th target gene is the hsa-miR-6781-5p gene, a congener thereof, a transcript thereof, or a variant or a derivative thereof. None of the previously known reports show that change in the expression of the gene or the transcript thereof can serve as a marker for prostate cancer.

The 56th target gene is the hsa-miR-6870-5p gene, a congener thereof, a transcript thereof, or a variant or a derivative thereof. None of the previously known reports show that change in the expression of the gene or the transcript thereof can serve as a marker for prostate cancer.

The 57th target gene is the hsa-miR-6729-5p gene, a congener thereof, a transcript thereof, or a variant or a derivative thereof. None of the previously known reports show that change in the expression of the gene or the transcript thereof can serve as a marker for prostate cancer.

The 58th target gene is the hsa-miR-4530 gene, a congener thereof, a transcript thereof, or a variant or a derivative thereof. None of the previously known reports show that change in the expression of the gene or the transcript thereof can serve as a marker for prostate cancer.

The 59th target gene is the hsa-miR-7847-3p gene, a congener thereof, a transcript thereof, or a variant or a derivative thereof. None of the previously known reports show that change in the expression of the gene or the transcript thereof can serve as a marker for prostate cancer.

The 60th target gene is the hsa-miR-6825-5p gene, a congener thereof, a transcript thereof, or a variant or a derivative thereof. None of the previously known reports show that change in the expression of the gene or the transcript thereof can serve as a marker for prostate cancer.

The 61st target gene is the hsa-miR-4674 gene, a congener thereof, a transcript thereof, or a variant or a derivative thereof. None of the previously known reports show that change in the expression of the gene or the transcript thereof can serve as a marker for prostate cancer.

The 62nd target gene is the hsa-miR-3917 gene, a congener thereof, a transcript thereof, or a variant or a derivative thereof. None of the previously known reports show that change in the expression of the gene or the transcript thereof can serve as a marker for prostate cancer.

The 63rd target gene is the hsa-miR-4707-3p gene, a congener thereof, a transcript thereof, or a variant or a derivative thereof. None of the previously known reports show that change in the expression of the gene or the transcript thereof can serve as a marker for prostate cancer.

The 64th target gene is the hsa-miR-6885-5p gene, a congener thereof, a transcript thereof, or a variant or a derivative thereof. None of the previously known reports show that change in the expression of the gene or the transcript thereof can serve as a marker for prostate cancer.

The 65th target gene is the hsa-miR-6722-3p gene, a congener thereof, a transcript thereof, or a variant or a derivative thereof. None of the previously known reports show that change in the expression of the gene or the transcript thereof can serve as a marker for prostate cancer.

The 66th target gene is the hsa-miR-4516 gene, a congener thereof, a transcript thereof, or a variant or a derivative thereof. None of the previously known reports show that change in the expression of the gene or the transcript thereof can serve as a marker for prostate cancer.

The 67th target gene is the hsa-miR-6757-5p gene, a congener thereof, a transcript thereof, or a variant or a derivative thereof. None of the previously known reports show that change in the expression of the gene or the transcript thereof can serve as a marker for prostate cancer.

The 68th target gene is the hsa-miR-6840-3p gene, a congener thereof, a transcript thereof, or a variant or a derivative thereof. None of the previously known reports show that change in the expression of the gene or the transcript thereof can serve as a marker for prostate cancer.

The 69th target gene is the hsa-miR-5195-3p gene, a congener thereof, a transcript thereof, or a variant or a derivative thereof. None of the previously known reports show that change in the expression of the gene or the transcript thereof can serve as a marker for prostate cancer.

The 70th target gene is the hsa-miR-6756-5p gene, a congener thereof, a transcript thereof, or a variant or a derivative thereof. None of the previously known reports show that change in the expression of the gene or the transcript thereof can serve as a marker for prostate cancer.

The 71st target gene is the hsa-miR-6800-5p gene, a congener thereof, a transcript thereof, or a variant or a derivative thereof. None of the previously known reports show that change in the expression of the gene or the transcript thereof can serve as a marker for prostate cancer.

The 72nd target gene is the hsa-miR-6727-5p gene, a congener thereof, a transcript thereof, or a variant or a derivative thereof. None of the previously known reports show that change in the expression of the gene or the transcript thereof can serve as a marker for prostate cancer.

The 73rd target gene is the hsa-miR-6126 gene, a congener thereof, a transcript thereof, or a variant or a derivative thereof. None of the previously known reports show that change in the expression of the gene or the transcript thereof can serve as a marker for prostate cancer.

The 74th target gene is the hsa-miR-6872-3p gene, a congener thereof, a transcript thereof, or a variant or a derivative thereof. None of the previously known reports show that change in the expression of the gene or the transcript thereof can serve as a marker for prostate cancer.

The 75th target gene is the hsa-miR-4446-3p gene, a congener thereof, a transcript thereof, or a variant or a derivative thereof. None of the previously known reports show that change in the expression of the gene or the transcript thereof can serve as a marker for prostate cancer.

The 76th target gene is the hsa-miR-1268a gene, a congener thereof, a transcript thereof, or a variant or a derivative thereof. None of the previously known reports show that change in the expression of the gene or the transcript thereof can serve as a marker for prostate cancer.

The 77th target gene is the hsa-miR-1908-3p gene, a congener thereof, a transcript thereof, or a variant or a derivative thereof. None of the previously known reports show that change in the expression of the gene or the transcript thereof can serve as a marker for prostate cancer.

The 78th target gene is the hsa-miR-3679-5p gene, a congener thereof, a transcript thereof, or a variant or a The 79th target gene is the hsa-miR-4534 gene, a congener thereof, a transcript thereof, or a variant or a derivative thereof. None of the previously known reports show that change in the expression of the gene or the transcript thereof can serve as a marker for prostate cancer.

The 80th target gene is the hsa-miR-4675 gene, a congener thereof, a transcript thereof, or a variant or a derivative thereof. None of the previously known reports show that change in the expression of the gene or the transcript thereof can serve as a marker for prostate cancer.

The 81st target gene is the hsa-miR-7108-5p gene, a congener thereof, a transcript thereof, or a variant or a derivative thereof. None of the previously known reports show that change in the expression of the gene or the transcript thereof can serve as a marker for prostate cancer.

The 82nd target gene is the hsa-miR-6799-5p gene, a congener thereof, a transcript thereof, or a variant or a derivative thereof. None of the previously known reports show that change in the expression of the gene or the transcript thereof can serve as a marker for prostate cancer.

The 83rd target gene is the hsa-miR-4695-5p gene, a congener thereof, a transcript thereof, or a variant or a derivative thereof. None of the previously known reports show that change in the expression of the gene or the transcript thereof can serve as a marker for prostate cancer.

The 84th target gene is the hsa-miR-3178 gene, a congener thereof, a transcript thereof, or a variant or a derivative thereof. None of the previously known reports show that change in the expression of the gene or the transcript thereof can serve as a marker for prostate cancer.

The 85th target gene is the hsa-miR-5090 gene, a congener thereof, a transcript thereof, or a variant or a derivative thereof. None of the previously known reports show that change in the expression of the gene or the transcript thereof can serve as a marker for prostate cancer.

The 86th target gene is the hsa-miR-3180 gene, a congener thereof, a transcript thereof, or a variant or a derivative thereof. None of the previously known reports show that change in the expression of the gene or the transcript thereof can serve as a marker for prostate cancer.

The 87th target gene is the hsa-miR-1237-5p gene, a congener thereof, a transcript thereof, or a variant or a derivative thereof. None of the previously known reports show that change in the expression of the gene or the transcript thereof can serve as a marker for prostate cancer.

The 88th target gene is the hsa-miR-4758-5p gene, a congener thereof, a transcript thereof, or a variant or a derivative thereof. None of the previously known reports show that change in the expression of the gene or the transcript thereof can serve as a marker for prostate cancer.

The 89th target gene is the hsa-miR-3184-5p gene, a congener thereof, a transcript thereof, or a variant or a derivative thereof. None of the previously known reports show that change in the expression of the gene or the transcript thereof can serve as a marker for prostate cancer.

The 90th target gene is the hsa-miR-4286 gene, a congener thereof, a transcript thereof, or a variant or a derivative thereof. None of the previously known reports show that change in the expression of the gene or the transcript thereof can serve as a marker for prostate cancer.

The 91st target gene is the hsa-miR-6784-5p gene, a congener thereof, a transcript thereof, or a variant or a derivative thereof. None of the previously known reports show that change in the expression of the gene or the transcript thereof can serve as a marker for prostate cancer.

The 92nd target gene is the hsa-miR-6768-5p gene, a congener thereof, a transcript thereof, or a variant or a derivative thereof. None of the previously known reports show that change in the expression of the gene or the transcript thereof can serve as a marker for prostate cancer.

The 93rd target gene is the hsa-miR-6785-5p gene, a congener thereof, a transcript thereof, or a variant or a derivative thereof. None of the previously known reports show that change in the expression of the gene or the transcript thereof can serve as a marker for prostate cancer.

The 94th target gene is the hsa-miR-4706 gene, a congener thereof, a transcript thereof, or a variant or a derivative thereof. None of the previously known reports show that change in the expression of the gene or the transcript thereof can serve as a marker for prostate cancer.

The 95th target gene is the hsa-miR-711 gene, a congener thereof, a transcript thereof, or a variant or a derivative thereof. None of the previously known reports show that change in the expression of the gene or the transcript thereof can serve as a marker for prostate cancer.

The 96th target gene is the hsa-miR-1260a gene, a congener thereof, a transcript thereof, or a variant or a derivative thereof. None of the previously known reports show that change in the expression of the gene or the transcript thereof can serve as a marker for prostate cancer.

The 97th target gene is the hsa-miR-6746-5p gene, a congener thereof, a transcript thereof, or a variant or a derivative thereof. None of the previously known reports show that change in the expression of the gene or the transcript thereof can serve as a marker for prostate cancer.

The 98th target gene is the hsa-miR-6089 gene, a congener thereof, a transcript thereof, or a variant or a derivative thereof. None of the previously known reports show that change in the expression of the gene or the transcript thereof can serve as a marker for prostate cancer.

The 99th target gene is the hsa-miR-6821-5p gene, a congener thereof, a transcript thereof, or a variant or a derivative thereof. None of the previously known reports show that change in the expression of the gene or the transcript thereof can serve as a marker for prostate cancer.

The 100th target gene is the hsa-miR-4667-5p gene, a congener thereof, a transcript thereof, or a variant or a derivative thereof. None of the previously known reports show that change in the expression of the gene or the transcript thereof can serve as a marker for prostate cancer.

The 101st target gene is the hsa-miR-8069 gene, a congener thereof, a transcript thereof, or a variant or a derivative thereof. None of the previously known reports show that change in the expression of the gene or the transcript thereof can serve as a marker for prostate cancer.

The 102nd target gene is the hsa-miR-4726-5p gene, a congener thereof, a transcript thereof, or a variant or a derivative thereof. None of the previously known reports show that change in the expression of the gene or the transcript thereof can serve as a marker for prostate cancer.

The 103rd target gene is the hsa-miR-6124 gene, a congener thereof, a transcript thereof, or a variant or a derivative thereof. None of the previously known reports show that change in the expression of the gene or the transcript thereof can serve as a marker for prostate cancer.

The 104th target gene is the hsa-miR-4532 gene, a congener thereof, a transcript thereof, or a variant or a derivative thereof. None of the previously known reports show that change in the expression of the gene or the transcript thereof can serve as a marker for prostate cancer.

The 105th target gene is the hsa-miR-4486 gene, a congener thereof, a transcript thereof, or a variant or a derivative thereof. None of the previously known reports show that change in the expression of the gene or the transcript thereof can serve as a marker for prostate cancer.

The 106th target gene is the hsa-miR-4728-5p gene, a congener thereof, a transcript thereof, or a variant or a derivative thereof. None of the previously known reports show that change in the expression of the gene or the transcript thereof can serve as a marker for prostate cancer.

The 107th target gene is the hsa-miR-4508 gene, a congener thereof, a transcript thereof, or a variant or a derivative thereof. None of the previously known reports show that change in the expression of the gene or the transcript thereof can serve as a marker for prostate cancer.

The 108th target gene is the hsa-miR-128-1-5p gene, a congener thereof, a transcript thereof, or a variant or a derivative thereof. None of the previously known reports show that change in the expression of the gene or the transcript thereof can serve as a marker for prostate cancer.

The 109th target gene is the hsa-miR-4513 gene, a congener thereof, a transcript thereof, or a variant or a derivative thereof. None of the previously known reports show that change in the expression of the gene or the transcript thereof can serve as a marker for prostate cancer.

The 110th target gene is the hsa-miR-6795-5p gene, a congener thereof, a transcript thereof, or a variant or a derivative thereof. None of the previously known reports show that change in the expression of the gene or the transcript thereof can serve as a marker for prostate cancer.

The 111th target gene is the hsa-miR-4689 gene, a congener thereof, a transcript thereof, or a variant or a derivative thereof. None of the previously known reports show that change in the expression of the gene or the transcript thereof can serve as a marker for prostate cancer.

The 112th target gene is the hsa-miR-6763-5p gene, a congener thereof, a transcript thereof, or a variant or a derivative thereof. None of the previously known reports show that change in the expression of the gene or the transcript thereof can serve as a marker for prostate cancer.

The 113th target gene is the hsa-miR-8072 gene, a congener thereof, a transcript thereof, or a variant or a derivative thereof. None of the previously known reports show that change in the expression of the gene or the transcript thereof can serve as a marker for prostate cancer.

The 114th target gene is the hsa-miR-6765-5p gene, a congener thereof, a transcript thereof, or a variant or a derivative thereof. None of the previously known reports show that change in the expression of the gene or the transcript thereof can serve as a marker for prostate cancer.

The 115th target gene is the hsa-miR-4419b gene, a congener thereof, a transcript thereof, or a variant or a derivative thereof. None of the previously known reports show that change in the expression of the gene or the transcript thereof can serve as a marker for prostate cancer.

The 116th target gene is the hsa-miR-7641 gene, a congener thereof, a transcript thereof, or a variant or a derivative thereof. None of the previously known reports show that change in the expression of the gene or the transcript thereof can serve as a marker for prostate cancer.

The 117th target gene is the hsa-miR-3928-3p gene, a congener thereof, a transcript thereof, or a variant or a derivative thereof. None of the previously known reports show that change in the expression of the gene or the transcript thereof can serve as a marker for prostate cancer.

The 118th target gene is the hsa-miR-1227-5p gene, a congener thereof, a transcript thereof, or a variant or a derivative thereof. None of the previously known reports show that change in the expression of the gene or the transcript thereof can serve as a marker for prostate cancer.

The 119th target gene is the hsa-miR-4492 gene, a congener thereof, a transcript thereof, or a variant or a derivative thereof. None of the previously known reports show that change in the expression of the gene or the transcript thereof can serve as a marker for prostate cancer.

The 120th target gene is the hsa-miR-296-3p gene, a congener thereof, a transcript thereof, or a variant or a derivative thereof. None of the previously known reports show that change in the expression of the gene or the transcript thereof can serve as a marker for prostate cancer.

The 121st target gene is the hsa-miR-6769a-5p gene, a congener thereof, a transcript thereof, or a variant or a derivative thereof. None of the previously known reports show that change in the expression of the gene or the transcript thereof can serve as a marker for prostate cancer.

The 122nd target gene is the hsa-miR-6889-5p gene, a congener thereof, a transcript thereof, or a variant or a derivative thereof. None of the previously known reports show that change in the expression of the gene or the transcript thereof can serve as a marker for prostate cancer.

The 123rd target gene is the hsa-miR-4632-5p gene, a congener thereof, a transcript thereof, or a variant or a derivative thereof. None of the previously known reports show that change in the expression of the gene or the transcript thereof can serve as a marker for prostate cancer.

The 124th target gene is the hsa-miR-4505 gene, a congener thereof, a transcript thereof, or a variant or a derivative thereof. None of the previously known reports show that change in the expression of the gene or the transcript thereof can serve as a marker for prostate cancer.

The 125th target gene is the hsa-miR-3154 gene, a congener thereof, a transcript thereof, or a variant or a derivative thereof. None of the previously known reports show that change in the expression of the gene or the transcript thereof can serve as a marker for prostate cancer.

The 126th target gene is the hsa-miR-3648 gene, a congener thereof, a transcript thereof, or a variant or a derivative thereof. None of the previously known reports show that change in the expression of the gene or the transcript thereof can serve as a marker for prostate cancer.

The 127th target gene is the hsa-miR-4442 gene, a congener thereof, a transcript thereof, or a variant or a derivative thereof. None of the previously known reports show that change in the expression of the gene or the transcript thereof can serve as a marker for prostate cancer.

The 128th target gene is the hsa-miR-3141 gene, a congener thereof, a transcript thereof, or a variant or a derivative thereof. None of the previously known reports show that change in the expression of the gene or the transcript thereof can serve as a marker for prostate cancer.

The 129th target gene is the hsa-miR-7113-3p gene, a congener thereof, a transcript thereof, or a variant or a derivative thereof. None of the previously known reports show that change in the expression of the gene or the transcript thereof can serve as a marker for prostate cancer.

The 130th target gene is the hsa-miR-6819-5p gene, a congener thereof, a transcript thereof, or a variant or a derivative thereof. None of the previously known reports show that change in the expression of the gene or the transcript thereof can serve as a marker for prostate cancer.

The 131st target gene is the hsa-miR-3195 gene, a congener thereof, a transcript thereof, or a variant or a derivative thereof. None of the previously known reports show that change in the expression of the gene or the transcript thereof can serve as a marker for prostate cancer.

The 132nd target gene is the hsa-miR-1199-5p gene, a congener thereof, a transcript thereof, or a variant or a derivative thereof. None of the previously known reports show that change in the expression of the gene or the transcript thereof can serve as a marker for prostate cancer.

The 133rd target gene is the hsa-miR-6738-5p gene, a congener thereof, a transcript thereof, or a variant or a derivative thereof. None of the previously known reports show that change in the expression of the gene or the transcript thereof can serve as a marker for prostate cancer.

The 134th target gene is the hsa-miR-4656 gene, a congener thereof, a transcript thereof, or a variant or a derivative thereof. None of the previously known reports show that change in the expression of the gene or the transcript thereof can serve as a marker for prostate cancer.

The 135th target gene is the hsa-miR-6820-5p gene, a congener thereof, a transcript thereof, or a variant or a derivative thereof. None of the previously known reports show that change in the expression of the gene or the transcript thereof can serve as a marker for prostate cancer.

The 136th target gene is the hsa-miR-615-5p gene, a congener thereof, a transcript thereof, or a variant or a derivative thereof. The previously known report shows that change in the expression of the gene or the transcript thereof can serve as a marker for prostate cancer (Patent Literature 1).

The 137th target gene is the hsa-miR-486-3p gene, a congener thereof, a transcript thereof, or a variant or a derivative thereof. The previously known report shows that change in the expression of the gene or the transcript thereof can serve as a marker for prostate cancer (Patent Literature 1).

The 138th target gene is the hsa-miR-1225-3p gene, a congener thereof, a transcript thereof, or a variant or a derivative thereof. The previously known report shows that change in the expression of the gene or the transcript thereof can serve as a marker for prostate cancer (Patent Literature 1).

The 139th target gene is the hsa-miR-760 gene, a congener thereof, a transcript thereof, or a variant or a derivative thereof. The previously known report shows that change in the expression of the gene or the transcript thereof can serve as a marker for prostate cancer (Patent Literature 1).

The 140th target gene is the hsa-miR-187-5p gene, a congener thereof, a transcript thereof, or a variant or a derivative thereof. The previously known report shows that change in the expression of the gene or the transcript thereof can serve as a marker for prostate cancer (Patent Literature 1).

The 141st target gene is the hsa-miR-1203 gene, a congener thereof, a transcript thereof, or a variant or a derivative thereof. The previously known report shows that change in the expression of the gene or the transcript thereof can serve as a marker for prostate cancer (Patent Literature 1).

The 142nd target gene is the hsa-miR-7110-5p gene, a congener thereof, a transcript thereof, or a variant or a derivative thereof. The previously known report shows that change in the expression of the gene or the transcript thereof can serve as a marker for prostate cancer (Patent Literature 1).

The 143rd target gene is the hsa-miR-371a-5p gene, a congener thereof, a transcript thereof, or a variant or a derivative thereof. The previously known report shows that change in the expression of the gene or the transcript thereof can serve as a marker for prostate cancer (Patent Literature 1).

The 144th target gene is the hsa-miR-939-5p gene, a congener thereof, a transcript thereof, or a variant or a derivative thereof. The previously known report shows that change in the expression of the gene or the transcript thereof can serve as a marker for prostate cancer (Patent Literature 1).

The 145th target gene is the hsa-miR-575 gene, a congener thereof, a transcript thereof, or a variant or a derivative thereof. The previously known report shows that change in the expression of the gene or the transcript thereof can serve as a marker for prostate cancer (Patent Literature 1).

The 146th target gene is the hsa-miR-92b-5p gene, a congener thereof, a transcript thereof, or a variant or a derivative thereof. The previously known report shows that change in the expression of the gene or the transcript thereof can serve as a marker for prostate cancer (Patent Literature 2).

The 147th target gene is the hsa-miR-887-3p gene, a congener thereof, a transcript thereof, or a variant or a derivative thereof. The previously known report shows that change in the expression of the gene or the transcript thereof can serve as a marker for prostate cancer (Patent Literature 1).

The 148th target gene is the hsa-miR-920 gene, a congener thereof, a transcript thereof, or a variant or a derivative thereof. The previously known report shows that change in the expression of the gene or the transcript thereof can serve as a marker for prostate cancer (Patent Literature 1).

The 149th target gene is the hsa-miR-1915-5p gene, a congener thereof, a transcript thereof, or a variant or a derivative thereof. The previously known report shows that change in the expression of the gene or the transcript thereof can serve as a marker for prostate cancer (Patent Literature 1).

The 150th target gene is the hsa-miR-1231 gene, a congener thereof, a transcript thereof, or a variant or a derivative thereof. The previously known report shows that change in the expression of the gene or the transcript thereof can serve as a marker for prostate cancer (Patent Literature 1).

The 151st target gene is the hsa-miR-663b gene, a congener thereof, a transcript thereof, or a variant or a derivative thereof. The previously known report shows that change in the expression of the gene or the transcript thereof can serve as a marker for prostate cancer (Patent Literature 1).

The 152nd target gene is the hsa-miR-1225-5p gene, a congener thereof, a transcript thereof, or a variant or a derivative thereof. The previously known report shows that change in the expression of the gene or the transcript thereof can serve as a marker for prostate cancer (Patent Literature 1).

The 153rd target gene is the hsa-miR-4763-3p gene, a congener thereof, a transcript thereof, or a variant or a derivative thereof. None of the previously known reports show that change in the expression of the gene or the transcript thereof can serve as a marker for prostate cancer.

The 154th target gene is the hsa-miR-3656 gene, a congener thereof, a transcript thereof, or a variant or a derivative thereof. None of the previously known reports show that change in the expression of the gene or the transcript thereof can serve as a marker for prostate cancer.

The 155th target gene is the hsa-miR-4488 gene, a congener thereof, a transcript thereof, or a variant or a derivative thereof. None of the previously known reports show that change in the expression of the gene or the transcript thereof can serve as a marker for prostate cancer.

The 156th target gene is the hsa-miR-125a-3p gene, a congener thereof, a transcript thereof, or a variant or a derivative thereof. The previously known report shows that change in the expression of the gene or the transcript thereof can serve as a marker for prostate cancer (Patent Literature 1).

The 157th target gene is the hsa-miR-1469 gene, a congener thereof, a transcript thereof, or a variant or a derivative thereof. None of the previously known reports show that change in the expression of the gene or the transcript thereof can serve as a marker for prostate cancer.

The 158th target gene is the hsa-miR-1228-5p gene, a congener thereof, a transcript thereof, or a variant or a derivative thereof. The previously known report shows that change in the expression of the gene or the transcript thereof can serve as a marker for prostate cancer (Patent Literature 1).

The 159th target gene is the hsa-miR-6798-5p gene, a congener thereof, a transcript thereof, or a variant or a derivative thereof. None of the previously known reports show that change in the expression of the gene or the transcript thereof can serve as a marker for prostate cancer.

The 160th target gene is the hsa-miR-1268b gene, a congener thereof, a transcript thereof, or a variant or a derivative thereof. The previously known report shows that change in the expression of the gene or the transcript thereof can serve as a marker for prostate cancer (Patent Literature 1).

The 161st target gene is the hsa-miR-6732-5p gene, a congener thereof, a transcript thereof, or a variant or a derivative thereof. None of the previously known reports show that change in the expression of the gene or the transcript thereof can serve as a marker for prostate cancer.

The 162nd target gene is the hsa-miR-1915-3p gene, a congener thereof, a transcript thereof, or a variant or a derivative thereof. The previously known report shows that change in the expression of the gene or the transcript thereof can serve as a marker for prostate cancer (Patent Literature 1).

The 163rd target gene is the hsa-miR-4433b-3p gene, a congener thereof, a transcript thereof, or a variant or a derivative thereof. None of the previously known reports show that change in the expression of the gene or the transcript thereof can serve as a marker for prostate cancer.

The 164th target gene is the hsa-miR-1207-5p gene, a congener thereof, a transcript thereof, or a variant or a derivative thereof. The previously known report shows that change in the expression of the gene or the transcript thereof can serve as a marker for prostate cancer (Patent Literature 1).

The 165th target gene is the hsa-miR-4433-3p gene, a congener thereof, a transcript thereof, or a variant or a derivative thereof. None of the previously known reports show that change in the expression of the gene or the transcript thereof can serve as a marker for prostate cancer.

The 166th target gene is the hsa-miR-6879-5p gene, a congener thereof, a transcript thereof, or a variant or a derivative thereof. None of the previously known reports show that change in the expression of the gene or the transcript thereof can serve as a marker for prostate cancer.

The 167th target gene is the hsa-miR-4417 gene, a congener thereof, a transcript thereof, or a variant or a derivative thereof. None of the previously known reports show that change in the expression of the gene or the transcript thereof can serve as a marker for prostate cancer.

The 168th target gene is the hsa-miR-30c-1-3p gene, a congener thereof, a transcript thereof, or a variant or a derivative thereof. The previously known report shows that change in the expression of the gene or the transcript thereof can serve as a marker for prostate cancer (Patent Literature 1).

The 169th target gene is the hsa-miR-4638-5p gene, a congener thereof, a transcript thereof, or a variant or a derivative thereof. None of the previously known reports show that change in the expression of the gene or the transcript thereof can serve as a marker for prostate cancer.

The 170th target gene is the hsa-miR-6088 gene, a congener thereof, a transcript thereof, or a variant or a derivative thereof. None of the previously known reports show that change in the expression of the gene or the transcript thereof can serve as a marker for prostate cancer.

The 171st target gene is the hsa-miR-4270 gene, a congener thereof, a transcript thereof, or a variant or a derivative thereof. None of the previously known reports show that change in the expression of the gene or the transcript thereof can serve as a marker for prostate cancer.

The 172nd target gene is the hsa-miR-6782-5p gene, a congener thereof, a transcript thereof, or a variant or a derivative thereof. None of the previously known reports show that change in the expression of the gene or the transcript thereof can serve as a marker for prostate cancer.

The 173rd target gene is the hsa-miR-665 gene, a congener thereof, a transcript thereof, or a variant or a derivative thereof. The previously known report shows that change in the expression of the gene or the transcript thereof can serve as a marker for prostate cancer (Patent Literature 1).

The 174th target gene is the hsa-miR-486-5p gene, a congener thereof, a transcript thereof, or a variant or a derivative thereof. The previously known report shows that change in the expression of the gene or the transcript thereof can serve as a marker for prostate cancer (Patent Literature 1).

The 175th target gene is the hsa-miR-4655-5p gene, a congener thereof, a transcript thereof, or a variant or a derivative thereof. None of the previously known reports show that change in the expression of the gene or the transcript thereof can serve as a marker for prostate cancer.

The 176th target gene is the hsa-miR-1275 gene, a congener thereof, a transcript thereof, or a variant or a derivative thereof. The previously known report shows that change in the expression of the gene or the transcript thereof can serve as a marker for prostate cancer (Patent Literature 1).

The 177th target gene is the hsa-miR-6806-5p gene, a congener thereof, a transcript thereof, or a variant or a derivative thereof. None of the previously known reports show that change in the expression of the gene or the transcript thereof can serve as a marker for prostate cancer.

The 178th target gene is the hsa-miR-614 gene, a congener thereof, a transcript thereof, or a variant or a derivative thereof. The previously known report shows that change in the expression of the gene or the transcript thereof can serve as a marker for prostate cancer (Patent Literature 1).

The 179th target gene is the hsa-miR-3937 gene, a congener thereof, a transcript thereof, or a variant or a derivative thereof. None of the previously known reports show that change in the expression of the gene or the transcript thereof can serve as a marker for prostate cancer.

The 180th target gene is the hsa-miR-6752-5p gene, a congener thereof, a transcript thereof, or a variant or a derivative thereof. None of the previously known reports show that change in the expression of the gene or the transcript thereof can serve as a marker for prostate cancer.

The 181st target gene is the hsa-miR-6771-5p gene, a congener thereof, a transcript thereof, or a variant or a derivative thereof. None of the previously known reports show that change in the expression of the gene or the transcript thereof can serve as a marker for prostate cancer.

The 182nd target gene is the hsa-miR-4450 gene, a congener thereof, a transcript thereof, or a variant or a derivative thereof. None of the previously known reports show that change in the expression of the gene or the transcript thereof can serve as a marker for prostate cancer.

The 183rd target gene is the hsa-miR-211-3p gene, a congener thereof, a transcript thereof, or a variant or a derivative thereof. The previously known report shows that change in the expression of the gene or the transcript thereof can serve as a marker for prostate cancer (Patent Literature 1).

The 184th target gene is the hsa-miR-663a gene, a congener thereof, a transcript thereof, or a variant or a derivative thereof. The previously known report shows that change in the expression of the gene or the transcript thereof can serve as a marker for prostate cancer (Patent Literature 1).

The 185th target gene is the hsa-miR-6842-5p gene, a congener thereof, a transcript thereof, or a variant or a derivative thereof. None of the previously known reports show that change in the expression of the gene or the transcript thereof can serve as a marker for prostate cancer.

The 186th target gene is the hsa-miR-7114-5p gene, a congener thereof, a transcript thereof, or a variant or a derivative thereof. None of the previously known reports show that change in the expression of the gene or the transcript thereof can serve as a marker for prostate cancer.

The 187th target gene is the hsa-miR-6779-5p gene, a congener thereof, a transcript thereof, or a variant or a derivative thereof. None of the previously known reports show that change in the expression of the gene or the transcript thereof can serve as a marker for prostate cancer.

The 580th target gene is the hsa-miR-204-3p gene, a congener thereof, a transcript thereof, or a variant or a derivative thereof. None of the previously known reports show that change in the expression of the gene or the transcript thereof can serve as a marker for prostate cancer.

The 581st target gene is the hsa-miR-642a-3p gene, a congener thereof, a transcript thereof, or a variant or a derivative thereof. None of the previously known reports show that change in the expression of the gene or the transcript thereof can serve as a marker for prostate cancer.

The 582nd target gene is the hsa-miR-762 gene, a congener thereof, a transcript thereof, or a variant or a derivative thereof. None of the previously known reports show that change in the expression of the gene or the transcript thereof can serve as a marker for prostate cancer.

The 583rd target gene is the hsa-miR-1202 gene, a congener thereof, a transcript thereof, or a variant or a derivative thereof. None of the previously known reports show that change in the expression of the gene or the transcript thereof can serve as a marker for prostate cancer.

The 584th target gene is the hsa-miR-3162-5p gene, a congener thereof, a transcript thereof, or a variant or a derivative thereof. None of the previously known reports show that change in the expression of the gene or the transcript thereof can serve as a marker for prostate cancer.

The 585th target gene is the hsa-miR-3196 gene, a congener thereof, a transcript thereof, or a variant or a derivative thereof. None of the previously known reports show that change in the expression of the gene or the transcript thereof can serve as a marker for prostate cancer.

The 586th target gene is the hsa-miR-3622a-5p gene, a congener thereof, a transcript thereof, or a variant or a derivative thereof. None of the previously known reports show that change in the expression of the gene or the transcript thereof can serve as a marker for prostate cancer.

The 587th target gene is the hsa-miR-3665 gene, a congener thereof, a transcript thereof, or a variant or a derivative thereof. None of the previously known reports show that change in the expression of the gene or the transcript thereof can serve as a marker for prostate cancer.

The 588th target gene is the hsa-miR-3940-5p gene, a congener thereof, a transcript thereof, or a variant or a derivative thereof. None of the previously known reports show that change in the expression of the gene or the transcript thereof can serve as a marker for prostate cancer.

The 589th target gene is the hsa-miR-4294 gene, a congener thereof, a transcript thereof, or a variant or a derivative thereof. None of the previously known reports show that change in the expression of the gene or the transcript thereof can serve as a marker for prostate cancer.

The 590th target gene is the hsa-miR-4466 gene, a congener thereof, a transcript thereof, or a variant or a derivative thereof. None of the previously known reports show that change in the expression of the gene or the transcript thereof can serve as a marker for prostate cancer.

The 591st target gene is the hsa-miR-4476 gene, a congener thereof, a transcript thereof, or a variant or a derivative thereof. None of the previously known reports show that change in the expression of the gene or the transcript thereof can serve as a marker for prostate cancer.

The 592nd target gene is the hsa-miR-4723-5p gene, a congener thereof, a transcript thereof, or a variant or a derivative thereof. None of the previously known reports show that change in the expression of the gene or the transcript thereof can serve as a marker for prostate cancer.

The 593rd target gene is the hsa-miR-4725-3p gene, a congener thereof, a transcript thereof, or a variant or a derivative thereof. None of the previously known reports show that change in the expression of the gene or the transcript thereof can serve as a marker for prostate cancer.

The 594th target gene is the hsa-miR-4730 gene, a congener thereof, a transcript thereof, or a variant or a derivative thereof. None of the previously known reports show that change in the expression of the gene or the transcript thereof can serve as a marker for prostate cancer.

The 595th target gene is the hsa-miR-4739 gene, a congener thereof, a transcript thereof, or a variant or a derivative thereof. None of the previously known reports show that change in the expression of the gene or the transcript thereof can serve as a marker for prostate cancer.

The 596th target gene is the hsa-miR-4787-5p gene, a congener thereof, a transcript thereof, or a variant or a derivative thereof. None of the previously known reports show that change in the expression of the gene or the transcript thereof can serve as a marker for prostate cancer.

The 597th target gene is the hsa-miR-5787 gene, a congener thereof, a transcript thereof, or a variant or a derivative thereof. None of the previously known reports show that change in the expression of the gene or the transcript thereof can serve as a marker for prostate cancer.

The 598th target gene is the hsa-miR-6085 gene, a congener thereof, a transcript thereof, or a variant or a derivative thereof. None of the previously known reports show that change in the expression of the gene or the transcript thereof can serve as a marker for prostate cancer.

The 599th target gene is the hsa-miR-6717-5p gene, a congener thereof, a transcript thereof, or a variant or a derivative thereof. None of the previously known reports show that change in the expression of the gene or the transcript thereof can serve as a marker for prostate cancer.

The 600th target gene is the hsa-miR-6724-5p gene, a congener thereof, a transcript thereof, or a variant or a derivative thereof. None of the previously known reports show that change in the expression of the gene or the transcript thereof can serve as a marker for prostate cancer.

The 601st target gene is the hsa-miR-6777-5p gene, a congener thereof, a transcript thereof, or a variant or a derivative thereof. None of the previously known reports show that change in the expression of the gene or the transcript thereof can serve as a marker for prostate cancer.

The 602nd target gene is the hsa-miR-6778-5p gene, a congener thereof, a transcript thereof, or a variant or a derivative thereof. None of the previously known reports show that change in the expression of the gene or the transcript thereof can serve as a marker for prostate cancer.

The 603rd target gene is the hsa-miR-6787-5p gene, a congener thereof, a transcript thereof, or a variant or a derivative thereof. None of the previously known reports show that change in the expression of the gene or the transcript thereof can serve as a marker for prostate cancer.

The 604th target gene is the hsa-miR-6789-5p gene, a congener thereof, a transcript thereof, or a variant or a derivative thereof. None of the previously known reports show that change in the expression of the gene or the transcript thereof can serve as a marker for prostate cancer.

The 605th target gene is the hsa-miR-6845-5p gene, a congener thereof, a transcript thereof, or a variant or a derivative thereof. None of the previously known reports show that change in the expression of the gene or the transcript thereof can serve as a marker for prostate cancer.

The 606th target gene is the hsa-miR-6893-5p gene, a congener thereof, a transcript thereof, or a variant or a derivative thereof. None of the previously known reports show that change in the expression of the gene or the transcript thereof can serve as a marker for prostate cancer.

The 607th target gene is the hsa-miR-16-5p gene, a congener thereof, a transcript thereof, or a variant or a derivative thereof. The previously known report shows that change in the expression of the gene or the transcript thereof can serve as a marker for prostate cancer (Patent Literature 2).

The 608th target gene is the hsa-miR-423-5p gene, a congener thereof, a transcript thereof, or a variant or a derivative thereof. The previously known report shows that change in the expression of the gene or the transcript thereof can serve as a marker for prostate cancer (Patent Literature 2).

The 609th target gene is the hsa-miR-451a gene, a congener thereof, a transcript thereof, or a variant or a derivative thereof. The previously known report shows that change in the expression of the gene or the transcript thereof can serve as a marker for prostate cancer (Patent Literature 2).

The 610th target gene is the hsa-miR-564 gene, a congener thereof, a transcript thereof, or a variant or a derivative thereof. The previously known report shows that change in the expression of the gene or the transcript thereof can serve as a marker for prostate cancer (Patent Literature 2).

The 611th target gene is the hsa-miR-671-5p gene, a congener thereof, a transcript thereof, or a variant or a derivative thereof. The previously known report shows that change in the expression of the gene or the transcript thereof can serve as a marker for prostate cancer (Patent Literature 2).

2. Nucleic Acid Probe or Primer for Detection of Prostate Cancer

In the present invention, a nucleic acid capable of specifically binding to any of the target nucleic acids as the prostate cancer markers described above can be used as a nucleic acid, for example, a nucleic acid probe or a primer, for the detection or diagnosis of prostate cancer.

In the present invention, the nucleic acid probe or the primer that can be used for detecting prostate cancer or for diagnosing prostate cancer permits qualitative and/or quantitative measurement of the presence, expression level, or abundance of any of the target nucleic acids as the prostate cancer markers described above, for example, human-derived hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p, or hsa-miR-6893-5p, or combinations thereof, congeners thereof, transcripts thereof, or variants or derivatives thereof.

The expression level of each target nucleic acid described above is increased or decreased (hereinafter, referred to as "increased/decreased") according to the type of the target nucleic acid(s) in a subject having prostate cancer as compared with a healthy subject. Hence, the nucleic acid of the present invention can be effectively used for measuring the expression level of the target nucleic acid(s) in a body fluid derived from a subject (e.g., a human) suspected of having prostate cancer and a body fluid derived from a healthy subject and detecting prostate cancer by the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 135 and 580 to 606, or a primer for amplifying a polynucleotide consisting of a nucleotide sequence represented by at least one of SEQ ID NOs: 1 to 135 and 580 to 606.

The nucleic acid probe or the primer that can be further used in the present invention can comprise a nucleic acid probe capable of specifically binding to a polynucleotide consisting of a nucleotide sequence represented by at least one of SEQ ID NOs: 136 to 152 and 607 to 611, or a primer for amplifying a polynucleotide consisting of a nucleotide sequence represented by at least one of SEQ ID NOs: 136 to 152 and 607 to 611.

The nucleic acid probe or the primer that can be further used in the present invention can comprise a nucleic acid probe capable of specifically binding to a polynucleotide consisting of a nucleotide sequence represented by at least one of SEQ ID NOs: 153 to 187, or a primer for amplifying a polynucleotide consisting of a nucleotide sequence represented by at least one of SEQ ID NOs: 153 to 187.

Specifically, these nucleic acid probes or primers comprise a combination of one or more polynucleotides selected from a polynucleotide group comprising nucleotide sequences represented by any of SEQ ID NOs: 1 to 684 or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the prostate cancer markers as target nucleic acids.

More specifically, examples of the nucleic acid probe or the primer that can be used in the present invention include one or more polynucleotide(s) selected from the group consisting of the following polynucleotides (a) to (e):
(a) a polynucleotide consisting of a nucleotide sequence represented by any of SEQ ID NOs: 1 to 135, 580 to 606 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 135, 580 to 606,
(c) a polynucleotide consisting of a nucleotide sequence complementary to a nucleotide sequence represented by any of SEQ ID NOs: 1 to 135, 580 to 606 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 135, 580 to 606 or a nucleotide sequence derived from the nucleotide sequence by the replacement of u with t, and
(e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise any of the following polynucleotides (f) to (j):
(f) a polynucleotide consisting of a nucleotide sequence represented by any of SEQ ID NOs: 136 to 152, 607 to 611 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 136 to 152, 607 to 611,
(h) a polynucleotide consisting of a nucleotide sequence complementary to a nucleotide sequence represented by any of SEQ ID NOs: 136 to 152, 607 to 611 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 136 to 152, 607 to 611 or a nucleotide sequence derived from the nucleotide sequence by the replacement of u with t, and
(j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise any of the following polynucleotides (k) to (o):
(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 153 to 187,
(m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 153 to 187 or a nucleotide sequence derived from the nucleotide sequence by the replacement of u with t, and
(o) a polynucleotide hybridizing under stringent conditions to any of the polynucleotides (k) to (n).

For these polynucleotides, the "fragment thereof comprising 15 or more consecutive nucleotides" can contain the number of nucleotides in the range of, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p, hsa-miR-6893-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564, hsa-miR-671-5p, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p represented by SEQ ID NOs: 1 to 187, and 580 to 611 are known in the art, and their obtainment methods are also known as mentioned above. Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 bases can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probes and the primers for detecting the polynucleotides consisting of a nucleotide sequence represented by any of SEQ ID NOs: 1 to 187, and 580 to 611 do not exist as miRNAs or precursors thereof in vivo. For example, the nucleotide sequences represented by SEQ ID NO: 7 and SEQ ID NO: 9 are formed from the precursor represented by SEQ ID NO: 194. This precursor has a hairpin-like structure as shown in FIG. 1, and the nucleotide sequences represented by SEQ ID NO: 7 and SEQ ID NO: 9 have mismatch sequences with each other. Therefore, a nucleotide sequence completely complementary to the nucleotide sequence represented by SEQ ID NO: 7 or SEQ ID NO: 9 does not naturally occur in vivo. Likewise, the nucleic acid probe and the primer for detecting the nucleotide sequence represented by any of SEQ ID NOs: 1 to 187, and 580 to 611 each have an artificial nucleotide sequence that does not exist in vivo.

3. Kit or Device for Detection of Prostate Cancer

The present invention also provides a kit or a device for the detection of prostate cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a prostate cancer marker.

The target nucleic acid as a prostate cancer marker according to the present invention is selected from the following group 1:

miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR- 4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

An additional target nucleic acid that can be optionally used in the measurement is selected from the following group 2: miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

An additional target nucleic acid that can be optionally further used in the measurement is selected from the following group 3: miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

The kit or the device of the present invention comprises nucleic acid(s) capable of specifically binding to any of the target nucleic acids as the prostate cancer markers described above, preferably one or more polynucleotide(s) selected from the nucleic acid probes or the primers described in the preceding Section 2, specifically, the polynucleotides described in the preceding Section 2, or variant(s) thereof, etc.

Specifically, the kit or the device of the present invention can comprise at least one or more polynucleotide(s) comprising (or consisting of) a nucleotide sequence represented by any of SEQ ID NOs: 1 to 135, 580 to 606 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 136 to 152, 607 to 611 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 153 to 187 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):
(1) a polynucleotide comprising 15 or more consecutive nucleotides in a nucleotide sequence derived from a nucleotide sequence represented by any of SEQ ID NOs: 1 to 135, 580 to 606 by the replacement of u with t, or a complementary sequence thereof;
(2) a polynucleotide comprising 15 or more consecutive nucleotides in a nucleotide sequence derived from a nucleotide sequence represented by any of SEQ ID NOs: 136 to 152, 607 to 611 by the replacement of u with t, or a complementary sequence thereof; and
(3) a polynucleotide comprising 15 or more consecutive nucleotides in a nucleotide sequence derived from a nucleotide sequence represented by any of SEQ ID NOs: 153 to 187 by the replacement of u with t, or a complementary sequence thereof.

In a preferred embodiment, the polynucleotide is a polynucleotide consisting of a nucleotide sequence represented by any of SEQ ID NOs: 1 to 135, 580 to 606 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 136 to 152, 607 to 611 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 153 to 187 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range of, for example, 15 consecutive nucleotides to less than the total number of bases of the sequence, 17 consecutive nucleotides to less than the total number of bases of the sequence, or 19 consecutive nucleotides to less than the total number of bases of the sequence, in the nucleotide sequence of each polynucleotide.

Specific examples of the aforementioned polynucleotide combination constituting the kit or the device of the present invention can include combinations of 1, 2, 3, 4, 5, 6, 7, 8, 9, 10 or more of the polynucleotides consisting of nucleotide sequences represented by SEQ ID NOs as shown in Table 1 (SEQ ID NOs: 1 to 187 and 580 to 611 corresponding to the miRNA markers in the table). However, these are given merely for illustrative purposes, and various other possible combinations are included in the present invention.

The aforementioned combination constituting the kit or the device for discriminating a prostate cancer patient from a healthy subject according to the present invention is desirably, for example, a combination of two or more of the polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a prostate cancer patient from a healthy subject is preferably a combination comprising at least one or more of newly found polynucleotides consisting of the nucleotide sequences represented by SEQ ID NOs: 1 to 135, among the combinations constituted by two of the polynucleotides consisting of the nucleotide sequences represented by SEQ ID NOs: 1 to 187, and 580 to 611.

The combination of polynucleotides with cancer type specificity capable of discriminating a prostate cancer patient not only from a healthy subject but also from other cancer patients is preferably, for example, a combination of multiple polynucleotides comprising at least one polynucleotide selected from the group consisting of polynucleotides of SEQ ID NOs: 1, 3, 4, 5, 6, 7, 9, 10, 12, 14, 15, 16, 17, 18, 20, 24, 29, 35, 37, 42, 51, 55, 58, 61, 63, 64, 67, 70, 72, 79, 82, 89, 91, 97, 98, 101, 103, 104, 112, 113, 114, 116, 119, 126, 135, 136, 139, 140, 141, 145, 147, 154, 155, 156, 158, 169, 173, 175, 178, 182, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610 and 611 (hereinafter, this group is referred to as "cancer type-specific polynucleotide group 1"), with any of the polynucleotides of the other SEQ ID NOs.

The combination of polynucleotides with cancer type specificity capable of discriminating a prostate cancer patient not only from a healthy subject but also from other cancer patients is more preferably a combination of multiple polynucleotides selected from the cancer type-specific polynucleotide group 1.

The combination of polynucleotides with cancer type specificity capable of discriminating a prostate cancer patient not only from a healthy subject but also from other cancer patients is more preferably a combination comprising at least one or more polynucleotide(s) selected from the group consisting of polynucleotides of SEQ ID NOs: 1, 12, 16, 37, 42, 63, 119, 126, 139 173, 178, 599. 609, and 611 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the aforementioned polynucleotides with cancer type specificity used in the combination can be 1, 2, 3, 4, 5, 6, 7, 8, 9, 10 or more for the combination and is more preferably 4 or more for the combination. Usually, the combination of 4 of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of three polynucleotides selected from the cancer type-specific polynucleotide group 1 or complementary sequences thereof will be listed below.

(1) a combination of SEQ ID NOs: 1, 63, 139, and 600 (markers: hsa-miR-4443, hsa-miR-4707-3p, hsa-miR-760, and hsa-miR-6724-5p);

(2) a combination of SEQ ID NOs: 1, 12, 63, and 599 (markers: hsa-miR-4443, hsa-miR-4745-5p, hsa-miR-4707-3p, and hsa-miR-6717-5p);

(3) a combination of SEQ ID NOs: 1, 141, 173, and 599 (markers: hsa-miR-4443, hsa-miR-1203, hsa-miR-665, and hsa-miR-6717-5p);

(4) a combination of SEQ ID NOs: 1, 16, 139, and 178 (markers: hsa-miR-4443, hsa-miR-92a-2-5p, hsa-miR-760, and hsa-miR-614); and (5) a combination of SEQ ID NOs: 1, 63, 173, and 599 (markers: hsa-miR-4443, hsa-miR-4707-3p, hsa-miR-665, and hsa-miR-6717-5p).

Non-limiting examples of the combination of the polynucleotide consisting of the nucleotide sequence represented by SEQ ID NO: 12 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 42, 63, and 609 (markers: hsa-miR-4745-5p, hsa-miR-4525, hsa-miR-4707-3p, and hsa-miR-451a);

(2) a combination of SEQ ID NOs: 12, 16, 135, and 156 (markers: hsa-miR-4745-5p, hsa-miR-92a-2-5p, hsa-miR-6820-5p, and hsa-miR-125a-3p);

(3) a combination of SEQ ID NOs: 12, 16, 169, and 178 (markers: hsa-miR-4745-5p, hsa-miR-92a-2-5p, hsa-miR-4638-5p, and hsa-miR-614);

(4) a combination of SEQ ID NOs: 12, 16, 139, and 601 (markers: hsa-miR-4745-5p, hsa-miR-92a-2-5p, hsa-miR-760, and hsa-miR-6777-5p); and (5) a combination of SEQ ID NOs: 12, 16, 42, and 607 (markers: hsa-miR-4745-5p, hsa-miR-92a-2-5p, hsa-miR-4525, and hsa-miR-16-5p).

Non-limiting examples of the combination of the polynucleotide consisting of the nucleotide sequence represented by SEQ ID NO: 16 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 18, 139, and 178 (markers: hsa-miR-92a-2-5p, hsa-miR-4448, hsa-miR-760, and hsa-miR-614);

(2) a combination of SEQ ID NOs: 12, 16, 37, and 178 (markers: hsa-miR-4745-5p, hsa-miR-92a-2-5p, hsa-miR-3619-3p, and hsa-miR-614);

(3) a combination of SEQ ID NOs: 12, 16, 37, and 599 (markers: hsa-miR-4745-5p, hsa-miR-92a-2-5p, hsa-miR-3619-3p, and hsa-miR-6717-5p);

(4) a combination of SEQ ID NOs: 12, 16, 37, and 97 (markers: hsa-miR-4745-5p, hsa-miR-92a-2-5p, hsa-miR-3619-3p, and hsa-miR-6746-5p); and (5) a combination of SEQ ID NOs: 12, 14, 16, and 599 (markers: hsa-miR-4745-5p, hsa-miR-3663-3p, hsa-miR-92a-2-5p, and hsa-miR-6717-5p).

Non-limiting examples of the combination of the polynucleotide consisting of the nucleotide sequence represented by SEQ ID NO: 37 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 37, 63, 139, and 611 (markers: hsa-miR-3619-3p, hsa-miR-4707-3p, hsa-miR-760, and hsa-miR-671-5p);

(2) a combination of SEQ ID NOs: 37, 42, 63, and 178 (markers: hsa-miR-3619-3p, hsa-miR-4525, hsa-miR-4707-3p, and hsa-miR-614);

(3) a combination of SEQ ID NOs: 37, 42, 63, and 599 (markers: hsa-miR-3619-3p, hsa-miR-4525, hsa-miR-4707-3p, and hsa-miR-6717-5p);

(4) a combination of SEQ ID NOs: 37, 42, 63, and 139 (markers: hsa-miR-3619-3p, hsa-miR-4525, hsa-miR-4707-3p, and hsa-miR-760); and (5) a combination of SEQ ID NOs: 12, 16, 37, and 603 (markers: hsa-miR-4745-5p, hsa-miR-92a-2-5p, hsa-miR-3619-3p, and hsa-miR-6787-5p).

Non-limiting examples of the combination of the polynucleotide consisting of the nucleotide sequence represented by SEQ ID NO: 42 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 42, 63, 607, and 611 (markers: hsa-miR-4525, hsa-miR-4707-3p, hsa-miR-16-5p, and hsa-miR-671-5p);

(2) a combination of SEQ ID NOs: 42, 63, 609, and 611 (markers: hsa-miR-4525, hsa-miR-4707-3p, hsa-miR-451a, and hsa-miR-671-5p);

(3) a combination of SEQ ID NOs: 42, 63, 173, and 599 (markers: hsa-miR-4525, hsa-miR-4707-3p, hsa-miR-665, and hsa-miR-6717-5p);

(4) a combination of SEQ ID NOs: 12, 16, 42, and 609 (markers: hsa-miR-4745-5p, hsa-miR-92a-2-5p, hsa-miR-4525, and hsa-miR-451a); and (5) a combination of SEQ ID NOs: 42, 63, 91, and 609 (markers: hsa-miR-4525, hsa-miR-4707-3p, hsa-miR-6784-5p, and hsa-miR-451a).

Non-limiting examples of the combination of the polynucleotide consisting of the nucleotide sequence represented by SEQ ID NO: 63 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 10, 42, 63, and 599 (markers: hsa-miR-642b-3p, hsa-miR-4525, hsa-miR-4707-3p, and hsa-miR-6717-5p);

(2) a combination of SEQ ID NOs: 42, 63, 599, and 609 (markers: hsa-miR-4525, hsa-miR-4707-3p, hsa-miR-6717-5p, and hsa-miR-451a);

(3) a combination of SEQ ID NOs: 42, 63, 583, and 609 (markers: hsa-miR-4525, hsa-miR-4707-3p, hsa-miR-1202, and hsa-miR-451a);

(4) a combination of SEQ ID NOs: 37, 42, 63, and 611 (markers: hsa-miR-3619-3p, hsa-miR-4525, hsa-miR-4707-3p, and hsa-miR-671-5p); and (5) a combination of SEQ ID NOs: 12, 63, 70, and 599 (markers: hsa-miR-4745-5p, hsa-miR-4707-3p, hsa-miR-6756-5p, and hsa-miR-6717-5p).

Non-limiting examples of the combination of the polynucleotide consisting of the nucleotide sequence represented by SEQ ID NO: 119 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 16, 37, and 119 (markers: hsa-miR-4745-5p, hsa-miR-92a-2-5p, hsa-miR-3619-3p, and hsa-miR-4492);

(2) a combination of SEQ ID NOs: 37, 63, 119, and 584 (markers: hsa-miR-3619-3p, hsa-miR-4707-3p, hsa-miR-4492, and hsa-miR-3162-5p);

(3) a combination of SEQ ID NOs: 63, 119, 173, and 178 (markers: hsa-miR-4707-3p, hsa-miR-4492, hsa-miR-665, and hsa-miR-614);

(4) a combination of SEQ ID NOs: 63, 119, 158, and 173 (markers: hsa-miR-4707-3p, hsa-miR-4492, hsa-miR-1228-5p, and hsa-miR-665); and (5) a combination of SEQ ID NOs: 63, 119, 173, and 605 (markers: hsa-miR-4707-3p, hsa-miR-4492, hsa-miR-665, and hsa-miR-6845-5p).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 126, 597, and 599 (markers: hsa-miR-92a-2-5p, hsa-miR-3648, hsa-miR-5787, and hsa-miR-6717-5p);

(2) a combination of SEQ ID NOs: 16, 42, 126, and 599 (markers: hsa-miR-92a-2-5p, hsa-miR-4525, hsa-miR-3648, and hsa-miR-6717-5p);

(3) a combination of SEQ ID NOs: 16, 126, 139, and 601 (markers: hsa-miR-92a-2-5p, hsa-miR-3648, hsa-miR-760, and hsa-miR-6777-5p);

(4) a combination of SEQ ID NOs: 16, 126, 593, and 599 (markers: hsa-miR-92a-2-5p, hsa-miR-3648, hsa-miR-4725-3p, and hsa-miR-6717-5p); and (5) a combination of SEQ ID NOs: 15, 16, 126, and 599 (markers: hsa-miR-3131, hsa-miR-92a-2-5p, hsa-miR-3648, and hsa-miR-6717-5p).

Non-limiting examples of the combination of the polynucleotide consisting of the nucleotide sequence represented by SEQ ID NO: 139 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 37, 63, 139, and 584 (markers: hsa-miR-3619-3p, hsa-miR-4707-3p, hsa-miR-760, and hsa-miR-3162-5p);
(2) a combination of SEQ ID NOs: 63, 139, 173, and 178 (markers: hsa-miR-4707-3p, hsa-miR-760, hsa-miR-665, and hsa-miR-614);
(3) a combination of SEQ ID NOs: 16, 63, 139, and 601 (markers: hsa-miR-92a-2-5p, hsa-miR-4707-3p, hsa-miR-760, and hsa-miR-6777-5p);
(4) a combination of SEQ ID NOs: 37, 63, 139, and 600 (markers: hsa-miR-3619-3p, hsa-miR-4707-3p, hsa-miR-760, and hsa-miR-6724-5p); and
(5) a combination of SEQ ID NOs: 16, 139, 178, and 586 (markers: hsa-miR-92a-2-5p, hsa-miR-760, hsa-miR-614, and hsa-miR-3622a-5p).

Non-limiting examples of the combination of the polynucleotide consisting of the nucleotide sequence represented by SEQ ID NO: 173 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 63, 139, 173, and 599 (markers: hsa-miR-4707-3p, hsa-miR-760, hsa-miR-665, and hsa-miR-6717-5p);
(2) a combination of SEQ ID NOs: 63, 119, 173, and 581 (markers: hsa-miR-4707-3p, hsa-miR-4492, hsa-miR-665, and hsa-miR-642a-3p);
(3) a combination of SEQ ID NOs: 63, 173, 582, and 599 (markers: hsa-miR-4707-3p, hsa-miR-665, hsa-miR-762, and hsa-miR-6717-5p);
(4) a combination of SEQ ID NOs: 63, 136, 173, and 599 (markers: hsa-miR-4707-3p, hsa-miR-615-5p, hsa-miR-665, and hsa-miR-6717-5p); and
(5) a combination of SEQ ID NOs: 29, 63, 173, and 178 (markers: hsa-miR-6726-5p, hsa-miR-4707-3p, hsa-miR-665, and hsa-miR-614).

Non-limiting examples of the combination of the polynucleotide consisting of the nucleotide sequence represented by SEQ ID NO: 178 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 139, 178, and 601 (markers: hsa-miR-92a-2-5p, hsa-miR-760, hsa-miR-614, and hsa-miR-6777-5p);
(2) a combination of SEQ ID NOs: 16, 37, 139, and 178 (markers: hsa-miR-92a-2-5p, hsa-miR-3619-3p, hsa-miR-760, and hsa-miR-614);
(3) a combination of SEQ ID NOs: 1, 12, 16, and 178 (markers: hsa-miR-4443, hsa-miR-4745-5p, hsa-miR-92a-2-5p, and hsa-miR-614);
(4) a combination of SEQ ID NOs: 1, 63, 173, and 178 (markers: hsa-miR-4443, hsa-miR-4707-3p, hsa-miR-665, and hsa-miR-614); and
(5) a combination of SEQ ID NOs: 16, 139, 178, and 597 (markers: hsa-miR-92a-2-5p, hsa-miR-760, hsa-miR-614, and hsa-miR-5787).

Non-limiting examples of the combination of the polynucleotide consisting of the nucleotide sequence represented by SEQ ID NO: 599 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 37, 63, and 599 (markers: hsa-miR-4745-5p, hsa-miR-3619-3p, hsa-miR-4707-3p, and hsa-miR-6717-5p);
(2) a combination of SEQ ID NOs: 42, 58, 63, and 599 (markers: hsa-miR-4525, hsa-miR-4530, hsa-miR-4707-3p, and hsa-miR-6717-5p);
(3) a combination of SEQ ID NOs: 1, 12, 16, and 599 (markers: hsa-miR-4443, hsa-miR-4745-5p, hsa-miR-92a-2-5p, and hsa-miR-6717-5p);
(4) a combination of SEQ ID NOs: 63, 119, 173, and 599 (markers: hsa-miR-4707-3p, hsa-miR-4492, hsa-miR-665, and hsa-miR-6717-5p); and
(5) a combination of SEQ ID NOs: 16, 18, 139, and 599 (markers: hsa-miR-92a-2-5p, hsa-miR-4448, hsa-miR-760, and hsa-miR-6717-5p).

Non-limiting examples of the combination of the polynucleotide consisting of the nucleotide sequence represented by SEQ ID NO: 609 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 42, 63, 585, and 609 (markers: hsa-miR-4525, hsa-miR-4707-3p, hsa-miR-3196, and hsa-miR-451a);
(2) a combination of SEQ ID NOs: 42, 63, 592, and 609 (markers: hsa-miR-4525, hsa-miR-4707-3p, hsa-miR-4723-5p, and hsa-miR-451a);
(3) a combination of SEQ ID NOs: 18, 42, 581, and 609 (markers: hsa-miR-4448, hsa-miR-4525, hsa-miR-642a-3p, and hsa-miR-451a);
(4) a combination of SEQ ID NOs: 12, 16, 599, and 609 (markers: hsa-miR-4745-5p, hsa-miR-92a-2-5p, hsa-miR-6717-5p, and hsa-miR-451a); and
(5) a combination of SEQ ID NOs: 16, 126, 599, and 609 (markers: hsa-miR-92a-2-5p, hsa-miR-3648, hsa-miR-6717-5p, and hsa-miR-451a).

Non-limiting examples of the combination of the polynucleotide consisting of the nucleotide sequence represented by SEQ ID NO: 611 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 16, 37, and 611 (markers: hsa-miR-4745-5p, hsa-miR-92a-2-5p, hsa-miR-3619-3p, and hsa-miR-671-5p);
(2) a combination of SEQ ID NOs: 1, 63, 139, and 611 (markers: hsa-miR-4443, hsa-miR-4707-3p, hsa-miR-760, and hsa-miR-671-5p);
(3) a combination of SEQ ID NOs: 63, 158, 173, and 611 (markers: hsa-miR-4707-3p, hsa-miR-1228-5p, hsa-miR-665, and hsa-miR-671-5p);
(4) a combination of SEQ ID NOs: 16, 37, 139, and 611 (markers: hsa-miR-92a-2-5p, hsa-miR-3619-3p, hsa-miR-760, and hsa-miR-671-5p); and
(5) a combination of SEQ ID NOs: 16, 37, 595, and 611 (markers: hsa-miR-92a-2-5p, hsa-miR-3619-3p, hsa-miR-4739, and hsa-miR-671-5p).

The kit or the device of the present invention can also contain a polynucleotide that is already known or that will be found in future, to enable detection of prostate cancer, in addition to the polynucleotide(s) (which can include a variant, a fragment, and a derivative) according to the present invention described above.

The kit of the present invention can also contain an antibody for measuring a marker for prostate cancer examination known in the art, such as PSA, in addition to the polynucleotide(s) according to the present invention described above, and a variant thereof or a fragment thereof.

These polynucleotides and the variants thereof or the fragments thereof contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid(s) through the use of hybridization using this array.

The kit or the device of the present invention comprises nucleic acids capable of specifically binding to the polynucleotides of at least one or more, preferably at least two or more, more preferably at least three or more, most preferably at least five or more to all of the prostate cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the prostate cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the prostate cancer marker miRNAs, respectively, of the group 3 described above.

The kit or the device of the present invention can be used for detecting prostate cancer as described in the Section 4 below.

4. Method for Detecting Prostate Cancer

The present invention further provides a method for detecting prostate cancer, comprising using the kit or the device of the present invention (including the nucleic acid(s) that can be used in the present invention) described in the preceding Section 3 to measure an expression level(s) of one or more prostate cancer-derived gene(s) represented by an expression level(s) of prostate cancer-derived gene(s) selected from the following group: miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p, optionally an expression level of prostate cancer-derived gene(s) selected from the following group: miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p, and optionally an expression level of prostate cancer-derived gene(s) selected from the following group: miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p in a sample in vitro, further comparing, for example, the expression level(s) of the gene(s) in the sample (e.g., blood, serum, or plasma) collected from a subject suspected of having prostate cancer with a control expression level in the sample collected from a healthy subject (including a non-prostate cancer patient), and evaluating the subject as having prostate cancer when the expression level of the target nucleic acid is statistically significantly different between the samples.

This method of the present invention permits limitedly invasive early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the prostate cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol® (Life Technologies Corp.) may be used. The prostate cancer-derived genes may be prepared by the addition of a reagent for RNA extraction containing acidic phenol, such as Trizol (Life Technologies Corp.) or Isogen (Nippon Gene Co., Ltd). Alternatively, a kit such as miRNeasy® Mini Kit (Qiagen N.V.) can be used, though the method is not limited thereto.

The present invention also provides use of the kit or the device of the present invention for detecting in vitro an expression product of a prostate cancer-derived miRNA gene(s) in a sample derived from a subject.

In the method of the present invention, a kit or a device comprising, each alone or in every possible composition, the polynucleotides that can be used in the present invention as described above is used as the kit or the device.

In the detection or (genetic) diagnosis of prostate cancer according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine of the subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of prostate cancer or the detection of the presence or absence of prostate cancer. Specifically, the detection of prostate cancer using the kit or the device can be performed by detecting in vitro an expression level(s) of a gene(s) using the nucleic acid probe(s) or the primer(s) contained in the kit or the device in a sample such as blood, serum, plasma, or urine from a subject suspected of having prostate cancer. The subject suspected of having prostate cancer can be evaluated as having prostate cancer when the expression level(s) of a target miRNA marker(s) measured using polynucleotide(s) (including any variant, any fragment, and any derivative thereof) consisting of a nucleotide sequence(s) represented by at least one or more of SEQ ID NOs: 1 to 135, 580 to 606, or a complementary sequence(s) thereof, optionally a nucleotide sequence(s) represented by one or more of SEQ ID NOs: 136 to 152, 607 to 611 or a complementary sequence(s) thereof, and optionally a nucleotide sequence(s) represented by one or more of SEQ ID NOs: 153 to 187 or a complementary sequence(s) thereof in the sample such as blood, serum, plasma, or urine of the subject is statistically significantly different from the expression level(s) thereof in the sample such as blood, serum, or plasma, or urine of a healthy subject.

The method of the present invention can be combined with rectal examination, transrectal ultrasonography of the prostate, or a diagnostic imaging method such as CT scan, MRI scan, or bone scintigraphy. The method of the present invention is capable of specifically detecting prostate cancer and can substantially discriminate prostate cancer from the other cancers.

The method for detecting the absence of an expression product of a prostate cancer-derived gene(s) or the presence of the expression product of a prostate cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotide(s) (including a variant, a fragment, and a derivative) selected from the polynucleotide group of the present invention, to evaluate the presence or absence of prostate cancer or to detect prostate cancer. The method for detecting prostate cancer according to the present invention can also evaluate or diagnose, for example, the presence or absence of amelioration of the disease or the degree of amelioration thereof in a prostate cancer patient given a therapeutic drug for the amelioration of the disease.

The method of the present invention can comprise, for example, the following steps (a), (b), and (c):

(a) contacting a sample derived from a subject with a polynucleotide(s) in the kit or the device of the present invention in vitro;

(b) measuring an expression level(s) of the target nucleic acid(s) in the sample using the polynucleotide(s) as a nucleic acid probe(s) or a primer(s); and (c) evaluating the presence or absence of prostate cancer (cells) in the subject on the basis of the step (b).

Specifically, the present invention provides a method for detecting prostate cancer, comprising measuring an expression level(s) of a target nucleic acid(s) in a sample of a subject using a nucleic acid(s) capable of specifically binding to at least one or more (preferably at least two or more) polynucleotide(s) selected from miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR- 6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p and evaluating in vitro the presence or absence of prostate cancer in the subject using the measured expression level(s) and a control expression level(s) of a healthy subject measured in the same way as above.

In the present specification, the term "evaluation" is evaluation support based on results of in vitro examination, not physician's judgment.

As described above, in the method of the present invention, specifically, miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

In the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

The method of the present invention can further use a nucleic acid capable of specifically binding to at least one or more polynucleotide(s) selected from miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

Specifically, miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

Specifically, the nucleic acid(s) is further selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

The method of the present invention can further use a nucleic acid(s) capable of specifically binding to at least one or more polynucleotide(s) selected from miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

Specifically, miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c-1-3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR-486-5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

Specifically, the nucleic acid further used is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a prostate tissue) or a body fluid such as blood, serum, plasma, or urine of the subject. The sample includes, specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

In the present specification, the subject refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of prostate cancer (cells) can comprise, for example, the following steps (a), (b), and (c):

(a) binding RNA prepared from the sample of the subject or a complementary polynucleotide (cDNA) transcribed therefrom to a polynucleotide in the kit or the device of the present invention;

(b) measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) evaluating the presence or absence of prostate cancer (or prostate cancer-derived gene expression) on the basis of the measurement results of the step (b).

For example, various hybridization methods can be used for detecting, examining, evaluating, or diagnosing prostate cancer (or prostate cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}$P, $^{33}$P, $^{35}$S, etc.), a fluorescent material, or the like, hybridizing the labeled product with the living tissue-derived RNA of the subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves preparing cDNA from the living tissue-derived RNA of the subject according to a routine method, hybridizing a pair of primers (consisting of a plus strand and a reverse strand binding to the cDNA) prepared from the polynucleotide for detection of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. Array in which a gene group immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes all of these arrays. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probe using an image detector (examples thereof can include Typhoon 9410 (GE Healthcare Japan Corp.) and 3D-Gene® scanner (Toray Industries, Inc.)).

The "stringent conditions" used in the present specification are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent conditions of washing. The hybridization conditions involves, for example, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the washing conditions, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include a treatment for approximately 15 seconds to 1 minute at 5 to 10° C. plus a Tm value calculated from the sequence of the primer, using a PCR buffer having composition such as 10 mM Tris-HCL (pH 8.3), 50 mM KCL, and 1 to 2 mM MgCl$_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.), LNA®-based MicroRNA PCR (Exiqon), or Ncode® miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measured samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a prostate cancer patient and a sample derived from a healthy subject as supervising samples, and determining or evaluating the presence and/or absence of the prostate cancer-derived gene in the sample.

Specifically, the present invention further provides the method comprising: a first step of measuring in vitro an expression level of a target gene in multiple samples, in which the presence and/or absence of the prostate cancer-derived gene has been known in the samples, using the polynucleotide, the kit, or the device (e.g., chip) for detection of the present invention, or a combination thereof; a second step of preparing a discriminant with the measurement values of the expression level of the target gene (target nucleic acid) obtained in the first step as supervising samples; a third step of measuring in vitro an expression level of the target gene in a sample derived from a subject in the same way as in the first step; and a fourth step of substituting the measurement value of the expression level of the target gene obtained in the third step into the discriminant obtained in the second step, and determining or evaluating the presence and/or absence of the prostate cancer-derived gene in the sample on the basis of the results obtained from the discriminant, wherein the target gene can be detected using the polynucleotide or using a polynucleotide for detection, a variant thereof, or a fragment thereof contained in the kit or the device (e.g., chip). In this context, the discriminant can be prepared by use of Fisher's linear discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this context, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's linear discriminant analysis, one type of linear discriminant analysis, is a dimension reduction method for selecting a dimension suitable for classification, and constructs a synthetic variable with high discriminant performance by focusing on the variance of the synthetic variables and minimizing the variance of data having the same label (Venables, W. N. et al., Modern Applied Statistics with S. Fourth edition. Springer, 2002). In the Fisher's linear discriminant analysis, direction w of projection is determined so as to maximize Formula 2. In this context, μ represents an average input, ng represents the number of data associated to class g, and μg represents an average input of the data associated to class g. The numerator and the denominator are intra-class variance and inter-class variance, respectively, when each data is projected in the direction of the vector w. Discriminant coefficient wi is determined by maximizing this ratio (Takafumi Kanamori et al., "Pattern Recognition", Kyoritsu Shuppan Co., Ltd., (2009); and Richard O. et al., Pattern Classification Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining, an associated cluster which has a closer Mahalanobis' distance from each cluster. In this context, μ represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1} (x - \mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set that has known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the results of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (radial basis function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of a C-SVC discriminant that can be used in the method of the present invention will be given below. First, all subjects are divided into two groups, i.e., a prostate cancer patient group and a healthy subject group. For example, prostate tissue examination can be used for a reference under which each subject is confirmed as a prostate cancer patient or a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables, and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_{a} \frac{1}{2} a^T Q a - e^T a \quad \text{Formula 4}$$

$$\text{subject to } y^T a = 0, 0 \le a_i \le C, i = 1, \ldots, l,$$

Formula 5 is a finally obtained discriminant, and an associated group can be determined on the basis of the sign of a value obtained according to the discriminant. In this context, x represents a support vector, y represents a label indicating the association with a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this context, x represents a support vector, and y represents a kernel parameter for adjusting the complexity of the hyperplane.

$$K(x_i, x_j) = \exp(-r\|x_i - x_j\|^2), r < 0 \quad \text{Formula 6}$$

In addition, an approach such as neural network, k-nearest neighbor algorithms, decision trees, or logistic regression analysis can be selected as a method for determining or evaluating the presence and/or absence of expression of a prostate cancer-derived target gene in a sample derived from a subject, or for evaluating the expression level thereof by comparison with a control derived from a healthy subject.

The method of the present invention can comprise, for example, the following steps (a), (b), and (c):

(a) measuring an expression level of a target gene in tissues containing prostate cancer-derived genes derived from prostate cancer patients and/or samples already known to be tissues containing no prostate cancer-derived gene derived from healthy subjects, using the polynucleotide, the kit, or the device (e.g., DNA chip) for detection according to the present invention;

(b) preparing the discriminants of Formulae 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, substituting the obtained measurement value into the discriminants prepared in the step (b), and determining or evaluating the presence and/or absence of the prostate cancer-derived target gene in the sample, or evaluating the expression level thereof by comparison with a healthy subject-derived control, on the basis of the obtained results.

In this context, in the discriminants of Formulae 1 to 3, 5, and 6, x represents an explanatory variable and includes a value obtained by measuring a polynucleotide selected from the polynucleotides described above in the Section 2, or any fragment thereof. Specifically, the explanatory variable for discriminating a prostate cancer patient from a healthy subject according to the present invention is a gene expression level selected from, for example, the following expression levels (1) to (3):

(1) a gene expression level in the serum of a prostate cancer patient or a healthy subject measured by any DNA comprising 15 or more consecutive nucleotides in a nucleotide sequence represented by any of SEQ ID NOs: 1 to 135, 580 to 606 or a complementary sequence thereof, (2) a gene expression level in the serum of a prostate cancer patient or a healthy subject measured by any DNA comprising 15 or more consecutive nucleotides in a nucleotide sequence represented by any of SEQ ID NOs: 136 to 152, 607 to 611 or a complementary sequence thereof, and (3) a gene expression level in the serum of a prostate cancer patient or a healthy subject measured by any DNA comprising 15 or more consecutive nucleotides in a nucleotide sequence represented by any of SEQ ID NOs: 153 to 187 or a complementary sequence thereof.

As described above, for the method for determining or evaluating the presence and/or absence of a prostate cancer-derived gene in a sample derived from a subject, a discriminant prepared from a training cohort is required. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a prostate cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of an analytical test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by an analytical test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a prostate cancer patient group and gene expression levels of a healthy subject group may be calculated to select a gene that is used for an explanatory variable for a discriminant. Alternatively, ROC curves based on the gene expression levels of a prostate cancer patient group and a healthy subject group may be used, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of a P value, and a method of constructing a discriminant by repetitively evaluating the genes for use while adding the genes one by one in a descending order of the gene expression difference (Furey T S. et al., 2000, Bioinformatics, Vol. 16, p. 906-14). A gene expression level of another independent prostate cancer patient or healthy subject is substituted as an explanatory variable into this discriminant to calculate a result of the discriminant analysis that indicates the group to which this independent prostate cancer patient or healthy subject associated. Specifically, the found gene set for diagnosis and the discriminant constructed using the gene set for diagnosis can be evaluated in an independent sample group to find a more universal gene set for diagnosis capable of detecting prostate cancer and a more universal method for discriminating prostate cancer.

Split-sample method is preferably used for evaluating the discriminant performance (generality) of the discriminant. Specifically, a data set is divided into a training cohort and a validation cohort, and gene selection by a statistical test and construction of a discriminant are performed in the training cohort. Accuracy, sensitivity, and specificity are calculated using results of discriminant analysis in a validation cohort according to the discriminant and a true group to which the validation cohort associated, to evaluate the discriminant performance. On the other hand, instead of dividing a data set, gene selection by a statistical test and construction of a discriminant may be performed using all of samples, and accuracy, sensitivity, and specificity can be calculated by the discriminant of newly prepared samples according to the discriminant to evaluate the discriminant performance.

The present invention provides a polynucleotide for detection or for disease diagnosis useful in the diagnosis and treatment of prostate cancer, a method for detecting prostate cancer using the polynucleotide, and a kit and a device for the detection of prostate cancer, comprising the polynucleotide. Particularly, in order to select a gene for diagnosis and prepare a discriminant so as to exhibit accuracy beyond a prostate cancer diagnosis method using existing tumor markers PSA, a gene set for diagnosis and a discriminant for the method of the present invention can be constructed, which exhibit accuracy beyond PSA, for example, by comparing genes expressed in serum derived from a patient who is confirmed to be negative using PSA but finally found to have prostate cancer by detailed examination such as computed tomography using a contrast medium, with genes expressed in serum derived from a patient who has no prostate cancer.

For example, the gene set for diagnosis is set to any combination selected from one or two or more of the polynucleotides based on a nucleotide sequence represented by any of SEQ ID NOs: 1 to 135, 580 to 606, or a complementary sequence thereof as described above, optionally one or two or more of the polynucleotides based on a nucleotide sequence represented by any of SEQ ID NOs: 136 to 152, 607 to 611, or a complementary sequence thereof, and optionally one or two or more of the polynucleotides based on a nucleotide sequence represented by any of SEQ ID NOs: 153 to 187, or a complementary sequence thereof. Further, a discriminant is constructed using expression levels of the gene set for diagnosis in samples derived from class I prostate cancer patients and samples derived from class II healthy subjects as a result of tissue diagnosis. As a result, the presence or absence of prostate cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Prostate Cancer Patient and Healthy Subject>

Serum was collected after obtainment of informed consent, using VENOJECT II vacuum blood collecting tube VP-AS109K60 (Terumo Corp.) from each of 94 healthy male subjects, and 35 prostate cancer patients (30 cases with stage II, 1 case with stage III, and 4 cases with stage IV) (Table 2-1) who were confirmed to have no cancer in organs other than the prostate, and used as a training cohort. Likewise, serum was collected after obtainment of informed consent, using VENOJECT II vacuum blood collecting tube VP-AS109K60 (Terumo Corp.) from each of 47 healthy male subjects, and 17 prostate cancer patients (15 cases with stage II and 2 cases with stage III) (Table 2-2) who were confirmed to have no cancer in organs other than the prostate, and used as a validation cohort.

<Extraction of Total RNA>

Total RNA was obtained from 300 µL of the serum sample obtained from each of 193 persons in total of 141 healthy male subjects and 52 prostate cancer patients in the training cohort and the validation cohort, using a reagent for RNA extraction in 3D-Gene® RNA extraction reagent from liquid sample kit (Toray Industries, Inc.) according to the protocol provided by the manufacturer.

<Measurement of Gene Expression Level> miRNAs in the total RNA obtained from the serum sample of each of 193 persons in total of 141 healthy male subjects and 52 prostate cancer patients in the aforementioned training cohort and the validation cohort were fluorescently labeled using 3D-Gene® miRNA Labeling kit (Toray Industries, Inc.) according to the protocol (ver 2.20) provided by the manufacturer. The oligo DNA chip used was 3D-Gene® Human miRNA Oligo chip (Toray Industries, Inc.) with mounted probes having sequences complementary to 2,555 miRNAs among the miRNAs registered in miR-Base Release 20. Hybridization of the miRNAs in the total RNA with the probes on the DNA chip under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 52 prostate cancer patients and the 141 healthy male subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Sample from Patients with Cancer Other than Prostate Cancer>

Serum was collected using VENOJECT II vacuum blood collecting tube VP-AS109K60 (Terumo Corp.) from each of 63 breast cancer patients who were confirmed to have no cancer in other organs after obtainment of informed consent, and used as a training cohort together with the samples of 35 prostate cancer patients and 99 healthy male subjects of Reference Example 1. Likewise, serum was collected using VENOJECT II vacuum blood collecting tube VP-AS109K60 (Terumo Corp.) from each of 30 breast cancer patients who were confirmed to have no cancer in other organs after obtainment of informed consent, and used as a validation cohort together with the samples of 17 prostate cancer patients who were confirmed to have no cancer in organs other than the prostate and 51 healthy male subjects of Reference Example 1. Subsequent operations were conducted in the same way as in Reference Example 1.

Example 1

<Selection of Gene Marker Using Samples in the Training Cohort, and Method for Evaluating Prostate Cancer Discriminant Performance with the Single Gene Marker Using Samples in the Validation Cohort>

In this Example, a gene marker for discriminating a prostate cancer patient from a healthy subject was selected from the training cohort and studied in samples of the validation cohort independent of the training cohort.

Specifically, first, the miRNA expression levels of the training cohort and the validation cohort obtained in the preceding Reference Examples 1 were combined and normalized by quantile normalization.

Next, genes for diagnosis were selected in the training cohort. Here, in order to acquire diagnostic markers with higher reliability, only genes that showed gene expression levels of $2^6$ or higher in 50% or more of the samples in either of the prostate cancer patient group in the training cohort or the healthy subject group in the training cohort were selected. In order to further acquire statistically significant genes for discriminating a prostate cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The obtained genes are described in Table 2.

In this way, hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsamiR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663 and hsa-miR-1225-5p genes, and the nucleotide sequences of SEQ ID NOs: 1 to 152 related thereto were found.

A discriminant for determining the presence or absence of prostate cancer was further prepared by Fisher's linear discriminant analysis with the expression levels of these genes as an index. Specifically, any newly found polynucleotide consisting of a nucleotide sequence represented by any of SEQ ID NOs: 1 to 135 among the 152 genes selected in the training cohort was applied to Formula 2 to construct a discriminant. Calculated accuracy, sensitivity, and specificity are shown in Table 4. In this respect, a discriminant coefficient and a constant term are shown in Table 5.

Figure 2:
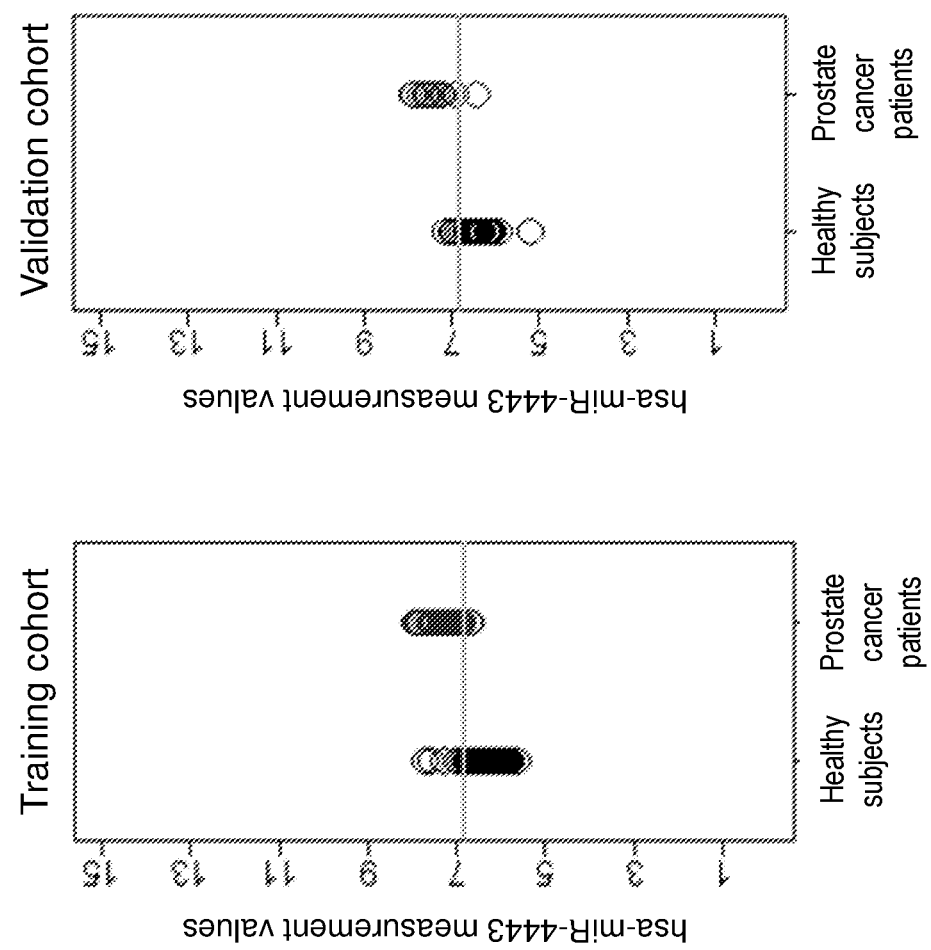
FIG. 2 Left diagram: the measurement values of hsa-miR-4443 (SEQ ID NO: 1) in healthy subjects (100 persons) and in prostate cancer patients (35 persons) selected as the training cohort were each plotted on the ordinate. The horizontal line in the diagram depicts a threshold (6.84) that was optimized by Fisher's linear discriminant analysis and discriminated between the two groups. Right diagram: the measurement values of hsa-miR-4443 (SEQ ID NO: 1) in healthy subjects (50 persons) and in prostate cancer patients (17 persons) selected as the validation cohort were each plotted on the ordinate. The horizontal line in the diagram depicts the threshold (6.84) that was set in the training cohort and discriminated between the two groups.

Next, accuracy, sensitivity, and specificity in the validation cohort were calculated using the discriminant thus prepared, and the discriminant performance of the selected polynucleotides was validated using the independent samples (Table 4). For example, the expression level measurement value of the nucleotide sequence represented by SEQ ID NO: 1 was compared between the healthy subjects (47 persons) and the prostate cancer patients (17 persons) in the validation cohort. The results showing that the gene expression level measurement values in the training cohort were significantly lower in the prostate cancer patient group than in the healthy subject group (see the left diagram of FIG. 2), were also reproducible in the validation cohort (see the right diagram of FIG. 2). Likewise, the results obtained about the other polynucleotides shown in SEQ ID NOs: 2 to 152 showed that the gene expression level measurement values were significantly lower (−) or higher (+) in the prostate cancer patient group than in the healthy subject group. These results were able to be validated in the validation cohort. For example, as for this nucleotide sequence represented by SEQ ID NO: 1, the number of samples that were correctly identified in the detection of prostate cancer was calculated using the threshold (6.84) that was set in the training cohort and discriminated between the two groups. As a result, 15 true positives, 44 true negatives, 3 false positive, and 2 false negatives were obtained. From these values, 92.2% accuracy, 88.2% sensitivity, and 93.6% specificity were obtained as detection performance. In this way, the detection performance was calculated as to all of the polynucleotides shown in SEQ ID NOs: 1 to 152, and described in Table 4.

Among the polynucleotides consisting of the nucleotide sequences represented by SEQ ID NOs: 1 to 152 shown in Table 3, for example, 141 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 103, 104, 105, 106, 107, 108, 109, 110, 111, 112, 113, 114, 116, 119, 120, 121, 123, 124, 126, 127, 128, 131, 132, 135, 136, 137, 138, 139, 140, 141, 142, 143, 144, 145, 146, 147, 148, 149, 150, 151 and 152 exhibited sensitivity of 88.2%, 94.1%, 76.5%, 88.2%, 88.2%, 94.1%, 76.5%, 64.7%, 88.2%, 76.5%, 64.7%, 82.4%, 70.6%, 88.2%, 52.9%, 47.1%, 70.6%, 94.1%, 70.6%, 76.5%, 76.5%, 70.6%, 70.6%, 29.4%, 58.8%, 88.2%, 58.8%, 76.5%, 64.7%, 76.5%, 64.7%, 47.1%, 76.5%, 82.4%, 70.6%, 47.1%, 64.7%, 58.8%, 52.9%, 82.4%, 64.7%, 70.6%, 64.7%, 70.6%, 70.6%, 76.5%, 58.8%, 58.8%, 52.9%, 64.7%, 47.1%, 41.2%, 70.6%, 52.9%, 29.4%, 35.3%, 41.2%, 58.8%, 52.9%, 41.2%, 70.6%, 52.9%, 35.3%, 64.7%, 29.4%, 70.6%, 70.6%, 76.5%, 58.8%, 70.6%, 35.3%, 58.8%, 58.8%, 47.1%, 70.6%, 76.5%, 58.8%, 82.4%, 23.5%, 52.9%, 41.2%, 47.1%, 64.7%, 41.2%, 41.2%, 35.3%, 47.1%, 47.1%, 41.2%, 29.4%, 41.2%, 64.7%, 35.3%, 70.6%, 29.4%, 47.1%, 29.4%, 52.9%, 64.7%, 47.1%, 23.5%, 35.3%, 47.1%, 35.3%, 35.3%, 52.9%, 23.5%, 35.3%, 47.1%, 52.9%, 23.5%, 23.5%, 29.4%, 52.9%, 41.2%, 23.5%, 23.5%, 41.2%, 47.1%, 29.4%, 58.8%, 29.4%, 23.5%, 29.4%, 58.8%, 88.2%, 76.5%, 58.8%, 52.9%, 47.1%, 35.3%, 52.9%, 29.4%, 47.1%, 76.5%, 58.8%, 29.4%, 29.4%, 29.4%, 41.2% and 23.5% respectively, in the validation cohort (Table 4). Non-Patent Literature 3 has reported that the existing prostate cancer marker PSA has general sensitivity of 20.5%. These results were able to demonstrate that, for example, the 141 polynucleotides consisting of the nucleotide sequences represented by SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 103, 104, 105, 106, 107, 108, 109, 110, 111, 112, 113, 114, 116, 119, 120, 121, 123, 124, 126, 127, 128, 131, 132, 135, 136, 137, 138, 139, 140, 141, 142, 143, 144, 145, 146, 147, 148, 149, 150, 151 and 152 can discriminate, each alone, prostate cancer in the validation cohort with sensitivity beyond PSA.

Example 2

<Method for Evaluating Prostate Cancer Discriminant Performance with Combination of Multiple Gene Markers Using Samples in the Validation Cohort>

In this Example, a method for evaluating prostate cancer discriminant performance with combination of the gene markers selected in Example 1 was studied.

Figure 3:
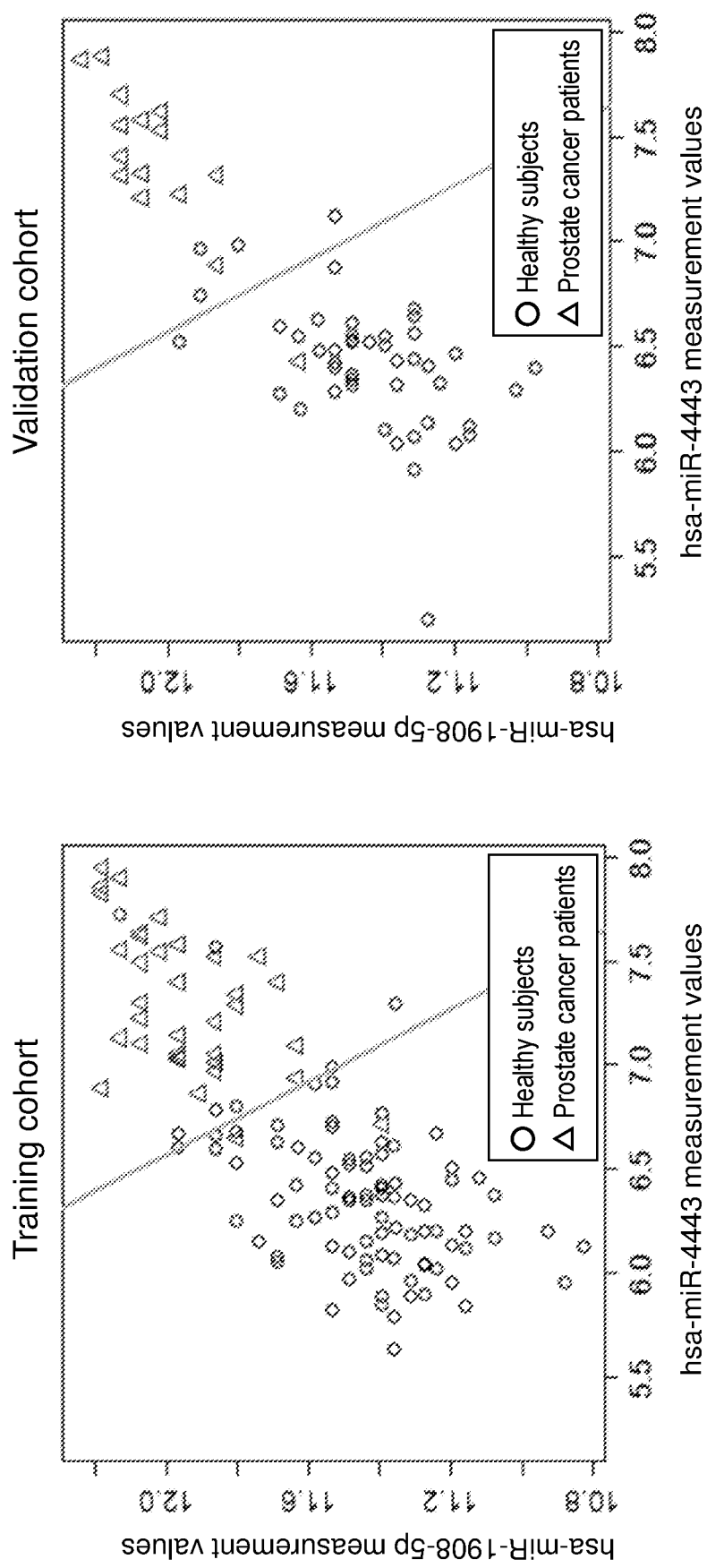
FIG. 3 Left diagram: the measurement values of hsa-miR-4443 (SEQ ID NO: 1) in healthy subjects (100 persons, circles) and in prostate cancer patients (35 persons, triangles) selected as the training cohort were each plotted on the abscissa against their measurement values of hsa-miR-1908-5p (SEQ ID NO: 2) on the ordinate. The line in the diagram depicts a discriminant function (0=1.15x+y+19.53) that was optimized by Fisher's linear discriminant analysis and discriminated between the two groups. Right diagram: the measurement values of hsa-miR-4443 (SEQ ID NO: 1) in healthy subjects (50 persons, circles) and in prostate cancer patients (17 persons, triangles) selected as the validation cohort were each plotted on the abscissa against their measurement values of hsa-miR-1908-5p (SEQ ID NO: 2) on the ordinate. The line in the diagram depicts the threshold (0=1.15x+y+19.53) that was set in the training cohort and discriminated between the two groups.

Specifically, Fisher's linear discriminant analysis was conducted as to 11,340 combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152 selected in Example 1, to construct a discriminant for determining the presence or absence of prostate cancer. Next, accuracy, sensitivity, and specificity in the validation cohort were calculated using the discriminant thus prepared, and the discriminant performance of the selected polynucleotides was validated using the independent samples. For example, the expression level measurement values of the nucleotide sequences represented by SEQ ID NO: 1 and SEQ ID NO: 2 were compared between the healthy subjects and the prostate cancer patients in the validation cohort. As a result, a scatter diagram that significantly separated the gene expression level measurement values of the prostate cancer patient group from those of the healthy subject group was obtained in the training cohort (see the left diagram of FIG. 3). These results were also reproducible for the validation cohort (see the right diagram of FIG. 3). Likewise, a scatter diagram that significantly separated the gene expression level measurement values of the prostate cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152. These results were able to be validated in the validation cohort. For example, as for these nucleotide sequences represented by SEQ ID NO: 1 and SEQ ID NO: 2, the number of samples correctly identified in the detection of prostate cancer was calculated using the threshold (0=1.15x+y+19.53) that was set in the training cohort and discriminated between the two groups. As a result, 16 true positives, 45 true negatives, 2 false positive, and 1 false negatives were obtained. From these values, 95.3% accuracy, 94.1% sensitivity, and 95.7% specificity were obtained as detection performance.

In this way, the detection performance was calculated as to all combinations (11,340 combinations) of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152. Among them, 151 combinations comprising the expression level measurement value of the polynucleotide consisting of the nucleotide sequence represented by SEQ ID NO: 1 and their detection performance are described in Table 6 as an example. For example, the combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 94.1%, 88.2%, 88.2%, and 94.1%, respectively, in the validation cohort (Table 6). In this way, 11,326 combinations of two expression level measurement values of the polynucleotides having sensitivity beyond the existing prostate cancer marker PSA (general sensitivity: 20.5%) were obtained in the validation cohort. All of the polynucleotides represented by the nucleotide sequences 1 to 152 described in Table 3 obtained in Example 1 were employed at least once in these combinations. These results were able to demonstrate that the combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152 has the performance of detecting prostate cancer with sensitivity beyond PSA.

Thus, markers capable of detecting prostate cancer with excellent sensitivity are obtained even if 3, 4, 5, 6, 7, 8, 9, 10 or more of the expression level measurement values of the polynucleotides consisting of the nucleotide sequences represented by SEQ ID NOs: 1 to 152 are combined. For example, the polynucleotides consisting of the nucleotide sequences represented by SEQ ID NOs: 1 to 135 newly found in Example 1 were ranked in the descending order of their P values which indicates statistical significance, and prostate cancer detection sensitivity was evaluated using combinations of one or more polynucleotides to which the polynucleotides (miRNAs) were added one by one from the top to the bottom of the rank accordingly. In short, the order to combine the polynucleotides (miRNAs) in this evaluation is in reverse in terms of SEQ ID NOs, such as SEQ ID NO: 135 to SEQ ID NOs: 134, 133, . . . , shown in Table 3. As a result, the sensitivity in the validation cohort was 29.4% for 1 polynucleotide, 47.1% for 2 polynucleotides, 76.5% for 3 polynucleotides, 82.4% for 5 polynucleotides, 82.4% for 10 polynucleotides, 88.2% for 20 polynucleotides, 100% for 50 polynucleotides, and 100% for 100 polynucleotides. These values of the sensitivity were higher than the general sensitivity (20.5%) of the existing prostate cancer marker PSA, demonstrating that even combinations of multiple (i.e., two or more) miRNAs can serve as excellent markers for the detection of prostate cancer. In this context, the combinations of multiple miRNAs are not limited to the combinations of the miRNAs added in the order of the statistically significant difference as described above, and any combination of multiple polynucleotides (miRNAs) can be used in the detection of prostate cancer.

From these results, it can be concluded that all of the polynucleotides consisting of the nucleotide sequences represented by SEQ ID NOs: 1 to 152 serve as excellent diagnostic markers.

TABLE 2

| Sample name | Cancer stage |
| --- | --- |
| Training cohort | |
| PR04 | II |
| PR06 | IV |
| PR08 | II |
| PR09 | II |
| PR12 | II |
| PR19 | II |
| PR21 | II |
| PR22 | II |
| PR23 | II |
| PR29 | II |
| PR30 | II |
| PR32 | III |
| PR46 | II |
| PR48 | II |
| PR51 | II |
| PR52 | II |
| PR53 | II |
| PR64 | II |
| PR65 | II |
| PR66 | II |
| PR69 | IV |
| PR73 | II |
| PR75 | II |
| PR80 | IV |
| PR81 | II |
| PR83 | II |
| PR84 | II |
| PR85 | II |
| PR87 | II |
| PR90 | II |
| PR93 | II |
| PR94 | II |
| PR97 | II |
| PR99 | IV |
| PR101 | II |
| Validation cohort | |
| PR01 | II |
| PR17 | II |
| PR26 | III |
| PR27 | II |
| PR28 | III |
| PR33 | II |
| PR40 | II |
| PR45 | II |
| PR59 | II |

TABLE 2-continued

| Sample name | Cancer stage |
|---|---|
| PR62 | II |
| PR67 | II |
| PR71 | II |
| PR82 | II |
| PR91 | II |
| PR92 | II |
| PR96 | II |
| PR100 | II |

TABLE 3

| SEQ ID NO: | Gene name | P value after Bonferroni correction | Expression level in prostate cancer patient relative to healthy subject |
|---|---|---|---|
| 1 | hsa-miR-4443 | 2.10E–23 | + |
| 2 | hsa-miR-1908-5p | 7.83E–18 | + |
| 3 | hsa-miR-4257 | 2.21E–17 | − |
| 4 | hsa-miR-3197 | 5.78E–17 | + |
| 5 | hsa-miR-3188 | 5.96.E–17 | + |
| 6 | hsa-miR-4649-5p | 6.34E–17 | − |
| 7 | hsa-miR-1343-3p | 2.48.E–16 | − |
| 8 | hsa-miR-6861-5p | 1.15.E–15 | − |
| 9 | hsa-miR-1343-5p | 3.73.E–15 | + |
| 10 | hsa-miR-642b-3p | 3.94.E–15 | − |
| 11 | hsa-miR-6741-5p | 3.03.E–14 | − |
| 12 | hsa-miR-4745-5p | 4.76.E–14 | − |
| 13 | hsa-miR-6826-5p | 1.27.E–13 | − |
| 14 | hsa-miR-3663-3p | 1.61.E–13 | − |
| 15 | hsa-miR-3131 | 5.67.E–13 | − |
| 16 | hsa-miR-92a-2-5p | 1.04.E–12 | + |
| 17 | hsa-miR-4258 | 1.59.E–12 | − |
| 18 | hsa-miR-4448 | 2.54.E–12 | + |
| 19 | hsa-miR-6125 | 4.39.E–12 | + |
| 20 | hsa-miR-6880-5p | 6.24.E–12 | + |
| 21 | hsa-miR-6132 | 8.70.E–12 | + |
| 22 | hsa-miR-4467 | 1.45.E–11 | + |
| 23 | hsa-miR-6749-5p | 1.46.E–11 | − |
| 24 | hsa-miR-2392 | 1.68.E–11 | + |
| 25 | hsa-miR-1273g-3p | 2.09.E–11 | − |
| 26 | hsa-miR-4746-3p | 2.43.E–11 | + |
| 27 | hsa-miR-1914-3p | 2.94.E–11 | − |
| 28 | hsa-miR-7845-5p | 3.03.E–11 | + |
| 29 | hsa-miR-6726-5p | 5.00.E–11 | − |
| 30 | hsa-miR-128-2-5p | 5.60.E–11 | − |
| 31 | hsa-miR-4651 | 6.14.E–11 | − |
| 32 | hsa-miR-6765-3p | 6.43.E–11 | − |
| 33 | hsa-miR-3185 | 7.07.E–11 | + |
| 34 | hsa-miR-4792 | 7.39.E–11 | + |
| 35 | hsa-miR-6887-5p | 9.57.E–11 | − |
| 36 | hsa-miR-5572 | 1.01.E–10 | + |
| 37 | hsa-miR-3619-3p | 1.89.E–10 | − |
| 38 | hsa-miR-6780b-5p | 2.55.E–10 | + |
| 39 | hsa-miR-4707-5p | 2.83.E–10 | + |
| 40 | hsa-miR-8063 | 2.93.E–10 | − |
| 41 | hsa-miR-4454 | 3.34.E–10 | − |
| 42 | hsa-miR-4525 | 3.73.E–10 | − |
| 43 | hsa-miR-7975 | 3.87.E–10 | − |
| 44 | hsa-miR-744-5p | 4.00.E–10 | + |
| 45 | hsa-miR-3135b | 4.73.E–10 | − |
| 46 | hsa-miR-4648 | 5.10.E–10 | + |
| 47 | hsa-miR-6816-5p | 6.76.E–10 | + |
| 48 | hsa-miR-4741 | 9.16.E–10 | + |
| 49 | hsa-miR-7150 | 1.34.E–09 | + |
| 50 | hsa-miR-6791-5p | 2.31.E–09 | + |
| 51 | hsa-miR-1247-3p | 3.07.E–09 | + |
| 52 | hsa-miR-7977 | 3.35.E–09 | − |
| 53 | hsa-miR-4497 | 4.19.E–09 | − |
| 54 | hsa-miR-6090 | 5.36.E–09 | + |
| 55 | hsa-miR-6781-5p | 8.00.E–09 | + |
| 56 | hsa-miR-6870-5p | 1.48.E–08 | + |
| 57 | hsa-miR-6729-5p | 1.56.E–08 | + |
| 58 | hsa-miR-4530 | 2.60.E–08 | + |
| 59 | hsa-miR-7847-3p | 3.09.E–08 | − |
| 60 | hsa-miR-6825-5p | 3.86.E–08 | + |
| 61 | hsa-miR-4674 | 3.88.E–08 | − |
| 62 | hsa-miR-3917 | 4.11.E–08 | − |
| 63 | hsa-miR-4707-3p | 4.52.E–08 | + |
| 64 | hsa-miR-6885-5p | 5.06.E–08 | − |
| 65 | hsa-miR-6722-3p | 5.76.E–08 | + |
| 66 | hsa-miR-4516 | 6.32.E–08 | − |
| 67 | hsa-miR-6757-5p | 6.81.E–08 | − |
| 68 | hsa-miR-6840-3p | 1.30.E–07 | − |
| 69 | hsa-miR-5195-3p | 1.45.E–07 | − |
| 70 | hsa-miR-6756-5p | 1.48.E–07 | − |
| 71 | hsa-miR-6800-5p | 1.61.E–07 | + |
| 72 | hsa-miR-6727-5p | 1.65.E–07 | − |
| 73 | hsa-miR-6126 | 1.87.E–07 | + |
| 74 | hsa-miR-6872-3p | 2.21.E–07 | − |
| 75 | hsa-miR-4446-3p | 3.28.E–07 | − |
| 76 | hsa-miR-1268a | 4.54.E–07 | + |
| 77 | hsa-miR-1908-3p | 5.41.E–07 | − |
| 78 | hsa-miR-3679-5p | 5.53.E–07 | + |
| 79 | hsa-miR-4534 | 7.45.E–07 | + |
| 80 | hsa-miR-4675 | 7.91.E–07 | − |
| 81 | hsa-miR-7108-5p | 1.01.E–06 | + |
| 82 | hsa-miR-6799-5p | 1.57.E–06 | + |
| 83 | hsa-miR-4695-5p | 3.59.E–06 | + |
| 84 | hsa-miR-3178 | 4.54.E–06 | + |
| 85 | hsa-miR-5090 | 4.93.E–06 | − |
| 86 | hsa-miR-3180 | 6.40.E–06 | + |
| 87 | hsa-miR-1237-5p | 9.54.E–06 | + |
| 88 | hsa-miR-4758-5p | 1.50.E–05 | − |
| 89 | hsa-miR-3184-5p | 1.60.E–05 | + |
| 90 | hsa-miR-4286 | 1.96.E–05 | − |
| 91 | hsa-miR-6784-5p | 2.81.E–05 | + |
| 92 | hsa-miR-6768-5p | 3.47.E–05 | + |
| 93 | hsa-miR-6785-5p | 3.51.E–05 | − |
| 94 | hsa-miR-4706 | 3.72.E–05 | + |
| 95 | hsa-miR-711 | 4.59.E–05 | + |
| 96 | hsa-miR-1260a | 5.06.E–05 | − |
| 97 | hsa-miR-6746-5p | 5.35.E–05 | − |
| 98 | hsa-miR-6089 | 7.26.E–05 | + |
| 99 | hsa-miR-6821-5p | 7.94.E–05 | + |
| 100 | hsa-miR-4667-5p | 8.38.E–05 | + |
| 101 | hsa-miR-8069 | 9.70.E–05 | + |
| 102 | hsa-miR-4726-5p | 1.11.E–04 | − |
| 103 | hsa-miR-6124 | 1.59.E–04 | + |
| 104 | hsa-miR-4532 | 1.87.E–04 | − |
| 105 | hsa-miR-4486 | 1.92.E–04 | + |
| 106 | hsa-miR-4728-5p | 1.96.E–04 | − |
| 107 | hsa-miR-4508 | 2.20.E–04 | + |
| 108 | hsa-miR-128-1-5p | 3.56.E–04 | − |
| 109 | hsa-miR-4513 | 3.75.E–04 | − |
| 110 | hsa-miR-6795-5p | 5.28.E–04 | − |
| 111 | hsa-miR-4689 | 5.85.E–04 | − |
| 112 | hsa-miR-6763-5p | 6.01.E–04 | − |
| 113 | hsa-miR-8072 | 6.56.E–04 | + |
| 114 | hsa-miR-6765-5p | 6.67.E–04 | + |
| 115 | hsa-miR-4419b | 7.40.E–04 | − |
| 116 | hsa-miR-7641 | 8.72.E–04 | − |
| 117 | hsa-miR-3928-3p | 9.57.E–04 | + |
| 118 | hsa-miR-1227-5p | 9.66.E–04 | + |
| 119 | hsa-miR-4492 | 1.12.E–03 | − |
| 120 | hsa-miR-296-3p | 1.39.E–03 | − |
| 121 | hsa-miR-6769a-5p | 1.42.E–03 | − |
| 122 | hsa-miR-6889-5p | 1.46.E–03 | + |
| 123 | hsa-miR-4632-5p | 1.74.E–03 | + |
| 124 | hsa-miR-4505 | 1.94.E–03 | + |
| 125 | hsa-miR-3154 | 1.97.E–03 | + |
| 126 | hsa-miR-3648 | 2.03.E–03 | − |
| 127 | hsa-miR-4442 | 2.15.E–03 | − |
| 128 | hsa-miR-3141 | 3.29.E–03 | + |
| 129 | hsa-miR-7113-3p | 3.29.E–03 | + |
| 130 | hsa-miR-6819-5p | 5.95.E–03 | − |
| 131 | hsa-miR-3195 | 6.78.E–03 | + |
| 132 | hsa-miR-1199-5p | 7.39.E–03 | − |
| 133 | hsa-miR-6738-5p | 8.00.E–03 | − |
| 134 | hsa-miR-4656 | 8.53.E–03 | |

TABLE 3-continued

| SEQ ID NO: | Gene name | P value after Bonferroni correction | Expression level in prostate cancer patient relative to healthy subject |
|---|---|---|---|
| 135 | hsa-miR-6820-5p | 9.18.E−03 | + |
| 136 | hsa-miR-615-5p | 1.89.E−11 | − |
| 137 | hsa-miR-486-3p | 4.76.E−11 | − |
| 138 | hsa-miR-1225-3p | 8.87.E−11 | + |
| 139 | hsa-miR-760 | 1.05.E−10 | − |
| 140 | hsa-miR-187-5p | 9.50.E−09 | − |
| 141 | hsa-miR-1203 | 6.86.E−08 | + |
| 142 | hsa-miR-7110-5p | 2.08.E−07 | + |
| 143 | hsa-miR-371a-5p | 4.75.E−07 | − |
| 144 | hsa-miR-939-5p | 9.56.E−07 | + |
| 145 | hsa-miR-575 | 2.41.E−06 | + |
| 146 | hsa-miR-92b-5p | 2.89.E−06 | + |
| 147 | hsa-miR-887-3p | 1.35.E−05 | + |
| 148 | hsa-miR-920 | 3.39.E−05 | − |
| 149 | hsa-miR-1915-5p | 2.55.E−04 | − |
| 150 | hsa-miR-1231 | 3.11.E−04 | + |
| 151 | hsa-miR-663b | 1.18.E−03 | − |
| 152 | hsa-miR-1225-5p | 8.49.E−03 | + |

TABLE 4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 93 | 85.7 | 95.7 | 92.2 | 88.2 | 93.6 |
| 2 | 87.6 | 85.7 | 88.3 | 92.2 | 94.1 | 91.5 |
| 3 | 89.9 | 77.1 | 94.7 | 89.1 | 76.5 | 93.6 |
| 4 | 85.3 | 71.4 | 90.4 | 95.3 | 88.2 | 97.9 |
| 5 | 89.1 | 77.1 | 93.6 | 92.2 | 88.2 | 93.6 |
| 6 | 88.4 | 77.1 | 92.6 | 92.2 | 94.1 | 91.5 |
| 7 | 86 | 74.3 | 90.4 | 82.8 | 76.5 | 85.1 |
| 8 | 86.8 | 74.3 | 91.5 | 84.4 | 64.7 | 91.5 |
| 9 | 83.7 | 74.3 | 87.2 | 92.2 | 88.2 | 93.6 |
| 10 | 86.8 | 68.6 | 93.6 | 92.2 | 76.5 | 97.9 |
| 11 | 86 | 68.6 | 92.6 | 85.9 | 64.7 | 93.6 |
| 12 | 86 | 74.3 | 90.4 | 90.6 | 82.4 | 93.6 |
| 13 | 89.1 | 77.1 | 93.6 | 89.1 | 70.6 | 95.7 |
| 14 | 79.8 | 42.9 | 93.6 | 95.3 | 88.2 | 97.9 |
| 15 | 83.7 | 68.6 | 89.4 | 76.6 | 52.9 | 85.1 |
| 16 | 87.6 | 77.1 | 91.5 | 73.4 | 47.1 | 83 |
| 17 | 82.9 | 57.1 | 92.6 | 81.2 | 70.6 | 85.1 |
| 18 | 88.4 | 65.7 | 96.8 | 93.8 | 94.1 | 93.6 |
| 19 | 88.4 | 82.9 | 90.4 | 84.4 | 70.6 | 89.4 |
| 20 | 82.9 | 57.1 | 92.6 | 92.2 | 76.5 | 97.9 |
| 21 | 87.6 | 62.9 | 96.8 | 92.2 | 76.5 | 97.9 |
| 22 | 82.2 | 60 | 90.4 | 89.1 | 70.6 | 95.7 |
| 23 | 82.2 | 60 | 90.4 | 89.1 | 70.6 | 95.7 |
| 24 | 84.5 | 57.1 | 94.7 | 71.9 | 29.4 | 87.2 |
| 25 | 87.6 | 62.9 | 96.8 | 82.8 | 58.8 | 91.5 |
| 26 | 84.5 | 65.7 | 91.5 | 93.8 | 88.2 | 95.7 |
| 27 | 82.2 | 65.7 | 88.3 | 76.6 | 58.8 | 83 |
| 28 | 81.4 | 57.1 | 90.4 | 89.1 | 76.5 | 93.6 |
| 29 | 87.6 | 68.6 | 94.7 | 85.9 | 64.7 | 93.6 |
| 30 | 85.3 | 60 | 94.7 | 87.5 | 76.5 | 91.5 |
| 31 | 82.2 | 57.1 | 91.5 | 82.8 | 64.7 | 89.4 |
| 32 | 84.5 | 60 | 93.6 | 79.7 | 47.1 | 91.5 |
| 33 | 83.7 | 65.7 | 90.4 | 90.6 | 76.5 | 95.7 |
| 34 | 89.9 | 74.3 | 95.7 | 87.5 | 82.4 | 89.4 |
| 35 | 81.4 | 57.1 | 90.4 | 85.9 | 70.6 | 91.5 |
| 36 | 79.8 | 57.1 | 88.3 | 78.1 | 47.1 | 89.4 |
| 37 | 84.5 | 60 | 93.6 | 87.5 | 64.7 | 95.7 |
| 38 | 81.4 | 54.3 | 91.5 | 82.8 | 58.8 | 91.5 |
| 39 | 79.1 | 54.3 | 88.3 | 87.5 | 52.9 | 100 |
| 40 | 83.7 | 74.3 | 87.2 | 90.6 | 82.4 | 93.6 |
| 41 | 85.3 | 60 | 94.7 | 79.7 | 64.7 | 85.1 |
| 42 | 79.1 | 48.6 | 90.4 | 89.1 | 70.6 | 95.7 |
| 43 | 81.4 | 54.3 | 91.5 | 85.9 | 64.7 | 93.6 |
| 44 | 85.3 | 54.3 | 96.8 | 90.6 | 70.6 | 97.9 |
| 45 | 89.9 | 74.3 | 95.7 | 89.1 | 70.6 | 95.7 |
| 46 | 82.9 | 60 | 91.5 | 84.4 | 76.5 | 87.2 |
| 47 | 83.7 | 60 | 92.6 | 79.7 | 58.8 | 87.2 |
| 48 | 82.9 | 54.3 | 93.6 | 82.8 | 58.8 | 91.5 |
| 49 | 84.5 | 57.1 | 94.7 | 79.7 | 52.9 | 89.4 |
| 50 | 78.3 | 48.6 | 89.4 | 87.5 | 64.7 | 95.7 |
| 51 | 82.2 | 48.6 | 94.7 | 75 | 47.1 | 85.1 |
| 52 | 80.6 | 51.4 | 91.5 | 79.7 | 41.2 | 93.6 |
| 53 | 79.8 | 60 | 87.2 | 85.9 | 70.6 | 91.5 |
| 54 | 80.6 | 42.9 | 94.7 | 87.5 | 52.9 | 100 |
| 55 | 82.9 | 57.1 | 92.6 | 76.6 | 29.4 | 93.6 |
| 56 | 80.6 | 54.3 | 90.4 | 76.6 | 35.3 | 91.5 |
| 57 | 85.3 | 51.4 | 97.9 | 81.2 | 41.2 | 95.7 |
| 58 | 80.6 | 54.3 | 90.4 | 81.2 | 58.8 | 89.4 |
| 59 | 79.1 | 51.4 | 89.4 | 81.2 | 52.9 | 91.5 |
| 60 | 78.3 | 51.4 | 88.3 | 76.6 | 41.2 | 89.4 |
| 61 | 81.4 | 48.6 | 93.6 | 85.9 | 70.6 | 91.5 |
| 62 | 82.9 | 54.3 | 93.6 | 82.8 | 52.9 | 93.6 |
| 63 | 82.9 | 60 | 91.5 | 78.1 | 35.3 | 93.6 |
| 64 | 80.6 | 42.9 | 94.7 | 89.1 | 64.7 | 97.9 |
| 65 | 78.3 | 40 | 92.6 | 79.7 | 29.4 | 97.9 |
| 66 | 80.6 | 45.7 | 93.6 | 84.4 | 70.6 | 89.4 |
| 67 | 80.6 | 57.1 | 89.4 | 84.4 | 70.6 | 89.4 |
| 68 | 79.1 | 42.9 | 92.6 | 85.9 | 76.5 | 89.4 |
| 69 | 82.2 | 48.6 | 94.7 | 81.2 | 58.8 | 89.4 |
| 70 | 79.8 | 51.4 | 90.4 | 92.2 | 70.6 | 100 |
| 71 | 79.8 | 45.7 | 92.6 | 79.7 | 35.3 | 95.7 |
| 72 | 79.8 | 51.4 | 90.4 | 78.1 | 58.8 | 85.1 |
| 73 | 77.5 | 42.9 | 90.4 | 81.2 | 58.8 | 89.4 |
| 74 | 81.4 | 51.4 | 92.6 | 73.4 | 47.1 | 83 |
| 75 | 79.1 | 54.3 | 88.3 | 82.8 | 70.6 | 87.2 |
| 76 | 76 | 42.9 | 88.3 | 84.4 | 76.5 | 87.2 |
| 77 | 78.3 | 51.4 | 88.3 | 79.7 | 58.8 | 87.2 |
| 78 | 80.6 | 51.4 | 91.5 | 92.2 | 82.4 | 95.7 |
| 79 | 78.3 | 42.9 | 91.5 | 68.8 | 23.5 | 85.1 |
| 80 | 79.1 | 40 | 93.6 | 84.4 | 52.9 | 95.7 |
| 81 | 79.1 | 45.7 | 91.5 | 81.2 | 41.2 | 95.7 |
| 82 | 79.1 | 45.7 | 91.5 | 78.1 | 47.1 | 89.4 |
| 83 | 76.7 | 42.9 | 89.4 | 89.1 | 64.7 | 97.9 |
| 84 | 80.6 | 45.7 | 93.6 | 78.1 | 41.2 | 91.5 |
| 85 | 79.8 | 37.1 | 95.7 | 84.4 | 41.2 | 100 |
| 86 | 79.8 | 45.7 | 92.6 | 75 | 35.3 | 89.4 |
| 87 | 78.1 | 32.4 | 94.7 | 85.9 | 47.1 | 100 |
| 88 | 79.1 | 31.4 | 96.8 | 84.4 | 47.1 | 97.9 |
| 89 | 75.2 | 34.3 | 90.4 | 76.6 | 41.2 | 89.4 |
| 90 | 76.7 | 37.1 | 91.5 | 76.6 | 29.4 | 93.6 |
| 91 | 74.4 | 34.3 | 89.4 | 70.3 | 17.6 | 89.4 |
| 92 | 83.7 | 51.4 | 95.7 | 79.7 | 41.2 | 93.6 |
| 93 | 77.5 | 42.9 | 90.4 | 84.4 | 64.7 | 91.5 |
| 94 | 79.8 | 42.9 | 93.6 | 76.6 | 35.3 | 91.5 |
| 95 | 82.2 | 48.6 | 94.7 | 89.1 | 70.6 | 95.7 |
| 96 | 78.3 | 45.7 | 90.4 | 73.4 | 29.4 | 89.4 |
| 97 | 76 | 34.3 | 91.5 | 75 | 47.1 | 85.1 |
| 98 | 74.4 | 25.7 | 92.6 | 76.6 | 29.4 | 93.6 |
| 99 | 78.3 | 42.9 | 91.5 | 85.9 | 52.9 | 97.9 |
| 100 | 73.6 | 22.9 | 92.6 | 87.5 | 64.7 | 95.7 |
| 101 | 79.8 | 45.7 | 92.6 | 84.4 | 47.1 | 97.9 |
| 102 | 76 | 37.1 | 90.4 | 67.2 | 17.6 | 85.1 |
| 103 | 79.1 | 31.4 | 96.8 | 76.6 | 23.5 | 95.7 |
| 104 | 77.5 | 28.6 | 95.7 | 81.2 | 35.3 | 97.9 |
| 105 | 77.5 | 34.3 | 93.6 | 81.2 | 47.1 | 93.6 |
| 106 | 73.6 | 31.4 | 89.4 | 79.7 | 35.3 | 95.7 |
| 107 | 77.5 | 25.7 | 96.8 | 75 | 35.3 | 89.4 |
| 108 | 76 | 34.3 | 91.5 | 84.4 | 52.9 | 95.7 |
| 109 | 76.7 | 34.3 | 92.6 | 75 | 23.5 | 93.6 |
| 110 | 76 | 22.9 | 95.7 | 78.1 | 35.3 | 93.6 |
| 111 | 75.2 | 14.3 | 97.9 | 84.4 | 47.1 | 97.9 |
| 112 | 72.9 | 20 | 92.6 | 85.9 | 52.9 | 97.9 |
| 113 | 75.2 | 22.9 | 94.7 | 78.1 | 23.5 | 97.9 |
| 114 | 73.6 | 17.1 | 94.7 | 76.6 | 23.5 | 95.7 |
| 115 | 76.7 | 28.6 | 94.7 | 73.4 | 17.6 | 93.6 |
| 116 | 73.6 | 28.6 | 90.4 | 75 | 29.4 | 91.5 |
| 117 | 79.1 | 34.3 | 95.7 | 75 | 17.6 | 95.7 |

TABLE 4-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 118 | 74.4 | 22.9 | 93.6 | 71.9 | 17.6 | 91.5 |
| 119 | 73.6 | 22.9 | 92.6 | 85.9 | 52.9 | 97.9 |
| 120 | 73.6 | 25.7 | 91.5 | 79.7 | 41.2 | 93.6 |
| 121 | 77.5 | 34.3 | 93.6 | 75 | 23.5 | 93.6 |
| 122 | 74.4 | 25.7 | 92.6 | 70.3 | 11.8 | 91.5 |
| 123 | 76.7 | 25.7 | 95.7 | 78.1 | 23.5 | 97.9 |
| 124 | 81.4 | 40 | 96.8 | 84.4 | 41.2 | 100 |
| 125 | 74.4 | 20 | 94.7 | 71.9 | 17.6 | 91.5 |
| 126 | 76.7 | 28.6 | 94.7 | 82.8 | 47.1 | 95.7 |
| 127 | 75.2 | 31.4 | 91.5 | 76.6 | 29.4 | 93.6 |
| 128 | 76.7 | 22.9 | 96.8 | 87.5 | 58.8 | 97.9 |
| 129 | 69.8 | 22.9 | 87.2 | 73.4 | 11.8 | 95.7 |
| 130 | 74.4 | 22.9 | 93.6 | 75 | 11.8 | 97.9 |
| 131 | 74.4 | 28.6 | 91.5 | 81.2 | 29.4 | 100 |
| 132 | 74.4 | 22.9 | 93.6 | 75 | 23.5 | 93.6 |
| 133 | 68.2 | 11.4 | 89.4 | 75 | 11.8 | 97.9 |
| 134 | 75.2 | 20 | 95.7 | 76.6 | 17.6 | 97.9 |
| 135 | 73.6 | 22.9 | 92.6 | 78.1 | 29.4 | 95.7 |
| 136 | 86.8 | 65.7 | 94.7 | 75 | 58.8 | 80.9 |
| 137 | 86 | 68.6 | 92.6 | 93.8 | 88.2 | 95.7 |
| 138 | 86.8 | 68.6 | 93.6 | 85.9 | 76.5 | 89.4 |
| 139 | 79.8 | 54.3 | 89.4 | 81.2 | 58.8 | 89.4 |
| 140 | 80.6 | 51.4 | 91.5 | 73.4 | 52.9 | 80.9 |
| 141 | 80.6 | 45.7 | 93.6 | 84.4 | 47.1 | 97.9 |
| 142 | 76 | 48.6 | 86.2 | 78.1 | 35.3 | 93.6 |
| 143 | 79.8 | 42.9 | 93.6 | 79.7 | 52.9 | 89.4 |
| 144 | 72.9 | 42.9 | 84 | 76.6 | 29.4 | 93.6 |
| 145 | 79.8 | 48.6 | 91.5 | 82.8 | 47.1 | 95.7 |
| 146 | 79.1 | 48.6 | 90.4 | 92.2 | 76.5 | 97.9 |
| 147 | 74.4 | 34.3 | 89.4 | 87.5 | 58.8 | 97.9 |
| 148 | 75.2 | 34.3 | 90.4 | 67.2 | 29.4 | 80.9 |
| 149 | 76 | 28.6 | 93.6 | 78.1 | 29.4 | 95.7 |
| 150 | 76 | 28.6 | 93.6 | 78.1 | 29.4 | 95.7 |
| 151 | 79.8 | 34.3 | 96.8 | 81.2 | 41.2 | 95.7 |
| 152 | 72.9 | 14.3 | 94.7 | 78.1 | 23.5 | 97.9 |

TABLE 5

| SEQ ID NO: | Discriminant coefficient | Constant term |
|---|---|---|
| 1 | 2.841 | 19.421 |
| 2 | 4.435 | 51.871 |
| 3 | 3.207 | 21.845 |
| 4 | 3.253 | 31.499 |
| 5 | 4.075 | 25.795 |
| 6 | 2.840 | 29.134 |
| 7 | 2.539 | 19.203 |
| 8 | 4.359 | 31.785 |
| 9 | 4.100 | 43.343 |
| 10 | 2.475 | 23.187 |
| 11 | 4.875 | 33.924 |
| 12 | 2.662 | 31.800 |
| 13 | 2.576 | 15.891 |
| 14 | 3.758 | 45.427 |
| 15 | 3.007 | 21.322 |
| 16 | 2.086 | 20.103 |
| 17 | 2.415 | 21.597 |
| 18 | 1.386 | 8.309 |
| 19 | 5.265 | 63.510 |
| 20 | 2.601 | 20.485 |
| 21 | 3.480 | 28.174 |
| 22 | 2.098 | 21.131 |
| 23 | 5.034 | 50.773 |
| 24 | 4.361 | 26.275 |
| 25 | 2.837 | 21.020 |
| 26 | 3.180 | 21.510 |
| 27 | 4.832 | 36.754 |
| 28 | 3.240 | 22.334 |
| 29 | 3.297 | 32.746 |
| 30 | 2.751 | 29.763 |
| 31 | 5.736 | 63.070 |
| 32 | 1.809 | 15.805 |
| 33 | 2.566 | 18.600 |
| 34 | 1.963 | 13.501 |
| 35 | 3.448 | 22.503 |
| 36 | 2.577 | 17.708 |
| 37 | 2.326 | 19.136 |
| 38 | 3.057 | 27.631 |
| 39 | 4.748 | 35.803 |
| 40 | 2.880 | 23.980 |
| 41 | 2.262 | 26.203 |
| 42 | 2.961 | 20.754 |
| 43 | 2.220 | 21.988 |
| 44 | 2.353 | 16.969 |
| 45 | 3.102 | 24.441 |
| 46 | 1.594 | 9.958 |
| 47 | 4.468 | 45.625 |
| 48 | 3.732 | 37.591 |
| 49 | 4.378 | 34.624 |
| 50 | 4.896 | 45.653 |
| 51 | 4.268 | 27.572 |
| 52 | 2.192 | 21.441 |
| 53 | 3.013 | 38.151 |
| 54 | 6.888 | 90.453 |
| 55 | 5.516 | 58.347 |
| 56 | 3.641 | 27.465 |
| 57 | 7.874 | 99.518 |
| 58 | 2.492 | 24.657 |
| 59 | 4.058 | 26.380 |
| 60 | 2.350 | 15.623 |
| 61 | 3.450 | 35.983 |
| 62 | 3.384 | 20.446 |
| 63 | 3.330 | 22.289 |
| 64 | 2.906 | 32.309 |
| 65 | 6.296 | 54.722 |
| 66 | 4.911 | 64.684 |
| 67 | 3.206 | 23.658 |
| 68 | 3.285 | 29.269 |
| 69 | 3.237 | 22.571 |
| 70 | 5.038 | 42.229 |
| 71 | 4.159 | 36.268 |
| 72 | 6.806 | 87.077 |
| 73 | 3.063 | 33.575 |
| 74 | 2.552 | 15.751 |
| 75 | 2.791 | 20.526 |
| 76 | 3.285 | 37.356 |
| 77 | 3.362 | 22.864 |
| 78 | 2.811 | 19.633 |
| 79 | 3.759 | 26.864 |
| 80 | 2.982 | 22.991 |
| 81 | 3.997 | 37.078 |
| 82 | 4.484 | 37.972 |
| 83 | 4.600 | 35.223 |
| 84 | 6.026 | 73.901 |
| 85 | 4.239 | 33.902 |
| 86 | 5.314 | 47.015 |
| 87 | 4.798 | 61.512 |
| 88 | 6.806 | 59.152 |
| 89 | 2.706 | 22.080 |
| 90 | 2.498 | 18.719 |
| 91 | 3.833 | 48.285 |
| 92 | 3.325 | 32.674 |
| 93 | 2.793 | 25.551 |
| 94 | 3.860 | 30.344 |
| 95 | 3.878 | 32.579 |
| 96 | 2.688 | 18.916 |
| 97 | 4.301 | 28.806 |
| 98 | 6.386 | 86.216 |
| 99 | 3.660 | 32.730 |
| 100 | 4.747 | 30.458 |
| 101 | 5.928 | 76.530 |
| 102 | 4.003 | 27.083 |
| 103 | 2.947 | 21.339 |
| 104 | 3.195 | 38.076 |
| 105 | 3.103 | 22.617 |
| 106 | 5.105 | 36.656 |

TABLE 5-continued

| SEQ ID NO: | Discriminant coefficient | Constant term |
|---|---|---|
| 107 | 8.087 | 105.473 |
| 108 | 2.927 | 22.240 |
| 109 | 4.111 | 25.157 |
| 110 | 4.803 | 30.149 |
| 111 | 3.332 | 31.704 |
| 112 | 3.855 | 27.615 |
| 113 | 4.606 | 57.067 |
| 114 | 4.801 | 51.079 |
| 115 | 3.144 | 19.952 |
| 116 | 1.519 | 11.331 |
| 117 | 3.217 | 19.269 |
| 118 | 6.074 | 58.552 |
| 119 | 5.508 | 57.411 |
| 120 | 2.408 | 14.813 |
| 121 | 4.332 | 28.554 |
| 122 | 3.286 | 24.338 |
| 123 | 4.276 | 34.402 |
| 124 | 3.879 | 33.369 |
| 125 | 4.935 | 30.296 |
| 126 | 2.311 | 30.293 |
| 127 | 3.246 | 31.192 |
| 128 | 4.684 | 33.975 |
| 129 | 3.468 | 20.714 |
| 130 | 6.033 | 46.013 |
| 131 | 3.614 | 30.304 |
| 132 | 2.869 | 19.654 |
| 133 | 4.117 | 30.189 |
| 134 | 3.842 | 27.896 |
| 135 | 3.012 | 23.016 |
| 136 | 2.496 | 16.713 |
| 137 | 3.062 | 24.479 |
| 138 | 3.805 | 22.035 |
| 139 | 3.410 | 30.192 |
| 140 | 2.159 | 21.828 |
| 141 | 2.667 | 17.063 |
| 142 | 1.850 | 14.572 |
| 143 | 3.628 | 27.064 |
| 144 | 2.613 | 20.101 |
| 145 | 1.927 | 12.938 |
| 146 | 3.654 | 29.801 |
| 147 | 2.419 | 17.967 |
| 148 | 2.581 | 15.080 |
| 149 | 1.552 | 10.112 |
| 150 | 3.511 | 23.568 |
| 151 | 3.078 | 27.364 |
| 152 | 3.739 | 27.780 |

TABLE 6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_2 | 96.1 | 91.4 | 97.9 | 95.3 | 94.1 | 95.7 |
| 1_3 | 94.6 | 94.3 | 94.7 | 96.9 | 88.2 | 100 |
| 1_4 | 94.6 | 91.4 | 95.7 | 92.2 | 88.2 | 93.6 |
| 1_5 | 93.8 | 88.6 | 95.7 | 95.3 | 94.1 | 95.7 |
| 1_6 | 93 | 88.6 | 94.7 | 92.2 | 88.2 | 93.6 |
| 1_7 | 96.1 | 94.3 | 96.8 | 93.8 | 88.2 | 95.7 |
| 1_8 | 94.6 | 91.4 | 95.7 | 93.8 | 88.2 | 95.7 |
| 1_9 | 93.8 | 88.6 | 95.7 | 93.8 | 88.2 | 95.7 |
| 1_10 | 93.8 | 88.6 | 95.7 | 95.3 | 94.1 | 95.7 |
| 1_11 | 96.1 | 97.1 | 95.7 | 95.3 | 94.1 | 95.7 |
| 1_12 | 94.6 | 94.3 | 94.7 | 96.9 | 94.1 | 97.9 |
| 1_13 | 96.1 | 91.4 | 97.9 | 95.3 | 88.2 | 97.9 |
| 1_14 | 93.8 | 85.7 | 96.8 | 92.2 | 88.2 | 93.6 |
| 1_15 | 94.6 | 91.4 | 95.7 | 95.3 | 88.2 | 97.9 |
| 1_16 | 96.9 | 94.3 | 97.9 | 92.2 | 88.2 | 93.6 |
| 1_17 | 93 | 85.7 | 95.7 | 92.2 | 88.2 | 93.6 |
| 1_18 | 93.8 | 88.6 | 95.7 | 95.3 | 88.2 | 97.9 |
| 1_19 | 93.8 | 88.6 | 95.7 | 92.2 | 88.2 | 93.6 |
| 1_20 | 93 | 85.7 | 95.7 | 95.3 | 94.1 | 95.7 |
| 1_21 | 91.5 | 77.1 | 96.8 | 96.9 | 88.2 | 100 |
| 1_22 | 93 | 85.7 | 95.7 | 93.8 | 94.1 | 93.6 |
| 1_23 | 91.5 | 82.9 | 94.7 | 92.2 | 88.2 | 93.6 |
| 1_24 | 93.8 | 88.6 | 95.7 | 92.2 | 88.2 | 93.6 |
| 1_25 | 93.8 | 88.6 | 95.7 | 95.3 | 94.1 | 95.7 |
| 1_26 | 93.8 | 88.6 | 95.7 | 95.3 | 94.1 | 95.7 |
| 1_27 | 92.2 | 82.9 | 95.7 | 93.8 | 94.1 | 93.6 |
| 1_28 | 93.8 | 88.6 | 95.7 | 93.8 | 88.2 | 95.7 |
| 1_29 | 93 | 88.6 | 94.7 | 95.3 | 94.1 | 95.7 |
| 1_30 | 93 | 85.7 | 95.7 | 93.8 | 88.2 | 95.7 |
| 1_31 | 94.6 | 91.4 | 95.7 | 93.8 | 94.1 | 93.6 |
| 1_32 | 93.8 | 91.4 | 94.7 | 90.6 | 88.2 | 91.5 |
| 1_33 | 94.6 | 91.4 | 95.7 | 95.3 | 94.1 | 95.7 |
| 1_34 | 96.1 | 94.3 | 96.8 | 93.8 | 88.2 | 95.7 |
| 1_35 | 94.6 | 91.4 | 95.7 | 95.3 | 88.2 | 97.9 |
| 1_36 | 93 | 85.7 | 95.7 | 90.6 | 88.2 | 91.5 |
| 1_37 | 93 | 88.6 | 94.7 | 95.3 | 88.2 | 97.9 |
| 1_38 | 93 | 82.9 | 96.8 | 93.8 | 88.2 | 95.7 |
| 1_39 | 92.2 | 82.9 | 95.7 | 95.3 | 94.1 | 95.7 |
| 1_40 | 93 | 85.7 | 95.7 | 92.2 | 88.2 | 93.6 |
| 1_41 | 94.6 | 88.6 | 96.8 | 92.2 | 88.2 | 93.6 |
| 1_42 | 95.3 | 91.4 | 96.8 | 98.4 | 94.1 | 100 |
| 1_43 | 94.6 | 91.4 | 95.7 | 92.2 | 88.2 | 93.6 |
| 1_44 | 93 | 85.7 | 95.7 | 93.8 | 88.2 | 95.7 |
| 1_45 | 94.6 | 88.6 | 96.8 | 92.2 | 88.2 | 93.6 |
| 1_46 | 93 | 85.7 | 95.7 | 93.8 | 88.2 | 95.7 |
| 1_47 | 93 | 85.7 | 95.7 | 92.2 | 88.2 | 93.6 |
| 1_48 | 94.6 | 91.4 | 95.7 | 93.8 | 88.2 | 95.7 |
| 1_49 | 93.8 | 85.7 | 96.8 | 93.8 | 88.2 | 95.7 |
| 1_50 | 95.3 | 91.4 | 96.8 | 93.8 | 94.1 | 93.6 |
| 1_51 | 93.8 | 85.7 | 96.8 | 95.3 | 88.2 | 97.9 |
| 1_52 | 93.8 | 88.6 | 95.7 | 92.2 | 88.2 | 93.6 |
| 1_53 | 92.2 | 85.7 | 94.7 | 93.8 | 94.1 | 93.6 |
| 1_54 | 92.2 | 82.9 | 95.7 | 96.9 | 94.1 | 97.9 |
| 1_55 | 92.2 | 82.9 | 95.7 | 92.2 | 88.2 | 93.6 |
| 1_56 | 92.2 | 85.7 | 94.7 | 92.2 | 88.2 | 93.6 |
| 1_57 | 93 | 85.7 | 95.7 | 96.9 | 94.1 | 97.9 |
| 1_58 | 93 | 85.7 | 95.7 | 93.8 | 88.2 | 95.7 |
| 1_59 | 92.2 | 85.7 | 94.7 | 93.8 | 88.2 | 95.7 |
| 1_60 | 92.2 | 85.7 | 94.7 | 90.6 | 88.2 | 91.5 |
| 1_61 | 93 | 85.7 | 95.7 | 93.8 | 88.2 | 95.7 |
| 1_62 | 93 | 85.7 | 95.7 | 93.8 | 88.2 | 95.7 |
| 1_63 | 93.8 | 91.4 | 94.7 | 93.8 | 88.2 | 95.7 |
| 1_64 | 93.8 | 88.6 | 95.7 | 92.2 | 88.2 | 93.6 |
| 1_65 | 93 | 85.7 | 95.7 | 92.2 | 88.2 | 93.6 |
| 1_66 | 91.5 | 82.9 | 94.7 | 95.3 | 88.2 | 97.9 |
| 1_67 | 92.2 | 85.7 | 94.7 | 93.8 | 88.2 | 95.7 |
| 1_68 | 93 | 85.7 | 95.7 | 92.2 | 88.2 | 93.6 |
| 1_69 | 93 | 82.9 | 96.8 | 93.8 | 88.2 | 95.7 |
| 1_70 | 93.8 | 94.3 | 93.6 | 95.3 | 94.1 | 95.7 |
| 1_71 | 93 | 85.7 | 95.7 | 92.2 | 88.2 | 93.6 |
| 1_72 | 91.5 | 85.7 | 93.6 | 90.6 | 88.2 | 91.5 |
| 1_73 | 93 | 85.7 | 95.7 | 92.2 | 88.2 | 93.6 |
| 1_74 | 94.6 | 88.6 | 96.8 | 92.2 | 88.2 | 93.6 |
| 1_75 | 92.2 | 85.7 | 94.7 | 92.2 | 88.2 | 93.6 |
| 1_76 | 92.2 | 82.9 | 95.7 | 93.8 | 88.2 | 95.7 |
| 1_77 | 93.8 | 88.6 | 95.7 | 92.2 | 88.2 | 93.6 |
| 1_78 | 94.6 | 91.4 | 95.7 | 93.8 | 94.1 | 93.6 |
| 1_79 | 95.3 | 91.4 | 96.8 | 96.9 | 94.1 | 97.9 |
| 1_80 | 93 | 85.7 | 95.7 | 92.2 | 88.2 | 93.6 |
| 1_81 | 93 | 85.7 | 95.7 | 92.2 | 88.2 | 93.6 |
| 1_82 | 93 | 85.7 | 95.7 | 92.2 | 88.2 | 93.6 |
| 1_83 | 93 | 85.7 | 95.7 | 92.2 | 88.2 | 93.6 |
| 1_84 | 94.6 | 91.4 | 95.7 | 95.3 | 94.1 | 95.7 |
| 1_85 | 94.6 | 91.4 | 95.7 | 95.3 | 88.2 | 97.9 |
| 1_86 | 93 | 85.7 | 95.7 | 92.2 | 88.2 | 93.6 |
| 1_87 | 93 | 85.3 | 95.7 | 92.2 | 88.2 | 93.6 |
| 1_88 | 91.5 | 80 | 95.7 | 96.9 | 94.1 | 97.9 |
| 1_89 | 93 | 85.7 | 95.7 | 92.2 | 88.1 | 91.5 |
| 1_90 | 94.6 | 91.4 | 95.7 | 92.2 | 88.2 | 93.6 |
| 1_91 | 92.2 | 82.9 | 95.7 | 93.8 | 88.2 | 95.7 |
| 1_92 | 92.2 | 82.9 | 95.7 | 92.2 | 88.2 | 93.6 |
| 1_93 | 93 | 85.7 | 95.7 | 92.2 | 88.2 | 93.6 |
| 1_94 | 92.2 | 85.7 | 94.7 | 93.8 | 88.2 | 95.7 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_95 | 95.3 | 91.4 | 96.8 | 93.8 | 88.2 | 95.7 |
| 1_96 | 94.6 | 88.6 | 96.8 | 90.6 | 88.2 | 91.5 |
| 1_97 | 94.6 | 91.4 | 95.7 | 92.2 | 88.2 | 93.6 |
| 1_98 | 92.2 | 82.9 | 95.7 | 93.8 | 88.2 | 95.7 |
| 1_99 | 93.8 | 91.4 | 94.7 | 95.3 | 94.1 | 95.7 |
| 1_100 | 94.6 | 88.6 | 96.8 | 90.6 | 88.2 | 91.5 |
| 1_101 | 93 | 85.7 | 95.7 | 92.2 | 88.2 | 93.6 |
| 1_102 | 94.6 | 88.6 | 96.8 | 95.3 | 94.1 | 95.7 |
| 1_103 | 93 | 85.7 | 95.7 | 93.8 | 88.2 | 95.7 |
| 1_104 | 93 | 82.9 | 96.8 | 95.3 | 88.2 | 97.9 |
| 1_105 | 92.2 | 85.7 | 94.7 | 92.2 | 88.2 | 93.6 |
| 1_106 | 93 | 88.6 | 94.7 | 95.3 | 88.2 | 97.9 |
| 1_107 | 92.2 | 85.7 | 94.7 | 92.2 | 94.1 | 91.5 |
| 1_108 | 93.8 | 88.6 | 95.7 | 92.2 | 88.2 | 93.6 |
| 1_109 | 93.8 | 85.7 | 96.8 | 92.2 | 88.2 | 93.6 |
| 1_110 | 93.8 | 88.6 | 95.7 | 95.3 | 94.1 | 95.7 |
| 1_111 | 93 | 85.7 | 95.7 | 93.8 | 88.2 | 95.7 |
| 1_112 | 91.5 | 82.9 | 94.7 | 92.2 | 88.2 | 93.6 |
| 1_113 | 93 | 85.7 | 95.7 | 92.2 | 88.2 | 93.6 |
| 1_114 | 93 | 85.7 | 95.7 | 92.2 | 88.2 | 93.6 |
| 1_115 | 92.2 | 85.7 | 94.7 | 95.3 | 88.2 | 97.9 |
| 1_116 | 93 | 88.6 | 94.7 | 93.8 | 94.1 | 93.6 |
| 1_117 | 93 | 88.6 | 94.7 | 93.8 | 88.2 | 95.7 |
| 1_118 | 93 | 85.7 | 95.7 | 93.8 | 88.2 | 95.7 |
| 1_119 | 93.8 | 85.7 | 96.8 | 93.8 | 94.1 | 93.6 |
| 1_120 | 92.2 | 82.9 | 95.7 | 95.3 | 88.2 | 97.9 |
| 1_121 | 93 | 85.7 | 95.7 | 93.8 | 88.2 | 95.7 |
| 1_122 | 93 | 85.7 | 95.7 | 92.2 | 88.2 | 93.6 |
| 1_123 | 93 | 85.7 | 95.7 | 93.8 | 88.2 | 95.7 |
| 1_124 | 91.5 | 80 | 95.7 | 92.2 | 88.2 | 93.6 |
| 1_125 | 94.6 | 88.6 | 96.8 | 93.8 | 94.1 | 93.6 |
| 1_126 | 93.8 | 85.7 | 96.8 | 92.2 | 88.2 | 93.6 |
| 1_127 | 93.8 | 88.6 | 95.7 | 93.8 | 88.2 | 95.7 |
| 1_128 | 93.8 | 91.4 | 94.7 | 92.2 | 88.2 | 93.6 |
| 1_129 | 93 | 85.7 | 95.7 | 92.2 | 88.2 | 93.6 |
| 1_130 | 93 | 82.9 | 96.8 | 95.3 | 88.2 | 97.9 |
| 1_131 | 90.7 | 82.9 | 93.6 | 93.8 | 88.2 | 95.7 |
| 1_132 | 93 | 85.7 | 95.7 | 92.2 | 88.2 | 93.6 |
| 1_133 | 94.6 | 88.6 | 96.8 | 95.3 | 88.2 | 97.9 |
| 1_134 | 93.8 | 88.6 | 95.7 | 95.3 | 94.1 | 95.7 |
| 1_135 | 93 | 85.7 | 95.7 | 93.8 | 88.2 | 95.7 |
| 1_136 | 96.9 | 97.1 | 96.8 | 93.8 | 94.1 | 93.6 |
| 1_137 | 91.5 | 80 | 95.7 | 92.2 | 88.2 | 93.6 |
| 1_138 | 93.8 | 88.6 | 95.7 | 93.8 | 94.1 | 93.6 |
| 1_139 | 92.2 | 85.7 | 94.7 | 96.9 | 94.1 | 97.9 |
| 1_140 | 94.6 | 88.6 | 96.8 | 92.2 | 88.2 | 93.6 |
| 1_141 | 95.3 | 91.4 | 96.8 | 93.8 | 88.2 | 95.7 |
| 1_142 | 93 | 85.7 | 95.7 | 92.2 | 88.2 | 93.6 |
| 1_143 | 92.2 | 82.9 | 95.7 | 92.2 | 88.2 | 93.6 |
| 1_144 | 93 | 85.7 | 95.7 | 92.2 | 88.2 | 93.6 |
| 1_145 | 93 | 85.7 | 95.7 | 92.2 | 88.2 | 93.6 |
| 1_146 | 93 | 85.7 | 95.7 | 93.8 | 88.2 | 95.7 |
| 1_147 | 93 | 85.7 | 95.7 | 92.2 | 88.2 | 93.6 |
| 1_148 | 93 | 85.7 | 95.7 | 93.8 | 88.2 | 95.7 |
| 1_149 | 92.2 | 82.9 | 95.7 | 93.8 | 88.2 | 95.7 |
| 1_150 | 93.8 | 88.6 | 95.7 | 96.9 | 94.1 | 97.9 |
| 1_151 | 93 | 85.7 | 95.7 | 93.8 | 88.2 | 95.7 |
| 1_152 | 92.2 | 85.7 | 94.7 | 92.2 | 88.2 | 93.6 |

Example 3

<Selection of Gene Marker Using all Samples and Method for Evaluating Prostate Cancer Discriminant Performance with Acquired Gene Marker>

In this Example, the samples in the training cohort and the validation cohort used in Examples 1 and 2 were integrated, and selection of a gene marker and evaluation of its prostate cancer discriminant performance were conducted using all of the samples.

Specifically, the miRNA expression levels in the serum of the 52 prostate cancer patients and the 141 healthy male subjects obtained in the preceding Reference Examples were normalized by quantile normalization. In order to acquire diagnostic markers with higher reliability, only genes that showed gene expression levels of $2^6$ or higher in 50% or more of the samples in either of the prostate cancer patient group or the healthy subject group were selected in the gene marker selection. In order to further acquire statistical significance for discriminating a prostate cancer patient group from a healthy subject group, the P value obtained by two-tailed t-test assuming equal variance as to each gene expression level was corrected by the Bonferroni method, and genes that satisfied $p<0.01$ were selected as gene markers for use in explanatory variables of a discriminant. The obtained genes are described in Table 7. In this way, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p genes, and the nucleotide sequences of SEQ ID NOs: 153 to 187 related thereto were found in addition to the genes described in Table 3. As with the nucleotide sequences of SEQ ID NOs: 1 to 152, the results obtained about the polynucleotides shown in the nucleotide sequences of SEQ ID NOs: 153 to 187 also showed that the measurement values were significantly lower (−) or higher (+) in the prostate cancer patient group than in the healthy subject group (Table 7). These results were able to be validated in the validation cohort. The presence or absence of prostate cancer in the newly obtained samples can be determined by the methods described in Examples 1 and 2 by using the gene expression level measurement values described in Table 7 either alone or in combination with the gene expression level measurement values described in Table 3.

TABLE 7

| SEQ ID NO: | Gene name | P value after Bonferroni correction | Expression level in prostate cancer patient with relative to healthy subject |
|---|---|---|---|
| 1 | hsa-miR-4443 | 1.11E−37 | + |
| 2 | hsa-miR-1908-5p | 1.13E−31 | + |
| 3 | hsa-miR-4257 | 6.48E−24 | − |
| 4 | hsa-miR-3197 | 1.28E−30 | + |
| 5 | hsa-miR-3188 | 5.67E−27 | + |
| 6 | hsa-miR-4649-5p | 3.70E−27 | − |
| 7 | hsa-miR-1343-3p | 7.09E−23 | − |
| 8 | hsa-miR-6861-5p | 1.80E−24 | − |
| 9 | hsa-miR-1343-5p | 2.82E−24 | + |
| 10 | hsa-miR-642b-3p | 1.07E−27 | − |
| 11 | hsa-miR-6741-5p | 6.82E−22 | − |
| 12 | hsa-miR-4745-5p | 1.13E−23 | − |
| 13 | hsa-miR-6826-5p | 3.61E−19 | − |
| 14 | hsa-miR-3663-3p | 3.08E−23 | − |
| 15 | hsa-miR-3131 | 3.50E−15 | − |
| 16 | hsa-miR-92a-2-5p | 4.74E−16 | + |
| 17 | hsa-miR-4258 | 5.92E−20 | − |
| 18 | hsa-miR-4448 | 7.18E−20 | + |
| 19 | hsa-miR-6125 | 2.60E−19 | + |
| 20 | hsa-miR-6880-5p | 4.86E−19 | + |
| 21 | hsa-miR-6132 | 2.01E−19 | + |
| 22 | hsa-miR-4467 | 7.91E−20 | + |
| 23 | hsa-miR-6749-5p | 1.81E−19 | − |
| 24 | hsa-miR-2392 | 2.70E−11 | + |

TABLE 7-continued

| SEQ ID NO: | Gene name | P value after Bonferroni correction | Expression level in prostate cancer patient with relative to healthy subject |
|---|---|---|---|
| 25 | hsa-miR-1273g-3p | 3.27E−19 | − |
| 26 | hsa-miR-4746-3p | 4.55E−21 | + |
| 27 | hsa-miR-1914-3p | 8.27E−15 | − |
| 28 | hsa-miR-7845-5p | 5.79E−19 | + |
| 29 | hsa-miR-6726-5p | 7.72E−19 | − |
| 30 | hsa-miR-128-2-5p | 5.33E−19 | − |
| 31 | hsa-miR-4651 | 5.90E−18 | − |
| 32 | hsa-miR-6765-3p | 8.39E−16 | − |
| 33 | hsa-miR-3185 | 1.60E−19 | + |
| 34 | hsa-miR-4792 | 1.45E−17 | + |
| 35 | hsa-miR-6887-5p | 1.16E−14 | − |
| 36 | hsa-miR-5572 | 4.90E−16 | + |
| 37 | hsa-miR-3619-3p | 2.51E−16 | − |
| 38 | hsa-miR-6780b-5p | 1.37E−16 | + |
| 39 | hsa-miR-4707-5p | 1.51E−17 | + |
| 40 | hsa-miR-8063 | 5.05E−20 | − |
| 41 | hsa-miR-4454 | 6.07E−14 | − |
| 42 | hsa-miR-4525 | 6.00E−19 | − |
| 43 | hsa-miR-7975 | 6.13E−15 | − |
| 44 | hsa-miR-744-5p | 5.25E−18 | + |
| 45 | hsa-miR-3135b | 1.17E−09 | − |
| 46 | hsa-miR-4648 | 9.53E−17 | + |
| 47 | hsa-miR-6816-5p | 2.60E−15 | + |
| 48 | hsa-miR-4741 | 5.52E−16 | + |
| 49 | hsa-miR-7150 | 2.35E−13 | + |
| 50 | hsa-miR-6791-5p | 6.63E−17 | + |
| 51 | hsa-miR-1247-3p | 6.77E−13 | + |
| 52 | hsa-miR-7977 | 2.22E−14 | − |
| 53 | hsa-miR-4497 | 4.39E−16 | − |
| 54 | hsa-miR-6090 | 4.58E−17 | + |
| 55 | hsa-miR-6781-5p | 1.08E−11 | + |
| 56 | hsa-miR-6870-5p | 4.41E−09 | + |
| 57 | hsa-miR-6729-5p | 6.57E−14 | + |
| 58 | hsa-miR-4530 | 1.48E−10 | + |
| 59 | hsa-miR-7847-3p | 6.31E−12 | − |
| 60 | hsa-miR-6825-5p | 3.31E−12 | + |
| 61 | hsa-miR-4674 | 7.19E−14 | − |
| 62 | hsa-miR-3917 | 1.78E−12 | − |
| 63 | hsa-miR-4707-3p | 6.32E−12 | + |
| 64 | hsa-miR-6885-5p | 1.69E−14 | − |
| 65 | hsa-miR-6722-3p | 1.09E−10 | + |
| 66 | hsa-miR-4516 | 9.57E−15 | − |
| 67 | hsa-miR-6757-5p | 1.02E−11 | − |
| 68 | hsa-miR-6840-3p | 6.73E−14 | − |
| 69 | hsa-miR-5195-3p | 1.21E−11 | − |
| 70 | hsa-miR-6756-5p | 1.46E−15 | − |
| 71 | hsa-miR-6800-5p | 3.18E−11 | + |
| 72 | hsa-miR-6727-5p | 2.88E−09 | − |
| 73 | hsa-miR-6126 | 4.50E−12 | + |
| 74 | hsa-miR-6872-3p | 4.58E−09 | − |
| 75 | hsa-miR-4446-3p | 1.90E−12 | − |
| 76 | hsa-miR-1268a | 1.09E−13 | + |
| 77 | hsa-miR-1908-3p | 2.75E−10 | − |
| 78 | hsa-miR-3679-5p | 4.14E−15 | + |
| 79 | hsa-miR-4534 | 1.65E−06 | + |
| 80 | hsa-miR-4675 | 8.56E−11 | − |
| 81 | hsa-miR-7108-5p | 5.97E−11 | + |
| 82 | hsa-miR-6799-5p | 1.21E−10 | + |
| 83 | hsa-miR-4695-5p | 2.08E−13 | + |
| 84 | hsa-miR-3178 | 1.33E−10 | + |
| 85 | hsa-miR-5090 | 6.85E−11 | − |
| 86 | hsa-miR-3180 | 1.01E−09 | + |
| 87 | hsa-miR-1237-5p | 7.78E−13 | + |
| 88 | hsa-miR-4758-5p | 1.97E−09 | − |
| 89 | hsa-miR-3184-5p | 4.70E−10 | + |
| 90 | hsa-miR-4286 | 2.39E−08 | − |
| 91 | hsa-miR-6784-5p | 1.24E−07 | + |
| 92 | hsa-miR-6768-5p | 2.85E−07 | + |
| 93 | hsa-miR-6785-5p | 2.78E−10 | − |
| 94 | hsa-miR-4706 | 3.20E−06 | − |
| 95 | hsa-miR-711 | 7.50E−11 | + |
| 96 | hsa-miR-1260a | 3.06E−07 | − |
| 97 | hsa-miR-6746-5p | 6.04E−06 | − |
| 98 | hsa-miR-6089 | 1.19E−08 | + |
| 99 | hsa-miR-6821-5p | 4.27E−10 | + |
| 100 | hsa-miR-4667-5p | 9.12E−07 | + |
| 101 | hsa-miR-8069 | 1.81E−09 | + |
| 102 | hsa-miR-4726-5p | 2.71E−05 | − |
| 103 | hsa-miR-6124 | 9.11E−05 | + |
| 104 | hsa-miR-4532 | 2.46E−09 | − |
| 105 | hsa-miR-4486 | 6.30E−09 | + |
| 106 | hsa-miR-4728-5p | 8.48E−09 | − |
| 107 | hsa-miR-4508 | 1.66E−06 | + |
| 108 | hsa-miR-128-1-5p | 2.04E−08 | + |
| 109 | hsa-miR-4513 | 1.44E−06 | − |
| 110 | hsa-miR-6795-5p | 1.12E−06 | + |
| 111 | hsa-miR-4689 | 8.95E−06 | − |
| 112 | hsa-miR-6763-5p | 2.59E−09 | + |
| 113 | hsa-miR-8072 | 1.32E−07 | + |
| 114 | hsa-miR-6765-5p | 4.48E−05 | + |
| 115 | hsa-miR-4419b | 1.22E−04 | − |
| 116 | hsa-miR-7641 | 3.99E−08 | − |
| 117 | hsa-miR-3928-3p | 7.30E−06 | + |
| 118 | hsa-miR-1227-5p | 6.47E−06 | + |
| 119 | hsa-miR-4492 | 3.11E−10 | − |
| 120 | hsa-miR-296-3p | 1.31E−06 | − |
| 121 | hsa-miR-6769a-5p | 2.26E−05 | − |
| 122 | hsa-miR-6889-5p | 5.29E−04 | + |
| 123 | hsa-miR-4632-5p | 3.39E−05 | + |
| 124 | hsa-miR-4505 | 6.21E−06 | + |
| 125 | hsa-miR-3154 | 1.41E−05 | + |
| 126 | hsa-miR-3648 | 2.83E−06 | − |
| 127 | hsa-miR-4442 | 2.03E−07 | − |
| 128 | hsa-miR-3141 | 3.73E−07 | + |
| 129 | hsa-miR-7113-3p | 4.11E−05 | + |
| 130 | hsa-miR-6819-5p | 5.08E−03 | − |
| 131 | hsa-miR-3195 | 1.18E−04 | + |
| 132 | hsa-miR-1199-5p | 8.59E−05 | − |
| 133 | hsa-miR-6738-5p | 2.49E−05 | − |
| 134 | hsa-miR-4656 | 1.45E−05 | − |
| 135 | hsa-miR-6820-5p | 3.40E−04 | + |
| 136 | hsa-miR-615-5p | 1.98E−14 | − |
| 137 | hsa-miR-486-3p | 9.28E−17 | + |
| 138 | hsa-miR-1225-3p | 3.41E−16 | + |
| 139 | hsa-miR-760 | 4.58E−15 | − |
| 140 | hsa-miR-187-5p | 7.21E−11 | − |
| 141 | hsa-miR-1203 | 8.06E−14 | + |
| 142 | hsa-miR-7110-5p | 7.39E−11 | + |
| 143 | hsa-miR-371a-5p | 3.27E−12 | − |
| 144 | hsa-miR-939-5p | 2.77E−11 | + |
| 145 | hsa-miR-575 | 1.85E−10 | + |
| 146 | hsa-miR-92b-5p | 7.45E−16 | + |
| 147 | hsa-miR-887-3p | 3.99E−12 | + |
| 148 | hsa-miR-920 | 1.63E−05 | − |
| 149 | hsa-miR-1915-5p | 1.24E−07 | − |
| 150 | hsa-miR-1231 | 1.35E−07 | + |
| 151 | hsa-miR-663b | 6.03E−07 | − |
| 152 | hsa-miR-1225-5p | 2.89E−06 | + |
| 153 | hsa-miR-4763-3p | 1.50E−07 | + |
| 154 | hsa-miR-3656 | 2.20E−06 | + |
| 155 | hsa-miR-4488 | 3.80E−06 | + |
| 156 | hsa-miR-125a-3p | 8.47E−06 | − |
| 157 | hsa-miR-1469 | 8.73E−06 | + |
| 158 | hsa-miR-1228-5p | 1.34E−05 | + |
| 159 | hsa-miR-6798-5p | 1.73E−05 | + |
| 160 | hsa-miR-1268b | 1.93E−05 | + |
| 161 | hsa-miR-6732-5p | 2.42E−05 | + |
| 162 | hsa-miR-1915-3p | 3.96E−05 | + |
| 163 | hsa-miR-4433b-3p | 4.24E−05 | + |
| 164 | hsa-miR-1207-5p | 4.14E−05 | + |
| 165 | hsa-miR-4433-3p | 4.84E−05 | + |
| 166 | hsa-miR-6879-5p | 5.79E−05 | + |
| 167 | hsa-miR-4417 | 8.44E−05 | + |
| 168 | hsa-miR-30c-1-3p | 8.49E−05 | + |
| 169 | hsa-miR-4638-5p | 7.97E−05 | + |
| 170 | hsa-miR-6088 | 2.07E−04 | − |
| 171 | hsa-miR-4270 | 2.44E−04 | − |
| 172 | hsa-miR-6782-5p | 6.53E−04 | + |
| 173 | hsa-miR-665 | 7.52E−04 | − |
| 174 | hsa-miR-486-5p | 9.25E−04 | + |

TABLE 7-continued

| SEQ ID NO: | Gene name | P value after Bonferroni correction | Expression level in prostate cancer patient with relative to healthy subject |
|---|---|---|---|
| 175 | hsa-miR-4655-5p | 1.04E−03 | + |
| 176 | hsa-miR-1275 | 1.11E−03 | + |
| 177 | hsa-miR-6806-5p | 1.78E−03 | − |
| 178 | hsa-miR-614 | 1.92E−03 | − |
| 179 | hsa-miR-3937 | 2.41E−03 | + |
| 180 | hsa-miR-6752-5p | 2.47E−03 | + |
| 181 | hsa-miR-6771-5p | 3.30E−03 | − |
| 182 | hsa-miR-4450 | 3.79E−03 | + |
| 183 | hsa-miR-211-3p | 6.22E−03 | − |
| 184 | hsa-miR-663a | 5.44E−03 | + |
| 185 | hsa-miR-6842-5p | 8.58E−03 | + |
| 186 | hsa-miR-7114-5p | 8.30E−03 | − |
| 187 | hsa-miR-6779-5p | 8.35E−03 | − |

Example 4

<Method for Evaluating Prostate Cancer-Specific Discriminant Performance with Combination of Multiple Gene Markers Using Samples in the Validation Cohort>

In this Example, gene expression levels of miRNAs in serum were compared between prostate cancer patients and a control group that consists of healthy subjects and breast cancer patients, in the same way as the method described in Example 1 in the training cohort obtained in Reference Example 2 to select a statistically significant gene for diagnosis. Polynucleotides consisting of the nucleotide sequences represented by SEQ ID NOs: 580 to 611 thus newly selected were each further combined with the gene markers selected in Example 1 to study a method for evaluating prostate cancer-specific discriminant performance.

Specifically, first, the miRNA expression levels in the training cohort and the validation cohort obtained in Reference Example 2 mentioned above were combined and normalized by quantile normalization. Next, Fisher's linear discriminant analysis was conducted as to combinations of 1 to 4 expression level measurement values comprising at least one or more of the expression level measurement values of the polynucleotides consisting of the nucleotide sequences represented by SEQ ID NOs: 1 to 187, 580 to 611, to construct a discriminant for determining the presence or absence of prostate cancer. Next, accuracy, sensitivity, and specificity in the validation cohort obtained in Reference Example 2 were calculated using the discriminant thus prepared, with the prostate cancer patient group as a positive sample group, and the healthy subject group and the breast cancer patient group as a negative sample group. The discriminant performance of the selected polynucleotides was validated using the independent samples.

Most of polynucleotides consisting of the nucleotide sequences represented by these SEQ ID NOs (SEQ ID NOs: 1 to 187, and 580 to 611 corresponding to the miRNA markers of Table 1) or complementary sequences thereof mentioned above were able to provide relatively high accuracy, sensitivity, and specificity in the determination of the presence or absence of prostate cancer, and furthermore, were able to specifically discriminate prostate cancer from the other cancers. For example, among the combinations of multiple polynucleotides selected from the group consisting of polynucleotides consisting of the nucleotide sequences represented by SEQ ID NOs: 1, 3, 4, 5, 6, 7, 9, 10, 12, 14, 15, 16, 17, 18, 20, 24, 29, 35, 37, 42, 51, 55, 58, 61, 63, 64, 67, 70, 72, 79, 82, 89, 91, 97, 98, 101, 103, 104, 112, 113, 114, 116, 119, 126, 135, 136, 139, 140, 141, 145, 147, 154, 155, 156, 158, 169, 173, 175, 178, 182, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610 and 611, or complementary sequences thereof (the cancer type-specific polynucleotide group 1) as polynucleotides capable of specifically binding to target markers, combinations comprising at least one or more polynucleotide(s) selected from the group consisting of polynucleotides of SEQ ID NOs: 1, 12, 16, 37, 42, 63, 119, 126, 139, 173, 178, 599, 609 and 611 (the cancer type-specific polynucleotide group 2) that were included in the cancer type-specific polynucleotide group 1, were able to specifically discriminate prostate cancer from the other cancers with high accuracy.

The number of the aforementioned polynucleotides with cancer type specificity in the combination can be 1, 2, 3, 4, 5, 6, 7, 8, 9, 10 or more for the combination. The combinations of 4 or more of these polynucleotides were able to exhibit discriminant accuracy of 85% or higher.

Specifically, the discriminant accuracy of the measurement using the polynucleotide consisting of the nucleotide sequence represented by SEQ ID NO: 1 or a complementary sequence thereof is shown in Table 8-1. The measurement using the combination of one polynucleotide comprising at least one polynucleotide consisting of the nucleotide sequence represented by SEQ ID NO: 1 or a complementary sequence thereof exhibited accuracy of 94.4% in the training cohort and accuracy of 91.8% in the validation cohort. Also, for example, the measurement using the combination of two polynucleotides comprising at least one polynucleotide consisting of the nucleotide sequence represented by SEQ ID NO: 1 or a complementary sequence thereof exhibited the highest accuracy of 96.4% in the training cohort and the highest accuracy of 90.8% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 98.5% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 95.4% in the training cohort and the highest accuracy of 92.9% in the validation cohort.

The discriminant accuracy of the measurement using the polynucleotide consisting of the nucleotide sequence represented by SEQ ID NO: 12 or a complementary sequence thereof is shown in Table 8-2. The measurement using the combination of one polynucleotide comprising at least one polynucleotide consisting of the nucleotide sequence represented by SEQ ID NO: 12 or a complementary sequence thereof exhibited accuracy of 65.5% in the training cohort and accuracy of 56.1% in the validation cohort. Also, for example, the measurement using the combination of two polynucleotides comprising at least one polynucleotide consisting of the nucleotide sequence represented by SEQ ID NO: 12 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 12 or a complementary sequence thereof exhibited the highest accuracy of 98.0% in the training cohort and the highest accuracy of 93.9% in the validation cohort. Furthermore, for example, the measurement using the combinations of four polynucleotides comprising at least one polynucleotide consisting of the nucleotide sequence represented by SEQ ID NO: 12 or a complementary sequence thereof exhibited the highest accuracy of 98.5% in the training cohort and the highest accuracy of 94.9% in the validation cohort.

The discriminant accuracy of the measurement using the polynucleotide consisting of the nucleotide sequence represented by SEQ ID NO: 16 or a complementary sequence thereof is shown in Table 8-3. The measurement using the combination of one polynucleotide comprising at least one polynucleotide consisting of the nucleotide sequence represented by SEQ ID NO: 16 or a complementary sequence thereof exhibited accuracy of 71.6% in the training cohort and accuracy of 74.5% in the validation cohort. Also, for example, the measurement using the combination of two polynucleotides comprising at least one polynucleotide consisting of the nucleotide sequence represented by SEQ ID NO: 16 or a complementary sequence thereof exhibited the highest accuracy of 95.4% in the training cohort and the highest accuracy of 93.9% in the validation cohort. Furthermore, for example, the measurement using the combinations of three polynucleotides comprising at least one polynucleotide consisting of the nucleotide sequence represented by SEQ ID NO: 16 or a complementary sequence thereof exhibited the highest accuracy of 97.5% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 16 or a complementary sequence thereof exhibited the highest accuracy of 98.0% in the training cohort and the highest accuracy of 88.8% in the validation cohort.

The discriminant accuracy of the measurement using the polynucleotide consisting of the nucleotide sequence represented by SEQ ID NO: 37 or a complementary sequence thereof is shown in Table 8-4. The measurement using the combination of one polynucleotide comprising at least one polynucleotide consisting of the nucleotide sequence represented by SEQ ID NO: 37 or a complementary sequence thereof exhibited accuracy of 73.6% in the training cohort and accuracy of 72.4% in the validation cohort. Also, for example, the measurement using the combination of two polynucleotides comprising at least one polynucleotide consisting of the nucleotide sequence represented by SEQ ID NO: 37 or a complementary sequence thereof exhibited the highest accuracy of 95.9% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 37 or a complementary sequence thereof exhibited the highest accuracy of 97.0% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 37 or a complementary sequence thereof exhibited the highest accuracy of 97.0% in the training cohort and the highest accuracy of 89.8% in the validation cohort.

The discriminant accuracy of the measurement using the polynucleotide consisting of the nucleotide sequence represented by SEQ ID NO: 42 or a complementary sequence thereof is shown in Table 8-5. The measurement using the combination of one polynucleotide comprising at least one polynucleotide consisting of the nucleotide sequence represented by SEQ ID NO: 42 or a complementary sequence thereof exhibited accuracy of 57.4% in the training cohort and accuracy of 59.2% in the validation cohort. Also, for example, the measurement using the combination of two polynucleotides comprising at least one polynucleotide consisting of the nucleotide sequence represented by SEQ ID NO: 42 or a complementary sequence thereof exhibited the highest accuracy of 95.4% in the training cohort and the highest accuracy of 93.9% in the validation cohort. Furthermore, for example, the measurement using the combinations of three polynucleotides comprising at least one polynucleotide consisting of the nucleotide sequence represented by SEQ ID NO: 42 or a complementary sequence thereof exhibited the highest accuracy of 97.5% in the training cohort and the highest accuracy of 95.9% in the validation cohort. Furthermore, for example, the measurement using the combinations of four polynucleotides comprising at least one polynucleotide consisting of the nucleotide sequence represented by SEQ ID NO: 42 or a complementary sequence thereof exhibited the highest accuracy of 96.9% in the training cohort and the highest accuracy of 94.9% in the validation cohort.

The discriminant accuracy of the measurement using the polynucleotide consisting of the nucleotide sequence represented by SEQ ID NO: 63 or a complementary sequence thereof is shown in Table 8-6. The measurement using the combination of one polynucleotide comprising at least one polynucleotide consisting of the nucleotide sequence represented by SEQ ID NO: 63 or a complementary sequence thereof exhibited accuracy of 72.6% in the training cohort and accuracy of 73.5% in the validation cohort. Also, for example, the measurement using the combination of two polynucleotides comprising at least one polynucleotide consisting of the nucleotide sequence represented by SEQ ID NO: 63 or a complementary sequence thereof exhibited the highest accuracy of 94.9% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 63 or a complementary sequence thereof exhibited the highest accuracy of 95.9% in the training cohort and the highest accuracy of 95.9% in the validation cohort. Furthermore, for example, the measurement using the combinations of four polynucleotides comprising at least one polynucleotide consisting of the nucleotide sequence represented by SEQ ID NO: 63 or a complementary sequence thereof exhibited the highest accuracy of 94.4% in the training cohort and the highest accuracy of 89.8% in the validation cohort.

The discriminant accuracy of the measurement using the polynucleotide consisting of the nucleotide sequence represented by SEQ ID NO: 119 or a complementary sequence thereof is shown in Table 8-7. The measurement using the combination of one polynucleotide comprising at least one polynucleotide consisting of the nucleotide sequence represented by SEQ ID NO: 119 or a complementary sequence thereof exhibited accuracy of 46.9% in the training cohort and accuracy of 48.0% in the validation cohort. Also, for example, the measurement using the combination of two polynucleotides comprising at least one polynucleotide consisting of the nucleotide sequence represented by SEQ ID NO: 119 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 119 or a complementary sequence thereof exhibited the highest accuracy of 97.4% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 119 or a complementary sequence thereof exhibited the highest accuracy of 96.4% in the training cohort and the highest accuracy of 89.8% in the validation cohort.

The discriminant accuracy of the measurement using the polynucleotide consisting of the nucleotide sequence represented by SEQ ID NO: 126 or a complementary sequence thereof is shown in Table 8-8. The measurement using the combination of one polynucleotide comprising at least one polynucleotide consisting of the nucleotide sequence represented by SEQ ID NO: 126 or a complementary sequence thereof exhibited accuracy of 66.0% in the training cohort and accuracy of 53.1% in the validation cohort. Also, for example, the measurement using the combination of two polynucleotides comprising at least one polynucleotide consisting of the nucleotide sequence represented by SEQ ID NO: 126 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited the highest accuracy of 96.4% in the training cohort and the highest accuracy of 90.8% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited the highest accuracy of 93.9% in the training cohort and the highest accuracy of 91.8% in the validation cohort.

The discriminant accuracy of the measurement using the polynucleotide consisting of the nucleotide sequence represented by SEQ ID NO: 139 or a complementary sequence thereof is shown in Table 8-9. The measurement using the combination of one polynucleotide comprising at least one polynucleotide consisting of the nucleotide sequence represented by SEQ ID NO: 139 or a complementary sequence thereof exhibited accuracy of 43.7% in the training cohort and accuracy of 40.8% in the validation cohort. Also, for example, the measurement using the combination of two polynucleotides comprising at least one polynucleotide consisting of the nucleotide sequence represented by SEQ ID NO: 139 or a complementary sequence thereof exhibited the highest accuracy of 94.4% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 139 or a complementary sequence thereof exhibited the highest accuracy of 96.4% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 139 or a complementary sequence thereof exhibited the highest accuracy of 92.4% in the training cohort and the highest accuracy of 91.8% in the validation cohort.

The discriminant accuracy of the measurement using the polynucleotide consisting of the nucleotide sequence represented by SEQ ID NO: 173 or a complementary sequence thereof is shown in Table 8-10. The measurement using the combination of one polynucleotide comprising at least one polynucleotide consisting of the nucleotide sequence represented by SEQ ID NO: 173 or a complementary sequence thereof exhibited accuracy of 43.7% in the training cohort and accuracy of 55.1% in the validation cohort. Also, for example, the measurement using the combination of two polynucleotides comprising at least one polynucleotide consisting of the nucleotide sequence represented by SEQ ID NO: 173 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 173 or a complementary sequence thereof exhibited the highest accuracy of 97.0% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 173 or a complementary sequence thereof exhibited the highest accuracy of 92.4% in the training cohort and the highest accuracy of 95.9% in the validation cohort.

The discriminant accuracy of the measurement using the polynucleotide consisting of the nucleotide sequence represented by SEQ ID NO: 178 or a complementary sequence thereof is shown in Table 8-11. The measurement using the combination of one polynucleotide comprising at least one polynucleotide consisting of the nucleotide sequence represented by SEQ ID NO: 178 or a complementary sequence thereof exhibited accuracy of 68.0% in the training cohort and the highest accuracy of 72.4% in the validation cohort. Also, for example, the measurement using the combination of two polynucleotides comprising at least one polynucleotide consisting of the nucleotide sequence represented by SEQ ID NO: 178 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 178 or a complementary sequence thereof exhibited the highest accuracy of 96.4% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 178 or a complementary sequence thereof exhibited the highest accuracy of 96.4% in the training cohort and the highest accuracy of 93.9% in the validation cohort.

The discriminant accuracy of the measurement using the polynucleotide consisting of the nucleotide sequence represented by SEQ ID NO: 599 or a complementary sequence thereof is shown in Table 8-12. The measurement using the combination of one polynucleotide comprising at least one polynucleotide consisting of the nucleotide sequence represented by SEQ ID NO: 599 or a complementary sequence thereof exhibited accuracy of 61.4% in the training cohort and the highest accuracy of 65.3% in the validation cohort. Also, for example, the measurement using the combination of two polynucleotides comprising at least one polynucleotide consisting of the nucleotide sequence represented by SEQ ID NO: 599 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 599 or a complementary sequence thereof exhibited the highest accuracy of 97.5% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 599 or a complementary sequence thereof exhibited the highest accuracy of 96.4% in the training cohort and the highest accuracy of 94.9% in the validation cohort.

The discriminant accuracy of the measurement using the polynucleotide consisting of the nucleotide sequence represented by SEQ ID NO: 609 or a complementary sequence thereof is shown in Table 8-13. The measurement using the combination of one polynucleotide comprising at least one polynucleotide consisting of the nucleotide sequence represented by SEQ ID NO: 609 or a complementary sequence thereof exhibited accuracy of 59.7% in the training cohort and accuracy of 65.3% in the validation cohort. Also, for example, the measurement using the combination of two polynucleotides comprising at least one polynucleotide consisting of the nucleotide sequence represented by SEQ ID NO: 609 or a complementary sequence thereof exhibited the highest accuracy of 95.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 609 or a complementary sequence thereof exhibited the highest accuracy of 96.4% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 609 or a complementary sequence thereof exhibited the highest accuracy of 96.4% in the training cohort and the highest accuracy of 88.8% in the validation cohort.

The discriminant accuracy of the measurement using the polynucleotide consisting of the nucleotide sequence represented by SEQ ID NO: 611 or a complementary sequence thereof is shown in Table 8-14. The measurement using the combination of one polynucleotide comprising at least one polynucleotide consisting of the nucleotide sequence represented by SEQ ID NO: 611 or a complementary sequence thereof exhibited accuracy of 55.8% in the training cohort and accuracy of 62.2% in the validation cohort. Also, for example, the measurement using the combination of two polynucleotides comprising at least one polynucleotide consisting of the nucleotide sequence represented by SEQ ID NO: 611 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 611 or a complementary sequence thereof exhibited the highest accuracy of 98.0% in the training cohort and the highest accuracy of 90.8% in the validation cohort. Furthermore, for example, the measurement using the combinations of four polynucleotides comprising at least one polynucleotide consisting of the nucleotide sequence represented by SEQ ID NO: 611 or a complementary sequence thereof exhibited the highest accuracy of 96.4% in the training cohort and the highest accuracy of 90.8% in the validation cohort.

Figure 4:
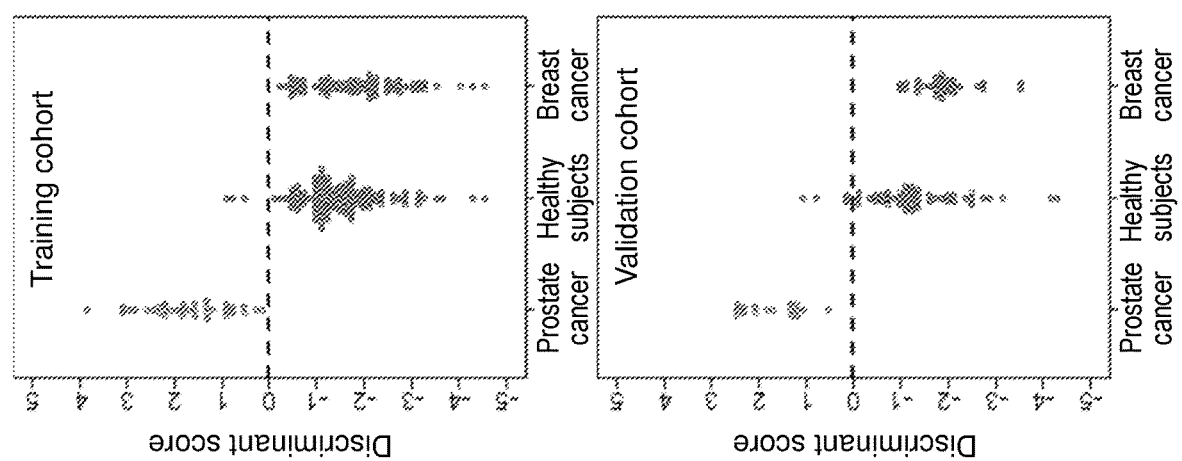
FIG. 4 Upper diagram: a discriminant (1.34×miR-92a-2-5p+1.56×miR-6820-5p−1.29×miR-4745-5p−0.76×miR-125a-3p−4.31) was prepared by use of Fisher's linear discriminant analysis from the measurement values of hsa-miR-4745-5p (SEQ ID NO: 12), hsa-miR-92a-2-5p (SEQ ID NO: 16), hsa-miR-6820-5p (SEQ ID NO: 135), and hsa-miR-125a-3p (SEQ ID NO: 156) in 35 prostate cancer patients, 99 healthy subjects, and 63 breast cancer patients selected as the training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared in the training cohort as to the measurement values of hsa-miR-4745-5p (SEQ ID NO: 12), hsa-miR-92a-2-5p (SEQ ID NO: 16), hsa-miR-6820-5p (SEQ ID NO: 135), and hsa-miR-125a-3p (SEQ ID NO: 156) in 17 prostate cancer patients, 51 healthy subjects, and 30 breast cancer patients selected as the validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 12, 16, 135, and 156 were compared among 35 prostate cancer patients, 99 healthy subjects, and 63 breast cancer patients in the training cohort. As a result, a scatter diagram that significantly separated the discriminant score of the prostate cancer patient group from the discriminant scores of the other groups was obtained in the training cohort (see the upper diagram of FIG. 4). These results were also reproducible in the validation cohort (see the lower diagram of FIG. 4).

TABLE 8-1

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 1 | 94.4 | 91.4 | 95.1 | 91.8 | 94.1 | 91.4 |
| 1_597 | 96.4 | 97.1 | 96.3 | 90.8 | 88.2 | 91.4 |
| 1_7_29 | 98.5 | 100 | 98.1 | 92.9 | 94.1 | 92.6 |
| 1_63_139_600 | 94.9 | 91.4 | 95.7 | 91.8 | 88.2 | 92.6 |
| 1_12_63_599 | 95.4 | 100 | 94.4 | 91.8 | 94.1 | 91.4 |
| 1_141_173_599 | 95.4 | 97.1 | 95.1 | 91.8 | 94.1 | 91.4 |
| 1_16_139_178 | 95.4 | 100 | 94.4 | 92.9 | 94.1 | 92.6 |
| 1_63_173_599 | 93.9 | 94.3 | 93.8 | 90.8 | 94.1 | 90.1 |

TABLE 8-2

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 12 | 65.5 | 74.3 | 63.6 | 56.1 | 70.6 | 53.1 |
| 1_12 | 94.9 | 94.3 | 95.1 | 91.8 | 94.1 | 91.4 |
| 1_7_12 | 98 | 100 | 97.5 | 93.9 | 94.1 | 93.8 |
| 12_42_63_609 | 92.3 | 97.1 | 91.3 | 89.8 | 100 | 87.7 |
| 12_16_135_156 | 98.5 | 100 | 98.1 | 94.9 | 100 | 93.8 |
| 12_16_169_178 | 94.9 | 100 | 93.8 | 88.8 | 100 | 86.4 |
| 12_16_139_601 | 94.9 | 100 | 93.8 | 91.8 | 100 | 90.1 |
| 12_16_42_607 | 97 | 100 | 96.3 | 93.9 | 100 | 92.6 |

TABLE 8-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 16 | 71.6 | 97.1 | 66 | 74.5 | 100 | 69.1 |
| 1_16 | 95.4 | 94.3 | 95.7 | 93.9 | 94.1 | 93.8 |
| 1_16_42 | 97.5 | 97.1 | 97.5 | 94.9 | 94.1 | 95.1 |
| 16_18_139_178 | 94.4 | 97.1 | 93.8 | 92.9 | 94.1 | 92.6 |
| 12_16_37_178 | 98 | 100 | 97.5 | 88.8 | 100 | 86.4 |
| 12_16_37_599 | 97.5 | 100 | 96.9 | 89.8 | 100 | 87.7 |
| 12_16_37_97 | 96.4 | 100 | 95.7 | 89.8 | 100 | 87.7 |
| 12_14_16_599 | 95.4 | 100 | 94.4 | 87.8 | 94.1 | 86.4 |

TABLE 8-4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 37 | 73.6 | 77.1 | 72.8 | 72.4 | 82.4 | 70.4 |
| 1_37 | 95.9 | 97.1 | 95.7 | 92.9 | 88.2 | 93.8 |
| 1_37_135 | 97 | 97.1 | 96.9 | 92.9 | 88.2 | 93.8 |
| 37_63_139_611 | 93.4 | 88.6 | 94.4 | 88.8 | 94.1 | 87.7 |
| 37_42_63_178 | 91.4 | 94.3 | 90.7 | 90.8 | 94.1 | 90.1 |
| 37_42_63_599 | 91.4 | 91.4 | 91.4 | 91.8 | 94.1 | 91.4 |
| 37_42_63_139 | 91.9 | 91.4 | 92 | 91.8 | 94.1 | 91.4 |
| 12_16_37_603 | 97 | 100 | 96.3 | 89.8 | 100 | 87.7 |

TABLE 8-5

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 42 | 57.4 | 48.6 | 59.3 | 59.2 | 52.9 | 60.5 |
| 1_42 | 95.4 | 94.3 | 95.7 | 93.9 | 94.1 | 93.8 |
| 1_3_42 | 97.5 | 94.3 | 98.1 | 95.9 | 94.1 | 96.3 |
| 42_63_607_611 | 90.4 | 88.6 | 90.7 | 90.8 | 100 | 88.9 |
| 42_63_609_611 | 90.8 | 88.6 | 91.3 | 91.8 | 100 | 90.1 |
| 42_63_173_599 | 89.3 | 91.4 | 88.9 | 90.8 | 100 | 88.9 |
| 12_16_42_609 | 96.9 | 100 | 96.3 | 94.9 | 100 | 93.8 |
| 42_63_91_609 | 88.3 | 91.4 | 87.6 | 90.8 | 100 | 88.9 |

TABLE 8-6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 63 | 72.6 | 88.6 | 69.1 | 73.5 | 88.2 | 70.4 |
| 1_63 | 94.9 | 91.4 | 95.7 | 92.9 | 94.1 | 92.6 |
| 1_42_63 | 95.9 | 94.3 | 96.3 | 95.9 | 94.1 | 96.3 |
| 10_42_63_599 | 92.9 | 97.1 | 92 | 91.8 | 100 | 90.1 |
| 42_63_599_609 | 88.8 | 91.4 | 88.2 | 91.8 | 100 | 90.1 |
| 42_63_583_609 | 94.4 | 91.4 | 95 | 89.8 | 100 | 87.7 |
| 37_42_63_611 | 93.9 | 91.4 | 94.4 | 94.9 | 100 | 93.8 |
| 12_63_70_599 | 90.9 | 100 | 88.9 | 89.8 | 94.1 | 88.9 |

TABLE 8-7

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 119 | 46.9 | 62.9 | 43.5 | 48 | 58.8 | 45.7 |
| 1_119 | 94.9 | 91.4 | 95.7 | 91.8 | 94.1 | 91.4 |
| 1_16_119 | 97.4 | 100 | 96.9 | 91.8 | 88.2 | 92.6 |
| 12_16_37_119 | 96.4 | 100 | 95.7 | 89.8 | 100 | 87.7 |
| 37_63_119_584 | 93.4 | 88.6 | 94.4 | 87.8 | 94.1 | 86.4 |
| 63_119_173_178 | 87.2 | 88.6 | 87 | 82.7 | 94.1 | 80.2 |
| 63_119_158_173 | 85.7 | 88.6 | 85.1 | 84.7 | 88.2 | 84 |
| 63_119_173_605 | 87.2 | 88.6 | 87 | 82.7 | 88.2 | 81.5 |

TABLE 8-8

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 126 | 66 | 71.4 | 64.8 | 53.1 | 64.7 | 50.6 |
| 1_126 | 94.4 | 94.3 | 94.4 | 91.8 | 94.1 | 91.4 |
| 1_126_597 | 96.4 | 97.1 | 96.3 | 90.8 | 88.2 | 91.4 |
| 16_126_597_599 | 90.9 | 100 | 88.9 | 81.6 | 88.2 | 80.2 |
| 16_42_126_599 | 92.9 | 94.3 | 92.6 | 92.9 | 100 | 91.4 |
| 16_126_139_601 | 93.9 | 100 | 92.6 | 91.8 | 100 | 90.1 |
| 16_126_593_599 | 89.8 | 97.1 | 88.3 | 85.7 | 94.1 | 84 |
| 15_16_126_599 | 91.4 | 97.1 | 90.1 | 81.6 | 94.1 | 79 |

TABLE 8-9

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 139 | 43.7 | 62.9 | 39.5 | 40.8 | 64.7 | 35.8 |
| 1_139 | 94.4 | 91.4 | 95.1 | 92.9 | 94.1 | 92.6 |
| 1_139_141 | 96.4 | 97.1 | 96.3 | 94.9 | 94.1 | 95.1 |
| 37_63_139_584 | 92.4 | 91.4 | 92.6 | 90.8 | 94.1 | 90.1 |
| 63_139_173_178 | 85.3 | 91.4 | 84 | 89.8 | 94.1 | 88.9 |
| 16_63_139_601 | 92.4 | 97.1 | 91.4 | 91.8 | 94.1 | 91.4 |
| 37_63_139_600 | 89.8 | 91.4 | 89.5 | 88.8 | 94.1 | 87.7 |
| 16_139_178_586 | 91.4 | 100 | 89.5 | 92.9 | 100 | 91.4 |

TABLE 8-10

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 173 | 43.7 | 51.4 | 42 | 55.1 | 58.8 | 54.3 |
| 1_173 | 94.9 | 94.3 | 95.1 | 91.8 | 94.1 | 91.4 |
| 1_15_173 | 97 | 97.1 | 96.9 | 91.8 | 94.1 | 91.4 |
| 63_139_173_599 | 84.8 | 88.6 | 84 | 89.8 | 94.1 | 88.9 |
| 63_119_173_581 | 90.3 | 91.4 | 90.1 | 89.8 | 94.1 | 88.9 |
| 63_173_582_599 | 88.3 | 91.4 | 87.7 | 84.5 | 88.2 | 83.8 |
| 63_136_173_599 | 92.4 | 94.3 | 92 | 95.9 | 94.1 | 96.3 |
| 29_63_173_178 | 87.8 | 91.4 | 87 | 88.8 | 88.2 | 88.9 |

TABLE 8-11

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 178 | 68 | 68.6 | 67.9 | 72.4 | 82.4 | 70.4 |
| 1_178 | 94.4 | 91.4 | 95.1 | 91.8 | 94.1 | 91.4 |
| 1_15_178 | 96.4 | 97.1 | 96.3 | 94.9 | 94.1 | 95.1 |
| 16_139_178_601 | 93.4 | 100 | 92 | 90.8 | 100 | 88.9 |
| 16_37_139_178 | 93.4 | 94.3 | 93.2 | 91.8 | 94.1 | 91.4 |
| 1_12_16_178 | 96.4 | 100 | 95.7 | 93.9 | 100 | 92.6 |
| 1_63_173_178 | 94.9 | 94.3 | 95.1 | 91.8 | 94.1 | 91.4 |
| 16_139_178_597 | 93.9 | 100 | 92.6 | 89.8 | 100 | 87.7 |

TABLE 8-12

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 599 | 61.4 | 74.3 | 58.6 | 65.3 | 82.4 | 61.7 |
| 1_599 | 94.4 | 91.4 | 95.1 | 91.8 | 94.1 | 91.4 |
| 3_112_599 | 97.5 | 97.1 | 97.5 | 92.9 | 94.1 | 92.6 |
| 12_37_63_599 | 91.9 | 97.1 | 90.7 | 88.8 | 94.1 | 87.7 |
| 42_58_63_599 | 90.9 | 94.3 | 90.1 | 87.8 | 94.1 | 86.4 |
| 1_12_16_599 | 96.4 | 100 | 95.7 | 94.9 | 100 | 93.8 |
| 63_119_173_599 | 87.2 | 88.6 | 87 | 80.6 | 88.2 | 79 |
| 16_18_139_599 | 94.9 | 97.1 | 94.4 | 92.9 | 94.1 | 92.6 |

TABLE 8-13

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 609 | 59.7 | 77.1 | 55.9 | 65.3 | 82.4 | 61.7 |
| 1_609 | 95.4 | 94.3 | 95.7 | 91.8 | 94.1 | 91.4 |
| 1_10_609 | 96.4 | 94.3 | 96.9 | 91.8 | 94.1 | 91.4 |
| 42_63_585_609 | 89.8 | 91.4 | 89.4 | 91.8 | 100 | 90.1 |
| 42_63_592_609 | 88.8 | 88.6 | 88.8 | 89.8 | 100 | 87.7 |
| 18_42_581_609 | 93.4 | 94.3 | 93.2 | 90.8 | 94.1 | 90.1 |

TABLE 8-13-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 12_16_599_609 | 96.4 | 100 | 95.7 | 88.8 | 100 | 86.4 |
| 16_126_599_609 | 87.2 | 97.1 | 85.1 | 84.7 | 88.2 | 84.0 |

TABLE 8-14

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 611 | 55.8 | 54.3 | 56.2 | 62.2 | 58.8 | 63 |
| 1_611 | 94.9 | 94.3 | 95.1 | 91.8 | 94.1 | 91.4 |
| 10_15_611 | 98 | 100 | 97.5 | 90.8 | 100 | 88.9 |
| 12_16_37_611 | 96.4 | 100 | 95.7 | 90.8 | 100 | 88.9 |
| 1_63_139_611 | 94.4 | 88.6 | 95.7 | 91.8 | 88.2 | 92.6 |
| 63_158_173_611 | 87.8 | 88.6 | 87.7 | 83.7 | 88.2 | 82.7 |
| 16_37_139_611 | 93.9 | 97.1 | 93.2 | 90.8 | 100 | 88.9 |
| 16_37_595_611 | 91.9 | 97.1 | 90.7 | 84.7 | 82.4 | 85.2 |

As shown in these Examples, the kit, device and the method of the present invention can detect prostate cancer more sensitively than the existing tumor markers and therefore permit early decision to carry out the surgical resection of the cancer site. As a result, improvement in 5-year survival rate and reduction in the rate of recurrence can be achieved.

INDUSTRIAL APPLICABILITY

According to the present invention, prostate cancer can be effectively detected by a simple and inexpensive method. This permits early detection, diagnosis and treatment of prostate cancer. The method of the present invention can detect prostate cancer with limited invasiveness using the blood of a patient and therefore allows prostate cancer to be detected conveniently and rapidly.

All publications, patents, and patent applications cited herein are incorporated herein by reference in their entirety.

---

The invention claimed is:

1. A method for detecting prostate cancer, comprising determining an expression level of hsa-miR-4443 in a sample comprising blood, serum, or plasma from a human subject using a kit comprising a nucleic acid(s), as a primer(s) for PCR, or a probe(s) for Northern blot, Southern blot, or in situ hybridization, capable of specifically binding to hsa-miR-4443, wherein the determining comprises the following steps of:
   (a) contacting hsa-miR-4443 in the sample or complementary polynucleotide(s) thereof prepared from hsa-miR-4443 with the nucleic acid(s);
   (b) measuring an expression level of hsa-miR-4443 by quantitative RT-PCR using the nucleic acid(s) as the primer(s), or Northern blot, Southern blot, or in situ hybridization using the nucleic acids as the probe(s); and
   (c) comparing the expression level of hsa-miR-4443 measured in the step (b) with a control expression level of hsa-miR-4443 in a control sample from a healthy subject measured in the same way as in the step (b),
   wherein a higher expression level of hsa-miR-4443 in the sample comprising blood, serum, or plasma from the subject as compared to the control expression level is detected and is indicative that the subject has prostate cancer; and
   treating the subject for prostate cancer or performing a diagnostic procedure on the prostate of the subject, wherein the treatment comprises surgery, radiotherapy, chemotherapy or the combination thereof, and wherein the diagnostic procedure comprises rectal examination, transrectal ultrasonography of the prostate, or imaging of prostate tissue.

2. A method for detecting prostate cancer, comprising determining an expression level of hsa-miR-4443 in a sample comprising blood, serum, or plasma from a human subject using a device comprising a nucleic acid(s), as a probe(s), capable of specifically binding to hsa-miR-4443, wherein the method determining comprises the following steps of:
   (a) binding hsa-miR-4443 in the sample or cDNA thereof prepared from hsa-miR-4443 to the nucleic acid(s) to measure an expression level of hsa-miR-4443 by hybridization using the nucleic acid(s); and
   (b) comparing the expression level of hsa-miR-4443 measured in the step (a) with a control expression level of hsa-miR-4443 in a sample from a healthy subject measured in the same way as in the step (a),
   wherein a higher expression level of hsa-miR-4443 in the sample comprising blood, serum, or plasma from the subject as compared to the control expression level is detected and is indicative that the subject has prostate cancer; and
   treating the subject for prostate cancer or performing a diagnostic procedure on the prostate of the subject, wherein the treatment comprises surgery, radiotherapy, chemotherapy or the combination thereof, and wherein the diagnostic procedure comprises rectal examination, transrectal ultrasonography of the prostate, or imaging of prostate tissue.

3. The method according to claim 1, wherein the step (c) further comprises preparing a discriminant based on a formula.

4. The method according to claim 3, wherein the discriminant is compared to a threshold.

5. The method according to claim 2, wherein the step (b) further comprises preparing a discriminant based on a formula.

6. The method according to claim 5, wherein the discriminant is compared to a threshold.

* * * * *